United States Patent
Valamehr et al.

(10) Patent No.: US 10,626,372 B1
(45) Date of Patent: *Apr. 21, 2020

(54) METHODS AND COMPOSITIONS FOR INDUCING HEMATOPOIETIC CELL DIFFERENTIATION

(71) Applicant: Fate Therapeutics, Inc., San Diego, CA (US)

(72) Inventors: Bahram Valamehr, San Diego, CA (US); Raedun Clarke, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/545,243

(22) PCT Filed: Jan. 26, 2016

(86) PCT No.: PCT/US2016/014918
§ 371 (c)(1),
(2) Date: Jul. 20, 2017

(87) PCT Pub. No.: WO2016/123100
PCT Pub. Date: Aug. 4, 2016

Related U.S. Application Data

(60) Provisional application No. 62/251,016, filed on Nov. 4, 2015, provisional application No. 62/107,517, filed on Jan. 26, 2015.

(51) Int. Cl.
| | |
|---|---|
| *C12N 5/07* | (2010.01) |
| *C12N 5/074* | (2010.01) |
| *C12N 5/077* | (2010.01) |
| *C12N 5/0783* | (2010.01) |
| *C12N 5/0789* | (2010.01) |
| *C12N 5/0775* | (2010.01) |
| *C12N 5/00* | (2006.01) |

(52) U.S. Cl.
CPC ......... *C12N 5/0647* (2013.01); *C12N 5/0018* (2013.01); *C12N 5/0607* (2013.01); *C12N 5/0636* (2013.01); *C12N 5/0646* (2013.01); *C12N 5/0662* (2013.01); *C12N 5/0696* (2013.01); *C12N 2501/10* (2013.01); *C12N 2501/115* (2013.01); *C12N 2501/125* (2013.01); *C12N 2501/14* (2013.01); *C12N 2501/145* (2013.01); *C12N 2501/155* (2013.01); *C12N 2501/165* (2013.01); *C12N 2501/22* (2013.01); *C12N 2501/23* (2013.01); *C12N 2501/2302* (2013.01); *C12N 2501/2303* (2013.01); *C12N 2501/2306* (2013.01); *C12N 2501/2307* (2013.01); *C12N 2501/2311* (2013.01); *C12N 2501/2315* (2013.01); *C12N 2501/26* (2013.01); *C12N 2501/40* (2013.01); *C12N 2501/415* (2013.01); *C12N 2501/42* (2013.01); *C12N 2501/727* (2013.01); *C12N 2506/02* (2013.01); *C12N 2506/11* (2013.01); *C12N 2506/45* (2013.01)

(58) Field of Classification Search
CPC .. C12N 5/0018; C12N 5/0607; C12N 5/0696; C12N 2501/10; C12N 2501/115; C12N 2501/155; C12N 2501/23; C12N 2501/165; C12N 2501/125; C12N 5/0647; C12N 2501/2303; C12N 2500/02; C12N 2501/2306; C12N 2501/2302; C12N 2501/2307; C12N 2501/2311; C12N 2501/26; C12N 2501/2315; C12N 5/0646; C12N 5/0662

See application file for complete search history.

(56) References Cited

U.S. PATENT DOCUMENTS

| | | | |
|---|---|---|---|
| 5,780,300 | A | 7/1998 | Artavanis-Tsakonas et al. |
| 5,858,358 | A | 1/1999 | June et al. |
| 5,883,223 | A | 3/1999 | Gray |
| 5,942,435 | A | 8/1999 | Wheeler |
| 6,140,081 | A | 10/2000 | Barbas |
| 6,352,694 | B1 | 3/2002 | June et al. |
| 6,453,242 | B1 | 9/2002 | Eisenberg et al. |

(Continued)

FOREIGN PATENT DOCUMENTS

| | | |
|---|---|---|
| EP | 1992360 A1 | 11/2008 |
| EP | 2606884 A1 | 6/2013 |

(Continued)

OTHER PUBLICATIONS

Bykovskaia et al. The generation of human dendritic and NK cells from hemopoietic progenitors induced by IL-15. J Leukoc Biol 66: 659-666, 1999.*

(Continued)

*Primary Examiner* — Bridget E Bunner
(74) *Attorney, Agent, or Firm* — Mintz, Levin, Cohn, Ferris, Glovsky and Popeo, P.C.

(57) ABSTRACT

The invention provides culture platforms, cell media, and methods of differentiating pluripotent cells into hematopoietic cells. The invention further provides pluripotent stem cell-derived hematopoietic cells generated using the culture platforms and methods disclosed herein, which enable feed-free, monolayer culturing and in the absence of EB formation. Specifically, pluripotent stem cell-derived hematopoietic cell of this invention include, and not limited to, iHSC, definitive hemogenic endothelium, hematopoietic multipotent progenitors, T cell progenitors, NK cell progenitors, T cells, and NK cells.

16 Claims, 56 Drawing Sheets

(56) References Cited

U.S. PATENT DOCUMENTS

| | | | |
|---|---|---|---|
| 6,534,055 B1 | 3/2003 | June et al. | |
| 6,534,261 B1 | 3/2003 | Cox et al. | |
| 6,534,476 B2 | 3/2003 | Miyazono et al. | |
| 6,689,744 B2 | 2/2004 | Gao et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,888,121 B2 | 2/2011 | Urnov et al. | |
| 7,972,854 B2 | 7/2011 | Miller et al. | |
| 8,044,201 B2 | 10/2011 | Xu et al. | |
| 8,168,428 B2 | 5/2012 | Zon et al. | |
| 8,389,282 B2 | 3/2013 | Sadelain et al. | |
| 9,220,728 B2 | 12/2015 | Sadelain et al. | |
| 9,452,186 B2 | 9/2016 | Shoemaker et al. | |
| 9,889,160 B2 | 2/2018 | Jantz et al. | |
| 10,287,606 B2 | 5/2019 | Valamehr et al. | |
| 2004/0067583 A1 | 4/2004 | Bernstein et al. | |
| 2004/0101519 A1 | 5/2004 | June et al. | |
| 2004/0171148 A1 | 9/2004 | Schmitt et al. | |
| 2005/0119203 A1 | 6/2005 | Steinbrecher et al. | |
| 2006/0034810 A1 | 2/2006 | Riley et al. | |
| 2006/0121005 A1 | 6/2006 | Berenson et al. | |
| 2011/0027235 A1 | 2/2011 | Gregory et al. | |
| 2011/0027886 A1 | 2/2011 | Han et al. | |
| 2011/0145940 A1 | 6/2011 | Voytas et al. | |
| 2012/0009676 A1* | 1/2012 | Mack | C12N 5/0696 435/372 |
| 2012/0039911 A1 | 2/2012 | Park et al. | |
| 2012/0264218 A1 | 10/2012 | Lin et al. | |
| 2013/0071414 A1 | 3/2013 | Dotti et al. | |
| 2013/0078226 A1 | 3/2013 | Nakauchi et al. | |
| 2013/0280222 A1 | 10/2013 | Kay et al. | |
| 2014/0155468 A1 | 6/2014 | Gregory et al. | |
| 2014/0171148 A1 | 9/2014 | Schmitt et al. | |
| 2014/0273211 A1 | 9/2014 | Slukvin et al. | |
| 2014/0349402 A1 | 11/2014 | Cooper et al. | |
| 2014/0369973 A1 | 12/2014 | Bernstein et al. | |
| 2015/0140665 A1 | 5/2015 | Calos et al. | |
| 2015/0174169 A1 | 6/2015 | Genovese et al. | |
| 2015/0342993 A1 | 12/2015 | Kloss et al. | |
| 2015/0376296 A1 | 12/2015 | Fedorov et al. | |
| 2017/0073643 A1 | 3/2017 | Valamehr et al. | |
| 2018/0072992 A1 | 3/2018 | Valamehr et al. | |
| 2018/0112180 A1 | 4/2018 | Robbins et al. | |
| 2018/0155717 A1 | 6/2018 | Valamehr et al. | |
| 2018/0320137 A1 | 11/2018 | Valamehr et al. | |
| 2019/0119638 A1 | 4/2019 | Sadelain et al. | |
| 2019/0271005 A1 | 9/2019 | Valamehr et al. | |

FOREIGN PATENT DOCUMENTS

| | | |
|---|---|---|
| WO | WO 1998/53058 A1 | 11/1998 |
| WO | WO 1998/53059 A1 | 11/1998 |
| WO | WO 1998/53060 A1 | 11/1998 |
| WO | WO 1999/001426 A1 | 1/1999 |
| WO | WO 2002/006213 A2 | 1/2002 |
| WO | WO 2002/016536 A1 | 2/2002 |
| WO | WO 2003/016496 A2 | 2/2003 |
| WO | WO 2003/077914 A2 | 9/2003 |
| WO | WO 2005/051301 A2 | 6/2005 |
| WO | WO 2005/117994 A2 | 12/2005 |
| WO | WO 2007/044084 A2 | 4/2007 |
| WO | WO 2008/006583 A1 | 1/2008 |
| WO | WO 2008/094597 A2 | 8/2008 |
| WO | WO 2009/091826 A2 | 7/2009 |
| WO | WO 2009/091826 A3 | 7/2009 |
| WO | WO 2009/091826 A9 | 7/2009 |
| WO | WO 2009/097140 A1 | 8/2009 |
| WO | WO-2010/096746 A1 | 8/2010 |
| WO | WO 2011/115308 A1 | 9/2011 |
| WO | WO 2011/159726 A2 | 12/2011 |
| WO | WO 2012/012667 A2 | 1/2012 |
| WO | WO 2012/021845 A2 | 2/2012 |
| WO | WO 2012/087965 A2 | 6/2012 |
| WO | WO-2013/009825 A1 | 1/2013 |
| WO | WO 2013/075222 A1 | 5/2013 |
| WO | WO 2013/086029 A1 | 6/2013 |
| WO | WO 2013/158292 A1 | 10/2013 |
| WO | WO 2013/163171 A1 | 10/2013 |
| WO | WO 2013/176916 A1 | 11/2013 |
| WO | WO 2014/011540 A1 | 1/2014 |
| WO | WO 2014/062138 A1 | 4/2014 |
| WO | WO 2014/152603 A1 | 9/2014 |
| WO | WO 2014/165131 A1 | 10/2014 |
| WO | WO 2016/123117 A1 | 8/2016 |
| WO | WO 2017/078807 A1 | 5/2017 |
| WO | WO 2017/079673 A1 | 5/2017 |
| WO | WO-2017/180989 A2 | 10/2017 |
| WO | WO-2017/180989 A3 | 10/2017 |

OTHER PUBLICATIONS

Li et al. Generation of human-induced pluripotent stem cells in the absence of exogenous Sox2. Stem Cells 27: 2992-3000, 2009.*

Nazareth et al. High-throughput fingerprinting of human pluripotent stem cell fate responses and lineage bias. Nature Methods 10(12): 1225-1231 (with online methods), 2013.*

Ninomiya et al. Improved efficiency of definitive endoderm induction from human induced pluripotent stem cells in feeder and serum-free culture system. In Vitro Cell Dev Biol 51: 1-8, 2015.*

Ogorevc et al. Cellular reprogramming in farm animals: an overview of iPSC generation in the mammalian farm animal species. J Animal Sci Biotech 7:10, 2016 (9 total pages).*

Paterson et al. Characterization of companion animal pluripotent stem cells. Cytometry Part A 93A: 137-148, 2018.*

Tsutsui et al. An optimized small molecular inhibitor cocktail that supports long-term maintenance of human embryonic stem cells. Nature Comm 2: 167, 2011 (8 total pages).*

Valamehr et al. Developing defined culture systems for human pluripotent stem cells. Regen Med 6(5): 623-634, 2011.*

Birch et al., "Suspension culture of mammalian cells," Bioprocess Technol., 10:251-270 (1990).

Brentjens et al., "Genetically targeted T cells eradicate systemic acute lymphoblastic leukemia xenografts," Clin. Cancer Res., 13(18Pt 1):5426-5435 (2007).

Brentjens et al., "Treatment of chronic lymphocytic leukemia with genetically targeted autologous T cells: case report of an unforeseen adverse event in a phase I clinical trial," Mol. Ther., 18(4):666-668 (2010).

Brown et al., "Derivation of induced pluripotent stem cells from human peripheral blood T lymphocytes," PLoSOne, 5(6):e11373 (2010).

Chang et al., "Transforming growth factor-beta signaling in breast cancer", Frontiers in Bioscience, 12: 4393-4401 (2007).

Choi et al., "Identification of the hemogenic endothelial progenitor and its direct precursor in human pluripotent stem cell differentiation cultures," Cell Rep., 2(3):553-567 (2012).

Cui et al., "Selective inhibition of TGF-β responsive genes by Smad-interacting peptide aptamers from FoxH1, Lef1 and CBP", Oncogene, 24: 3864-3874 (2005).

Dacosta et al., "SB-505124 is a selective inhibitor of transforming growth factor-beta type I receptors ALK4, ALK5, and ALK7," Mol. Pharmacol., 65(3):744-752 (2004).

De Gouville and Huet, "Inhibition of ALK5 as a new approach to treat liver fibrotic diseases", Drug News Perspective, 19(2): 85-90 (2006).

Figueiredo et al., "Class-, gene-, and group-specific HLA silencing by lentiviral shRNA delivery," J. Mol. Med., 84(5):425-437 (2006).

(56) References Cited

OTHER PUBLICATIONS

French et al., "Human induced pluripotent stem cell-derived B lymphocytes express sIgM and can be generated via a hemogenic endothelium intermediate," Stem Cells and Development, 24(9):1082-1095 (2015).
Gellibert et al., "Discovery of 4-{4-[3-(Pyridin-2-yl)-1H-pyrazol-4-yl]pyridin-2-yl}-N-(tetrahydro-2H-pyran-4-yl)benzamide (GW788388): A Potent, Selective, and Orally Active Transforming Growth Factor-β Type I Receptor Inhibitor", Journal Medicinal Chemistry, 49(7): 2210-2221 (2006).
Gong et al., "Cancer patient T cells genetically targeted to prostate-specific membrane antigen specifically lyse prostate cancer cells and release cytokines in response to prostate-specific membrane antigen," Neoplasia, 1(2):123-127 (1999).
Hu et al., "Large-scale mammalian cell culture," Curr. Opin. Biotechnol., 8(2):148-153 (1997).
Huang et al., "Pivotal role for glycogen synthase kinase-3 in hematopoietic stem cell homeostasis in mice," J. Clin. Invest., 119(12):3519-3529 (2009).
Inman et al., "SB-431542 is a potent and specific inhibitor of transforming growth factor-β Superfamily Type I Activin Receptor-Like Kinase (ALK) Receptors ALK4, ALK5, and ALK7", Molecular Pharmacology, 62(1): 65-74 (2002).
Kaminska, et al., "TGF beta signalling and its role in tumour pathogenesis", Acta Biochimica Polonica, 52(2): 329-337 (2005).
Kennedy et al., "T lymphocyte potential marks the emergence of definitive hematopoietic progenitors in human pluripotent stem cell differentiation cultures," Cell Rep., 2(6):1722-1735 (2012).
Kim, et al., "Pharmacokinetics and tissue distribution of 3-((5-(6-methylpyridin-2-yl)-4-(quinoxalin-6-yl)-1H-imidazol-2-yl)methyl)benzamide; a novel ALK5 inhibitor and a potential anti-fibrosis drug", Xenobiotica, 38(3): 325-339 (2008).
Kitano, "Serum-free media," in Animal Cell Bioreactors, eds. Ho and Wang, Butterworth-Heinemann, Stoneham, MA, Chapter 4, pp. 73-106 (1991).
Knorr et al., "Clinical-scale derivation of natural killer cells from human pluripotent stem cells for cancer therapy," Stem Cells Transl. Med., 2(4):274-283 (2013).
Knorr et al., "Engineering Human Pluripotent Stem Cells for Enhanced Lymphocyte Development and Function A Dissertation Submitted to the Faculty of the Graduate School of the University of Minnesota by," Oct. 2012, Retrieved from the Internet: URL:http://conservancy.umn.edu/bitstream/handle/11299/142741/Knorr_umn_0130E_13251.pdf?seque nce=1 &isAllowed=y [retrieved on Oct. 5, 2015].
Knorr et al., "Pluripotent stem cell-derived natural killer cells for cancer therapy," Transl. Res., 156(3):147-154 (2010).
Lian et al., "Efficient differentiation of human pluripotent stem cells to endothelial progenitors via small-molecule activation of WNT signaling," Stem Cell Reports, 3(5):804-816 (2014).
Maher et al., "Human T-lymphocyte cytotoxicity and proliferation directed by a single chimeric TCRzeta /CD28 receptor," Nat. Biotechnol., 20(1):70-75 (2002).
Nishimura et al., "Generation of rejuvenated antigen-specific T cells by reprogramming to pluripotency and redifferentiation," Cell Stem Cell, 12(1):114-126 (2013).
Papapetrou et al., "Genomic safe harbors permit high β-globin transgene expression in thalassemia induced pluripotent stem cells," Nat. Biotechnol., 29(1):73-78 (2011).
Poirot et al., "Multiplex genome-edited T-cell manufacturing platform for "off-the-shelf" adoptive T-cell immunotherapies," Cancer Res., 75(18):3853-3864 (2015).
Rathjen et al., "Properties and uses of embryonic stem cells: prospects for application to human biology and gene therapy," Reprod. Fertil. Dev., 10:31-47 (1998).
Robertston, "Derivation and maintenance of embryonic stem cell cultures," Methods Mol. Biol., 75:173-184 (1997).
Sadelain et al., "The promise and potential pitfalls of chimeric antigen receptors," Curr. Opin. Immunol., 21(2):215-223 (2009).

Schmitt et al., "Induction of T cell development and establishment of T cell competence from embryonic stem cells differentiated in vitro," Nat. Immunol., 5(4):410-417 (2004).
Schmitt et al., "Induction of T cell development from hematopoietic progenitor cells by delta-like-1 in vitro," Immunity, 17(6):749-756 (2002).
Shimanuki et al., "Modulation of the functional binding sites for TGF-beta on the type II receptor leads to suppression of TGF-beta signaling", Oncogene, 26: 3311-3320 (2007).
Spier, "Large-scale mammalian cell culture: methods, applications and products," Curr. Opin. Biotechnol., 2(3):375-379 (1991).
Suzuki et al., "A novel small-molecule inhibitor of transforming growth factor beta type I receptor kinase (SM16) inhibits murine mesothelioma tumor growth in vivo and prevents tumor recurrence after surgical resection", Cancer Research, 67(5): 2351-2359 (2007).
Tojo, et al., "The ALK-5 inhibitor A-83-01 inhibits Smad signaling and epithelia-to-mesenchymal transition by transforming growth factor-β," Cancer Sci, 96(11): 791-800 (2005).
Torikai et al., "A foundation for universal T-cell based immunotherapy: T cell engineered to express a CD19-specific chimeric-antigen-receptor and eliminate expression of endogenous TCR," Blood, 119(24):5697-5705 (2012).
Valamehr et al., "A novel platform to enable the high-throughput derivation and characterization of feeder-free human iPSCs," Sci. Rep., 2:213 (2012).
Valamehr et al., "Platform for induction and maintenance of transgene-free hiPSCs resembling ground state pluripotent stem cells," Stem Cell Reports, 2:366-381 (2014).
Wang et al., "WNT and BMP signaling are both required for hematopoietic cell development from human ES cells," Stem Cell Res., 3(2-3):113-125 (2009).
Wiles, "Embryonic stem cell differentiation in vitro," Methods Enzymol., 225:900-918 (1993).
Wrzesinski, et al., "Transforming growth factor-beta and the immune response: implications for anticancer therapy", Clinical Cancer Research, 13(18): 5262-5270 (2007).
Yamane et al., "Expression of AA4.1 marks lymphohematopoietic progenitors in early mouse development," Proc. Natl. Acad. Sci. USA, 106(22):8953-8958 (2009).
Zhao et al., "Inhibition of transforming growth factor-beta1-induced signaling and epithelial-to-mesenchymal transition by the Smad-binding peptide aptamer Trx-SARA", Molecular Biology of the Cell, 17(9): 3819-3831 (2006).
Ameri et al., "FGF2 specifies hESC-derived definitive endoderm into foregut/midgut cell lineages in a concentration-dependent manner," Stem Cells, 28(1):45-56 (2010).
Ansari et al., "The programmed death-1 (PD-1) pathway regulates autoimmune diabetes in nonobese diabetic (NOD) mice," J. Exp. Med., 198(1):63-69 (2003).
Beilhack et al., "Purified allogeneic hematopoietic stem cell transplantation blocks diabetes pathogenesis in NOD mice," Diabetes, 52:59-68 (2003).
Brevini et al., "No shortcuts to pig embryonic stem cells," Theriogenology, 74(4):544-550 (2010).
Chiang et al., "Differentiation of an embryonic stem cell to hemogenic endothelium by defined factors: essential role of bone morphogenetic protein 4," Development, 138(13):2833-2843 (2011).
D'Addio et al., "Autologous nonmyeloablative hematopoietic stem cell transplantation in new-onset type 1 diabetes: a multicenter analysis," Diabetes, 63:3041-3046 (2014).
Eiselleova et al., "A complex role for FGF-2 in self-renewal, survival, and adhesion of human embryonic stem cells," Stem Cells, 27(8):1847-1857 (2009).
Fiorina et al., "Targeting the CXCR4-CXCL12 axis mobilizes autologous hematopoietic stem cells and prolongs islet allograft survival via programmed death ligand 1," J. Immunol., 186:121-131 (2011).
Hoggatt et al., "Prostaglandin E2 enhances hematopoietic stem cell homing, survival, and proliferation," Blood, 113(22):5444-5455 (2009).
Joo et al., "ROCK suppression promotes differentiation and expansion of endothelial cells from embryonic stem cell-derived Flk1(+) mesodermal precursor cells," Blood, 120(13):2733-2744 (2012).

(56) References Cited

OTHER PUBLICATIONS

Krawetz et al., "Inhibition of Rho kinase regulates specification of early differentiation events in P19 embryonal carcinoma stem cell," PLoS One, 6(11):e26484 (2011).

Menon et al., "Lymphoid regeneration from gene-corrected SCID-X1 subject-derived iPSCs," *Cell Stem Cell*, 16(4):367-372 (2015).

Munoz et al., "Constraints to progress in embryonic stem cells from domestic species," Stem Cell Rev. Rep., 5:6-9 (2009).

Munoz et al., "Conventional pluripotency markers are unspecific for bovine embryonic-derived cell-lines," Theriogenology, 69(9):1159-1164 (2008).

Ozkaynak et al., "Programmed death-1 targeting can promote allograft survival," *J. Immunol.*, 169:6546-6553 (2002).

Paris et al., "Equine embryos and embryonic stem cells: defining reliable markers of pluripotency," *Theriogenology*, 74:516-524 (2010).

Pearson et al., "The stepwise specification of embryonic stem cells to hematopoietic fate is driven by sequential exposure to Bmp4, activin A, bFGF and VEGF," Development, 135:1525-1535 (2008).

Rahman et al., "Rescue of DNA-PK Signaling and T-Cell Differentiation by Targeted Genome Editing in a prkdc Deficient iPSC Disease Model," *PLoS Genet.*, 11(5):e1005239 (2015).

Riella et al., "Role of the PD-1 pathway in the immune response," *Am. J. Transplant.*, 12:2575-2587 (2012).

Song et al., "Improved hematopoietic differentiation efficiency of gene-corrected beta-thalassemia induced pluripotent stem cells by CRISPR/Cas9 system," *Stem Cells Dev.*, 24(9):1053-1065 (2015).

Vijayaragavan et al., "Noncanonical Wnt signaling orchestrates early developmental events toward hematopoietic cell fate from human embryonic stem cells," Cell Stem Cell, 4:248-262 (2009).

Vodyanik et al., "Leukosialin (CD43) defines hematopoietic progenitors in human embryonic stem cell differentiation cultures," *Blood*, 108:2095-2105 (2006).

Voltarelli et al., "Autologous nonmyeloablative hematopoietic stem cell transplantation in newly diagnosed type 1 diabetes mellitus," *JAMA*, 297(14):1568-1576 (2007).

Xu et al., "BMP4 initiates human embryonic stem cell differentiation to trophoblast," *Nat. Biotechnol.*, 20:1261-1264 (2002).

Zheng et al., "Ex vivo expanded hematopoietic stem cells overcome the MHC barrier in allogeneic transplantation," *Cell Stem Cell*, 9:119-130 (2011).

Eyquem, J. et al. (Mar. 2, 2017, e-published Feb. 22, 2017). "Targeting a CAR to the TRAC locus with CRISPR/Cas9 enhances tumour rejection," Nature 543(7643):113-117.

MacLeod, D.T. et al. (Apr. 5, 2017, e-published Feb. 23, 2017). "Integration of a CD19 CAR into the TCR Alpha Chain Locus Streamlines Production of Allogeneic Gene-Edited CAR T Cells," Mol Ther 25(4):949-961.

Smith, C. et al. (Mar. 2015, e-published Nov. 24, 2014). "Efficient and allele-specific genome editing of disease loci in human iPSCs," Mol Ther 23(3):570-577.

Themeli, M. et al. (Oct. 2013, e-published Aug. 11, 2013). "Generation of tumor-targeted human T lymphocytes from induced pluripotent stem cells for cancer therapy," Nat Biotechnol 31(10):928-933.

Themeli, M. et al. (Apr. 2, 2015). "New cell sources for T cell engineering and adoptive immunotherapy," Cell Stem Cell 16(4):357-366.

\* cited by examiner iHSC and iTC differentiation platform iHSC platform hiPSC → Mesoderm → Hemogeneic endothelium → Sort CD34+/45mid Definitive hematopoiesis HSC → T cell progenitors → T cell maturation Monolayer, FF | Suspension, FF iHSC-A
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- CHIR99021 iHSC-B
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- CHIR99021
- [+] add
  - SB431542 iHSC-C
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- [+] add
  - VEGF
  - SCF
  - FLT3L
  - IL15
  - IL3
  - IL6
  - IGF
  - TPO
- [-] remove
  - SB431542
  - CHIR99021 iTC platform iTC-A
- Suspension
- Stempro 34
- Glut & NEAA & ITS
- FBS
- Serum Replacement 3
- Ascorbic Acid
- BME
- MTG
- bFGF
- IL3
- IL6
- BMP4
- SCF
- FLT3L
- [+] add
  - DLL-1
  - DLL-4
  - IL7
  - IL2
- [-] remove
  - VEGF, BMP4, IL15
  - Fibronectin iTC-B
- Suspension
- Stempro 34
- Glut & NEAA & ITS
- FBS
- Serum Replacement 3
- Ascorbic Acid
- BME
- MTG
- bFGF
- IL6
- IL2
- IGF
- SCF
- FLT3L
- DLL-3
- DLL-4
- IL7
- [-] remove
  - BMP4

*FIG. 1* iHSC and iNK differentiation platform hiPSC → Mesoderm → Hemogeneic endothelium → Sort CD34+/45mid → Definitive hematopoiesis HSC → NK cell progenitors → NK cell maturation

Monolayer, FF ... Suspension, FF ... Suspension, FF iHSC-A
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- CHIR99021 iHSC-B
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- CHIR99021
- [+] add
  - SB431542 iHSC-C
- Matrigel (adherent)
- Stempro 34
- Glut & NEAA & ITS
- FBS
- Serum Replacement 3
- Ascorbic Acid
- BME
- MTG
- bFGF
- BMP4
- Fibronectin
- [+] add
  - VEGF
  - SCF
  - FLT3L
  - IL15
  - IL3
  - IL6
  - IGF
  - TPO
- [-] remove
  - SB431542
  - CHIR99021 iNK-A
- Suspension
- Stempro 34
- Glut & NEAA & ITS
- FBS
- Serum Replacement 3
- Ascorbic Acid
- BME
- MTG
- bFGF
- IL3
- IL6
- VEGF
- IL15
- BMP4
- SCF
- FLT3L
- [+] add
  - IL2
- [-] remove
  - VEGF iNK-B
- Suspension
- Stempro 34
- Glut & NEAA & ITS
- FBS
- Serum Replacement 3
- Ascorbic Acid
- BME
- MTG
- bFGF
- IL3
- IL6
- IL2
- IGF
- IL15
- SCF
- FLT3L
- IL7
- [-] remove
  - BMP4

*iHSC platform* | *iNK platform*

*FIG. 2*

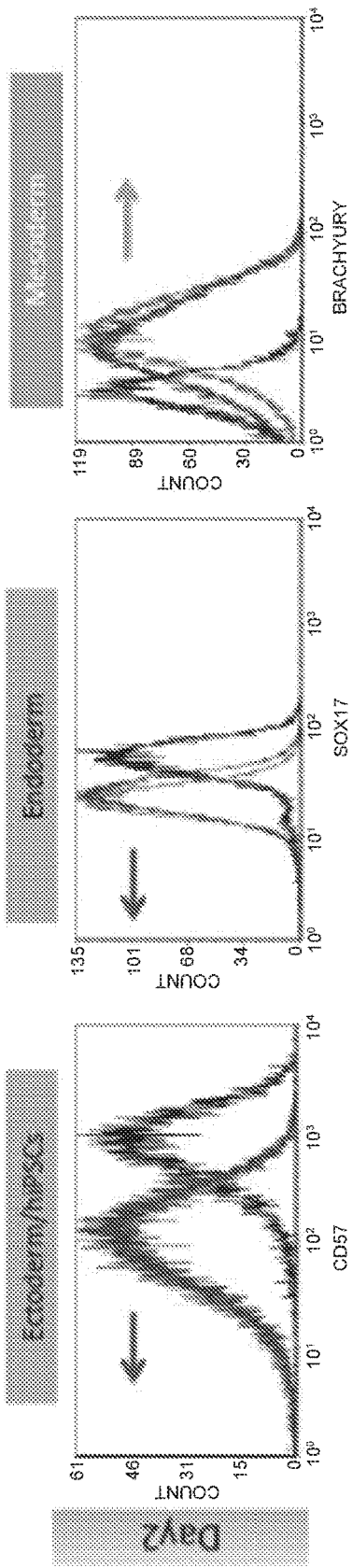
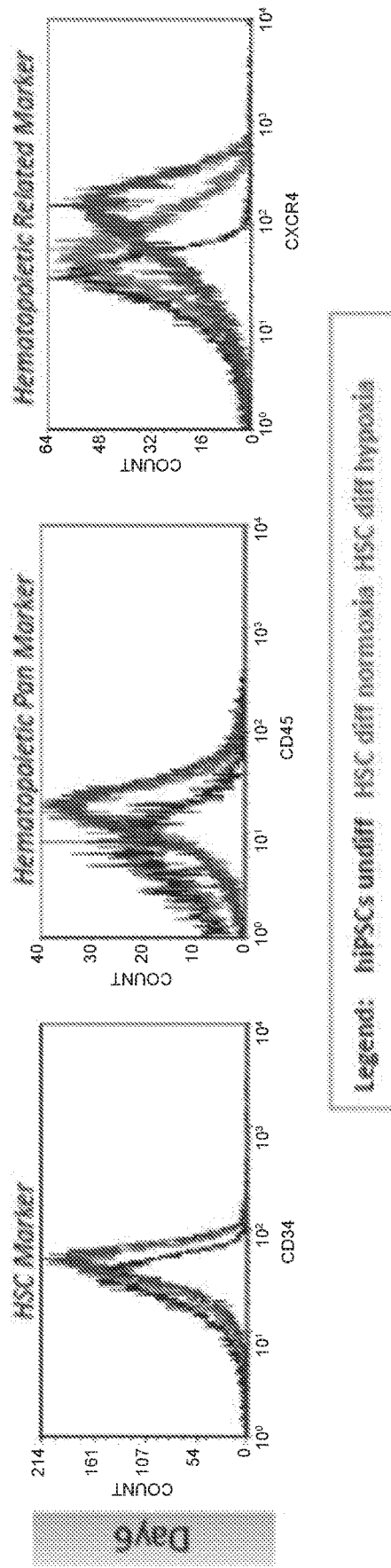
FIG. 4C
FIG. 4D

Fibroblast derived
OCT4/SOX2/T

Fibroblast derived
OCT4/SOX2/NANOG/T

Cord Blood derived
OCT4/SOX2/NANOG/LIN28/MYC/T

Platforms for CD34+ hemogenic endothelium (HE) and multipotent progenitors (MPP)

Naive hiPSC
- Matrigel
- DMEM/F12
- KOSR
- Glut & NEAA & ITS
- bME
- CHIR99021
- Thiazovivin
- PD0325901
- LIF
- bFGF iCD34-A
- Matrigel
- StemPro 34
- Glut & ITS
- AA
- MTG
- BMP4

Mesoderm iCD34-B
- Matrigel
- StemPro 34
- Glut & ITS
- AA
- MTG
- BMP4
- bFGF
- CHIR99012 iCD34-C
- Matrigel
- StemPro 34
- Glut & ITS
- AA
- MTG
- VEGF
- bFGF
- SCF
- IL6
- IL11
- Y27632

Sort CD34+HE

Definitive Hemogenic Endothelium iMPP-A
- Matrigel
- StemPro 34
- Glut & ITS
- AA
- MTG
- VEGF
- bFGF
- SCF
- IL6
- IL11
- BMP4
- TPO
- IL3
- GMCSF
- GCSF
- EPO
- Y27632

Pre-HSC iMPP-B
- Matrigel
- StemPro 34
- Glut & ITS
- AA
- MTG
- VEGF
- bFGF
- SCF
- IL6
- IL11
- BMP4
- TPO
- IL3
- GMCSF
- GCSF
- EPO Multipotent Progenitors

FIG. 12

Platforms for CD34+ hemogenic endothelium (HE) and T cell progenitors

Naive hiPSC → Mesoderm → Sort CD34+HE Definitive Hemogenic Endothelium → Pre-T cell progenitors → T cell progenitors or T cell

Naive hiPSC:
- Matrigel
- DMEM/F12
- KOSR
- Glut & NEAA & ITS
- bME
- CHIR99021
- Thiazovivin
- PD0325901
- LIF
- bFGF iCD34-A:
- Matrigel
- StemPro 34
- Glut & ITS
- -AA
- -MTG
- -BMP4 iCD34-B:
- Matrigel
- StemPro 34
- Glut & ITS
- -AA
- -MTG
- -BMP4
- -bFGF iCD34-B:
- Matrigel
- StemPro 34
- Glut & ITS
- -AA
- -MTG
- -BMP4
- -bFGF
- -CHIR99012 iCD34-C:
- Matrigel
- StemPro 34
- Glut & ITS
- -AA
- -MTG
- -VEGF
- -bFGF
- -SCF
- -IL6
- -IL11
- -Y27632 iT-A:
- StemPro 34
- Glut & ITS
- -AA
- -MTG
- -VEGF
- -bFGF
- -SCF
- -BMP4
- -Flt3L
- -IL7
- -Y27632 iT-B:
- Matrigel, FF or Stromal
- aMEM
- -FBS
- -Glut
- -SCF
- -Flt3L
- -IL7 iCD34 platform | iT platform

FIG. 13

Platforms for CD34+ hemogenic endothelium (HE) and NK cell progenitors

| | | Mesoderm | | Definitive Hemogenic Endothelium | Pre-NK cell progenitors | NK cell progenitors or NK cell |
|---|---|---|---|---|---|---|
| Naive hiPSC | iCD34-A | iCD34-B | iCD34-C | | | |
| -Matrigel<br>-DMEM/F12<br>-KOSR<br>-Glut & NEAA & ITS<br>-bME<br>-CHIR99021<br>-Thiazovivin<br>-PD0325901<br>-LIF<br>-bFGF | -Matrigel<br>-StemPro 34<br>-Glut & ITS<br>-AA<br>-MTG<br>-BMP4 | -Matrigel<br>-StemPro 34<br>-Glut & ITS<br>-AA<br>-MTG<br>-BMP4<br>-bFGF | -Matrigel<br>-StemPro 34<br>-Glut & ITS<br>-AA<br>-MTG<br>-BMP4<br>-bFGF<br>-CHIR99012 | Sort CD34+HE<br>-Matrigel<br>-StemPro 34<br>-Glut & ITS<br>-AA<br>-MTG<br>-VEGF<br>-bFGF<br>-SCF<br>-IL6<br>-IL11<br>-IL3<br>-Y27632 | -StemPro 34<br>-Glut & ITS<br>-AA<br>-MTG<br>-VEGF<br>-bFGF<br>-SCF<br>-BMP4<br>-Flt3L<br>-IL7<br>-IL15<br>-IL3<br>-Y27632 | -Matrigel, FF or Stromal<br>-aMEM<br>-FBS<br>-Glut<br>-SCF<br>-Flt3L<br>-IL7<br>-IL15<br>-IL3 |

*FIG. 14*

Optimization of protocol leads to enhanced differentiation, demonstrating that each component plays a critical role.

iPSC-derived, iCD34 differentiated towards T cells.

iPSC-derived, iCD34 differentiated towards T cells.

iPSC-derived, iCD34 differentiated towards NK cells.
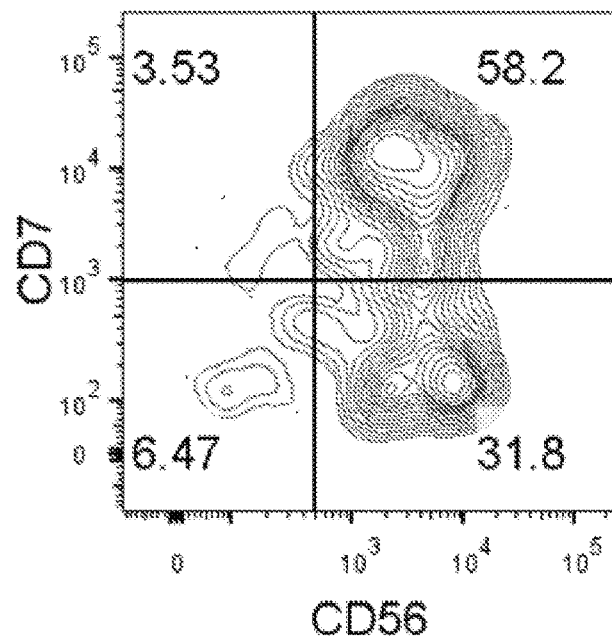
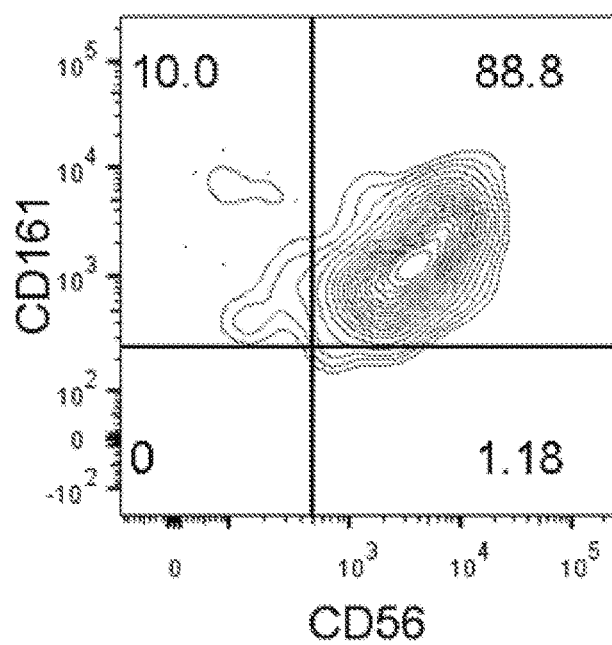
FIG. 22A iPSC-derived, iCD34 differentiated towards NK cells.
Mature NK lineage markers
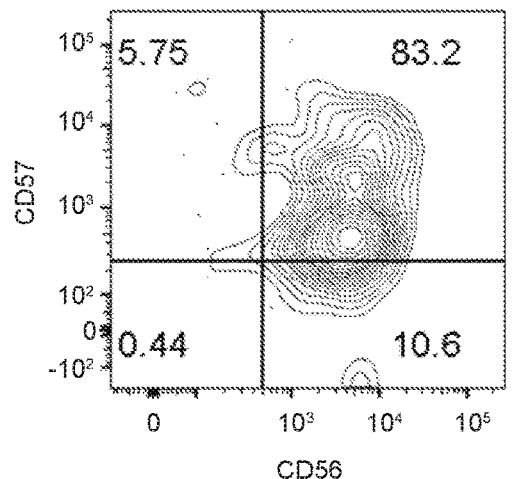
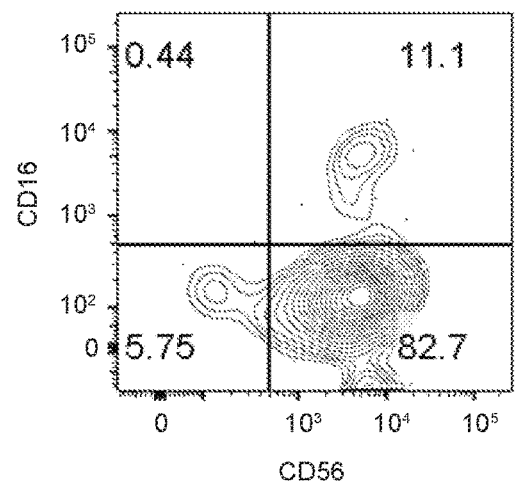
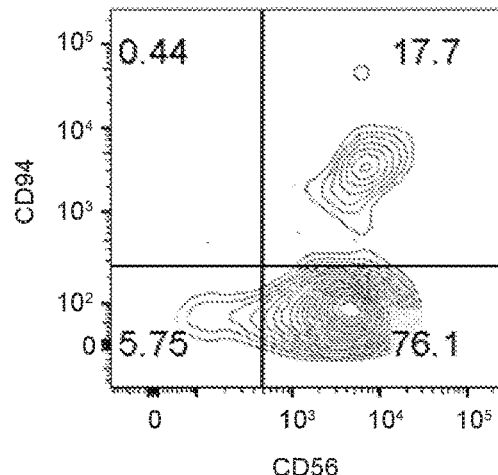
*FIG. 22B* iPSC-derived, iCD34 differentiated towards NK cells.
Day 5: UCB CD34+ cells versus iCD34+ cells
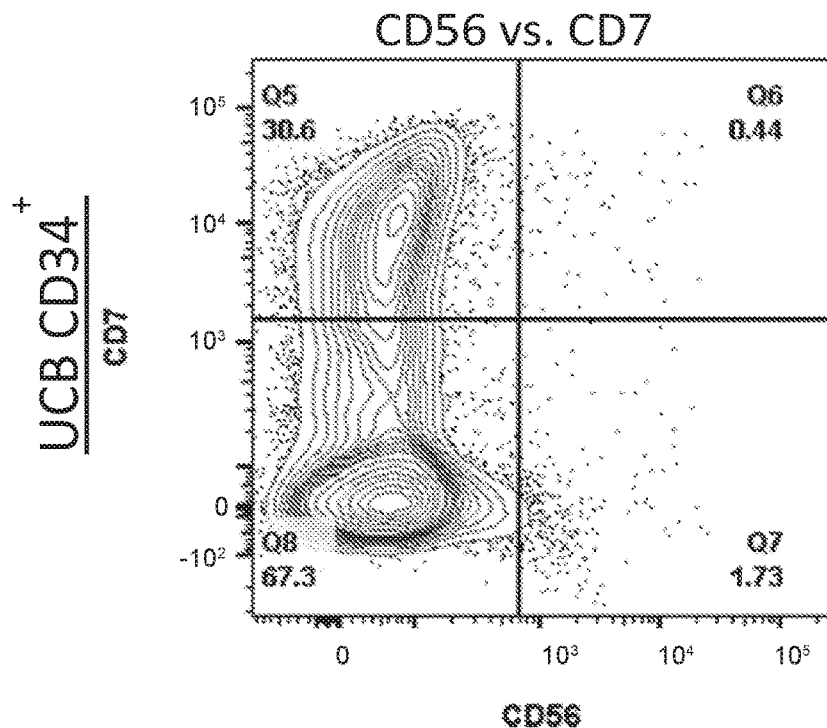
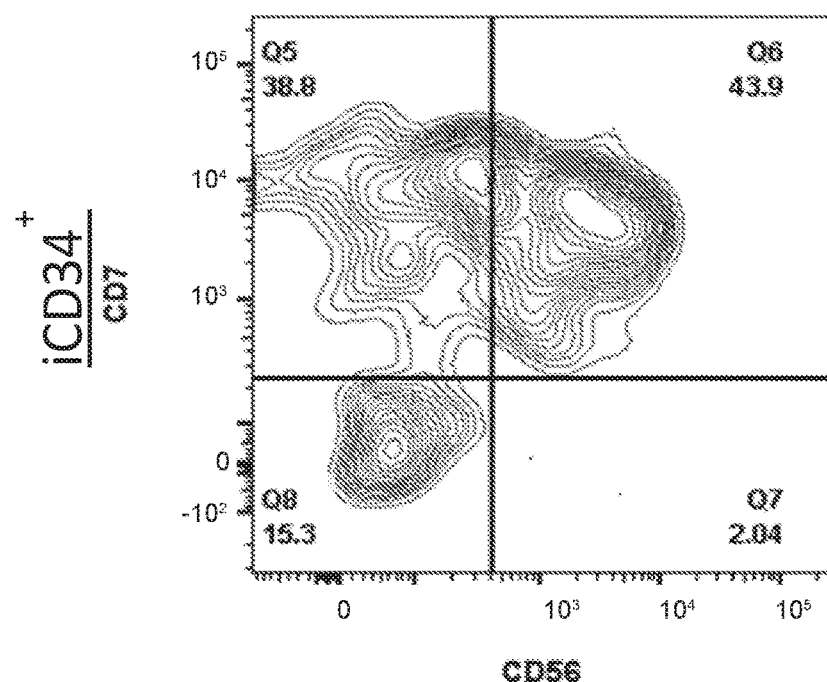
FIG. 22C Monolayer hiPSC hematopoietic differentiation platform allows for a scalable expansion strategy that is not seen during EB formation hiPSCs were seeded as monolayer and differentiated for 8 days prior to analysis for CD34, 43, CXCR4 and CD73.

METHODS AND COMPOSITIONS FOR INDUCING HEMATOPOIETIC CELL DIFFERENTIATION

RELATED APPLICATION

This application claims priority to U.S. Provisional Application Ser. No. 62/107,517, filed Jan. 26, 2015 and U.S. Provisional Patent Application No. 62/251,016, filed Nov. 4, 2015, the disclosures of which are hereby incorporated by reference in their entirety.

FIELD OF INVENTION

The invention relates generally to compositions and methods for manufacturing cells of all hematopoietic lineages from pluripotent stem cells. In particular, the invention relates to improved culture platforms for manufacturing cells of all hematopoietic lineages from pluripotent stem cells including human induced pluripotent stem cells.

BACKGROUND

Human induced pluripotent stem cell (hiPSC) technology represents a highly promising and potentially unlimited source of therapeutically viable hematopoietic cells for the treatment of numerous hematological and non-hematological malignancies including cancer. To advance the promise of hiPSC and genomically engineered hiPSC technology as an allogeneic source of hematopoietic cellular therapeutics, it is essential to be able to efficiently and reproducibly generate not only hematopoietic stem and progenitor cells (HSCs) but also immune effector populations, including the diverse subsets of T, B, NKT, and NK lymphoid cells, and progenitor cells thereof.

The in vitro derivation of HSCs with the potential to generate lymphocytes is complicated by the existence of at least two temporally and spatially distinct waves of blood formation during embryonic development: primitive and definitive hematopoiesis. Primitive hematopoiesis initiates in the extraembryonic yolk sac and generates a transient and restricted hematopoietic repertoire mainly including primitive erythroid and myeloid cells, but not HSCs. Nascent HSCs only emerge later during the definitive wave from a specialized endothelial progenitor within the arterial vasculature termed definitive hemogenic endothelium (HE). Definitive HE then undergoes an endothelial-to-hematopoietic transition to give rise to HSCs, which then ultimately migrate to the bone marrow where they sustain multi-lineage hematopoiesis, including T, B, NKT, and NK lymphoid cells, throughout adult life. Therefore the generation of HSCs and lymphoid effector cells from pluripotent stem cells is dependent upon the ability to accurately recapitulate the intricate stages of early embryonic hematopoietic development towards the definitive program through well-designed and validated methods and compositions.

A limited number of studies have described the directed differentiation of hiPSCs to definitive HE in vitro. A major hurdle in utilizing hiPSCs for therapeutic purposes has been the requirement to initially co-culture such cells with murine- or human-derived stromal cells in the presence of ill-defined serum-containing media in order to maintain pluripotency and induce differentiation. In addition, the existing protocols have also employed a strategy consisting of culturing iPSC to form an embryoid body (EB), which is a heterogeneous aggregate of cells comprising various differentiated cells including ectoderm, mesoderm, and endoderm cells. Those procedures either require aggregating pluripotent cells by for example spinning to form clumps, allowing the cells to settle and aggregate in wells or allowing for passive aggregation and clump formation in suspension culture. The formed EBs are maintained for certain duration in differentiation inducing culture systems, typically seven to ten days, to allow for proper differentiation, then the EBs are either transferred to adherent culture for further maturation or dissociated into single cells for cell type selection in order to proceeding to the subsequent differentiation steps. (Kennedy et al., Cell Reports 2012:1722-1735; Knorr, et al., Stem Cells Translational Medicine 2013 (2):274-283). For example, Kennedy et al. teach to generate EBs for iPSCs differentiation, where pluripotent cells were treated with collagenase and trypsin to allow for scraping of the cells to form small aggregates which were then cultured to form EBs. EB formation has been shown to facilitate pluripotent stem cell differentiation, however the requirement of forming aggregates and subsequent EBs is labor intensive, the cell numbers minimally increase in this process, the cellular content in the three dimensional EB aggregates are exposed to the media factors inconsistently and unevenly, which leads to heterogeneous cells products that are in variable differention stages, and greatly hinders the scalability and reproducibility of a manufacturing process that is required to be efficient and streamlined.

Therefore, there is a need for methods and compositions of differentiating stem cell to definitive hematopoiesis without relying on co-culturing or serum-containing media, and without requiring the formation of embryoid body aggregates as intermediates.

SUMMARY OF THE INVENTION

The present invention relates generally to cell culture conditions, media, culture platforms, and methods for culturing and differentiating stem cells to a hematopoietic cell fate.

Specifically, the present invention provides methods and compositions for the generation of hematopoietic cell lineages through definitive hemogenic endothelium (HE) and definitive hematopoietic stem cells (HSC) derived from pluripotent stem cells, including hiPSCs under serum/feeder-free conditions and in a scalable and monolayer culturing platform without the need of EB formation. Cells that may be differentiated according to the methods of the invention range from pluripotent stem cells, to progenitor cells that are committed to a particular terminally differentiated cell and transdifferentiated cells, cells of various lineages directly transitioned to hematopoietic fate withoug going through a pluripotent intermediate. Similarly, the cells produced by differentiation of stem cells range from multipotent stem or progenitor cells to terminally differentiated stem cells, and all intervening hematopoietic cell lineages.

The present invention provides methods and compositions for differentiating and expanding cells of the hematopoietic lineage from pluripotent stem cells in monolayer culturing, which comprises contacting the pluripotent sterm cells with a BMP pathway activator, and optionally, bFGF. As such, pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

Provided herein is a monolayer differentiation platform that facilitates differentiation towards definitive hemogenic endothelium resulting in the derivation of hematopoietic stem cells and differentiated progeny such as T, B, NKT and NK cells. The demonstrated monolayer differentiation strategy combines enhanced differentiation efficiency with large-scale expansion enables the delivery of therapeutically relevant number of pluripotent stem cell-derived hematopoietic cells for various therapeutic applications. Further, the present invention disclosed that monolayer culturing using the methods provided herein leads to functional hematopoietic lineage cells that enable full range of in vitro differentiation, ex vivo modulation, and in vivo long term hematopoietic self-renewal, reconstitution and engraftment.

One aspect of the present invention provides a culture platform for obtaining pluripotent stem cell-derived hematopoietic lineage cells, which comprises: group I: (i) a culture medium comprising a BMP activator, and one or more growth factors and cytokines selected from the group consisting of VEGF, SCF, Flt3L, IL15, IL3, IL6, IGF, and TPO, wherein the culture medium is optionally free of Wnt pathway activators and TGFβ receptor/ALK inhibitors, and is suitable for differentiating and expanding definitive HSCs from definitive hemogenic endothelium; (ii) a culture medium comprising a GSK3 inhibitor, a BMP activator, and optionally, a TGFβ receptor/ALK inhibitor, wherein the culture medium is suitable for differentiating and expanding definitive hemogenic endothelium from mesodermal cells; and (iii) a culture medium comprising a GSK3 inhibitor, a BMP activator, wherein the culture medium is suitable for differentiating and expanding mesodermal cells from pluripotent stem cells.

Alternatively, the culture platform for obtaining pluripotent stem cell-derived hematopoietic lineage cells comprises group II: (i) a culture medium comprising a ROCK inhibitor, one or more growth factors and cytokines selected from the group consisting of bFGF, VEGF, SCF, IL6, and IL11, and is optionally free of TGFβ receptor/ALK inhibitor, wherein the medium is suitable for differentiating and expanding definitive hemogenic endothelium from mesodermal cells having definitive hemogenic endothelium potential; (ii) a culture medium comprising a BMP activator, bFGF, and a GSK3 inhibitor, and is optionally free of TGFβ receptor/ALK inhibitor, wherein the medium is suitable for obtaining mesodermal cell having definitive hemogenic endothelium potential; and (iii) a culture medium that comprises a BMP activator, and optionally bFGF, wherein the medium is suitable for differentiating and expanding mesodermal cells from pluripotent stem cells. In some embodiment, the pluripotent stem cells of the above culture platform are iPSCs. In some embodiments, the iPSCs are naïve iPSCs. In some embodiment, the Group (II) of the above culture platform further comprises: (iv) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells.

In some embodiments of the above culture platform, each of the Group (I) and (II) further comprises additional culture media.

Group (I) may further comprise: (i) a culture medium comprising one or more growth factors and cytokines selected from the group consisting of SCF, Flt3L, IL7, IGF, IL2, IL3, and IL6; and one or more Notch pathway activators; wherein the culture medium is free of BMP activator, and is suitable for differentiating pluripotent stem cell-derived T cell progenitors to T cells, or (ii) a culture medium comprising a BMP activator; one or more growth factors and cytokines selected from the group consisting of SCF, Flt3L, IL7, IL2, IL3, and IL6; and one or more Notch pathway activators, wherein the culture medium is suitable for differentiating pluripotent stem cell-derived definitive HSC to T cell progenitors. These additional culture media are suitable for generating pluripotent stem cell-derived T lineage cells.

Group (II) may further comprise: (i) a culture medium comprising one or more growth factors and cytokines selected from the group consisting of SCF, Flt3L, and IL7, but free of one or more of VEGF, bFGF, BMP activators and ROCK inhibitors, wherein the culture medium is suitable for differentiating pluripotent stem cell-derived pre-T cell progenitors to T cell progenitor or T cells; or (ii) a culture medium comprising a BMP activator, a ROCK inhibitor, and one or more growth factors and cytokines selected from the group consisting of VEGF, bFGF, SCF, Flt3L, and IL7, wherein the culture medium is suitable for differentiating pluripotent stem cell-derived definitive hemogenic endothelium to pre-T cell progenitor; and these additional culture media are suitable for generating pluripotent stem cell-derived T lineage cells.

In some embodiments of the above culture platform, each of the Group (I) and (II) again further comprises additional culture media:

Group (I) may further comprise: (i) a culture medium comprising one or more growth factors and cytokines selected from the group consisting of SCF, Flt3L, IGF, IL7, IL2, IL3, IL6, and IL15, wherein the culture medium is free of BMP activators, and is suitable for differentiating pluripotent stem cell-derived NK cell progenitors to NK cells; or (ii) a culture medium comprises a BMP activator; one or more growth factors and cytokines selected from the group consisting of SCF, Flt3L, VEGF, IL2, IL3, IL6, and IL15; wherein the culture medium is suitable for differentiating pluripotent stem cell-derived definitive HSC to NK cell progenitors; and these additional media are suitable for generating pluripotent stem cell-derived NK lineage cells.

As to Group (II), in addition to above mentioned media, it may further comprise: (i) a medium comprising one or more growth factors and cytokines selected from the group consisting of SCF, Flt3L, IL3, IL7, and IL15, wherein the medium is free of one or more of VEGF, bFGF, BMP activators and ROCK inhibitors and is suitable for differentiating pluripotent stem cell-derived pre-NK cell progenitors to NK cell progenitors or NK cells; or (ii) a medium comprising a BMP activator, a ROCK inhibitor, and one or more growth factors and cytokines selected from the group consisting of VEGF, bFGF, SCF, Flt3L, IL3, IL7, and IL15, wherein the medium is suitable for differentiating pluripotent stem cell-derived definitive hemogenic endothelium into pre-NK cell progenitors; and these additional media are suitable for generating pluripotent stem cell-derived NK lineage cells.

In yet another embodiment, the group (II) of the provided culture platform further comprises: (i) a culture medium comprising a BMP activator, one or more growth factors and cytokines selected from the group consisting of TPO, IL3, GMCSF, EPO, bFGF, VEGF, SCF, IL6, and IL11, but free of ROCK inhibitor, wherein the culture medium is suitable for differentiating pluripotent stem cell-derived pre-HSCs to hematopoietic multipotent progenitors; (ii) a culture medium comprising a BMP activator, a ROCK inhibitor, and one or more growth factors and cytokines selected from the group consisting of TPO, IL3, GMCSF, EPO, bFGF, VEGF, SCF, IL6 and IL11, a wherein the culture medium is suitable for differentiating pluripotent stem cell-derived definitive hemogenic endothelium to pre-HSCs; and these culture media are provided for generating pluripotent stem cell-derived hematopoiesis multipotent progenitors.

Another aspect of the present invention provides a composition for differentiating and expanding pluripotent stem cell-derived hematopoietic cells, which comprises one or more of the following Group (I) or (II).

Group (I): (i) a culture medium comprising a BMP activator; one or more growth factors and cytokines selected from the group consisting of VEGF, SCF, Flt3L, IL15, IL3, IL6, IGF, and TPO; and pluripotent stem cell-derived definitive hemogenic endothelium, wherein the culture medium is optionally free of Wnt pathway activators and TGFβ receptor/ALK inhibitors, and is suitable for differentiating and expanding definitive HSCs from pluripotent stem cell-derived definitive hemogenic endothelium; (ii) a culture medium comprising a GSK3 inhibitor, a BMP activator, and optionally, a TGFβ receptor/ALK inhibitor; and pluripotent stem cell-derived mesodermal cells, wherein the culture medium is suitable for differentiating and expanding definitive hemogenic endothelium from pluripotent stem cell-derived mesodermal cells; and (iii) a culture medium comprising a GSK3 inhibitor, a BMP activator; and iPSC, wherein the culture medium is suitable for differentiating and expanding mesodermal cells from pluripotent stem cells.

Group (II): (i) a culture medium comprising a ROCK inhibitor, one or more growth factors and cytokines selected from the group consisting of bFGF, VEGF, SCF, IL6, and IL11; and pluripotent stem cell-derived mesodermal cells with definitive hemogenic endothelium potential, wherein the medium is optionally free of TGFβ receptor/ALK inhibitor, wherein the medium is suitable for differentiating and expanding definitive hemogenic endothelium from the pluripotent stem cell-derived mesodermal cells with hemogenic endothelium potential; (ii) a culture medium comprising a BMP activator, bFGF, and a GSK3 inhibitor, but free of TGFβ receptor/ALK inhibitor; and pluripotent stem cell-derived mesodermal cells, wherein the medium is suitable for differentiating and expanding mesodermal cells having definitive hemogenic endothelium potential from pluripotent stem cell-derived mesodermal cells; and (iii) a culture medium that comprises a BMP activator, and optionally bFGF; and iPSCs, wherein the medium is suitable for differentiating and expanding mesodermal cells from pluripotent stem cells.

In some embodiments of the composition for differentiating and expanding pluripotent stem cell-derived hematopoietic cells, the pluripotent stem cells are iPSCs. In some embodiments, the iPSCs are naïve iPSCs.

In some embodiments of the composition for differentiating and expanding pluripotent stem cell-derived hematopoietic cells, the Group (II) comprises an additional composition, such as (vi) a culture medium that comprises a MEK inhibitor, a GSK3 inhibitor, and a ROCK inhibitor, and is free of TGFβ receptor/ALK inhibitors; and pluripotent stem cells; wherein the medium is suitable for seeding and expanding the pluripotent stem cells. In some embodiments, the pluripotent stem cells are iPSCs. In some embodiments, the iPSCs are naïve iPSCs.

In some embodiments of the above composition for differentiating and expanding pluripotent stem cell-derived hematopoietic cells, the Group (I) additionally comprises: (i) a culture medium comprising one or more growth factors and cytokines selected from the group consisting of SCF, Flt3L, IL7, IGF, IL2, IL3, and IL6; and one or more Notch pathway activators; and pluripotent stem cell-derived T cell progenitors, wherein the culture medium is free of BMP activator, and is suitable for differentiating pluripotent stem cell-derived T cell progenitors to T cells, or (ii) a culture medium comprising a BMP activator, one or more growth factors and cytokines selected from the group consisting of SCF, Flt3L, IL7, IL2, IL3, and IL6; one or more Notch pathway activators; and pluripotent stem cell-derived definitive HSC, wherein the culture medium is suitable for differentiating pluripotent stem cell-derived definitive HSCs to T cell progenitors; and these additional media are suitable for generating pluripotent stem cell-derived T lineage cells.

As to Group (II) of the above composition for differentiating and expanding pluripotent stem cell-derived hematopoietic cells, in some embodiments, it further comprises: (i) a culture medium comprising one or more growth factors and cytokines selected from the group consisting of SCF, Flt3L, and IL7, but free of one or more of VEGF, bFGF, BMP activators and ROCK inhibitors; and pluripotent stem cell-derived pre-T cell progenitors, wherein the culture medium is suitable for differentiating the pluripotent stem cell-derived pre-T cell progenitors to T cell progenitors or T cells; or (ii) a culture medium comprising a BMP activator, a ROCK inhibitor, one or more growth factors and cytokines selected from the group consisting of VEGF, bFGF, SCF, Flt3L, and IL7, and pluripotent stem cell-derived definitive hemogenic endothelium, wherein the culture medium is suitable for differentiating the definitive hemogenic endothelium into pre-T cell progenitor. These additional media are suitable for generating pluripotent stem cell-derived T lineage cells.

In yet some other embodiment of the above composition for differentiating and expanding pluripotent stem cell-derived hematopoietic cells, Group (I) further comprises (i) a culture medium comprising one or more growth factors and cytokines selected from the group consisting of SCF, Flt3L, IGF, IL7, IL2, IL3, IL6, and IL15; and pluripotent stem cell-derived NK cell progenitors, wherein the culture medium is free of BMP activators, and is suitable for differentiating the NK cell progenitors to NK cells; or (ii) a culture medium comprises a BMP activator, one or more growth factors and cytokines selected from the group consisting of SCF, Flt3L, VEGF, IL2, IL3, IL6, and IL15; and pluripotent stem cell-derived definitive HSC, wherein the culture medium is suitable for differentiating pluripotent stem cell-derived definitive HSC to NK cell progenitors. These additional media are suitable for generating pluripotent stem cell-derived NK lineage cells. Alternatively, Group (II) of the above composition for differentiating and expanding pluripotent stem cell-derived hematopoietic cells further comprises: (i) a medium comprising one or more growth factors and cytokines selected from the group consisting of SCF, Flt3L, IL3, IL7, and IL15, is free of one or more of VEGF, bFGF, BMP activators and ROCK inhibitors; and pluripotent stem cell-derived pre-NK cell progenitors, wherein the medium is suitable for differentiating the pre-NK cell progenitors to NK cell progenitors or NK cells; or (ii) a medium comprising a BMP activator, a ROCK inhibitor, one or more growth factors and cytokines selected from the group consisting of VEGF, bFGF, SCF, Flt3L, IL3, IL7, and IL15, and pluripotent stem cell-derived definitive hemogenic endothelium, wherein the medium is suitable for differentiating the definitive hemogenic endothelium into pre-NK cell progenitors. These culture media are suitable for generating pluripotent stem cell-derived NK lineage cells.

In still some other embodiment, the group (II) of the above composition for differentiating and expanding pluripotent stem cell-derived hematopoietic cells further comprises one or more medium for generating pluripotent stem cell-derived hematopoiesis multipotent progenitors, wherein the medium comprises: (i) a culture medium comprising a BMP activator, one or more growth factors and cytokines selected from the group consisting of TPO, IL3, GMCSF, EPO, bFGF, VEGF, SCF, IL6, and IL11, but free of ROCK inhibitor, and pluripotent stem cell-derived pre-HSC, wherein the culture medium is suitable for differentiating the pre-HSC to hematopoietic multipotent progenitors; and/or (ii) a culture medium comprising a BMP activator, a ROCK inhibitor, one or more growth factors and cytokines selected from the group consisting of TPO, IL3, GMCSF, EPO, bFGF, VEGF, SCF, IL6 and IL11, and pluripotent stem cell-derived definitive hemogenic endothelium, wherein the culture medium is suitable for differentiating the definitive hemogenic endothelium to pre-HSC.

One aspect of the present invention provides a culture platform for generating pluripotent stem cell-derived T lineage cells, which comprises: group I—(i) a culture medium comprising a GSK3 inhibitor, a BMP activator, wherein the culture medium is suitable for differentiating and expanding pluripotent stem cell-derived mesodermal cells drom pluripotent stem cells; (ii) a culture medium comprising a GSK3 inhibitor, a BMP activator, and optionally, a TGFβ receptor/ALK inhibitor, wherein the culture medium is suitable for differentiating and expanding definitive hemogenic endothelium from mesodermal cells; (iii) a culture medium comprising a BMP activator, one or more growth factors and cytokines selected from the group consisting of VEGF, SCF, Flt3L, IL15, IL3, IL6, IGF, and TPO; wherein the culture medium is optionally free of Wnt pathway activators and TGFβ receptor/ALK inhibitors, and is suitable for differentiating and expanding definitive HSC from definitive hemogenic endothelium; and (iv) a culture medium comprising a BMP activator; one or more growth factors and cytokines selected from the group consisting of SCF, Flt3L, IL7, IL2, IL3, and IL6; and one or more Notch pathway activators, wherein the culture medium is suitable for differentiating T cell progenitors from definitive HSC; and optionally, (v) a culture medium comprising one or more growth factors and cytokines selected from the group consisting of SCF, Flt3L, IL7, IGF, IL2, IL3, and IL6; and one or more Notch pathway activators; wherein the culture medium is free of BMP activator, and is suitable for differentiating T cells from T cell progenitors.

Alternatively, the culture platform for generating pluripotent stem cell-derived T lineage cells comprises: group II—(i) a culture medium that comprises a BMP activator, and optionally bFGF, wherein the medium is suitable for differentiating and expanding pluripotent stem cell-derived mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive HE potential from the mesodermal cells; (iii) a culture medium comprising a ROCK inhibitor, one or more growth factors and cytokines selected from the group consisting of bFGF, VEGF, SCF, IL6, and IL11; and optionally free of TGFβ receptor/ALK inhibitor, wherein the medium is suitable for differentiating and expanding definitive hemogenic endothelium from the mesodermal cells with definitive hemogenic endothelium potential; (iv) a culture medium comprising a BMP activator, a ROCK inhibitor, one or more growth factors and cytokines selected from the group consisting of VEGF, bFGF, SCF, Flt3L, and IL7, and pluripotent stem cell-derived definitive hemogenic endothelium, wherein the culture medium is suitable for differentiating the definitive hemogenic endothelium into pre-T cell progenitor; and (v) a culture medium comprising one or more growth factors and cytokines selected from the group consisting of SCF, Flt3L, and IL7, but free of one or more of VEGF, bFGF, BMP activators and ROCK inhibitors; and pluripotent stem cell-derived pre-T cell progenitors, wherein the culture medium is suitable for differentiating the pre-T cell progenitors to T cell progenitors or T cells.

In some embodiments of the above culture platform for generating pluripotent stem cell-derived T lineage cells, the culture platform of group II further comprises: (vi) a culture medium that comprises a MEK inhibitor, a GSK3 inhibitor, and a ROCK inhibitor, and is optionally free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs.

Another aspect of the present invention provides a culture platform for generating pluripotent stem cell-derived NK cells, which comprises: group I— (i) a culture medium comprising a GSK3 inhibitor, a BMP activator, wherein the culture medium is suitable for differentiating pluripotent stem cells to mesodermal cells; (ii) a culture medium comprising a GSK3 inhibitor, a BMP activator, and optionally, a TGFβ receptor/ALK inhibitor, wherein the culture medium is suitable for differentiating mesodermal cells to definitive hemogenic endothelium; (iii) a culture medium comprising a BMP activator, one or more growth factors and cytokines selected from the group consisting of VEGF, SCF, Flt3L, IL15, IL3, IL6, IGF, and TPO, wherein the culture medium is optionally free of Wnt pathway activators and TGFβ receptor/ALK inhibitors, and is suitable for differentiating definitive hemogenic endothelium to definitive HSCs; (iv) a culture medium comprising a BMP activator, one or more growth factors and cytokines selected from the group consisting of SCF, Flt3L, VEGF, IL2, IL3, IL6, and IL15; wherein the culture medium is suitable for differentiating definitive HSCs to NK cell progenitors; and optionally, (v) a culture medium comprising one or more growth factors and cytokines selected from the group consisting of SCF, Flt3L, IGF, IL7, IL2, IL3, IL6, and IL15, wherein the culture medium is free of BMP activators, and is suitable for differentiating NK cell progenitors to NK cells.

Alternatively, the culture platform for generating pluripotent stem cell-derived NK cells comprises: group II— (i) a culture medium that comprises a BMP activator, and optionally bFGF, wherein the medium is suitable for differentiating and expanding mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from mesodermal cells; (iii) a culture medium comprising a ROCK inhibitor, one or more growth factors and cytokines selected from the group consisting of bFGF, VEGF, SCF, IL6, and IL11, and optionally free of TGFβ receptor/ALK inhibitor, wherein the medium is suitable for differentiating definitive hemogenic endothelium from mesodermal cells having definitive hemogenic endothelium potential; (iv) a culture medium comprising a BMP activator, a ROCK inhibitor, and one or more growth factors and cytokines selected from the group consisting of VEGF, bFGF, SCF, Flt3L, IL3, IL7, and IL15, wherein the medium is suitable for differentiating definitive hemogenic endothelium into pre-NK cell progenitor; and (v) a medium comprising one or more growth factors and cytokines selected from the group consisting of SCF, Flt3L, IL3, IL7, and IL15, wherein the medium is free of one or more of VEGF, bFGF, BMP activators and ROCK inhibitors and is suitable for differentiating pre-NK cell progenitors to NK cell progenitors or NK cells.

In some embodiment of the above culture platform for generating pluripotent stem cell-derived NK cells, the culture platform of group II further comprises: (vi) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs.

Yet another aspect of the present invention provides a culture platform for generating pluripotent stem cell-derived definitive hemogenic endothelium (iHE), which comprises: (i) a culture medium that comprises a BMP activator, and optionally bFGF, wherein the medium is suitable for differentiating and expanding mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from the pluripotent stem cell-derived mesodermal cells; and (iii) a culture medium comprising a ROCK inhibitor, and one or more growth factors and cytokines selected from the group consisting of bFGF, VEGF, SCF, IL6, IL11, wherein the medium is optionally free of TGFβ receptor/ALK inhibitor, and wherein the medium is suitable for differentiating and expanding definitive hemogenic endothelium from the mesodermal cells having definitive hemogenic endothelium potential.

In some embodiments of the culture platform for generating pluripotent stem cell-derived definitive hemogenic endothelium (iHE), the culture platform further comprises (iv) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells.

Still another aspect of the invention provides a culture platform for generating pluripotent stem cell-derived hematopoiesis multipotent progenitors, which comprises: (i) a culture medium that comprises a BMP activator, and optionally bFGF, wherein the medium is suitable for differentiating and expanding mesodermal cells from pluripotent stem cell-derived mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from the pluripotent stem cell-derived mesodermal cells; (iii) a culture medium comprising a ROCK inhibitor, one or more growth factors and cytokines selected from the group consisting of bFGF, VEGF, SCF, IL6, and IL11; wherein the medium is optionally free of TGFβ receptor/ALK inhibitor, wherein the medium is suitable for differentiating and expanding definitive hemogenic endothelium from mesodermal cells having definitive hemogenic endothelium potential; (iv) a culture medium comprising a BMP activator, a ROCK inhibitor, one or more growth factors and cytokines selected from the group consisting of TPO, IL3, GMCSF, EPO, bFGF, VEGF, SCF, IL6 and IL11; wherein the culture medium is suitable for differentiating definitive hemogenic endothelium to pre-HSC; and (v) a culture medium comprising a BMP activator, one or more growth factors and cytokines selected from the group consisting of TPO, IL3, GMCSF, EPO, bFGF, VEGF, SCF, IL6, and IL11, wherein the medium is free of ROCK inhibitor, wherein the culture medium is suitable for differentiating pre-HSC to hematopoietic multipotent progenitors. In some embodiments, the culture platform further comprises (vi) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs.

Another aspect of the invention provides a method for directing differentiation of pluripotent stem cells into cells of a definitive hematopoietic lineage, which comprises: group I—(i) contacting pluripotent stem cells with a composition comprising a GSK3 inhibitor, a BMP activator, to initiate differentiation and expansion of pluripotent stem cell-derived mesodermal cells from pluripotent stem cells; (ii) contacting pluripotent stem cell-derived mesodermal cells with a composition comprising a GSK3 inhibitor, a BMP activator, and optionally, a TGFβ receptor/ALK inhibitor, to initiate differentiation and expansion of pluripotent stem cell-derived definitive hemogenic endothelium cell from the pluripotent stem cell-derived mesodermal cellss; and (iii) contacting pluripotent stem cell-derived definitive hemogenic endothelium with a composition comprising a BMP activator, one or more growth factors and cytokines selected from the group consisting of VEGF, SCF, Flt3L, IL15, IL3, IL6, IGF, and TPO, wherein the composition is optionally free of Wnt pathway activators and TGFβ receptor/ALK inhibitors, to initiate differentiation and expansion of the pluripotent stem cell-derived definitive HSCs from hemogenic endothelium cell.

Alternatively, the method for directing differentiation of pluripotent stem cells into cells of a definitive hematopoietic lineage comprises: group II— (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor, one or more growth factors and cytokines selected from the group consisting of bFGF, VEGF, SCF, IL6, and IL11; wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential; and optionally, subjecting pluripotent stem cells, pluripotent stem cell-derived mesodermal cells, mesodermal cells having hemogenic endothelium, and/or definitive hemogenic endothelium under low oxygen tension between about 2% to about 10%.

In some embodiments of the method for directing differentiation of pluripotent stem cells into cells of a hematopoietic lineage, the method of group (II) further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs. In some embodiments, the iPSCs are naïve iPSCs.

In some embodiments of the method for directing differentiation of pluripotent stem cells into cells of a hematopoietic lineage, the differentiation of the pluripotent stem cells into cells of hematopoietic lineage is void of generation of embryoid bodies, and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−.

In some other embodiments of the above method, group I further comprises (i) contacting pluripotent stem cell-derived definitive HSCs with a composition comprising a BMP activator, one or more growth factors and cytokines selected from the group consisting of SCF, Flt3L, IL7, IL2, IL3, and IL6, and one or more Notch pathway activators, to initiate the differentiation of the pluripotent stem cell-derived definitive HSCs to T cell progenitors, and optionally, contacting the T cell progenitors with a composition comprising one or more growth factors and cytokines selected from the group consisting of SCF, Flt3L, IL7, IGF, IL2, IL3, and IL6; and one or more Notch pathway activators, to initiate the differentiation of the T cell progenitors to T cells. In some embodiments, group II of the method further comprises (i) contacting pluripotent stem cell-derived definitive hemogenic endothelium with a composition comprising a BMP activator, a ROCK inhibitor, one or more growth factors and cytokines selected from the group consisting of VEGF, bFGF, SCF, Flt3L, and IL7, to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, BMP activators and ROCK inhibitors, to initiate the differentiation of the pre-T cell progenitors to T cell progenitors or T cells. In some embodiments of the method, the pluripotent stem cell-derived T cell progenitors are CD34+CD7+.

In yet some other embodiments of the above method for directing differentiation of pluripotent stem cells into cells of a hematopoietic lineage, group I of the method further comprises: (i) contacting pluripotent stem cell-derived definitive HSCs with a composition comprising a BMP activator, one or more growth factors and cytokines selected from the group consisting of SCF, Flt3L, VEGF, IL2, IL3, IL6, and IL15, to initiate differentiation of the definitive HSC to NK cell progenitors; and optionally, (ii) contacting the NK cell progenitors with a composition comprising one or more growth factors and cytokines selected from the group consisting of SCF, Flt3L, IGF, IL7, IL2, IL3, IL6, and IL15, but free of BMP activators, to initiate differentiation of the NK cell progenitors to NK cells; or group II of the method further comprises: (i) contacting pluripotent stem cell-derived definitive hemogenic endothelium with a composition comprising a BMP activator, a ROCK inhibitor, and one or more growth factors and cytokines selected from the group consisting of VEGF, bFGF, SCF, Flt3L, IL3, IL7, and IL15, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, BMP activators and ROCK inhibitors, to initiate differentiation of the pre-NK cell progenitors to NK cell progenitors or NK cells. In some embodiments, group II of the method further comprises: (i) contacting pluripotent stem cell-derived definitive hemogenic endothelium with a composition comprising a BMP activator, a ROCK inhibitor, and one or more growth factors and cytokines selected from the group consisting of TPO, IL3, GMCSF, EPO, bFGF, VEGF, SCF, IL6 and IL11, to initiate differentiation of definitive hemogenic endothelium to pre-HSCs; (ii) a culture medium comprising a BMP activator, one or more growth factors and cytokines selected from the group consisting of TPO, IL3, GMCSF, EPO, bFGF, VEGF, SCF, IL6, and IL11, but free of ROCK inhibitor, wherein the culture medium is suitable for differentiating pluripotent stem cell-derived pre-HSC to hematopoietic multipotent progenitors. In some embodiments, the pluripotent stem cell-derived definitive HSCs obtained using the above method are CD34+CD45+, and are suitable for long-term engraftment.

Another aspect of the invention provides a method for generating pluripotent stem cell-derived T lineage cells, which comprises: group I— (i) contacting pluripotent stem cells with a composition comprising a GSK3 inhibitor, a BMP activator, to initiate differentiation and expansion of mesodermal cells from pluripotent stem cells; (ii) contacting mesodermal cells with a composition comprising a GSK3 inhibitor, a BMP activator, and optionally, a TGFβ receptor/ALK inhibitor, to initiate differentiation and expansion of definitive hemogenic endothelium from the mesodermal cells; (iii) contacting definitive hemogenic endothelium with a composition comprising a BMP activator, one or more growth factors and cytokines selected from the group consisting of VEGF, SCF, Flt3L, IL15, IL3, IL6, IGF, and TPO; wherein the composition is free of Wnt pathway activators and TGFβ receptor/ALK inhibitors, to initiate differentiation and expansion of definitive HSCs from definitive hemogenic endothelium; and (iv) contacting definitive HSCs with a composition comprising a BMP activator, one or more growth factors and cytokines selected from the group consisting of SCF, Flt3L, IL7, IL2, IL3, and IL6, and one or more Notch pathway activators, to initiate differentiation of the definitive HSC to T cell progenitors; and optionally, (v) contacting the T cell progenitors with a composition comprising one or more growth factors and cytokines selected from the group consisting of SCF, Flt3L, IL7, IGF, IL2, IL3, and IL6; one or more Notch pathway activators; but free of BMP activators, to initiating differentiation of T cell progenitors to T cells.

Alternatively, the method for generating pluripotent stem cell-derived T lineage cells comprises: group II—(i) contacting pluripotent stem cells with a composition comprising a BMP activator, and optionally bFGF, to initiate differentiation and expansion of mesodermal cells from pluripotent stem cells; (ii) contacting the mesodermal cells with a composition comprising a BMP activator, bFGF, and a GSK3 inhibitor, but free of TGFβ receptor/ALK inhibitor, to initiate differentiation and expansion of the mesodermal cells having definitive HE potential from the mesodermal cells; (iii) contacting mesodermal cells having definitive HE potential with a composition comprising a ROCK inhibitor, one or more growth factors and cytokines selected from the group consisting of bFGF, VEGF, SCF, IL6, and IL11; wherein the composition is free of TGFβ receptor/ALK inhibitor, to initiate differentiation and expansion of definitive hemogenic endothelium from mesodermal cells having definitive HE potential; (iv) contacting definitive hemogenic endothelium with a composition comprising a BMP activator, a ROCK inhibitor, one or more growth factors and cytokines selected from the group consisting of VEGF, bFGF, SCF, Flt3L, and IL7, to initiate differentiation of the definitive hemogenic endothelium to pre-T cell progenitors; and (v) contacting the pre-T cell progenitors with a composition comprising one or more growth factors and cytokines selected from the group consisting of SCF, Flt3L, and IL7, wherein the composition is free of one or more of VEGF, bFGF, BMP activators and ROCK inhibitors; to initiate differentiation of the pre-T cell progenitors to T cell progenitors or T cells; and optionally, the seeded pluripotent stem cells, mesodermal cells, mesodermal cells having definitive HE potential, and/or definitive hemogenic endothelium may be subject to low oxygen tension between about 2% to about 10%. In some embodiments, group II of the above method further comprises: contacting iPSCs with a composition comprising a MEK inhibitor, a GSK3 inhibitor, and a ROCK inhibitor, but free of TGFβ receptor/ALK inhibitors, to seed and expand pluripotent stem cells; and/or wherein the pluripotent stem cells. In some embodiments, the pluripotent stem cells are iPSCs. In some embodiments, the iPSCs are naïve iPSC. In some embodiments of the method, the differentiation of the pluripotent stem cells into T cell lineages is void of generation of embryoid bodies, and is in a monolayer culturing format.

Yet another aspect of the invention provides a method for generating pluripotent stem cell-derived NK lineage cells, which comprises: group I— (i) contacting pluripotent stem cells with a composition comprising a GSK3 inhibitor, a BMP activator, to initiate differentiation of the pluripotent stem cells to mesodermal cells; (ii) contacting the mesodermal cells with a composition comprising a GSK3 inhibitor, a BMP activator, and optionally, a TGFβ receptor/ALK inhibitor, to initiate differentiation of mesodermal cells to definitive hemogenic endothelium; (iii) contacting the definitive hemogenic endothelium with a composition comprising a BMP activator, one or more growth factors and cytokines selected from the group consisting of VEGF, SCF, Flt3L, IL15, IL3, IL6, IGF, and TPO, wherein the composition is free of Wnt pathway activators and TGFβ receptor/ALK inhibitors; to initiate differentiation of pluripotent stem cells-derived definitive hemogenic endothelium to definitive HSCs; and (iv) contacting definitive HSCs with a composition comprising a BMP activator, one or more growth factors and cytokines selected from the group consisting of SCF, Flt3L, VEGF, IL2, IL3, IL6, and IL15 to initiate differentiation of definitive HSCs to NK cell progenitors; and optionally, (v) contacting pluripotent stem cell-derived NK cell progenitors with a composition comprising one or more growth factors and cytokines selected from the group consisting of SCF, Flt3L, IGF, IL7, IL2, IL3, IL6, and IL15, but free of BMP activators, to initiate differentiation NK cell progenitors to NK cells. Alternatively, the method for generating pluripotent stem cell-derived NK lineage cells comprises: group II—(i) contacting pluripotent stem cells with a composition comprising a BMP activator, and optionally bFGF, to initiate differentiation and expansion of mesodermal cells from the pluripotent stem cells; (ii) contacting mesodermal cells with a composition comprising a BMP activator, bFGF, and a GSK3 inhibitor, and optionally free of TGFβ receptor/ALK inhibitor, to initiate differentiation and expansion of mesodermal cells having definitive HE potential from mesodermal cells; (iii) contacting mesodermal cells having definitive HE potential with a composition comprising one or more growth factors and cytokines selected from the group consisting of bFGF, VEGF, SCF, IL6, and IL11; and a ROCK inhibitor, and optionally free of TGFβ receptor/ALK inhibitor, to initiate differentiation and expansion of pluripotent stem cell-derived definitive hemogenic endothelium from the pluripotent stem cell-derived mesodermal cells having definitive HE potential; (iv) contacting pluripotent stem cell-derived definitive hemogenic endothelium with a composition comprising one or more growth factors and cytokines selected from the group consisting of VEGF, bFGF, SCF, Flt3L, IL3, IL7, and IL15, a BMP activator, and a ROCK inhibitor, to initiate differentiation of the pluripotent stem cell-derived definitive hemogenic endothelium to pre-NK cell progenitors; and (v) contacting pluripotent stem cell-derived pre-NK cell progenitors with a composition comprising one or more growth factors and cytokines selected from the group consisting of SCF, Flt3L, IL3, IL7, and IL15, but free of one or more of VEGF, bFGF, BMP activators and ROCK inhibitors, to initiate differentiation of the pluripotent stem cell-derived pre-NK cell progenitors to pluripotent stem cell-derived NK cell progenitors or NK cells; and optionally, subjecting seeded pluripotent stem cells, pluripotent stem cell-derived-mesodermal cells, and/or definitive hemogenic endothelium under low oxygen tension between about 2% to about 10%. In some embodiments, the method for generating pluripotent stem cell-derived NK lineage cells of group II further comprises contacting iPSCs with a composition comprising a MEK inhibitor, a GSK3 inhibitor, and a ROCK inhibitor, but free of TGFβ receptor/ALK inhibitors, to seed and expand the iPSCs. In some embodiments, the iPSCs are naïve iPSCs. In some embodiments, the method for generating pluripotent stem cell-derived NK lineage cells is void of generation of embryoid bodies, and is in a monolayer culturing format.

Another aspect of the invention provides a method for generating pluripotent stem cell-derived definitive hemogenic endothelium, comprising: (i) contacting iPSCs with a composition comprising a BMP activator, and optionally bFGF, to initiate differentiation and expansion of pluripotent stem cell-derived mesodermal cells from pluripotent stem cells; (ii) contacting pluripotent stem cell-derived mesodermal cells with a composition comprising a BMP activator, bFGF, and a GSK3 inhibitor, and optionally free of TGFβ receptor/ALK inhibitor, to initiate differentiation and expansion of pluripotent stem cell-derived mesodermal cells having definitive HE potential from pluripotent stem cell-derived mesodermal cells; (iii) contacting pluripotent stem cell-derived mesodermal cells having definitive HE potential with a composition comprising one or more growth factors and cytokines selected from the group consisting of bFGF, VEGF, SCF, IL6, and IL11; and a ROCK inhibitor, and optionally free of TGFβ receptor/ALK inhibitor, to initiate differentiation and expansion of pluripotent stem cell-derived definitive hemogenic endothelium from the pluripotent stem cell-derived mesodermal cells having definitive HE potential; and optionally, subjecting seeded pluripotent stem cells, pluripotent stem cell-derived mesodermal cells, and/or definitive hemogenic endothelium under low oxygen tension between about 2% to about 10%. In some embodiments, the above method for generating pluripotent stem cell-derived definitive hemogenic endothelium, further comprises: contacting iPSCs with a composition comprising a MEK inhibitor, a GSK3 inhibitor, and a ROCK inhibitor, but free of TGFβ receptor/ALK inhibitors, to seed and expand the iPSCs; and/or wherein the iPSCs are naïve iPSCs. In some embodiments, the above method of differentiating iPSCs into cells of a definitive hemogenic endothelium is void of generation of embryoid bodies, and is in monolayer culturing format.

Another aspect of the invention provides a method for generating pluripotent stem cell-derived multipotent progenitors of hematopoietic lineage, comprising: (i) contacting iPSCs with a composition comprising a BMP activator, and optionally bFGF, to initiate differentiation and expansion of pluripotent stem cell-derived mesodermal cells from iPSCs; (ii) contacting pluripotent stem cell-derived mesodermal cells with a composition comprising a BMP activator, bFGF, and a GSK3 inhibitor, but free of TGFβ receptor/ALK inhibitor, to initiate differentiation and expansion of the mesodermal cells having definitive HE potential from the mesodermal cells; (iii) contacting mesodermal cells having definitive HE potential with a composition comprising a ROCK inhibitor, one or more growth factors and cytokines selected from the group consisting of bFGF, VEGF, SCF, IL6, and IL11, wherein the composition is free of TGFβ receptor/ALK inhibitor, to initiate differentiation and expansion of definitive hemogenic endothelium from mesodermal cells having definitive HE potential; (iv) contacting definitive hemogenic endothelium with a composition comprising a BMP activator, a ROCK inhibitor, one or more growth factors and cytokines selected from the group consisting of TPO, IL3, GMCSF, EPO, bFGF, VEGF, SCF, IL6 and IL11, to initiate differentiation of definitive hemogenic endothelium to pre-HSC; and (v) contacting pre-HSC with a composition comprising a BMP activator, one or more growth factors and cytokines selected from the group consisting of TPO, IL3, GMCSF, EPO, bFGF, VEGF, SCF, IL6, and IL11, but free of ROCK inhibitor, to initiate differentiation of the pre-HSC to hematopoietic multipotent progenitors; and optionally, subjecting seeded pluripotent stem cells, mesodermal cells, and/or definitive hemogenic endothelium under low oxygen tension between about 2% to about 10%. In some embodiments, the above method for generating pluripotent stem cell-derived hematopoiesis multipotent progenitors further comprises contacting pluripotent stem cells with a composition comprising a MEK inhibitor, a GSK3 inhibitor, and a ROCK inhibitor, but free of TGFβ receptor/ALK inhibitors, to seed and expand the pluripotent stem cells. In some embodiments, the pluripotent stem cells are iPSCs. In some embodiments, the iPSCs are naïve iPSCs. In some embodiments, the differentiation of the pluripotent stem cells into hematopoiesis multipotent progenitors using the above method is void of generation of embryoid bodies, and is in monolayer culturing format.

A further aspect of the invention provides a composition comprising: one or more cell populations generated from the culture platform disclosed herein: pluripotent stem cells-derived (i) CD34+ definitive hemogenic endothelium (iCD34), wherein the iCD34 cells have capacity to differentiate into multipotent progenitor cells, T cell progenitors, NK cell progenitors, T cells and NK cells, and wherein the iCD34 cells are CD34+CD43−; (ii) definitive hemogenic endothelium (iHE), wherein the iHE cells are CD34+; (iii) pluripotent stem cell-derived definitive HSCs, wherein the iHSC is CD34+CD45+; (iv) hematopoietic multipotent progenitor cells, wherein the iMPP cells are CD34+CD45+; (v) T cell progenitors, wherein the T cell progenitors are CD34+CD7+; (vi) T cells, wherein the T cells are CD4+ or CD8+; (vii) NK cell progenitors, wherein the NK cell progenitors are CD56+CD7+CD161+; and (viii) NK cells, wherein the NK cells are CD56+CD57+CD16+CD94−.

Still a further aspect of the invention provides one or more cell lines, or clonal cells generated using the methods disclosed herein: pluripotent stem cell-derived (i) CD34+ definitive hemogenic endothelium (iCD34), wherein the iCD34 cells have capacity to differentiate into multipotent progenitor cells, T cell progenitors, NK cell progenitors, T cells and NK cells, and wherein the iCD34 cells are CD34+CD43−; (ii) definitive hemogenic endothelium (iHE), wherein the iHE cell line or clonal cells are CD34+; (iii) definitive HSCs, wherein the iHSCs is CD34+CD45+; (iv) hematopoietic multipotent progenitor cells (iMPP), wherein the iMPP cells are CD34+CD45+; (v) T cell progenitors, wherein the T cell progenitors are CD34+CD7+; (vi) T cells, wherein the T cells are CD4+ or CD8+; (vii) NK cell progenitors, wherein the NK cell progenitors are CD56+CD7+CD161+; and (viii) NK cells, wherein the NK cells are CD56+CD57+CD16+CD94−.

Another aspect of the present invention provides a method of promoting hematopoietic self-renewal, reconstitution or engraftment using one or more of cell populations, cell lines or clonal cells generated using methods as disclosed: pluripotent stem cell-derived (i) CD34+ definitive hemogenic endothelium (iCD34), wherein the iCD34 cells have capacity to differentiate into multipotent progenitor cells, T cell progenitors, NK cell progenitors, T cells and NK cells, and wherein the iCD34 cells are CD34+CD43−; (ii) definitive hemogenic endothelium (iHE), wherein the iHE cell line or clonal cells are CD34+; (iii) definitive HSCs, wherein the iHSCs are CD34+CD45+; (iv) hematopoietic multipotent progenitor cells, wherein the iMPP cells are CD34+CD45+; (v) T cell progenitors, wherein the T cell progenitors are CD34+CD7+; (vi) T cells, wherein the T cells are CD4+ or CD8+; (vii) NK cell progenitors, wherein the NK cell progenitors are CD56+CD7+CD161+; and (viii) NK cells, wherein the NK cells are CD56+CD57+CD16+CD94−.

In summary, the present invention provides methods and compositions enabling a direct differentiation of pluripotent stem cells in monolayer without generating embryoid bodies from pluripotent stem cells, thereby achieving differentiation and expansion of mesodermal cells, definitive HE, and definitive HSCs, from which other hematopoietic lineage cells can be obtained in a scalable, reliable manner with a very high level of efficiency.

BRIEF DESCRIPTION OF THE DRAWINGS

FIG. 1 shows an exemplary schematic diagram for a multi-staged process for the hematopoietic differentiation of human induced pluripotent stem cells (hiPSCs) to fully differentiated T cells.

FIG. 2 shows an exemplary schematic diagram for a multi-staged process for the hematopoietic differentiation of hiPSCs to fully differentiated NK cells.

FIGS. 4A-4D show the expression profile of stem cells as they completely transition away from pluripotency towards a hematopoietic fate.

FIG. 12 shows a schematic diagram for a multi-staged culture process for the hematopoietic differentiation of induced pluripotent stem cells (iPSCs) to definitive hemogenic endothelium (iHE) and multipotent progenitors (iMPP). Note that culture can be converted to fully defined with the substitution of Matrigel™ for Vitronectin.

FIG. 13 shows a schematic diagram for a multi-staged culture process for the hematopoietic differentiation of induced pluripotent stem cells to T cell progenitors (iproT) and fully differentiated T (iT) cells. Note that culture can be converted to fully defined with the substitution of Matrigel™ for Vitronectin.

FIG. 14 shows a schematic diagram for a multi-staged culture process for the hematopoietic differentiation of induced pluripotent stem cells to NK cell progenitors (iproNK) and fully differentiated NK (iNK) cells. Note that culture can be converted to fully defined with the substitution of Matrigel™ for Vitronectin.

FIG. 22A-C shows early CD56+CD7+CD161+ NK cell progenitors and mature CD56+CD16+CD8+ NK cell subsets derived from hiPSCs utilizing a CD45+ gating strategy. A) Early NK lineage markers mark the presence of iproNK cells as defined by CD7 and CD56. B) Mature NK lineage markers mark the presence of mature NK cells as defined by CD57, CD16, CD94 and CD56. C) 5 day NK cell differentiation comparing the potential of CD34 positive cells from umbilical cord blood and iCD34 positive cells to give rise to iproNK cells.

DETAILED DESCRIPTION OF THE INVENTION

Figure 3A:
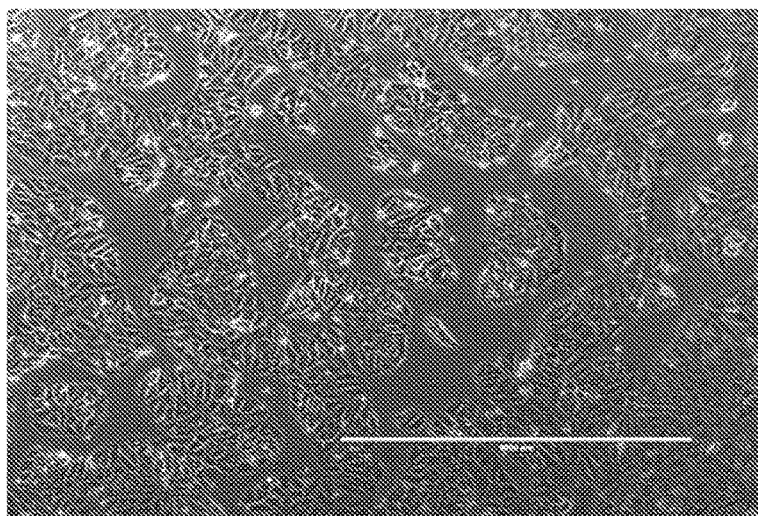
FIGS. 3A-3E show morphological changes over a 9 day course demonstrating the transition from hiPSCs towards hematopoietic cells.
Figure 3B:
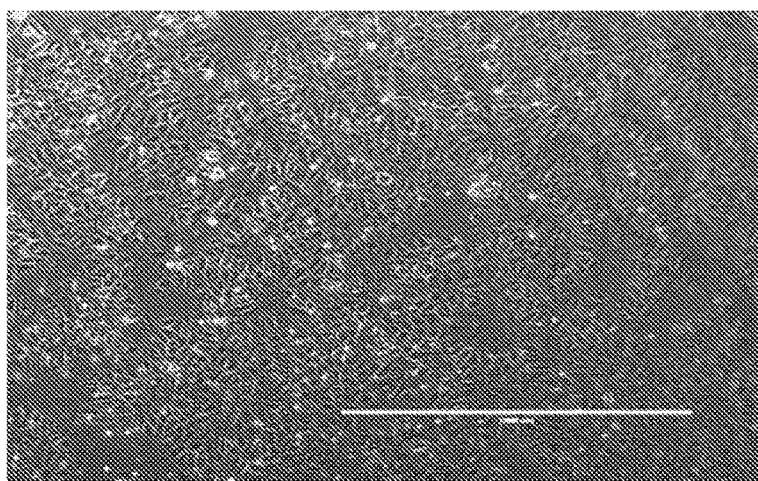
Figure 3C:
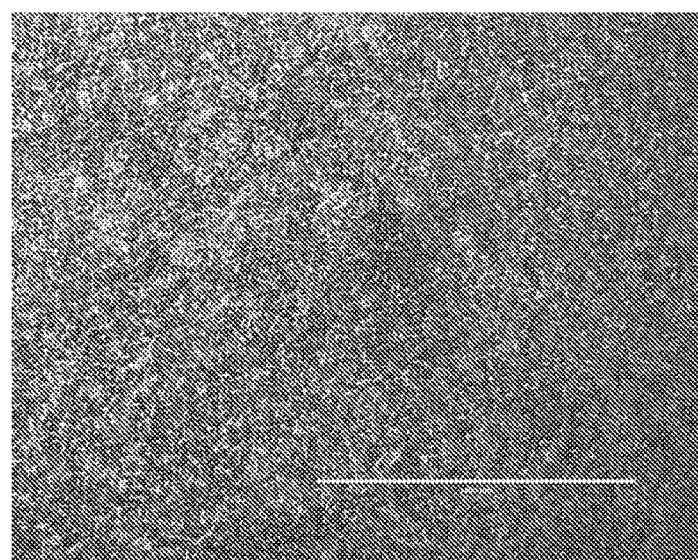
Figure 3D:
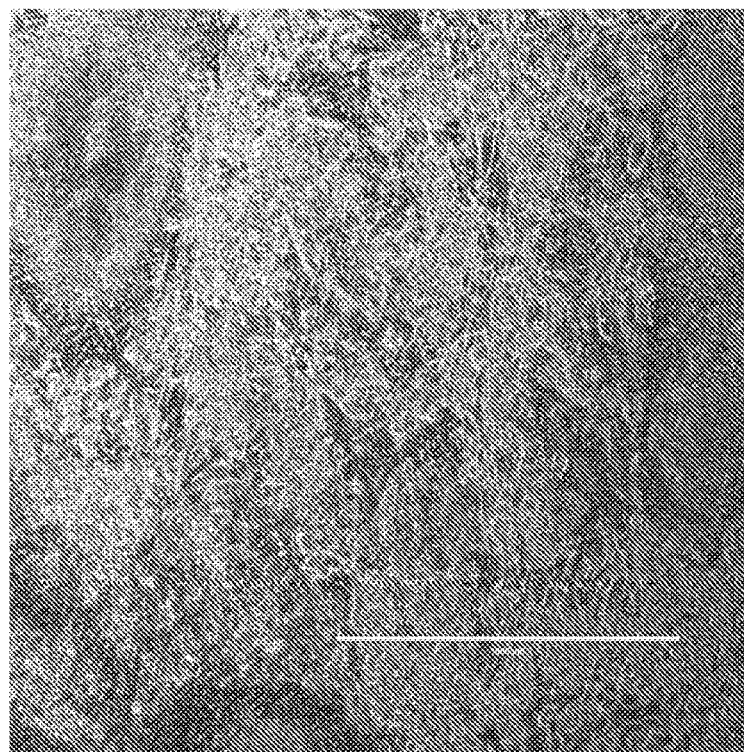
Figure 3E:
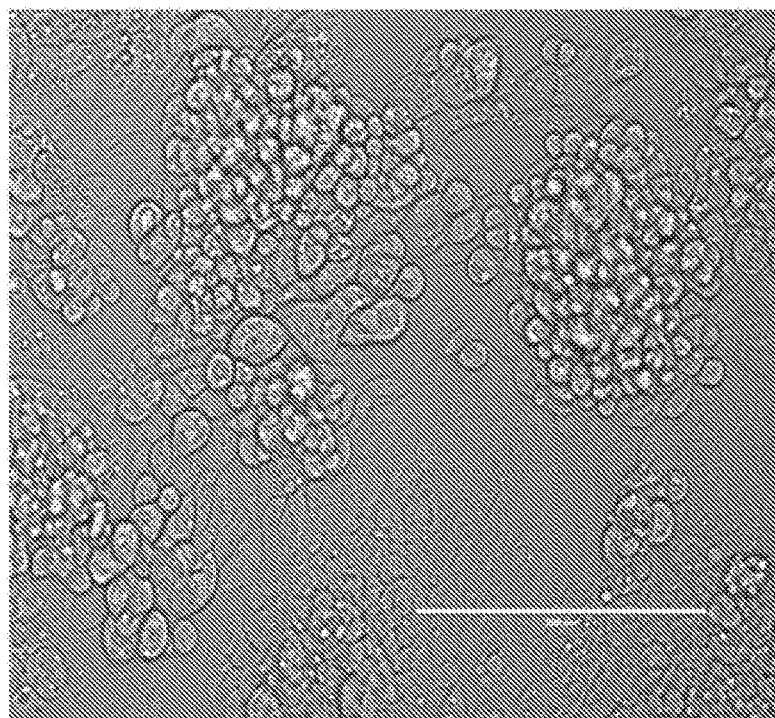

The invention generally relates to methods and compositions for differentiating stem cells toward a definitive hematopoietic cell fate. More particularly, the invention provides a multi-stage differentiation platform wherein iPSC or iPSC-derived cells at various stages of development can be induced to assume a definitive hematopoietic phenotype, ranging from definitive hemogenic endothelium, to fully differentiated hematopoietic cells including, T cells, B cells, NKT cells, and NK cells. That is, the invention provides methods and compositions for making a cell more susceptible to assuming a definitive hematopoietic fate, for example, a CD34+ definitive hematopoietic stem cell. Alternatively, the method and compositions of the present invention generate definitive hemogenic endothelium (HE) from naïve iPSCs in a scalable manner by avoiding the formation of EBs or aggregates.

A. Definitions

Unless defined otherwise, all technical and scientific terms used herein have the same meaning as commonly understood by those of ordinary skill in the art to which the invention belongs. For the purposes of the present invention, the following terms are defined below. The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

As used herein, the term "appreciable" refers to a range of quantity, level, value, number, frequency, percentage, dimension, size, amount, weight or length or an event that is readily detectable by one or more standard methods. The terms "not-appreciable" and "not appreciable" and equivalents refer to a range of quantity, level, value, number, frequency, percentage, dimension, size, amount, weight or length or an event that is not readily detectable or undetectable by standard methods. In one embodiment, an event is not appreciable if it occurs less than 5%, 4%, 3%, 2%, 1%, 0.1%, 0.01%, 0.001% or less of the time.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the term "mesoderm" refers to one of the three germinal layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem cell," or "definitive hematopoietic stem cell" as used herein, refers to CD34+ stem cells capable of giving rise to both mature myeloid and lymphoid cell types including T cells, natural killer cells and B cells.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "differentiation marker gene," or "differentiation gene," refers to genes whose expression are indicative of cell differentiation occurring within a cell, such as a pluripotent cell. Differentiation marker genes include, but are not limited to, the following genes: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury), ZIC1, GATA1, GATA2, HDAC4, HDAC5, HDAC7, HDAC9, NOTCH1, NOTCH2, NOTCH4, PAX5, RBPJ, RUNX1, STAT1 and STAT3.

As used herein, the term "differentiation marker gene profile," or "differentiation gene profile," "differentiation gene expression profile," "differentiation gene expression signature," "differentiation gene expression panel," "differentiation gene panel," or "differentiation gene signature" refers to the expression or levels of expression of a plurality of differentiation marker genes.

As used herein, the term "potency" refers to the sum of all developmental options accessible to the cell (i.e., the developmental potency). The continuum of cell potency includes, but is not limited to, totipotent cells, pluripotent cells, multipotent cells, oligopotent cells, unipotent cells, and terminally differentiated cells.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta, i.e., are not totipotent.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. EBs are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogenous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to induce differentiation of pluripotent stem cells and/or to expand the populations of pluripotent stem cell derived cells. For example, during aggregate-based pluripotent stem cell expansion, culture media are selected to maintain proliferation and pluripotency. Cells proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are minimal as compared to all three germ layer differentiation in EB.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, S SEAS, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) preinactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical intercell spacing.

As used herein, "feeder cells" or "feeders" are terms describing cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Adhere" refers to cells attaching to a vessel, for example, a cell attaching to a sterile plastic (or coated plastic) cell culture dish or flask in the presence of an appropriate culture medium. Certain classes of cells are not sustained or do not grow in a culture unless they adhere to the cell culture vessel. Certain classes of cells ("non-adherent cells") are maintained and/or proliferate in culture without adhering.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

B. Overview

The invention generally relates to a multistage process of differentiating a naïve pluripotent cell to non-pluripotent cells or a partially differentiated cells, including, mesodermal cells, definitive hemogenic endothelium, definitive hematopoietic stem or progenitor cells, CD34+ cells, multipotent progenitors (MPP) (capable of differentiating into myeloid, including neutrophil progenitors), T cell progenitors, NK cell progenitors; or fully differentiated terminal hematopoietic cells, such as, for example, T cells, B cells, NKT cells, or NK cells. The invention also relates to the compositions used in the disclosed methods; and cell populations, cell lines, or clonal cells generated using the disclosed methods.

In contrast to the methods used in the art, the present invention has avoided the formation of EB in iPSC differentiation. As provided, hematopoietic lineages cells derived from iPSC were obtained by seeding clonal iPSC cells in a TGFβ free culture medium to maintain their ground or naïve state of pluripotency, differentiating the clonal iPSCs in a monolayer format without EB formation, and utilizing a step-wise strategy to apply proper combination of small chemicals, growth factors and cytokines in the early and mid-stage of the differentiation. As such, the present invention enables direct transfer of expanded clonal iPSC to adherent culture in a form of monolayer for immediate differentiation without requiring formation of EB from iPSC.

The present invention thus provides culture platforms that enable differentiating stem cell to definitive hematopoiesis and functional hematopoietic lineage cells with high efficiency, without using TGFβ receptor/ALK inhibitors including SB431532. Furthermore, unlike previous studies, the present invention also provides a culture platform using feeder-free, serum-free conditions that support direct differentiation of iPSC in monolayer culture without the need for EB or aggregate intermediates from iPSC.

C. Culture Platforms

Existing methods for culturing pluripotent cells rely heavily on feeder cells or media pre-conditioned with feeder cells and containing fetal bovine serum; however, such environments may be unsuitable for producing cells for clinical and therapeutic use. For example, cells cultivated in such xeno-contaminated environments are generally considered unsuitable for human cell transplantation because the exposure to animal components may present a serious risk of immune rejection and transmitting unidentified pathogens to the treated patients, and could potentially reactivate animal retroviruses. Culture systems using animal-free culture media, such as the feeder-free environments contemplated herein, facilitate the manufacture of clinical-grade cell lines, particularly hESC, hiPSC, and pluripotent stem cell derived HSC, T, B, NKT, or NK cell lines.

In particular embodiments, the feeder-free environment is essentially free of human feeder cells and is not pre-conditioned by feeder cells, including without limitation, mouse embryonic fibroblasts, human fibroblasts, keratinocytes, and embryonic stem cells. The feeder-free cell culture medium is suitable for use in culturing pluripotent cells, reprogramming cells, single-cell culture, dissociation, and passaging of pluripotent cells, cell sorting of pluripotent cells, generation of ground state pluripotent cells, maintenance of ground state pluripotency, induction of pluripotent cell differentiation. In particular embodiments, the feeder-free environment is used to induce pluripotency, improve the efficiency of reprogramming, increase or maintain the potency of a cell, and/or induce differentiation. In certain embodiments, the feeder-free environment is additionally substantially free of cytokines and growth factors, including bFGF.

In some aspects of the invention, one or more, of the stages of iPSC differentiation described above may be carried out under feeder-free conditions. Such feeder-free conditions may be in forms including, but not limited to, monolayer culture and suspension culture. In one embodiment of the invention, the differentiation of a pluripotent cell to a mesodermal cell is carried out under monolayer feeder-free conditions. In another embodiment of the invention, the differentiation of a mesodermal cell to a definitive hemogenic endothelial cell is carried out under monolayer feeder-free conditions. In yet another embodiment of the invention, the differentiation of a definitive hemogenic endothelial cell to a hematopoietic stem cell is carried out under monolayer feeder-free conditions. In one embodiment of the invention, the differentiation of a definitive hematopoietic stem cell to a multipotent progenitor, a T cell progenitor or a NK cell progenitor is carried out under suspension feeder-free conditions, or under monolayer feeder-free conditions followed by suspension feeder-free conditions. In another embodiment of the invention, the differentiation of a T cell progenitor to a fully differentiated T cell, or a NK cell progenitor to a fully differentiated NK cell, is carried out under suspension feeder-free conditions, or under monolayer feeder-free followed by suspension feeder-free conditions.

Any suitable vessel or cell culture container may be used as a support for cell cultures in the basal media and/or the cell culture supplements. In some embodiments, coating the surface of a culture vessel with adhesion-promoting matrics/substrata (for example, collagens, fibronectins, RGD-containing polypeptides, gelatins, and the like) however promotes attachment of the cells, and in particular embodiments may enhance the effect of the cell culture media and supplements disclosed herein. Suitable substrates for culturing and passaging cells are known in the art and include, without limitation, vitronectin, gelatin, laminin, fibronectin, collagen, elastin, osteopontin, thrombospondin, mixtures of naturally occurring cell line-produced matrices such as Matrigel™, and synthetic or man-made surfaces such as polyamine monolayers and carboxy-terminated monolayers. In some embodiments, providing feeder-free conditions comprise culturing the cells on a matrix-coated surface. In one embodiment, a culture platform contemplated herein comprises a matrix/substrate comprising Matrigel™ or vitronectin. In some embodiments of the cultures, Matrigel™ is used, and thus the culture is fully defined.

In some aspects of the invention, one or more of the stages of differentiation described above may be carried out under serum-free conditions. Examples of commercially available serum-free media suitable for cell attachment and/or induction include mTeSR™1 or TeSR™2 from Stem Cell Technologies (Vancouver, Canada), Primate ES/iPS cell medium from ReproCELL (Boston, Mass.), StemPro®-34 from Invitrogen (Carlsbad, Calif.), StemPro® hESC SFM from Invitrogen, and X-VIVO™ from Lonza (Basel, Switzerland).

In additional embodiments, one or more of the media of the culture platform is a feeder-free environment, and optionally is substantially free of cytokines and/or growth factors. In other embodiments, the cell culture media contains supplements such as serums, extracts, growth factors, hormones, cytokines and the like. Generally, the culture platform comprises one or more of stage specific feeder-free, serum-free media, each of which further comprises one or more of the followings: nutrients/extracts, growth factors, hormones, cytokines and medium additives. Suitable nutrients/extracts may include, for example, DMEM/F-12 (Dulbecco's Modified Eagle Medium/Nutrient Mixture F-12), which is a widely used basal medium for supporting the growth of many different mammalian cells; KOSR (knock-out serum replacement); L-glut; NEAA (Non-Essential Amino Acids). Other medium additives may include, but not limited to, MTG, ITS, (ME, anti-oxidants (for example, ascorbic acid). In some embodiments, a culture medium of the present invention comprises one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), bone morphogenetic protein (BMP4), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ) and other cytokines having effects upon stem cells such as stem cell factor (SCF) and erythropoietin (EPO). These cytokines may be obtained commercially, for example from R&D Systems (Minneapolis, Minn.), and may be either natural or recombinant. In some other embodiments, the culture medium of the present invention comprises one or more of bone morphogenetic protein (BMP4), insulin-like growth factor-1 (IGF-1), basic fibroblast growth factor (bFGF), vascular endothelial growth factor (VEGF), hematopoietic growth factor (for example, SCF, GMCSF, GCSF, EPO, IL3, TPO, EPO), Fms-Related Tyrosine Kinase 3 Ligand (Flt3L); and one or more cytokines from Leukemia inhibitory factor (LIF), IL3, IL6, IL7, IL11, IL15. In some embodiments, the growth factors/mitogens and cytokines are stage and/or cell type specific in concentrations that are determined empirically or as guided by the established cytokine art.

Generally, techniques for differentiating an induced pluripotent cell involve modulation of specific cellular pathways, either directly or indirectly, using polynucleotide-, polypeptide- and/or small molecule-based approaches. The developmental potency of a cell may be modulated, for example, by contacting a cell with one or more modulators. "Contacting", as used herein, can involve culturing cells in the presence of one or more factors (such as, for example, small molecules, proteins, peptides, etc.). In some embodiments, a cell is contacted with one or more agents to induce cell differentiation. Such contact, may occur for example, by introducing the one or more agents to the cell during in vitro culture. Thus, contact may occur by introducing the one or more agents to the cell in a nutrient cell culture medium. The cell may be maintained in the culture medium comprising one or more agents for a period sufficient for the cell to achieve the differentiation phenotype that is desired. In some other embodiments, "contact" occurs when one or more factors are introduced into the cell via vectors. In some embodiments, the one or more vectors are introduced by a retrovirus, Sendai virus, an adenovirus, an episome, minicircle, vector system with expression cassette, or mRNA.

In other embodiments, one or more of stage specific feeder-free, serum-free media of the culture platform as disclosed herein further comprise one or more small molecules. In some embodiments, the culture platform comprises a cell culture medium comprising a GSK-3 inhibitor, a MEK inhibitor, a Rho Kinase (ROCK) inhibitor, and does not comprise, or is free of, a small molecule inhibitor of a TGFβ/activin signaling pathway including but not limited to TGFβ receptor or ALK5 inhibitors.

The culture platforms contemplated herein also offer numerous advantages by utilizing a homogenous population of industrial- or clinical-grade pluripotent cells having reduced spontaneous differentiation and/or having achieved ground state pluripotency. In one embodiment, the homogenous iPSC is maintained in a composition comprising a GSK-3 inhibitor, a MEK inhibitor, and a Rho Kinase (ROCK) inhibitor; and the composition is free of TGFβ receptor/ALK inhibitors. As used herein, the term "homogenous" refers to a population of cells wherein each cell is the same or substantially the same as the other cells in the population. In one embodiment, a cell is the same as other cells in the population if each cell expresses one or more of the same pluripotency markers as contemplated herein, e.g., SSEA4 and TRA1-81. In one embodiment, the population is homogenous if at least 90%, at least 95%, at least 96%, at least 97%, at least 98%, at least 99%, or more of the cells are the same or substantially the same as other cells in the population.

In various embodiments, the cell culture media of the culture platform for generating hematopoietic cell lineages through definitive heogenic endothelium herein do not comprise, or is essentially free of, an inhibitor of TGFβ/activin signaling pathways, including TGFβ receptor (TGFβR) inhibitors and ALK5 inhibitors. In one embodiment, the culture platform comprises a seeding medium for maintaining a naïve hiPSC, which medium comprises a GSK-3 inhibitor, a MEK inhibitor, and a Rho Kinase (ROCK) inhibitor. Without wishing to be bound to any particular theory, the inventors discovered that while TGFβR/ALK5 inhibitors increase the efficiency of reprogramming, these inhibitors counteract the long-term maintenance, quality and homogeneity of a pluripotent cell population. That is, while the inhibition of TGFβ pathway signaling improved the efficiency of cellular reprogramming, relief from this inhibition contributes to subsequent maintenance of the pluripotent cell population in in vitro culture systems, particularly in systems using feeder-cell free and single cell, enzymatic passage where a homogeneous pluripotent population with reduced spontaneous differentiation, and remaining in the "ground" or "naïve" pluripotency state is preferred. As used herein, the term "long-term," as measured by, without being limited to, the number of passages, often means at least 10, 15, 20, 25, 30, 35, 40, 45, 50, or more passages. As defined, "passage" refers to the act of subdividing and plating cells into multiple cell culture surfaces or vessels when the cells have proliferated to a desired extent. In addition, culturing metastable pluripotent cells in media comprising a GSK3 inhibitor and a MEK inhibitor and optionally a ROCK inhibitor, but free of, TGFβR/ALK5 inhibitors, as disclosed herein, transition pluripotent cells to achieve reduced spontaneous differentiation, and/or to achieve ground state pluripotency.

Achieving the ground or naïve pluripotency of the iPSC is also important to obtain hematopoietic lineage cells by differentiating iPSC without forming EB intermediates. In addition, the efficiency of naïve iPSC differentiation into definitive HE is also greatly impacted by the use of monolayer culturing without forming EB and aggregates thereof. In some embodiments, the culture platform comprises a medium that comprises a ROCK inhibitor, and is free of, or essentially free of, TGFβR/ALK5 inhibitors. In some other embodiments, the culture platform comprises a medium comprising a GSK3 inhibitor, but free of TGFβR/ALK5 inhibitors, which medium promotes the generation of definitive HE and/or definitive HSC cells using the culture platforms provided herein.

1. TGFβ Receptor/ALK Inhibitors

TGFβ receptor (e.g., ALK5) inhibitors can include antibodies to, dominant negative variants of, and antisense nucleic acids that suppress expression of, TGFβ receptors (e.g., ALK5). Exemplary TGFβ receptor/ALK inhibitors include, but are not limited to, SB431542 (see, e.g., Inman, et al., Molecular Pharmacology 62(1):65-74 (2002)); A-83-01, also known as 3-(6-Methyl-2-pyridinyl)-N-phenyl-4-(4-quinolinyl)-1H-pyrazole-1-carbothioamide (see, e.g., Tojo, et al., Cancer Science 96(11):791-800 (2005) and commercially available from, e.g., Toicris Bioscience); 2-(3-(6-Methylpyridin-2-yl)-1H-pyrazol-4-yl)-1,5-naphthyridine; Wnt3a/BIO (see, e.g., Dalton, et al., WO2008/094597, herein incorporated by reference); GW788388 (-{4-[3-(pyridin-2-yl)-1H-pyrazol-4-yl]pyridin-2-yl}-N-(tetrahydro-2H-pyran-4-yl)benzamide) (see, e.g., Gellibert, et al., Journal of Medicinal Chemistry 49(7):2210-2221 (2006)); SM16 (see, e.g., Suzuki, et al., Cancer Research 67(5):2351-2359 (2007)); IN-1130 (3-45-(6-methylpyridin-2-yl)-4-(quinoxalin-6-yl)-1H-imidazol-2-yl)methyl)benzamide) (see, e.g., Kim, et al., Xenobiotica 38(3):325-339 (2008)); GW6604 (2-phenyl-4-(3-pyridin-2-yl-1H-pyrazol-4-yl)pyridine) (see, e.g., de Gouville, et al., Drug News Perspective 19(2):85-90 (2006)); SB-505124 (2-(5-benzo[1,3]dioxol-5-yl-2-tert-butyl-3H-imidazol-4-yl)-6-methylpyridine hydrochloride) (see, e.g., DaCosta, et al., Molecular Pharmacology 65(3): 744-752 (2004)); and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data showing the effect of inhibiting ALK5, it is believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor (TGFβR) inhibitors can include antibodies to, dominant negative variants of and siRNA or antisense nucleic acids that target TGFβ receptors. Specific examples of TGFβ receptor inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID 11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., Clinical Cancer Research 13(18):5262-5270 (2007); Kaminska, et al., Acta Biochimica Polonica 52(2):329-337 (2005); and Chang, et al., Frontiers in Bioscience 12:4393-4401 (2007).)

Inhibitors of SMAD 2/3 phosphorylation can include antibodies to, dominant negative variants of and antisense nucleic acids that target SMAD2 or SMAD3. Specific examples of inhibitors include PD169316; SB203580;

SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et al., EP1992360, incorporated herein by reference.)

Inhibitors of the interaction of SMAD 2/3 and SMAD4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., Oncogene 24:3864-3874 (2005) and Zhao, et al., Molecular Biology of the Cell, 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to Smad7-as PTO-oligonucleotides. (See, e.g., Miyazono, et al., U.S. Pat. No. 6,534,476, and Steinbrecher, et al., US2005119203, both incorporated herein by reference.

2. WNT Pathway Agonists

As used herein, the terms "Wnt signal-promoting agent," "Wnt pathway activator," "Wnt pathway activating agent," or "Wnt pathway agonist," refers to an agonist of the Wnt signaling pathway, including but not limited to an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, and Wnt16. Wnt pathway agonists further include, but are not limited to, one or more of the following polypeptides or a fragment thereof: a Dkk polypeptide, a crescent polypeptide, a cerberus polypeptide, an axin polypeptide, a Frzb polypeptide, a T-cell factor polypeptide, or a dominant negative disheveled polypeptide.

Non-limiting examples of Wnt pathway agonists further include one or more of the following: a nucleic acid comprising a nucleotide sequence that encodes a Wnt polypeptide, a polypeptide comprising an amino acid sequence of a Wnt polypeptide, a nucleic acid comprising a nucleotide sequence that encodes an activated Wnt receptor, a polypeptide comprising an amino acid sequence of an activated Wnt receptor, a small organic molecule that promotes Wnt/β-catenin signaling, a small organic molecule that inhibits the expression or activity of a Wnt antagonist, an antisense oligonucleotide that inhibits expression of a Wnt antagonist, a ribozyme that inhibits expression of a Wnt antagonist, an RNAi construct, siRNA, or shRNA that inhibits expression of a Wnt antagonist, an antibody that binds to and inhibits the activity of a Wnt antagonist, a nucleic acid comprising a nucleotide sequence that encodes a β-catenin polypeptide, a polypeptide comprising an amino acid sequence of a β-catenin polypeptide, a nucleic acid comprising a nucleotide sequence that encodes a Lef-1 polypeptide, and a polypeptide comprising an amino acid sequence of a Lef-1 polypeptide.

Wnt pathway agonists further include GSK3 inhibitors, such as, for example, a nucleic acid comprising a nucleotide sequence that encodes a dominant negative GSK-3, GSK3α, or GSK3 polypeptide, a polypeptide comprising an amino acid sequence of a dominant negative GSK-3, GSK3α, or GSK3 polypeptide, a small organic molecule that binds to and inhibits the expression or activity of GSK-3, GSK3α, or GSK3, an RNAi construct, siRNA, or shRNA that binds to and inhibits the expression and/or activity of GSK-3, GSK3α, or GSK3, an antisense oligonucleotide that binds to and inhibits the expression of GSK-3, GSK3α, or GSK3, an antibody that binds to and inhibits the expression and/or activity of GSK-3, GSK3α, or GSK3, a ribozyme that binds to and inhibits the expression of GSK-3, GSK3a, or GSK3, and any GSK-3-independent reagent that activates β-catenin target genes similar in effect to GSK-3 inhibition.

3. GSK3 Inhibitors

GSK3 inhibitors are specific exemplary Wnt pathway agonists suitable for use in compositions contemplated herein, and may include, but are not limited to, polynucleotides, polypeptides, and small molecules. GSK3 inhibitors contemplated herein may decrease GSK3α/β expression and/or GSK3α/β activity. Illustrative examples of GSK3 inhibitors contemplated herein include, but are not limited to, anti-GSK3 antibodies, dominant negative GSK3 variants, siRNA, shRNA, miRNA and antisense nucleic acids that target GSK3.

Other illustrative GSK3 inhibitors include, but are not limited to: Kenpaullone, 1-Azakenpaullone, CHIR99021, CHIR98014, AR-A014418, CT 99021, CT 20026, SB216763, AR-A014418, lithium, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione, TWS1 19 pyrrolopyrimidine compound, L803 H-KEAPPAPPQSpP-NH2 or its myristoylated form, 2-Chloro-1-(4,5-dibromo-thiophen-2-yl)-ethanone, GF109203X, RO318220, TDZD-8, TIBPO, and OTDZT.

In particular illustrative embodiments, the GSK3 inhibitor is CHIR99021, BIO, or Kenpaullone.

In a preferred embodiment, the GSK3 inhibitor is CHIR99021.

In another embodiment, the GSK3 inhibitor is BRD0705.

4. ERK/MEK Inhibitors

ERK/MEK inhibitors suitable for use in compositions contemplated herein include, but are not limited to, polynucleotides, polypeptides, and small molecules. ERK/MEK inhibitors contemplated herein may decrease MEK or ERK expression and/or MEK or ERK activity. Illustrative examples of MEK/ERK inhibitors contemplated herein include, but are not limited to, anti-MEK or anti-ERK antibodies, dominant negative MEK or ERK variants, siRNA, shRNA, miRNA and antisense nucleic acids that target MEK or ERK.

Other illustrative ERK/MEK inhibitors include, but are not limited to, PD0325901, PD98059, UO126, SL327, ARRY-162, PD184161, PD184352, sunitinib, sorafenib, Vandetanib, pazopanib, Axitinib, GSK1 120212, ARRY-438162, RO5126766, XL518, AZD8330, RDEA1 19, AZD6244, FR180204 and PTK787.

Additional illustrative MEK/ERK inhibitors include those compounds disclosed in International Published Patent Applications WO 99/01426, WO 02/06213, WO 03/077914, WO 05/051301 and WO2007/044084.

Further illustrative examples of MEK/ERK inhibitors include the following compounds: 6-(4-Bromo-2-chloro-phenylamino)-7-fluoro-3-methyl-3H-benzoimidazol-e-5-carboxylic acid (2,3-dihydroxy-propoxy)-amide, 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimida-zol-5-yl]-2-hydroxy-ethanone, 6-(4-Bromo-2-chloro-phenylamino)-7-fluoro-3-methyl-3H-benzoimidazol-e-5-carboxylic acid (2-hydroxy-1,1-dimethyl-ethoxy)-amide, 6-(4-Bromo-2- chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phe-nylamino)-7-fluoro-3-methyl-3H-benzoimidazol-e-5-car-boxylic acid (2-hydroxy-ethoxy)-amide, referred to herein-after as MEK inhibitor 1, 2-[(2-fluoro-4-iodophenyl)amino]-N-(2-hydroxyethoxy)-1,5-dimethyl-6-oxo-1,6-dihydropyridine-3-carboxamide (referred to hereinafter as MEK inhibitor 2), 4-(4-bromo-2-fluorophenylamino)-N-(2-hydroxyethoxy)-1,5-dimethyl-6-oxo-1,6-dihydro-pyridazine-3-carboxamide, and a pharmaceutically accept-able salt thereof.

In a preferred embodiment, the MEK/ERK inhibitor is PD98059.

5. Rock Inhibitors

Rho associated kinases (ROCK) are serine/threonine kinases that serve downstream effectors of Rho kinases (of which three isoforms exist—RhoA, RhoB and RhoC). ROCK inhibitors suitable for use in compositions contem-plated herein include, but are not limited to, polynucleotides, polypeptides, and small molecules. ROCK inhibitors con-templated herein may decrease ROCK expression and/or ROCK activity. Illustrative examples of ROCK inhibitors contemplated herein include, but are not limited to, anti-ROCK antibodies, dominant negative ROCK variants, siRNA, shRNA, miRNA and antisense nucleic acids that target ROCK.

Illustrative ROCK inhibitors contemplated herein include, but are not limited to: thiazovivin, Y27632, Fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, and (R)-(+)-trans-N-(4-Pyridyl)-4-(1-aminoethyl)-cyclohexanecarboxamide, and ROCK inhibitors disclosed in U.S. Pat. No. 8,044,201, which is herein incorporated by reference in its entirety.

In one embodiment, the ROCK inhibitor is thiazovivin, Y27632, or pyrintegrin.

In a preferred embodiment, the ROCK inhibitor is thiaz-ovivin.

The amount of the small molecules in the compositions and cell culture media contemplated herein can vary and may be optimized according to the specific culture condi-tions, including the specific molecules and combinations used, the type of cell being cultured in the media, and the specific application. In one embodiment, a small molecule is present in a composition at a concentration sufficient to induce pluripotency, improve the efficiency of reprogram-ming, increase or maintain the potency of a cell, or induce or maintain ground state pluripotency.

Another aspect of the invention concerns Notch activators for use with the invention. Notch encompasses all members of the Notch receptor family, including, but not limited to, Notch1. Notch activators, include, but are not limited to, agonists of Notch receptor. The Notch agonist will bind Notch receptor, and as well, initiate or mediate the signaling event associated with the Notch receptor, such as, for example, to cause the intracellular domain of Notch to be cleaved and translocated to the nucleus. Notch activators include, but are not limited to, Jag1, Jag2, DLL-1, DLL-3 and DLL-4. Notch activators include, but are not limited to, those disclosed in EP 2606884, U.S. Pat. Nos. 6,689,744, and 5,780,300, the disclosures of which are incorporated herein by reference. In some embodiments, one or more of the Notch ligand can be introduced as soluble peptide, or immobilized on a solid material. The solid material may include, but not limited to, polystyrene plates, or beads. The beads for Notch ligands immobilization may be agarose beads, magnetic beads, and latex beads. In one embodiment, the Notch ligand peptide is conjugated/immobilized to beads. In another embodiment, the Notch ligand peptide is conjugated/immobilized to the surface of a polystyrene plate. In some embodiments, the immobilization of the Notch ligand is non-covalent. In some embodiments, the Notch ligand peptide is presented by cells.

Yet another aspect of the invention concerns BMP path-way activators, which include those agents disclosed in the following publications, the disclosures of which are incor-porated herein by reference: WO 2014011540, WO 2014062138, and WO 2005117994. BMP pathway activa-tors for use with the invention include, but are not limited to, BMP-5, BMP-6, BMP-7, BMP-8, BMP-2, and BMP-4. In one non-limiting embodiment of the invention, the BMP pathway activator is BMP-4. BMPs are multifunctional cytokines which are members of the transforming growth factor-beta superfamily. Bone morphogenetic protein (BMP) receptors mediate BMP signaling through activating Smad. BBMP ligands bind to the BMP receptors BMPRI and BMPRII. After BMPRII phosphorylated, following activates BMPRI. Phosphorylated BMPRI subsequently phosphory-lates receptor-activated Smad proteins (R-Smads), which associate with common mediator-Smad (co-Smad) and enter the nucleus, where they regulate gene expression. In one embodiment, the BMP pathway activator is BMP4.

The present invention provides compositions for obtain-ing hematopoietic lineage cells from iPSC either through definitive HSC differentiated from iPSCs or through defini-tive hemogenic endothelium differentiated from iPSCs, and each of the approaches is void of the EB formation from iPSC for desired cell differentiation.

6. hiPSC Differentiation Platfroms

I. iHSC Platform

One aspect of the present invention provides a culture medium for obtaining mesodermal cells from pluripotent stem cells including iPSCs. In some embodiments, the iPSCs are naïve iPSC. In one embodiment, the culture medium comprises a Wnt pathway activator, and a BMP activator. In one embodiment, the culture medium comprises a Wnt pathway activator, and an iHSC base medium com-prising a BMP activator. In one embodiment, the Wnt pathway activator in the culture medium is a GSK3 inhibitor. In one embodiment, the GSK3 inhibitor is CHIR99021. In one embodiment, the BMP activator is BMP4. In some embodiments, the culture medium comprises an extracellu-lar matrix protein. In other embodiments, the culture medium herein comprises small molecules, growth factors, and/or cytokines in concentration ranges as shown in Table 1. In some embodiments, the culture medium is fully defined when Matrigel™ instead of Vitronectin is being used.

TABLE 1 iHSC-A culture medium for obtaining mesodermal cells from iPSC

| iHSC base medium | StemPro 34 |
|---|---|
| | Glutamine |
| | Non-Essential Amino Acids & ITS |
| | FBS |
| | Serum Replacement 3 |
| | Ascorbic Acid (1-250 ng/ml) |
| | βME (0.4-100 μM) |

TABLE 1-continued

| iHSC-A culture medium for obtaining mesodermal cells from iPSC | |
|---|---|
| | MTG (10-2500 μM) |
| | BMP4 (0.05-15 ng/ml) |
| | bFGF (0.2-50 ng/ml) |
| | Fibronectin (0.05-15 μg/mL) |
| CHIR99021 (0.1-15 μM) | |
| Feeder-free, in combination with Matrigel™ or Vitronectin | |

One aspect of the present invention provides a culture medium for obtaining definitive hemogenic endothelium from mesodermal cells. In one embodiment, the culture medium comprises a Wnt pathway activator, a BMP activator, and optionally, a TGFβ receptor/ALK inhibitor. In one embodiment, the culture medium comprises a Wnt pathway activator, a BMP activator, and the culture medium is free, or essentially free, of TGFβ receptor/ALK inhibitor. In one embodiment, the culture medium comprises a Wnt pathway activator, and optionally, a TGFβ receptor/ALK inhibitor, and an iHSC base medium comprising a BMP activator. In one embodiment, the Wnt pathway activator in the culture medium is a GSK3 inhibitor. In one embodiment, the GSK3 inhibitor is CHIR99021. In one embodiment, the BMP activator is BMP4. In one embodiment, the optional TGFβ receptor/ALK inhibitor is SB431542. In some embodiments, the culture medium herein comprises an extracellular matrix protein. In other embodiments, the culture medium comprises small molecules, growth factors, and/or cytokines in concentration ranges as shown in Table 2. In some embodiments, the culture medium is fully defined with the substitution of Matrigel™ for Vitronectin.

TABLE 2

| iHSC-B culture medium for obtaining hemogenic endothelium from mesodermal cells | |
|---|---|
| iHSC base medium | StemPro 34 |
| | Glutamine |
| | Non-Essential Amino Acids & ITS |
| | FBS |
| | Serum Replacement 3 |
| | Ascorbic Acid (1-250 ng/ml) |
| | βME (0.4-100 μM) |
| | MTG (10-2500 μM) |
| | BMP4 (0.05-15 ng/ml) |
| | bFGF (0.2-50 ng/ml) |
| | Fibronectin (0.05-15 μg/mL) |
| CHIR99021 (0.1-15 μM) | |
| SB431542 (0.1-15 μM) (optional) | |
| Feeder-free, in combination with Matrigel™ or Vitronectin | |

One aspect of the present invention provides a culture medium for obtaining definitive HSC from hemogenic endothelium. In one embodiment, the culture medium comprises a BMP activator, and one or more growth factors and cytokines selected from the group consisting of VEGF, SCF, Flt3L, IL15, IL3, IL6, IGF, and TPO. In one embodiment, the culture medium comprising a BMP activator, and one or more growth factors and cytokines selected from the group consisting of VEGF, SCF, Flt3L, IL15, IL3, IL6, IGF and TPO, is free of Wnt pathway activators and TGFβ receptor/ALK inhibitors. In one embodiment, the culture medium comprises an iHSC base medium comprising a BMP activator, and one or more growth factors and cytokines selected from the group consisting of VEGF, SCF, Flt3L, IL15, IL3, IL6, IGF and TPO. In one embodiment, the BMP activator is BMP4. In some embodiments, the culture medium comprises an extracellular matrix protein. In other embodiments, the culture medium herein comprises small molecules, growth factors, and/or cytokines in concentration ranges as shown in Table 3. In some embodiments, the culture medium is fully defined with the substitution of Matrigel™ for Vitronectin.

TABLE 3

| iHSC-C culture medium for obtaining definitive HSC from hemogenic endothelium | |
|---|---|
| iHSC base medium | StemPro 34 |
| | Glutamine |
| | Non-Essential Amino Acids & ITS |
| | FBS |
| | Serum Replacement 3 |
| | Ascorbic Acid (1-250 ng/ml) |
| | βME (0.4-100 μM) |
| | MTG (10-2500 μM) |
| | BMP4 (5-125 ng/ml) |
| | bFGF (0.2-50 ng/ml) |
| | Fibronectin (0.05-15 μg/mL) |
| VEGF (0.5-125 ng/mL), SCF (2-500 ng/mL), Flt3L (1-250 ng/mL), IL15 (0.1-15 ng/mL), IL3 (0.4-100 ng/mL), IL6 (0.5-50 ng/mL), IGF (0.2-50 ng/mL), TPO (0.5-125 ng/mL) | |
| Feeder-free, in combination with Matrigel™ or Vitronectin | |

One aspect of the present invention provides a culture medium for obtaining T cell progenitors from definitive HSC. In one embodiment, the culture medium comprises a BMP activator, and one or more growth factors and cytokines selected from the group consisting of SCF, Flt3L, and IL7. In one embodiment, the culture medium comprises SCF, Flt3L, IL7, a BMP activator, and an iTC base medium comprising one or more growth factors and cytokines selected from the group consisting of IL2, IL3, and IL6, and one or more Notch pathway activators. In one embodiment, the iTC base medium comprises a combination of IL2, IL3, IL6, one or more Notch pathway activators. In one embodiment, the iTC base medium is free of fibronectin. In one embodiment, the BMP activator is BMP4. In one embodiment, the Notch pathway activators are Notch ligands including, but not limited to, Jag1, Jag2, DLL-1, DLL-3, and DLL-4. In some embodiments, DLL-1 and -4 can be introduced as soluble peptide, peptide conjugated to beads, peptide conjugated to the surface, or peptide presented by cells. In some embodiments, the culture medium comprises an extracellular matrix protein. In other embodiments, the culture medium herein comprises small molecules, growth factors, and/or cytokines in concentration ranges as shown in Table 4. In some embodiments, the culture medium is fully defined with the substitution of Matrigel™ for Vitronectin.

TABLE 4

| iTC-A1 culture medium for obtaining T cell progenitors from definitive HSC | |
|---|---|
| iTC base medium | StemPro 34 |
| | Glutamine |
| | Non-Essential Amino Acids & ITS |
| | FBS |
| | Serum Replacement 3 |
| | Ascorbic Acid (1-250 ng/ml) |
| | βME (0.4-100 μM) |
| | MTG (10-2500 μM) |
| | bFGF (0.2-50 ng/ml) |
| | IL2 (0.4-100 ng/mL) |
| | IL3 (0.4-100 ng/mL) |
| | IL6 (0.2-50 ng/mL) |
| | DLL-1 (5-1500 ng/mL) |
| | DLL-4 (5-1500 ng/mL) |

TABLE 4-continued iTC-A1 culture medium for obtaining T cell progenitors from definitive HSC BMP4 (0.5-50 ng/ml)
SCF (1-250 ng/mL)
Flt3L (0.5-125 ng/mL)
IL-7 0.2-50 ng/mL)
Feeder-free, in combination with Matrigel™ or Vitronectin One aspect of the present invention provides a culture medium for obtaining T cells from T cell progenitors. In one embodiment, the culture medium comprises one or more growth factors and cytokines selected from the group consisting of SCF, Flt3L, IL7, and IGF. In one embodiment, the culture medium comprising one or more growth factors and cytokines selected from the group consisting of SCF, Flt3L, IL7, and IGF is free of BMP activators. In one embodiment, the culture medium comprises a combination of growth factors and cytokines selected from the group consisting of SCF, Flt3L, IL7, IGF, and an iTC base medium comprising one or more growth factors and cytokines selected from the group consisting of IL2, IL3, and IL6, and one or more Notch pathway activators. In one embodiment, the iTC base medium comprises a combination of IL2, IL3, IL6, one or more Notch pathway activators. In one embodiment, the Notch pathway activators are Jag1, Jag2, DLL-1, DLL-3 and DLL-4. In some embodiments, DLL-1 and/or -4 can be introduced as soluble peptide, peptide conjugated to beads, peptide conjugated to the surface, or peptide presented by cells. In some embodiments, the BMP activators comprise BMP4. In some embodiments, the culture medium comprises an extracellular matrix protein. In other embodiments, the culture medium herein comprises small molecules, growth factors, and/or cytokines in concentration ranges as shown in Table 5. In some embodiments, the culture medium is fully defined with the substitution of Matrigel™ for Vitronectin.

TABLE 5 iTC-B1 culture medium for obtaining T cells from T cell progenitors

| iTC base medium | StemPro 34 |
| --- | --- |
| | Glutamine |
| | Non-Essential Amino Acids & ITS |
| | FBS |
| | Serum Replacement 3 |
| | Ascorbic Acid (1-250 ng/ml) |
| | βME (0.4-100 µM) |
| | MTG (10-2500 µM) |
| | bFGF (0.2-50 ng/ml) |
| | IL2 (0.4-100 ng/mL) |
| | IL3 (0.4-100 ng/mL) |
| | IL6 (0.2-50 ng/mL) |
| | DLL-1 (5-1500 ng/mL) |
| | DLL-4 (5-1500 ng/mL) |
| SCF (0.2-50 ng/mL) | |
| Flt3L (0.2-50 ng/mL) | |
| IL7 (0.04-10 ng/mL) | |
| IGF (0.2-50 ng/mL) | |
| Feeder-free, in combination with Matrigel™ or Vitronectin | |

One aspect of the present invention provides a culture medium for obtaining NK cell progenitors from definitive HSC. In one embodiment, the culture medium comprises a BMP activator, and one or more growth factors and cytokines selected from the group consisting of SCF, Flt3L, and VEGF. In one embodiment, the culture medium comprises SCF, Flt3L, VEGF, and a BMP activator, and iNK base medium comprising one or more growth factors and cytokines selected from the group consisting of IL2, IL3, IL6, and IL15. In one embodiment, the iNK base medium comprising a combination of IL2, IL3, IL6, and IL15. In one embodiment, the BMP activator is BMP4. In some embodiments, the culture medium comprises an extracellular matrix protein. In other embodiments, the culture medium herein comprises small molecules, growth factors, and/or cytokines in concentration ranges as shown in Table 6. In some embodiments, the culture medium is fully defined with the substitution of Matrigel™ for Vitronectin.

TABLE 6 iNK-A1 culture medium for obtaining NK cell progenitors from definitive HSC

| iNK base medium | StemPro 34 |
| --- | --- |
| | Glutamine |
| | Non-Essential Amino Acids & ITS |
| | FBS |
| | Serum Replacement 3 |
| | Ascorbic Acid (5-250 ng/ml) |
| | βME (0.4-100 µM) |
| | MTG (10-2500 µM) |
| | bFGF (0.2-50 ng/ml) |
| | IL2 (0.4-100 ng/mL) |
| | IL3 (0.4-100 ng/mL), |
| | IL6 (0.2-50 ng/mL), |
| | IL15 (0.1-25 ng/mL) |
| SCF (1-250 ng/mL) | |
| Flt3L (0.5-125 ng/mL) | |
| VEGF (0.5-125 ng/mL) | |
| BMP4 (0.2-50 ng/mL) | |
| Feeder-free, in combination with Matrigel™ or Vitronectin | |

One aspect of the present invention provides a culture medium for obtaining NK cells from NK cell progenitors. In one embodiment, the culture medium comprises one or more growth factors and cytokines selected from the group consisting of SCF, Flt3L, IGF, and IL7. In one embodiment, the culture medium comprises SCF, Flt3L, IGF, IL7, and iNK base medium comprising one or more growth factors and cytokines selected from the group consisting of IL2, IL3, IL6, and IL15, wherein the culture medium is free of BMP activators. In one embodiment, the iNK base medium comprising a combination of IL2, IL3, IL6, and IL15. In some embodiments, the culture medium comprises an extracellular matrix protein. In other embodiments, the culture medium herein comprises small molecules, growth factors, and/or cytokines in concentration ranges as shown in Table 7. In some embodiments, the culture medium is fully defined with the substitution of Matrigel™ for Vitronectin. In some embodiments, artificial antigens to stimulate NK growth, development, and maturation are introduced in the forms of bead conjugation, plasma membrane particles or antigen presenting cells.

TABLE 7 iNK-B1 culture medium for obtaining NK cells from NK cell progenitors

| iNK base medium | StemPro 34 |
| --- | --- |
| | Glutamine |
| | Non-Essential Amino Acids & ITS |
| | FBS |
| | Serum Replacement 3 |
| | Ascorbic Acid (1-250 ng/ml) |
| | βME (0.4-100 µM) |
| | MTG (10-2500 µM) |
| | bFGF (0.2-50 ng/ml) |

TABLE 7-continued iNK-B1 culture medium for obtaining NK cells from NK cell progenitors

| |
|---|
| IL2 (0.4-100 ng/mL) |
| IL3 (0.4-100 ng/mL), |
| IL6 (0.2-50 ng/mL), |
| IL15 (0.1-25 ng/mL) |
| SCF (0.2-50 ng/mL) |
| Flt3L (0.2-50 ng/mL) |
| IGF (0.2-50 ng/mL) |
| IL7 (0.04-10 ng/mL) |
| Feeder-free, in combination with Matrigel ™ or Vitronectin |

Another aspect of the present invention provides a culture platform for obtaining a T cell, which comprises one or more of (i) a culture medium comprising one or more growth factors and cytokines selected from the group consisting of SCF, Flt3L, IL7 and IGF, and a iTC base medium comprising one or more growth factors and cytokines selected from the group consisting of IL2, IL3, and IL6, and one or more Notch pathway activators, wherein the culture medium is free of BMP activators, and is suitable for generating T cells from T cell progenitors; (ii) a culture medium comprising a BMP activator, one or more growth factors and cytokines selected from the group consisting of SCF, Flt3L, and IL7, and the iTC base medium, wherein the culture medium is suitable for generating T cell progenitors from definitive HSC; (iii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating definitive HSC from hemogenic endothelium; (iv) a culture medium comprising a GSK3 inhibitor, and optionally, a TGFβ receptor/ALK inhibitor, and the iHSC base medium comprising a BMP activator, wherein the culture medium is suitable for generating hemogenic endothelium from mesodermal cells; and (v) a culture medium comprising a GSK3 inhibitor and the base iHSC base medium comprising a BMP activator, wherein the culture medium is suitable for generating mesodermal cells from iPSC. In some embodiments, the iPSC is naïve iPSC.

In one embodiment, the culture platform for obtaining a T cell comprises (i) a culture medium comprising one or more growth factors and cytokines selected from the group consisting of SCF, Flt3L, IGF, and IL7, and a iTC base medium comprising one or more growth factors and cytokines selected from the group consisting of IL2, IL3, and IL6, and one or more Notch pathway activators, wherein the culture medium is free of BMP activators, and is suitable for generating T cells from T cell progenitors. In one embodiment, the culture platform comprising the culture medium (i) further comprises (ii) a culture medium comprising a BMP activator, one or more growth factors and cytokines selected from the group consisting of SCF, Flt3L, and IL7, and the iTC base medium, wherein the culture medium (ii) is suitable for generating T cell progenitors from definitive HSC. In one embodiment, the culture platform comprising the culture media (i) and (ii) further comprises (iii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium (iii) is free of Wnt pathway activators and TGFβ receptor/ALK inhibitors, and is suitable for generating definitive HSC from hemogenic endothelium. In one embodiment, the culture platform comprising the culture media (i), (ii) and (iii), further comprises (iv) a culture medium comprising a GSK3 inhibitor, and optionally, a TGFβ receptor/ALK inhibitor, and the iHSC base medium, wherein the culture medium (iv) is suitable for generating definitive hemogenic endothelium from mesodermal cells. In another embodiment, the culture platform comprising the culture media (i), (ii), (iii) and (iv), further comprises (v) a culture medium comprising a GSK3 inhibitor and the base iHSC base medium, wherein the culture medium (v) is suitable for generating mesodermal cells from iPSC. In some embodiments, the iPSC is naïve iPSC.

One aspect of the present invention provides a culture platform for obtaining a T cell progenitor, which comprises one or more of (i) a culture medium comprising a BMP activator, one or more growth factors and cytokines selected from the group consisting of SCF, Flt3L, and IL7, and the iTC base medium, wherein the culture medium is suitable for generating T cell progenitors from definitive HSC; (ii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating HSC from definitive hemogenic endothelium; (iii) a culture medium comprising a GSK3 inhibitor, and optionally, a TGFβ receptor/ALK inhibitor, and the iHSC base medium, wherein the culture medium is suitable for generating definitive hemogenic endothelium from mesodermal cells; and (iv) a culture medium comprising a GSK3 inhibitor and the base iHSC base medium, wherein the culture medium is suitable for generating mesodermal cells from iPSC. In some embodiments, the iPSC is naïve iPSC.

In one embodiment, the culture platform for obtaining a T cell progenitor comprises (i) a culture medium comprising a BMP activator, one or more growth factors and cytokines selected from the group consisting of SCF, Flt3L and IL7, and iTC base medium, wherein the culture medium (i) is suitable for generating T cell progenitors from definitive HSC. In one embodiment, the culture platform comprising the culture medium (i) further comprises (ii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium (ii) is free of Wnt pathway activators and TGFβ receptor/ALK inhibitors, and is suitable for generating HSC from definitive hemogenic endothelium. In one embodiment, the culture platform comprising the culture media (i) and (ii), further comprises (iii) a culture medium comprising a GSK3 inhibitor, and optionally, a TGFβ receptor/ALK inhibitor, and the iHSC base medium, wherein the culture medium (iii) is suitable for generating definitive hemogenic endothelium from mesodermal cells. In another embodiment, the culture platform comprising the culture media (i), (ii), and (iii), further comprises (iv) a culture medium comprising a GSK3 inhibitor and the base iHSC base medium, wherein the culture medium (iv) is suitable for generating mesodermal cells from iPSC. In some embodiments, the iPSC is naïve iPSC.

One aspect of the present invention provides a culture platform for obtaining a definitive HSC, which comprises one or more of (i) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating HSC from definitive hemogenic endothelium; (ii) a culture medium comprising a GSK3 inhibitor, and optionally, a TGFβ receptor/ALK inhibitor, and the iHSC base medium, wherein the culture medium is suitable for generating definitive hemogenic endothelium from mesodermal cells; (iii) a culture medium comprising a GSK3 inhibitor and the base iHSC base medium, wherein the culture medium is suitable for generating mesodermal cells from iPSC. In some embodiments, the iPSC is naïve iPSC.

In one embodiment, the culture platform for obtaining a definitive HSC comprises (i) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium (i) is free of Wnt pathway activators and TGFβ receptor/ALK inhibitors, and is suitable for generating HSC from definitive hemogenic endothelium. In one embodiment, the culture platform comprising the culture media (i), further comprises (ii) a culture medium comprising a GSK3 inhibitor, and optionally, a TGFβ receptor/ALK inhibitor, and the iHSC base medium, wherein the culture medium (ii) is suitable for generating definitive hemogenic endothelium from mesodermal cells. In another embodiment, the culture platform comprising the culture media (i), and (ii), further comprises (iii) a culture medium comprising a GSK3 inhibitor and the base iHSC base medium, wherein the culture medium (iii) is suitable for generating mesodermal cells from iPSC. In some embodiments, the obtained definitive HSCs are CD34+ HSCs. In some embodiments, the iPSC is naïve iPSC.

Still another aspect of the present invention provides a culture platform for obtaining hemogenic endothelium, which comprises one or more of (i) a culture medium comprising a GSK3 inhibitor, and optionally, a TGFβ receptor/ALK inhibitor, and a iHSC base medium comprising a BMP activator, wherein the culture medium is suitable for generating definitive hemogenic endothelium from mesodermal cells; and (ii) a culture medium comprising a GSK3 inhibitor and the base iHSC base medium, wherein the culture medium is suitable for generating mesodermal cells from iPSC. In some embodiments, the iPSC is naïve iPSC.

In one embodiment, the culture platform for obtaining hemogenic endothelium comprises (i) a culture medium comprising a GSK3 inhibitor, and optionally, a TGFβ receptor/ALK inhibitor, and a iHSC base medium comprising a BMP activator, wherein the culture medium (i) is suitable for generating definitive hemogenic endothelium from mesodermal cells. In another embodiment, the culture platform comprising the culture medium (i), further comprises (ii) a culture medium comprising a GSK3 inhibitor and the base iHSC base medium, wherein the culture medium (ii) is suitable for generating mesodermal cells from iPSC. In some embodiments, the iPSC is naïve iPSC.

A further aspect of the present invention provides a culture platform for obtaining a NK cell, which comprises one or more of (i) a culture medium that comprises one or more growth factors and cytokines selected from the group consisting of SCF, Flt3L, IGF, and IL7, and a iNK base medium comprising one or more growth factors and cytokines selected from the group consisting of IL2, IL3, IL6, and IL15, wherein the culture medium is free of BMP activators, and is suitable for generating NK cells from NK cell progenitors; (ii) a culture medium comprising one or more growth factors and cytokines selected from the group consisting of SCF, Flt3L, and VEGF, a BMP activator, and the iNK base medium, wherein the culture medium is suitable for generating NK cell progenitors from definitive HSC; (iii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating HSC from definitive hemogenic endothelium; (iv) a culture medium comprising a GSK3 inhibitor, and optionally, a TGFβ receptor/ALK inhibitor, and the iHSC base medium comprising a BMP activator, wherein the culture medium is suitable for generating definitive hemogenic endothelium from mesodermal cells; and (v) a culture medium comprising a GSK3 inhibitor and the base iHSC base medium, wherein the culture medium is suitable for generating mesodermal cells from iPSC. In some embodiments, the iPSC is naïve iPSC.

One embodiment of the culture platform for obtaining a NK cell comprises (i) culture medium that comprises one or more growth factors and cytokines selected from the group consisting of SCF, Flt3L, and IL7, and a iNK base medium comprising one or more growth factors and cytokines selected from the group consisting of IL2, IL3, IL6, and IL15, wherein the culture medium (i) is free of BMP activators, and is suitable for generating NK cells from NK cell progenitors. In one embodiment, the culture platform comprising the culture medium (i), further comprises (ii) a culture medium comprising one or more growth factors and cytokines selected from the group consisting of SCF, Flt3L, and VEGF, a BMP activator, and the iNK base medium comprising one or more growth factors and cytokines selected from the group consisting of IL2, IL3, IL6, and IL15, wherein the culture medium (ii) is suitable for generating NK cell progenitors from definitive HSC. In one embodiment, the culture platform comprising the culture media (i) and (ii) further comprises (iii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium (iii) is free of Wnt pathway activators and TGFβ receptor/ALK inhibitors, and is suitable for generating HSC from definitive hemogenic endothelium. In one embodiment, the culture platform comprising the culture media (i), (ii) and (iii), further comprises (iv) a culture medium comprising a GSK3 inhibitor, and optionally, a TGFβ receptor/ALK inhibitor, and the iHSC base medium, wherein the culture medium (iv) is suitable for generating definitive hemogenic endothelium from mesodermal cells. In another embodiment, the culture platform comprising the culture media (i), (ii), (iii) and (iv) further comprises (v), a culture medium comprising a GSK3 inhibitor and the base iHSC base medium, wherein the culture medium (v) is suitable for generating mesodermal cells from iPSC. In some embodiments, the iPSC is naïve iPSC.

Another aspect of the present invention provides a culture platform for obtaining a NK cell progenitor, which comprises one or more of (i) a culture medium comprising a BMP activator, one or more growth factors and cytokines selected from the group consisting of SCF, Flt3L, VEGF, and a iNK base medium comprising one or more growth factors and cytokines selected from the group consisting of IL2, IL3, IL6, and IL15, wherein the culture medium is suitable for generating NK cell progenitors from definitive HSC; (ii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating HSC from definitive hemogenic endothelium; (iii) a culture medium comprising a GSK3 inhibitor, and optionally, a TGFβ receptor/ALK inhibitor, and the iHSC base medium, wherein the culture medium is suitable for generating definitive hemogenic endothelium from mesodermal cells; and (iv) a culture medium comprising a GSK3 inhibitor and the base iHSC base medium, wherein the culture medium is suitable for generating mesodermal cells from iPSC. In some embodiments, the iPSC is naïve iPSC.

One embodiment of the culture platform for obtaining a NK cell progenitor comprises (i) a culture medium comprising a BMP activator, one or more growth factors and cytokines selected from the group consisting of SCF, Flt3L, and VEGF, and a iNK base medium comprising one or more growth factors and cytokines selected from the group consisting of IL2, IL3, IL6, and IL15, wherein the culture medium (i) is suitable for generating NK cell progenitors from definitive HSC. In one embodiment, the culture platform comprising the culture medium (i), further comprises (ii) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium (ii) is free of Wnt pathway activators and TGFβ receptor/ALK inhibitors, and is suitable for generating HSC from definitive hemogenic endothelium. In one embodiment, the culture platform comprising the culture media (i) and (ii), further comprises (iii) a culture medium comprising a GSK3 inhibitor, and optionally, a TGFβ receptor/ALK inhibitor, and the iHSC base medium, wherein the culture medium (iii) is suitable for generating definitive hemogenic endothelium from mesodermal cells. In another embodiment, the culture platform comprising the culture media (i), (ii), and (iii), further comprises (iv) a culture medium comprising a GSK3 inhibitor and the base iHSC base medium, wherein the culture medium (v) is suitable for generating mesodermal cells from iPSC. In some embodiments, the iPSC is naïve iPSC.

One embodiment of the culture platform for obtaining a NK cell progenitor comprises one or more of artificial antigens in the forms of bead conjugation, plasma membrane particles and/or antigen presenting cells for stimulating NK growth, development, and maturation.

Still another aspect of the invention provides a culture platform for generating definitive CD34+ cells, which comprises one or more of (i) a culture medium comprising one or more growth factors and cytokines selected from the group consisting of VEGF, SCF, Flt3L, IL15, IL3, IL6, IGF, and TPO, and a iHSC base medium comprising a BMP activator, wherein the culture medium is free of Wnt pathway activators and TGFβ receptor/ALK inhibitors, and is suitable for generating HSC from definitive hemogenic endothelium; (ii) a culture medium comprising a GSK3 inhibitor, and optionally, a TGFβ receptor/ALK inhibitor, and the iHSC base medium, wherein the culture medium is suitable for generating definitive hemogenic endothelium from mesodermal cells; and (iii) a culture medium comprising a GSK3 inhibitor and the base iHSC base medium, wherein the culture medium is suitable for generating mesodermal cells from pluripotent stem cells including iPSC. In some embodiments, the iPSC is naïve iPSC.

II. iCD34 Platform

An additional aspect of the present invention provides a culture platform for obtaining definitive hemogenic endothelium using pluripotent stem cells. As used herein, definitive hemogenic endothelium is a hemogenic cell population directed towards definitive hematopoiesis with the capacity to give rise to all hematopoietic cells including, but not limited to, definitive HSCs, hematopoietic multipotent progenitors (MPP), T cell progenitors, NK cell progenitors, mature T cell and/or NK cells.

In one embodiment, the culture platform for obtaining definitive hemogenic endothelium using pluripotent stem cells including iPSCs comprises a seeding medium comprising MEKi, GSKi, and ROCKi. In some embodiments, the seeding medium is free of, or essentially free of, TGFβ receptor/ALK inhibitors. In one embodiment, the combinations of the small molecules in the seeding culture media of the invention are shown in Table 9 as Fate Maintenance Medium (FMM). The components of the medium may be present in the medium in amounts within the concentration ranges shown in Table 9. In one embodiment, the iPSC used for obtaining definitive hemogenic endothelium was a cell line generated using the Fate Reprogramming Medium (FRM), and further maintained in FMM to establish and sustain the ground or naïve state of the iPSC cell line, which is suitable for stage specific differentiation as disclosed herein. The ground or naïve iPSC so obtained is amenable to cryopreservation. In the present invention, an iPSC cell line or a clonal iPSC preserved may be seeded in FMM for the subsequence differentiation into definitive hemogenic endothelium.

TABLE 9

Seeding culture for Naïve iPSC to obtain CD34+ definitive hemogenic endothelium, multipotent progenitors, T cell progenitors and NK cell progenitors:

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum | Knockout Serum | Knockout Serum |
|  | N2 |  |
|  | B27 |  |
| Glutamine | Glutamine | Glutamine (1x) |
| Non-Essential Amino Acids | Non-Essential Amino Acids | Non-Essential Amino Acids |
| β-mercaptoethanol | β-mercaptoethanol | β-mercaptoethanol |
| bFGF (0.2-50 ng/mL) | bFGF (2-500 ng/mL) | bFGF (2-500 ng/mL) |
|  | LIF (0.2-50 ng/mL) | LIF (0.2-50 ng/mL) |
|  | Thiazovivin (0.1-25 µM) | Thiazovivin (0.1-25 µM) |
|  | PD0325901 (0.005-2 µM) | PD0325901 (0.005-2 µM) |
|  | CHIR99021 (0.02-5 µM) | CHIR99021 (0.02-5 µM) |
|  | SB431542 (0.04-10 µM) |  |
| In combination with MEF | Feeder-free, in combination with Matrigel™ or Vitronectin | |

One aspect of the present invention provides a culture medium for mesoderm differentiation and expansion from pluripotent stem cells including iPSCs. In some embodiments, the iPSC is naïve iPSC. In one embodiment, the culture medium comprises a BMP activator, and optionally a bFGF, and a CD34 base medium comprising small molecules in a combination as shown in Table 10. In some embodiments, the culture medium comprises an extracellular matrix protein. In other embodiments, the culture medium herein comprises small molecules, growth factors, and/or cytokines in concentration ranges as shown in Table 10. In some embodiments, the culture medium is fully defined with the substitution of Matrigel™ for Vitronectin.

TABLE 10 iCD34-A culture medium for obtaining mesoderm from naïve iPSC

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 μM) |
| BMP4 (0.05-15 ng/ml) | |
| Feeder-free, in combination with Matrigel ™ or Vitronectin | |

In one embodiment, the above culture medium for mesoderm differentiation and expansion from pluripotent stem cells further comprises bFGF between 0.2-50 ng.

One aspect of the present invention provides a culture medium for obtaining mesodermal cells with definitive hemogenic endothelium potential from pluripotent stem cells including iPSCs. In some embodiments, the iPSC is naïve iPSC. In one embodiment, the culture medium comprises a BMP activator, a GSK3 inhibitor and bFGF. In one embodiment, the culture medium comprising GSK3 inhibitor is only applied after mesodermal cell specification in order to achieve definitive HE potential. In one embodiment the culture medium comprising a BMP activator, a GSK3 inhibitor and bFGF, further comprises a CD34 base medium comprising small molecules in a combination as shown in Table 11. In one embodiment, the above culture medium is free of TGFβ receptor/ALK inhibitors. In some embodiments, the culture medium comprises an extracellular matrix protein. In other embodiments, the culture medium herein comprises small molecules, growth factors, and/or cytokines in concentration ranges as shown in Table 11. In some embodiments, the culture medium is fully defined with the substitution of Matrigel™ for Vitronectin.

TABLE 11 iCD34-B culture medium for obtaining mesodermal cells with definitive hemogenic endothelium potential

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 μM) |
| BMP4 (0.05-15 ng/ml) | |
| bFGF (0.2-50 ng/ml) | |
| CHIR99012 (0.04-10 μM) | |
| Feeder-free, in combination with Matrigel ™ or Vitronectin | |

One aspect of the present invention provides a culture medium for obtaining definitive hemogenic endothelium from mesodermal cells. In one embodiment, the culture medium comprises a ROCK inhibitor, and one or more growth factors and cytokines selected from the group consisting of VEGF, bFGF, SCF, IL6, and IL11. In one embodiment, the culture medium comprises VEGF, bFGF, SCF, IL6, IL11 and a ROCK inhibitor, and a CD34 base medium comprising small molecules in a combination as shown in Table 12. In one embodiment the culture medium comprising VEGF, bFGF, SCF, IL6, IL11 and a ROCK inhibitor is free of IGF1 and/or EPO. In other embodiments, the culture medium herein comprises small molecules, growth factors, and/or cytokines in concentration ranges as shown in Table 12.

TABLE 12 iCD34-C culture medium for obtaining definitive hemogenic endothelium from mesoderm

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 μM) |
| VEGF (0.2-50 ng/ml) | |
| bFGF (0.1-25 ng/ml) | |
| SCF (1-250 ng/ml) | |
| IL6 (0.2-50 ng/ml) | |
| IL11 (0.2-50 ng/ml) | |
| Y27632 (0.2-50 μM) | |
| Feeder-free, in combination with Matrigel ™ or Vitronectin | |

One aspect of the present invention provides a culture platform for obtaining multipotent progenitor (MPP) cells from definitive hemogenic endothelium. The MPP can be further differentiated into myeloid, including neutrophil progenitors. In one embodiment, the culture platform comprises (i) a culture medium comprising a BMP activator, a ROCK inhibitor, and one or more growth factors and cytokines selected from the group consisting of TPO, IL3, GMCSF, EPO, bFGF, VEGF, SCF, IL6 and IL11, wherein the culture medium is suitable for differentiating definitive hemogenic endothelium into a pre-HSC (Table 13). In another embodiment the culture platform comprising the culture medium for differentiating definitive hemogenic endothelium into a pre-HSC, further comprises (ii) a culture medium comprising a BMP activator, TPO, IL3, GMCSF, EPO, bFGF, VEGF, SCF, IL6, and IL11, wherein the culture medium is free of ROCK inhibitor and is suitable to differentiate the pre-HSC into multipotent progenitors. In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 13.

TABLE 13 iMPP-A culture medium for obtaining multipotent progenitors from definitive HE

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 μM) |
| VEGF (0.2-50 ng/ml) | |
| bFGF (0.2-25 ng/ml) | |
| SCF (1-250 ng/ml) | |
| IL6 (0.2-50 ng/ml) | |
| IL11 (0.2-50 ng/ml) | |
| Y27632 (0.2-50 μM)* not included when differentiating the pre-HSC into multipotent progenitors | |
| BMP4 (0.5-150 ng/ml) | |
| TPO (0.5-150 ng/ml) | |
| IL3 (0.5-150 ng/ml) | |
| GMCSF (0.1-25 ng/ml) | |
| EPO (0.02-5 ng/ml) | |
| Feeder-free, in combination with Matrigel ™ or Vitronectin | |

One aspect of the present invention provides a culture platform for generating T cell progenitors or T-cells from definitive hemogenic endothelium. In one embodiment, the culture platform comprises (i) a medium comprising a BMP activator, a ROCK inhibitors, one or more growth factors and cytokines selected from the group consisting of VEGF, bFGF, SCF, Flt3L, and IL7, wherein the medium is suitable for differentiating definitive hemogenic endothelium into pre-T cell progenitor (pre-proT); and (ii) a medium comprising one or more growth factors and cytokines selected from the group consisting of SCF, Flt3L, and IL7, wherein the medium is free of one or more of VEGF, bFGF, BMP activators and ROCK inhibitors, and is suitable for differentiating the pre-T cell progenitors to T cell progenitors or T cells (Table 14). In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 14.

TABLE 14 iTC-A2 culture medium for obtaining pre-T cell progenitors from definitive HE

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 µM) |
| Flt3L (0.2-50 ng/ml) | |
| IL7 (0.2-50 ng/ml) | |
| SCF (1-250 ng/ml) | |
| *: Not included in iTC-B2 for obtaining pre-T progenitors to T cell progenitors or T cells | BMP4 (0.5-150 ng/ml)* |
| | VEGF (0.2-50 ng/ml)* |
| | bFGF (0.1-25 ng/ml)* |
| | Y27632 (0.2-50 µM)* |
| Feeder-free, Suspension or monolayer | |

One aspect of the present invention provides a culture platform for generating NK cell progenitors or NK cells from definitive hemogenic endothelium. In one embodiment, the culture platform comprises (i) a medium comprising a BMP activator, a ROCK inhibitor, one or more growth factors and cytokines selected from the group consisting of VEGF, bFGF, SCF, Flt3L, IL3, IL7, and IL15, wherein the medium is suitable for differentiating definitive hemogenic endothelium into pre-NK cell progenitor (pre-proNK); and (ii) a medium comprising one or more growth factors and cytokines selected from the group consisting of SCF, Flt3L, IL3, IL7, and IL15, wherein the medium is free of one or more of VEGF, bFGF, BMP activators and ROCK inhibitors and is suitable for differentiating the pre-NK cell progenitors to NK cell progenitors or NK cells. In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 15.

TABLE 15 iNK-A2 culture medium for obtaining pre-NK cell progenitors from definitive HE

| | |
|---|---|
| iCD34 base medium | StemPro 34 |
| | Glutamine |
| | Non-Essential Amino Acids |
| | Ascorbic Acid (1-250 ng/ml) |
| | MTG (10-2500 µM) |
| SCF (1-250 ng/ml) | |
| Flt3L (0.2-50 ng/ml) | |

TABLE 15-continued iNK-A2 culture medium for obtaining pre-NK cell progenitors from definitive HE

| | |
|---|---|
| IL7 (0.2-50 ng/ml) | |
| IL15 (0.4-100 ng/ml) | |
| IL3 (0.1-25 ng/ml) | |
| *: Not included in iNK-B2 for obtaining pre-NK progenitors to NK progenitors or NK cells | VEGF (0.2-50 ng/ml)* |
| | bFGF (0.1-25 ng/ml)* |
| | BMP4 (0.5-150 ng/ml)* |
| | Y27632 (0.2-50 µM)* |
| Feeder-free, Suspension, monolayer | |

Another aspect of the present invention provides a culture platform for obtaining a T cell progenitor or T cell, which comprises one or more of (i) a medium that comprises one or more growth factors and cytokines selected from the group consisting of SCF, Flt3L, and IL7, and is free, or essentially free, of one or more of VEGF, bFGF, BMP activators and ROCK inhibitors, which medium is suitable for differentiating the pre-T cell progenitor to T cell progenitor or T cell; (ii) a medium that comprises a BMP activator, a ROCK inhibitor, one or more growth factors and cytokines selected from the group consisting of VEGF, bFGF, SCF, Flt3L, and IL7, and is suitable for differentiating definitive hemogenic endothelium into pre-T cell progenitor; (iii) a culture medium that comprises a ROCK inhibitor, one or more growth factors and cytokines selected from the group consisting of bFGF, VEGF, SCF, IL6, and IL11, and is suitable for definitive hemogenic endothelium differentiation and expansion from mesodermal cells; (iv) a culture medium that comprises a BMP activator, bFGF, and a GSK3 inhibitor, and is suitable for obtaining definitive hemogenic endothelium potential in mesodermal cells; (v) a culture medium that comprises a BMP activator, and optionally bFGF, and is suitable for generating and expanding mesodermal cells from iPSC; and (vi) a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

In one embodiment, the culture platform for generating a T cell progenitor or T cell comprises (i) a medium that comprises SCF, Flt3L, and IL7, is free, or essentially free, of one or more of VEGF, bFGF, BMP activators and ROCK inhibitors, and is suitable for differentiating the pre-T cell progenitor to T cell progenitors or T cells. In another embodiment, the culture platform for generating a T cell progenitor or T cell comprising medium (i), further comprises (ii) a medium that comprises a BMP activator, a ROCK inhibitor, one or more growth factors and cytokines selected from the group consisting of VEGF, bFGF, SCF, Flt3L, and IL7, and is suitable for differentiating definitive hemogenic endothelium into pre-T cell progenitor. In another embodiment, the culture platform for generating a T cell progenitor or T cell comprising medium (i) and (ii), further comprises (iii) a culture medium that comprises a ROCK inhibitor, one or more growth factors and cytokines selected from the group consisting of bFGF, VEGF, SCF, IL6, and IL11, and is suitable for definitive hemogenic endothelium differentiation and expansion from mesodermal cells. In still another embodiment, the culture platform for generating a T cell progenitor or T cell comprising medium (i), (ii) and (iii), further comprises (iv), a culture medium that comprises a BMP activator, bFGF, and a GSK3 inhibitor, and is suitable for obtaining definitive hemogenic endothelium potential in mesodermal cells. In yet another embodiment, the culture platform for generating a T cell progenitor or T cell comprising medium (i), (ii), (iii) and (iv) further comprises (v), a culture medium that comprises a BMP activator, and optionally bFGF, and is suitable for generating and expanding mesodermal cells from iPSC. In another embodiment, the culture platform for generating a T cell progenitor or T cell comprising medium (i), (ii), (iii), (iv) and (v) further comprises (vi), a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, Notch factors are used in the culture platform for generating a T cell progenitor or T cell. In some embodiments, Notch factors including Jag1, Jag2, DLL-1, DLL-3 and DLL-4 can be introduced as soluble peptide, peptide conjugated to beads, peptide conjugated to the surface, or peptide presented by cells.

Another aspect of the present invention provides a culture platform for obtaining a NK cell progenitor or NK cell comprising one or more of (i) a medium comprising one or more growth factors and cytokines selected from the group consisting of SCF, Flt3L, IL3, IL7, and IL15, wherein the medium is free, or essentially free, of one or more of VEGF, bFGF, BMP activators and ROCK inhibitors and is suitable for differentiating the pre-NK cell progenitors to NK cell progenitors or NK cells; (ii) a medium comprising a BMP activator, a ROCK inhibitor, one or more growth factors and cytokines selected from the group consisting of VEGF, bFGF, SCF, Flt3L, IL3, IL7, and IL15, wherein the medium is suitable for differentiating definitive hemogenic endothelium into pre-NK cell progenitor; (iii) a culture medium that comprises a ROCK inhibitor, one or more growth factors and cytokines selected from the group consisting of bFGF, VEGF, SCF, IL6, and IL11, and is suitable for definitive hemogenic endothelium differentiation and expansion from mesodermal cells to; (iv) a culture medium that comprises a BMP activator, bFGF, and a GSK3 inhibitor, and is suitable for obtaining definitive hemogenic endothelium potential in mesodermal cells; (v) a culture medium that comprises a BMP activator, and optionally bFGF, and is suitable for generating and expanding mesodermal cells from iPSCs; (vi) a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, NK maturation is conducted using one or more of artificial antigens to stimulate NK growth, development, and maturation, introduced in the forms of bead conjugation, plasma membrane particles and/or antigen presenting cells.

In one embodiment, the culture platform for generating a NK cell progenitor or NK cell comprises (i) a medium comprising one or more growth factors and cytokines selected from the group consisting of SCF, Flt3L, IL3, IL7, and IL15, wherein the medium is free, or essentially free, of one or more of VEGF, bFGF, BMP activators and ROCK inhibitors and is suitable for differentiating the pre-NK cell progenitors to NK cell progenitors or NK cells. In some embodiments, NK maturation is conducted using one or more of artificial antigens to stimulate NK growth, development, and maturation, introduced in the forms of bead conjugation, plasma membrane particles and/or antigen presenting cells. In another embodiment, the culture platform for generating a NK cell progenitor or NK cell comprising medium (i), further comprises (ii) a medium comprising a BMP activator, a ROCK inhibitor, one or more growth factors and cytokines selected from the group consisting of VEGF, bFGF, SCF, Flt3L, IL3, IL7, and IL15, wherein the medium is suitable for differentiating definitive hemogenic endothelium into pre-NK cell progenitor. In another embodiment, the culture platform for generating a NK cell progenitor or NK cell comprising medium (i) and (ii), further comprises (iii), a culture medium that comprises a ROCK inhibitor, one or more growth factors and cytokines selected from the group consisting of bFGF, VEGF, SCF, IL6, and IL11, and is suitable for definitive hemogenic endothelium differentiation and expansion from mesodermal cells. In still another embodiment, the culture platform for generating a NK cell progenitor or NK cell comprising medium (i), (ii) and (iii), further comprises (iv), a culture medium that comprises a BMP activator, bFGF, and a GSK3 inhibitor, and is suitable for obtaining definitive hemogenic endothelium potential in mesodermal cells. In yet another embodiment, the culture platform for generating a NK cell progenitor or NK cell comprising medium (i), (ii), (iii) and (iv), further comprises (v), a culture medium that comprises a BMP activator, and optionally bFGF, and is suitable for generating and expanding mesodermal cells from iPSCs. In another embodiment, the culture platform for generating a NK cell progenitor or NK cell comprising medium (i), (ii), (iii), (iv) and (v) further comprises (vi), a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating definitive hemogenic endothelium, which comprises one or more of (i) a culture medium for definitive hemogenic endothelium differentiation and expansion from mesoderm cells, comprising a ROCK inhibitor, and one or more growth factors and cytokines selected from the group consisting of bFGF, VEGF, SCF, IL6, and IL11; (ii) a culture medium for obtaining definitive hemogenic potential in mesodermal cells, comprising a BMP activator, bFGF, and a GSK3 inhibitor; (iii) a culture medium for differentiating and expanding mesodermal cells from naïve iPSC, comprising a BMP activator, and optionally bFGF; and (iv) a naïve iPSC seeding and expansion culture comprising MEKi, GSKi, and ROCKi, and the seeding culture is free of TGFβ receptor/ALK inhibitors. In some embodiments, the definitive hemogenic endothelium are CD34+. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

In one embodiment, the culture platform for obtaining a definitive hemogenic endothelium comprises (i) a culture medium comprising a ROCK inhibitor, and one or more growth factors and cytokines selected from the group consisting of bFGF, VEGF, SCF, IL6, and IL11, wherein the culture medium is suitable for differentiating and expanding definitive hemogenic endothelium from mesodermal cells. In one embodiment, the culture platform comprising the culture media (i), further comprises (ii), a culture medium comprising a BMP activator, bFGF, and a GSK3 inhibitor, wherein the culture medium (ii) is suitable for obtaining definitive hemogenic potential in mesodermal cells. In another embodiment, the culture platform comprising the culture media (i), and (ii), further comprises (iii), a culture medium comprising a BMP activator, and optionally bFGF, wherein the culture medium (iii) is suitable for differentiating and expanding mesodermal cells from naïve iPSCs. In yet another embodiment, the culture platform comprising the culture media (i), (ii) and (iii), further comprises (iv), a culture medium comprising MEKi, GSKi, and ROCKi, and the culture meduium (v) is free, or essentially free, of TGFβ receptor/ALK inhibitors, wherein the culture medium (v) is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating CD34+ definitive hemogenic endothelium, which comprises one or more of (i) a culture medium for differentiating and expanding definitive hemogenic endothelium from mesodermal cells, comprising a ROCK inhibitor, and one or more growth factors and cytokines selected from the group consisting of bFGF, VEGF, SCF, IL6, and IL11, wherein the definitive hemogenic endothelium comprises CD34+ definitive hemogenic endothelium; (ii) a culture medium for obtaining definitive hemogenic potential in mesodermal cells, comprising a BMP activator, bFGF, and a GSK3 inhibitor; (iii) a culture medium for differentiating and expanding mesodermal cells from naïve iPSC, comprising a BMP activator, and optionally bFGF; and (iv) a naïve iPSC seeding or expanding culture comprising MEKi, GSKi, and ROCKi, and the seeding culture is free, or essentially free, of TGFβ receptor/ALK inhibitors. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating mesodermal cells, which comprises one or more of (i) a culture medium for differentiating and expanding mesodermal cells from naïve iPSC, comprising a BMP activator, and optionally bFGF; and (ii) a naïve iPSC seeding or expanding culture comprising MEKi, GSKi, and ROCKi, and the seeding culture is free, or essentially free, of TGFβ receptor/ALK inhibitors. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, the culture platform for generating mesodermal cells may further comprise (iii) a culture medium comprising a BMP activator, bFGF, and a GSK3 inhibitor, wherein the culture medium is for obtaining definitive hemogenic potential in mesodermal cells. In some embodiments, the culture medium comprising a BMP activator, bFGF, and a GSK3 inhibitor is free of TGFβ receptor/ALK inhibitors.

C. Method of Obtaining CD34+ Cells, Definitive Hemogenic Endothelium, Multipotent Progenitors, T Cell or NK Cell Progenitors, T Cells and/or NK Cells The present invention provides a method of generating pluripotent stem cell-derived definitive hematopoietic cells using a multi-staged culture platform comprising one or more culture media. The method is suitable for feeder-free conditions. The method is also suitable for monolayer culturing, and thus without requiring EB formation or aggregate intermediates in order for pluripotent stem cell differentiation as compared to the methods known in the art. The method, as provided, generates, and at the same time, expands pluripotent stem cell-derived definitive hemogenic endothelium (iHE), definitive HSC (iHSC), CD34+ HE (iCD34), which are capable of being further differentiated into multipotent progenitor cells (iMPP), natural killer cell progenitors (ipro-NK), T cell progenitors (ipro-T), mature NK cells (iNK) and T cells (iT). Additional aspect of the invention also provides a method of generating myeloid cells differentiated from pluripotent stem cell-derived CD34+, HE, HSC, and/or MPP.

In one embodiment, the invention provides a method for differentiating and expanding cells of the hematopoietic lineage from pluripotent cells in monolayer culturing, which comprises contacting the pluripotent cells with a BMP pathway activator, and optionally, bFGF, wherein pluripotent stem cell-derived mesodermal cells are obtained and expanded without forming embryoid bodies from pluripotent stem cells, which are then subjected to contact with a BMP pathway activator, bFGF, and a WNT pathway activator to obtain expanded pluripotent stem cell-derived mesodermal cells having definitive hemogenic endothelium (HE) potential without forming embryoid bodies from pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The provided methods for obtaining cells of the hematopoietic lineage are superior to EB-mediated pluripotent stem cell differentiation, because EB formation does not lead to cell expansion, does not allow monolayer culturing, and is laborious and low efficiency. Additionally, the present invention disclosed that monolayer culturing using the methods provided herein leads to functional hematopoietic lineage cells that enable in vivo long-term hematopoietic self-renewal, reconstitution and engraftment.

As detailed below, the invention provides a method of obtaining hematopoietic lineage cells from pluripotent cells through obtaining definitive HSCs or definitive hemogenic endothelium. Particularly, the invention provides a method of directing hematopoietic lineage cell differentiation from pluripotent cells without forming EBs for differentiation.

I. Ihsc Platform

1. Differentiating and Expanding iHSC from Pluripotent Stem Cells, Pluripotent Stem Cell-Derived Mesodermal, or HE-iHSC Platform One aspect of the invention provides a method of using a multistage process to generate and expand definitive HSC (iHSC). Generally, the method begins with a first stage wherein a pluripotent stem cell is differentiated to a mesodermal cell, then the mesodermal cells are differentiated and expanded to hemogenic endothelium (HE) in the second stage. In the third stage, the HE cells are differentiated into definitive HSCs (iHSC), which are also expanded at the same time. The invention also provides a method of generating definitive HSC (iHSC) that comprises differentiating and expanding pluripotent stem cell-derived mesodermal cells to HE, and differentiating the HE to iHSC. Alternatively, the invention provides a method of generating and expanding definitive HSC (iHSC) that comprises differentiating pluripotent stem cell-derived HE to iHSC. In some embodiments of the above methods, pluripotent stem cells comprise iPSCs. In some embodiments, the iPSCs are naïve iPSCs.

In one embodiment of the method of producing definitive HSC (iHSC) from naïve pluripotent stem cells, the method comprises (1) differentiating the pluripotent stem cells to mesodermal cells by contacting the pluripotent cells with a medium comprising at least one of a BMP pathway activator and a Wnt pathway activator, and an extracellular matrix protein, wherein the differentiated mesodermal cells expand; (2) differentiating the mesodermal cells to definitive hemogenic endothelium by contacting the mesodermal cell with a second medium comprising at least one of the BMP pathway activator and the Wnt pathway activator, and optionally, a TGFβ receptor inhibitor, wherein the definitive HE cells expand; and (3) differentiating the definitive HE cells to definitive HSCs, wherein the definitive HSCs expand, by contacting the definitive HE cells with a third medium comprising a BMP activator, and one or more growth factors and cytokines selected from the group consisting of VEGF, SCF, Flt3L, IL15, IL3, IL6, IGF, and TPO. In some embodiments, the pluripotent stem cells comprise iPSCs. In some embodiments, the iPSCs are naïve iPSCs. In some embodiments, the iHSC cells obtained from the above method express CD34. In some embodiments, the above method further comprises sorting the obtained HSC (iHSC) using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the above method comprises differentiating the mesodermal cells to definitive hemogenic endothelium by contacting the mesodermal cell with media comprising at least one of the BMP pathway activator and the Wnt pathway activator, and a TGFβ receptor inhibitor.

In one embodiment of the method of generating and expanding definitive HSC (iHSC) from pluripotent stem cell-derived mesodermal cells, the method comprises differentiating the mesodermal cells into definitive HE cells by contacting the mesodermal cells with a medium comprising at least one of the BMP pathway activator and the Wnt pathway activator, and optionally, a TGFβ receptor inhibitor, wherein the definitive HE cells expand; and (2) differentiating the obtained HE cells into iHSC by contacting the HE cells with a second medium comprising a BMP activator, one or more growth factors and cytokines selected from the group consisting of VEGF, SCF, Flt3L, IL15, IL3, IL6, IGF, and TPO, wherein the iHSC expand. In some embodiments, the iHSC cells obtained from the above method express CD34. In some embodiments, the above method further comprises sorting the obtained HSC (iHSC) using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating and expanding definitive HSC (iHSC) from pluripotent stem cell-derived HE, the method comprises contacting the HE cells with a medium comprising a BMP activator, and one or more growth factors and cytokines selected from the group consisting of VEGF, SCF, Flt3L, IL15, IL3, IL6, IGF, and TPO, wherein the iHSCs are differentiated and expanded from the pluripotent stem cell-derived HE. In some embodiments, the iHSC cells obtained from the above method express CD34. In some embodiments, the above method further comprises sorting the obtained HSC (iHSC) using CD34, CD43, CD73, and/or CXCR4.

2. Differentiating and Expanding HE from Pluripotent Stem Cells, or Pluripotent Stem Cell Derived Mesodermal iHSC Platform One aspect of the invention provides a method of using a multistage process to generate and expand definitive hemogenic endothelium. In general, the method begins with a first stage wherein pluripotent stem cells are differentiated to mesodermal cells, and then the mesodermal cells are expanded and differentiated to hemogenic endothelium in the second stage. The starting pluripotent cells include, but are not limited to, induced ground or naïve pluripotent stem cells and embryonic stem cells. In some embodiments, the generated and expanded hemogenic endothelium are definitive. In some embodiments, the generated definitive hemogenic endothelium are CD34 positive. Alternatively, the invention provides a method of generating and expand hemogenic endothelium by differentiating pluripotent stem cell-derived mesodermal cells to definitive hemogenic endothelium.

In one embodiment of the method of differentiating and expanding definitive hemogenic endothelium from pluripotent stem cells, the method comprises (1) differentiating the pluripotent stem cells to mesodermal cells by contacting the cells with a first medium comprising at least one of a BMP pathway activator and a Wnt pathway activator, and an extracellular matrix protein; (2) differentiating the mesodermal cells to hemogenic endothelium by contacting the mesodermal cell with a second medium comprising at least one of the BMP pathway activator and the Wnt pathway activator, and optionally, a TGFβ receptor inhibitor, wherein the definitive HE cells expand. In some embodiments, the HE cells obtained from the above method express CD34. In some embodiments, the above method comprises a GSK3 inhibitor as a Wnt pathway activator. In some embodiments, the above method comprises CHIR99021 or BIO as a GSK3 inhibitor. In some embodiments, the above method comprises CHIR99021 as a GSK3 inhibitor. In some embodiments, the above method comprises SB431542 or A83-01 as a TGFβ receptor inhibitor. In some embodiments, the above method comprises SB431542 as a TGFβ receptor inhibitor.

In one embodiment of the method of differentiating and expanding hemogenic endothelium from pluripotent stem cell-derived mesodermal cells, the method comprises differentiating the mesodermal cells to hemogenic endothelium by contacting the mesodermal cells with a medium comprising at least one of the BMP pathway activator and the Wnt pathway activator, and optionally, a TGFβ receptor inhibitor. In some embodiments, the definitive HE cells obtained from the above method express CD34.

3. Differentiating and Expanding Mesodermal Cells from iPSC-iHSC Platform

One aspect of the invention provides a method of generating mesodermal cells from pluripotent stem cells. The starting pluripotent cells include, but are not limited to, induced ground or naïve pluripotent stem cells and embryonic stem cells.

In one embodiment of the method of generating and expanding mesodermal cells from pluripotent stem cells, the method comprises differentiating the pluripotent stem cells to mesodermal cells by contacting the pluripotent stem cells with a medium comprising at least one of a BMP pathway activator and a Wnt pathway activator, and an extracellular matrix protein. In some embodiments, the above method comprises a GSK3 inhibitor as a Wnt pathway activator. In some embodiments, the above method comprises CHIR99021 or BIO as a GSK3 inhibitor. In some embodiments, the above method comprises CHIR99021 as a GSK3 inhibitor.

4. Obtaining T Cell Progenitors from Pluripotent Stem Cells, from Pluripotent Stem Cell-Derived Mesodermal Cells, HE, or Definitive HSC-iHSC and iTC Platform One aspect of the invention provides a method of using a multistage process to generate T cell progenitors from pluripotent stem cells. Generally, the method begins with a first stage wherein pluripotent stem cells are differentiated to mesodermal cells, wherein the mesodermal cells are expanded, and then hemogenic endothelium are differentiated and expanded in the second stage. In the third stage, the HE cells are differentiated into definitive HSCs (iHSC), wherein the iHSCs expand. In the fourth stage, the iHSC are differentiated into T cell progenitors. The invention also provides a method of generating T cell progenitors that comprises differentiating pluripotent stem cell-derived mesodermal cell to HE, then differentiating the HE to iHSC, and then differentiating the iHSC to T cell progenitors. The invention further provides a method of generating T cell progenitors that comprises differentiating pluripotent stem cell-derived HE to iHSC, and then differentiating the iHSC to T cell progenitors. Alternatively, the invention provides a method of generating T cell progenitors that comprises differentiating pluripotent stem cell-derived iHSC to T cell progeitors.

In one embodiment of the method of producing T cell progenitors from pluripotent stem cells, the method comprises (1) differentiating the pluripotent stem cells to mesodermal cells by contacting the pluripotent cells with a medium comprising at least one of a BMP pathway activator and a Wnt pathway activator, and an extracellular matrix protein, wherein the mesodermal cells expand; (2) differentiating the mesodermal cells to hemogenic endothelium by contacting the mesodermal cell with a second medium comprising at least one of the BMP pathway activator and the Wnt pathway activator, and optionally, a TGFβ receptor inhibitor, wherein the HE cells expand; (3) differentiating the HE cells to definitive HSC by contacting the HE cells with a third medium comprising a BMP activator, one or more growth factors and cytokines selected from the group consisting of VEGF, SCF, Flt3L, IL15, IL3, IL6, IGF, and TPO, wherein the iHSCs expand; and (4) differentiating the iHSC to T cell progenitors by contacting the iHSC with a fourth medium comprising a BMP activator, one or more growth factors and cytokines selected from the group consisting of SCF, Flt3L, IL7, IL2, IL3, and IL6, and one or more Notch pathway activators. In some embodiments, the iHSC cells obtained from the above method express CD34. In some embodiments, the above method further comprises sorting the obtained HSC (iHSC) using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the BMP activator is BMP4. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cell progenitor from pluripotent stem cell-derived mesodermal cells, the method comprises differentiating the mesodermal cells into HE cells by contacting the mesodermal cells with a medium comprising at least one of the BMP pathway activator and the Wnt pathway activator, and optionally, a TGFβ receptor inhibitor, wherein the HE expand; (2) differentiating the obtained HE cells into iHSC by contacting the HE cells with a second medium comprising a BMP activator, and one or more growth factors and cytokines selected from the group consisting of VEGF, SCF, Flt3L, IL15, IL3, IL6, IGF, and TPO, wherein the iHSCs expand; and (3) differentiating the iHSC to T cell progenitors by contacting the iHSC with a third medium comprising a BMP activator, one or more growth factors and cytokines selected from the group consisting of SCF, Flt3L, IL7, IL2, IL3, and IL6, and one or more Notch pathway activators. In some embodiments, the iHSC cells obtained from the above method express CD34. In some embodiments, the above method further comprises sorting the obtained HSC (iHSC) using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cell progenitors from pluripotent stem cell-derived HE, the method comprises (1) differentiating the HE to iHSC by contacting the HE cells with a medium comprising a BMP activator, and one or more growth factors and cytokines selected from the group consisting of VEGF, SCF, Flt3L, IL15, IL3, IL6, IGF, and TPO, wherein the iHSCs expand; and (2) differentiating the iHSC to T cell progenitors by contacting the iHSC with a second medium comprising a BMP activator, and one or more growth factors and cytokines selected from the group consisting of SCF, Flt3L, IL7, IL2, IL3, and IL6, and one or more Notch pathway. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating T cell progenitors from pluripotent stem cell-derived iHSC, the method comprises differentiating the iHSC to T cell progenitors by contacting the iHSC with a medium comprising a BMP activator, one or more growth factors and cytokines selected from the group consisting of SCF, Flt3L, IL7, IL2, IL3, and IL6, and one or more Notch pathway activators. In some embodiments, the above method further comprises sorting and obtaining pluripotent stem cell-derived HSC (iHSC) using CD34, CD43, CD73, and/or CXCR4. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

5. Obtaining T Cells from Pluripotent Stem Cells, from Pluripotent Stem Cell-Derived Mesodermal Cells, HE, iHSC, or T Cell Progenitors—iHSC and iTC Platform One aspect of the invention provides a method of using a multistage process to generate T cells from pluripotent stem cells. Generally, the method begins with a first stage wherein a pluripotent stem cell is differentiated to a mesodermal cell, which expand while differentiating, then the mesodermal cells are differentiated to hemogenic endothelium in the second stage, wherein the HE cells expand. In the third stage, the HE cells are differentiated into definitive HSC (iHSC), wherein the iHSCs expand. In the fourth stage, the iHSC are differentiated into T cell progenitors (ipro-T). In the fifth stage, the iHSC are differentiated into T cells. The invention also provides a method of generating T cells that comprises differentiating pluripotent stem cell-derived mesodermal cell to HE, differentiating the HE to iHSC, differentiating the iHSC to T cell progenitors, and then differentiating T cell progenitors to T cells. The invention further provides a method of generating T cells that comprises differentiating pluripotent stem cell-derived HE to iHSC, differentiating the iHSC to T cell progenitors, and differentiating T cell progenitors to T cells. Alternatively, the invention provides a method of generating T cells that comprises differentiating pluripotent stem cell-derived iHSC to T cell progenitors, and differentiating the T cell progenitors to T cells. Further, the invention provides a method of generating T cells that comprises differentiating pluripotent stem cell-derived T cell progenitors to T cells.

In one embodiment of the method of producing T cells from pluripotent stem cells, the method comprises (1) differentiating the pluripotent stem cells to mesodermal cells by contacting the pluripotent stem cells with a medium comprising at least one of a BMP pathway activator and a Wnt pathway activator, and an extracellular matrix protein, wherein mesodermal cells expand; (2) differentiating the mesodermal cells to hemogenic endothelium by contacting the mesodermal cell with a second medium comprising at least one of the BMP pathway activator and the Wnt pathway activator, and optionally, a TGFβ receptor inhibitor, wherein HE cells expand; (3) differentiating the HE cells to iHSC by contacting the HE cells with a third medium comprising a BMP activator, and one or more growth factors and cytokines selected from the group consisting of VEGF, SCF, Flt3L, IL15, IL3, IL6, IGF, and TPO, wherein iHSCs expand; (4) differentiating the iHSC to T cell progenitors by contacting the iHSC with a fourth medium comprising a BMP activator, one or more growth factors and cytokines selected from the group consisting of SCF, Flt3L, IL7, IL2, IL3, and IL6, and one or more Notch pathway activators; and (5) differentiating the T cell progenitors to T cells by contacting the T cell progenitors with a fifth medium comprising one or more growth factors and cytokines selected form the group consisting of SCF, Flt3L, IL7, IGF, IL2, IL3, and IL6, and one or more Notch pathway activators. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the BMP activator is BMP4. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cells from pluripotent stem cell-derived mesodermal cells, the method comprises differentiating the mesodermal cells into HE cells by contacting the mesodermal cells with a medium comprising at least one of the BMP pathway activator and the Wnt pathway activator, and optionally, a TGFβ receptor inhibitor, wherein the definitive HE cells expand; (2) differentiating the obtained HE cells into iHSCs by contacting the HE cells with a second medium comprising a BMP activator, and one or more growth factors and cytokines selected from the group consisting of VEGF, SCF, Flt3L, IL15, IL3, IL6, IGF, and TPO, wherein iHSCs expand; (3) differentiating the iHSC to T cell progenitors by contacting the iHSC with a third medium comprising a BMP activator, one or more growth factors and cytokines selected from the group consisting of SCF, Flt3L, IL7, IL2, IL3, and IL6, and one or more Notch pathway activators; and (4) differentiating the T cell progenitors to T cells by contacting the T cell progenitors with a fourth medium comprising one or more growth factors and cytokines selected form the group consisting of SCF, Flt3L, IL7, IGF, IL2, IL3, and IL6, and one or more Notch pathway activators. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cells from pluripotent stem cell-derived HE, the method comprises (1) differentiating the pluripotent stem cell-derived HE to iHSC by contacting the HE cells with a medium comprising a BMP activator, and one or more growth factors and cytokines selected from the group consisting of VEGF, SCF, Flt3L, IL15, IL3, IL6, IGF, and TPO, wherein the iHSCs expand; (2) differentiating the iHSC to T cell progenitors by contacting the iHSC with a second medium comprising a BMP activator, one or more growth factors and cytokines selected from the group consisting of SCF, Flt3L, IL7, IL2, IL3, and IL6, and one or more Notch pathway activators; and (3) differentiating the T cell progenitors to T cells by contacting the T cell progenitors with a third medium comprising one or more growth factors and cytokines selected form the group consisting of SCF, Flt3L, IL7, IGF, IL2, IL3, and IL6, and one or more Notch pathway activators. In some embodiments, the iHSC cells obtained from the above method express CD34. In some embodiments, the above method further comprises sorting the obtained iHSC using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cells from pluripotent stem cell-derived iHSC, the method comprises (1) differentiating the iHSC to T cell progenitors by contacting the iHSC with a medium comprising a BMP activator, one or more growth factors and cytokines selected from the group consisting of SCF, Flt3L, IL7, IL2, IL3, and IL6, and one or more Notch pathway activators, wherein the iHSCs expand; and (2) differentiating the T cell progenitors to T cells by contacting the T cell progenitors with a medium comprising one or more growth factors and cytokines selected form the group consisting of SCF, Flt3L, IL7, IGF, IL2, IL3, and IL6, and one or more Notch pathway activators. In some embodiments, the above method further comprises sorting and obtaining pluripotent stem cell-derived HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In one embodiment, the Notch pathway activators are Jag1, Jag2, DLL-1, DLL-3 and DLL-4. In some embodiments, DLL-1 and -4 can be introduced as soluble peptide, peptide conjugated to beads, peptide conjugated to the surface, or peptide presented by cells.

In one embodiment of the method of generating T cells from pluripotent stem cell-derived T cell progenitors, the method comprises differentiating the T cell progenitors to T cells by contacting the T cell progenitors with a medium comprising one or more growth factors and cytokines selected form the group consisting of SCF, Flt3L, IL7, IGF, IL2, IL3, and IL6, and one or more Notch pathway activators.

6. Obtaining NK Cell Progenitors Pluripotent Stem Cell, from Pluripotent Stem Cell-Derived Mesodermal Cells, HE, or iHSC-iHSC and iNK Platform One aspect of the invention provides a method of using a multistage process to generate NK cell progenitors from pluripotent stem cells. Generally, the method begins with a first stage wherein pluripotent stem cells are differentiated to mesodermal cells, wherein the mesodermal cells expand; then the mesodermal cells are differentiated to hemogenic endothelium in the second stage, wherein the HE cells expand. In the third stage, the HE cells are differentiated into definitive HSC, wherein the definitive HSCs expand. In the fourth stage, the iHSC are differentiated into NK cell progenitors. The invention also provides a method of generating NK cell progenitors that comprises differentiating pluripotent stem cell-derived mesodermal cell to HE, then differentiating the HE to iHSC, and then differentiating the iHSC to NK cell progenitors. The invention further provides a method of generating NK cell progenitors that comprises differentiating pluripotent stem cell-derived HE to iHSC, and then differentiating the iHSC to NK cell progenitors. Alternatively, the invention provides a method of generating NK cell progenitors that comprises differentiating pluripotent stem cell-derived iHSC to NK cell progenitors.

In one embodiment of the method of producing NK cell progenitors from pluripotent stem cells, the method comprises (1) differentiating the pluripotent stem cells to mesodermal cells by contacting the pluripotent stem cells with a medium comprising at least one of a BMP pathway activator and a Wnt pathway activator, and an extracellular matrix protein, wherein the mesodermal cells expand; (2) differentiating the mesodermal cells to hemogenic endothelium by contacting the mesodermal cell with a second medium comprising at least one of the BMP pathway activator and the Wnt pathway activator, and optionally, a TGFβ receptor inhibitor, wherein the HE cells expand; (3) differentiating the HE cells to iHSC by contacting the HE cells with a third medium comprising a BMP activator, one or more growth factors and cytokines selected from the group consisting of VEGF, SCF, Flt3L, IL15, IL3, IL6, IGF, and TPO, wherein the iHSCs expand; and (4) differentiating the iHSC to NK cell progenitors by contacting the iHSC with a fourth medium comprising a BMP activator, and one or more growth factors and cytokines selected from the group consisting of SCF, Flt3L, VEGF, IL2, IL3, IL6, and IL15. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating NK cell progenitor from pluripotent stem cell-derived mesodermal cells, the method comprises differentiating the pluripotent stem cell-derived mesodermal cells into HE cells by contacting the mesodermal cells with a medium comprising at least one of the BMP pathway activator and the Wnt pathway activator, and optionally, a TGFβ receptor inhibitor, wherein the HE cells expand; (2) differentiating the obtained HE cells into iHSC by contacting the HE cells with a second medium comprising a BMP activator, and one or more growth factors and cytokines selected from the group consisting of VEGF, SCF, Flt3L, IL15, IL3, IL6, IGF, and TPO, wherein the iHSCs expand; and (3) differentiating the iHSC to NK cell progenitors by contacting the iHSC with a third medium comprising a BMP activator, and one or more growth factors and cytokines selected from the group consisting of SCF, Flt3L, VEGF, IL2, IL3, IL6, and IL15. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating NK cell progenitors from pluripotent stem cell-derived HE, the method comprises (1) differentiating the pluripotent stem cell-derived HE to iHSC by contacting the HE cells with a medium comprising a BMP activator, and one or more growth factors and cytokines selected from the group consisting of VEGF, SCF, Flt3L, IL15, IL3, IL6, IGF, and TPO, wherein iHSCs expand; and (2) differentiating the iHSCs to NK cell progenitors by contacting the iHSCs with a second medium comprising a BMP activator, and one or more growth factors and cytokines selected from the group consisting of SCF, Flt3L, VEGF, IL2, IL3, IL6, and IL15. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating NK cell progenitors from pluripotent stem cell-derived iHSC, the method comprises differentiating the iHSC to NK cell progenitors by contacting the iHSC with a medium comprising a BMP activator, and one or more growth factors and cytokines selected from the group consisting of SCF, Flt3L, VEGF, IL2, IL3, IL6, and IL15. In some embodiments, the above method further comprises sorting and obtaining pluripotent stem cell-derived HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

7. Obtaining NK Cells from Pluripotent Stem Cells, from Pluripotent Stem Cell-Derived Mesodermal Cells, HE, iHSC, or NK Cell Progenitors—iHSC and iNK Platform One aspect of the invention provides a method of using a multistage process to generate NK cells from pluripotent stem cells. Generally, the method begins with a first stage wherein pluripotent stem cells are differentiated to mesodermal cells, wherein the mesodermal cells expand, and then the mesodermal cells are differentiated to hemogenic endothelium in the second stage, wherein the HE cells expand. In the third stage, the HE cells are differentiated into definitive HSCs (iHSC); wherein the HSCs expand. In the fourth stage, the iHSC are differentiated into NK cell progenitors (ipro-NK). In the fifth stage, the iHSC are differentiated into NK cells. The invention also provides a method of generating NK cells that comprises differentiating pluripotent stem cell-derived mesodermal cell to HE, differentiating the HE to iHSC, differentiating the iHSC to NK cell progenitors, and then differentiating NK cell progenitors to NK cells. The invention further provides a method of generating NK cells that comprises differentiating pluripotent stem cell-derived HE to iHSC, differentiating the iHSC to NK cell progenitors, and differentiating NK cell progenitors to NK cells. Alternatively, the invention provides a method of generating NK cells that comprises pluripotent stem cell-derived iHSC to NK cell progenitors, and differentiating pluripotent stem cell-derived NK cell progenitors to NK cells. Further, the invention provides a method of generating NK cells that comprises differentiating pluripotent stem cell-derived NK cell progenitors to NK cells.

In one embodiment of the method of producing NK cells from pluripotent stem cells, the method comprises (1) differentiating the pluripotent stem cells to mesodermal cells by contacting the pluripotent stem cells with a medium comprising at least one of a BMP pathway activator and a Wnt pathway activator, and an extracellular matrix protein, wherein the mesodermal cells expand; (2) differentiating the mesodermal cells to definitive hemogenic endothelium by contacting the mesodermal cell with a second medium comprising at least one of the BMP pathway activator and the Wnt pathway activator, and optionally, a TGFβ receptor inhibitor, wherein the HE cells expand; (3) differentiating the HE cells to iHSC by contacting the HE cells with a third medium comprising a BMP activator, and one or more growth factors and cytokines selected from the group consisting of VEGF, SCF, Flt3L, IL15, IL3, IL6, IGF, and TPO, wherein the iHSCs expand; (4) differentiating the iHSC to NK cell progenitors by contacting the iHSC with a fourth medium comprising a BMP activator, and one or more growth factors and cytokines selected from the group consisting of SCF, Flt3L, VEGF, IL2, IL3, IL6, and IL15; and (5) differentiating the NK cell progenitors to NK cells by contacting the NK cell progenitors with a fifth medium comprising one or more growth factors and cytokines selected form the group consisting of SCF, Flt3L, IL7, IL2, IL3, IL6, and IL15. In some embodiments, the iHSC cells obtained from the above method express CD34. In some embodiments, the above method further comprises sorting the obtained HSC (iHSC) using CD34, CD43, CD73, and/or CXCR4. In some embodiments, the above method comprises differentiating the mesodermal cells to definitive hemogenic endothelium by contacting the mesodermal cell with media comprising at least one of the BMP pathway activator and the Wnt pathway activator, and a TGFβ receptor inhibitor. In one embodiment, the BMP activator is BMP4.

In one embodiment of the method of generating NK cells from pluripotent stem cell-derived mesodermal cells, the method comprises differentiating the pluripotent stem cell-derived mesodermal cells into HE cells by contacting the mesodermal cells with a medium comprising at least one of the BMP pathway activator and the Wnt pathway activator, and optionally, a TGFβ receptor inhibitor, wherein the mesodermal cells expand; (2) differentiating the obtained HE cells into iHSC by contacting the HE cells with a second medium comprising a BMP activator, and one or more growth factors and cytokines selected from the group consisting of VEGF, SCF, Flt3L, IL15, IL3, IL6, IGF, and TPO, wherein the definitive HE cells expand; (3) differentiating the iHSC to NK cell progenitors by contacting the iHSC with a third medium comprising a BMP activator, and one or more growth factors and cytokines selected from the group consisting of SCF, Flt3L, VEGF, IL2, IL3, IL6, and IL15; and (4) differentiating the NK cell progenitors to NK cells by contacting the NK cell progenitors with a fourth medium comprising one or more growth factors and cytokines selected form the group consisting of SCF, Flt3L, IL7, IL2, IL3, IL6, and IL15. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the above method comprises differentiating the mesodermal cells to definitive hemogenic endothelium by contacting the mesodermal cell with media comprising at least one of the BMP pathway activator and the Wnt pathway activator, and a TGFβ receptor inhibitor.

In one embodiment of the method of generating NK cells from pluripotent stem cell-derived HE, the method comprises (1) differentiating the pluripotent stem cell-derived definitive HE to iHSC by contacting the HE cells with a medium comprising a BMP activator, and one or more growth factors and cytokines selected from the group consisting of VEGF, SCF, Flt3L, IL15, IL3, IL6, IGF, and TPO, wherein the iHSCs expand; (2) differentiating the iHSC to NK cell progenitors by contacting the iHSC with a second medium comprising a BMP activator, and one or more growth factors and cytokines selected from the group consisting of SCF, Flt3L, VEGF, IL2, IL3, IL6, and IL15; and (3) differentiating the NK cell progenitors to NK cells by contacting the NK cell progenitors with a third medium comprising one or more growth factors and cytokines selected form the group consisting of SCF, Flt3L, IL7, IL2, IL3, IL6, and IL15. In some embodiments, the iHSC cells obtained from the above method express CD34. In some embodiments, the above method further comprises sorting the obtained HSC (iHSC) using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative.

In one embodiment of the method of generating NK cells from pluripotent stem cell-derived iHSC, the method comprises (1) differentiating the iHSC to NK cell progenitors by contacting the iHSC with a medium comprising a BMP activator, and one or more growth factors and cytokines selected from the group consisting of SCF, Flt3L, VEGF, IL2, IL3, IL6, and IL15; and (2) differentiating the NK cell progenitors to NK cells by contacting the NK cell progenitors with a second medium comprising one or more growth factors and cytokines selected form the group consisting of SCF, Flt3L, IL7, IL2, IL3, IL6, and IL15. In some embodiments, the above method further comprises sorting and obtain pluripotent stem cell-derived HSC (iHSC) using CD34, CD43, CD73 and/or CXCR4.

In one embodiment of the method of generating NK cells from pluripotent stem cell-derived NK cell progenitors, the method comprises differentiating the NK cell progenitors to NK cells by contacting the NK cell progenitors with a fifth medium comprising one or more growth factors and cytokines selected form the group consisting of SCF, Flt3L, IL7, IL2, IL3, IL6, and IL15.

II. iCD34 Platform

1. Deriving and Expanding Definitive iHE-iCD34 Platform

One aspect of the invention provides a method of using an optimized multistage process to generate definitive hemogenic endothelium (iHE). Generally, the method begins with a first stage wherein pluripotent stem cells are seeded and expanded. The pluripotent stem cells are then differentiated to mesodermal cells, which expand in this stage. The expanded mesodermal population is then differentiated to a mesodermal population with definitive hemogenic endothelium potential, definitive hemogenic endothelium are then differentiated and expanded from the mesodermal cells with definitive hemogenic endothelium potential. Alternatively, the invention provides a method of generating definitive hemogenic endothelium (iHE) that comprises differentiating and expanding mesodermal cells from pluripotent stem cells; then definitive hemogenic endothelium (iHE) are differentiated and expanded from mesodermal cells. In some embodiments, the pluripotent stem cells are iPSCs. In some embodiments, the iPSCs are naïve iPSCs. The invention further provides a method of generating and expanding definitive hemogenic endothelium (iHE) that comprises differentiating and expanding pluripotent stem cell-derived mesodermal cells, and obtaining mesodermal cells having definitive iHE potential, which are then differentiated into iHE. Alternatively, the invention provides a method of generating and expanding definitive hemogenic endothelium comprises differentiating pluripotent stem cell-derived mesodermal cells to iHE. The methods disclosed herein utilize the optimized monolayer iCD34 culture platform without EB formation, and is free, or essentially free, of TGFβ receptor/ALK inhibitors.

In one embodiment of the method of producing definitive hemogenic endothelium (iHE) from pluripotent stem cells, the method comprises (1) differentiating and expanding a mesodermal population from the pluripotent stem cells by contacting the cells with a medium comprising a BMP activator, and optionally bFGF; (2) differentiating and expanding the mesodermal population to obtain definitive HE potential in the mesodermal cells by contacting the cells with a medium comprising a BMP activator, a Wnt pathway activator and bFGF; (3) differentiating and expanding the mesodermal cells with definitive HE potential to definitive HE cells by contacting the cells with a medium comprising a ROCK inhibitor, and one or more of the growth factors and cytokines selected from the group consisting of VEGF, bFGF, SCF, IL6, and IL11. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, sorting uses CD34 positive, CD43 negative, and CD73 negative. In some other embodiments, the sorting uses CD34 positive, CD43 negative, CD73 negative, and CXCR4 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, contacting cell with a culture medium comprising GSK3 inhibitor is only after mesodermal cell specification in order to achieve definitive HE potential. In some embodiments, the method above further comprises subjecting the seeded iPSC, and/or mesodermal cells under a low oxygen tension between about 2% and about 10%. In some embodiments, the method above further comprises seeding the pluripotent stem cells by contacting the pluripotent cells with a medium comprising a MEKi, a GSKi, and a ROCKi, wherein the pluripotent stem cells expand.

In one embodiment of the method of generating definitive hemogenic endothelium (iHE) from seeded pluripotent stem cells, the method comprises (1) differentiating and expanding mesodermal cells from pluripotent stem cells by contacting the pluripotent stem cells with a medium comprising a BMP activator, and optionally bFGF; (2) obtaining mesodermal cells having definitive iHE potential by contacting the mesodermal cells with a medium comprising a BMP activator, a Wnt pathway activator and bFGF; (3) differentiating and expanding definitive HE cells from the mesodermal cells with iHE potential by contacting the mesodermal cells with a medium comprising a ROCK inhibitor, and one or more of the growth factors and cytokines selected from the group consisting of VEGF, bFGF, SCF, IL6, and IL11. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iHE cells using CD34, CD43, CD73 and/or CXCR4. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the seeded iPSC, and/or mesodermal cells under a low oxygen tension between about 2% and about 10%.

In one embodiment of the method of generating definitive hemogenic endothelium (iHE) from pluripotent stem cell-derived mesodermal cells, the method comprises (1) obtaining mesodermal cells having definitive HE potential by contacting the mesodermal cells with a medium comprising a BMP activator, a Wnt pathway activator and bFGF; (2) differentiating and expanding definitive HE cells from the mesodermal cells having definitive HE potential by contacting the mesodermal cells with a medium comprising a ROCK inhibitor, and one or more of the growth factors and cytokines selected from the group consisting of VEGF, bFGF, SCF, IL6, and IL11. In some embodiments, the iHE cells obtained from the above method express CD34. In some embodiments, the pluripotent stem cells are iPSCs. In some embodiments, the iPSCs are naïve iPSCs. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the mesodermal cells under a low oxygen tension between about 2% and about 10%.

In one embodiment of the method of obtaining definitive hemogenic endothelium (iHE) potential in pluripotent stem cell-derived mesodermal cells, the method comprises contacting the mesodermal cells with a medium comprising a ROCK inhibitor, and one or more of the growth factors and cytokines selected from the group consisting of VEGF, bFGF, SCF, IL6, and IL11, wherein the mesodermal cells expand. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iHE cells using CD34, CD43, CD73, and/or CXCR4. In some embodiments, the media in the above method are free, or essentially free, of TGFβ receptor inhibitor. In some embodiments, the Wnt pathway activator is a GSK3 inhibitor. In some embodiments, the method above further comprises subjecting the mesodermal cells under a low oxygen tension between about 2% and about 10%.

2. Deriving and Expanding Pluripotent Stem Cell-Derived Mesodermal Cells with Definitive Hemogenic Endothelium Potential iCD34 Platform One aspect of the invention provides a method of using an optimized multistage process to generate pluripotent stem cell-derived mesodermal cells. Generally, the method begins with a first stage wherein a pluripotent stem cell is seeded. The seeded pluripotent stem cell is then developed into mesoderm. The mesoderm is further differentiated to a mesodermal cell with definitive hemogenic endothelium potential in the third stage. Alternatively, the invention provides a method of generating pluripotent stem cell-derived mesodermal cells that comprises differentiating seeded pluripotent stem cell to mesoderm, and a method of differentiating mesoderm to mesodermal cells with definitive hemogenic potential. The invention further provides a method of generating pluripotent stem cell-derived mesodermal cells having definitive HE potential, and the method comprises differentiating a pluripotent stem cell-derived mesoderm to mesodermal cells with definitive hemogenic endothelium potential. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors.

In one embodiment of the method of obtaining definitive hemogenic endothelium potential in mesodermal cells derived from pluripotent stem cells, the method comprises (1) differentiating and expanding mesodermal cells from pluripotent stem cells by contacting the pluripotent stem cells with a medium comprising a BMP activator, and optionally bFGF; and (2) obtaining definitive hemogenic endothelium potential in the mesodermal cells by contacting the cells with a medium comprising a BMP activator, a Wnt pathway activator and bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the pluripotent stem cells under a low oxygen tension between about 2% and about 10%. In some embodiments, the above method further comprises seeding pluripotent stem cells by contacting the cells with a medium comprising a MEKi, a GSKi, and a ROCKi.

In one embodiment of the method of generating pluripotent stem cell-derived mesodermal cells having definitive hemogenic endothelium potential from pluripotent stem cell-derived mesoderm, the method comprises differentiating the mesoderm to mesodermal cells with definitive hemogenic endothelium potential by contacting the cells with a medium comprising a BMP activator, a Wnt pathway activator and bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the mesodermal cells under a low oxygen tension between about 2% and about 10%.

3. Deriving and Expanding Mesoderm from Pluripotent Stem Cell

One aspect of the invention provides a method of using an optimized multistage process to generate pluripotent stem cell-derived mesoderm. Generally, the method begins with a first stage wherein a pluripotent stem cell is seeded, and the seeded cell is then differentiated into mesoderm in the second stage. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors.

In one embodiment of the method of producing pluripotent stem cell-derived mesoderm from a pluripotent cell, the method comprises differentiating and expanding mesoderm cells from the seeded pluripotent stem cell by contacting the cell with a medium comprising a BMP activator, and optionally bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the method above further comprises subjecting the seeded iPSC under a low oxygen tension between about 2% and about 10%. In some embodiment, the above method further comprises seeding and expanding the iPSCs by contacting the pluripotent cells with a medium comprising a MEKi, a GSKi, and a ROCK.

4. Deriving Hematopoietic Multipotent Progenitors (iMPP)-iCD34 Platform and iMPP Platform One aspect of the invention provides a method of using an optimized multistage process to generate pluripotent stem cell-derived multipotent progenitors (iMPP). Generally, the method begins with a first stage wherein a pluripotent stem cell is seeded. The seeded cell is expanded and differentiated into mesodermal cells. The mesoderm is expanded and differentiated to a mesodermal cell with definitive hemogenic endothelium potential, and subsequently, the mesodermal cells are differentiated to definitive hemogenic endothelium. The HE cells are expanded and differentiated to pre-HSC, and then multipotent progenitors that are capable of differentiating into myeloids, including neutrophil progenitors. Alternatively, the invention provides a method of generating pluripotent stem cell-derived multipotent progenitors (iMPP) that comprises differentiating seeded pluripotent cells to mesoderm, differentiating mesoderm to mesodermal cells with definitive hemogenic endothelium potential, then the mesodermal cells are differentiated to definitive iHE, which are then differentiated into iMPP. The invention further provides a method of generating pluripotent stem cell-derived iMPP that comprises differentiating pluripotent stem cell-derived mesoderm to mesodermal cells with definitive hemogenic endothelium potential, then the mesodermal cells are differentiated to definitive iHE, which are then differentiated into iMPP. Alternatively, the invention provides a method of generating pluripotent stem cell-derived iMPP that comprises differentiating pluripotent stem cell-derived mesodermal cells to definitive iHE, which are then differentiated into iMPP. Further, the invention provides a method of generating pluripotent stem cell-derived iMPP that comprises differentiating pluripotent stem cell-derived iHE into iMPP. In some embodiments, the pluripotent stem cells are iPSCs. In some embodiments, the iPSCs are naïve iPSCs. The methods disclosed herein utilize the optimized monolayer iCD34 culture platform without EB formation, which is free, or essentially free, of TGFβ receptor/ALK inhibitors.

In one embodiment of the method of producing hematopoiesis multipotent progenitors (iMPP) from pluripotent stem cells, the method comprises (1) differentiating and expanding mesodermal cells from pluripotent stem cells by contacting the pluripotent cells with a medium comprising a BMP activator, and optionally bFGF; (2) obtaining definitive hemogenic endothelium potential in mesodermal cells by contacting the mesodermal cells with a medium comprising a BMP activator, a Wnt pathway activator and bFGF; (3) differentiating and expanding definitive HE cells from the mesodermal cells having definitive hemogenic endothelium potential by contacting the cells with a medium comprising a ROCK inhibitor, one or more of the growth factors and cytokines selected from the group consisting of VEGF, bFGF, SCF, IL6, and IL11; and (4) differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, and IL11, and optionally, a ROCK inhibitor. In some embodiments, the above method further comprises seeding and expanding the pluripotent stem cells by contacting the cells with a medium comprising a MEKi, a GSKi, and a ROCKi. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, and IL11. In other embodiments, the method comprising differentiating the definitive HE cells to pre-HSC, further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the method above further comprises subjecting the seeded pluripotent stem cells, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the BMP activator of the method is BMP4. In some embodiments, the Wnt pathway activator is a GSK3 inhibitor. In some embodiments, the ROCK inhibitor is Y27632 or thiazovivin.

In one embodiment of the method of generating pluripotent stem cell-derived multipotent progenitors (iMPP) from pluripotent stem cell-derived mesoderm, the method comprises (1) obtaining definitive hemogenic endothelium potential in pluripotent stem cell-derived mesodermal cells by contacting the mesodermal cells with a medium comprising a BMP activator, a Wnt pathway activator and bFGF; (2) differentiating and expanding definitive HE cells from the mesodermal cells with definitive hemogenic endothelium potential by contacting the cells with a medium comprising a ROCK inhibitor, and one or more of the growth factors and cytokines selected from the group consisting of VEGF, bFGF, SCF, IL6, and IL11; (3) differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, and IL11. In other embodiments, the method comprising differentiating the definitive HE cells to pre-HSC, further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting the mesoderm, and/or mesodermal cells with definitive hemogenic endothelium potential under a low oxygen tension between about 2% and about 10%.

In one embodiment of the method of generating pluripotent stem cell-derived multipotent progenitors (iMPP) from pluripotent stem cell-derived mesodermal cells with definitive hemogenic endothelium potential, the method comprises (1) differentiating and expanding definitive HE cells from the pluripotent stem cell-derived mesodermal cells with definitive hemogenic endothelium potential by contacting the cells with a medium comprising one or more of the growth factors and cytokines selected from the group consisting of VEGF, bFGF, SCF, IL6, and IL11, and a ROCK inhibitor; and (2) differentiating the definitive HE cells to iMPP by contacting the HE cells with a medium comprising a BMP activator, and one or more of the growth factors and cytokines selected from the group consisting of TPO, IL3, GMCSF, EPO, bFGF, VEGF, SCF, IL6, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, and IL11. In other embodiments, the method comprising differentiating the definitive HE cells to pre-HSC further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting mesodermal cells with definitive hemogenic endothelium potential under a low oxygen tension between about 2% and about 10%.

In one embodiment of the method of generating pluripotent stem cell-derived multipotent progenitors (iMPP) from pluripotent stem cell-derived definitive HE cells, the method comprises differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, and IL11. In other embodiments, the method comprising differentiating the definitive HE cells to pre-HSC further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting mesodermal cells with definitive hemogenic endothelium potential under a low oxygen tension between about 2% and about 10%.

5. Deriving Pluripotent Stem Cell-Derived T Cell Progenitors (Ipro-T) or T Cells—iCD34 Platform and iT Platform One aspect of the invention provides a method of using an optimized multistage process to generate pluripotent stem cell-derived T cell progenitors (ipro-T) or pluripotent stem cell-derived T cells. Generally, the method begins with pluripotent stem cells, from which mesodermal cells are differentiated and expanded. In some embodiments, the pluripotent stem cells are iPSCs. In some embodiments, the iPSCs are naïve iPSCs. The mesoderm is then differentiated to a mesodermal cell with definitive hemogenic endothelium potential. The mesodermal cells with definitive hemogenic endothelium potential are subsequently differentiated to definitive hemogenic endothelium, which are at the same time expanded in the medium. The definitive HE cells are then differentiated to pre-proT, and then to T cell progenitors (pro-T), which can be continuously differentiated into T cells in the same medium. Alternatively, the invention provides a method of generating pluripotent stem cell-derived T cell progenitors (ipro-T) or T cells that comprises differentiating seeded pluripotent stem cells to mesoderm, differentiating mesoderm to mesodermal cells with definitive hemogenic endothelium potential, then the mesodermal cells with definitive hemogenic endothelium potential are differentiated to iHE, which are then differentiated into T cell progenitors or T cells. The invention further provides a method of generating pluripotent stem cell-derived T cell progenitors (ipro-T) or T cells that comprises differentiating pluripotent stem cell-derived mesoderm to mesodermal cells with definitive hemogenic endothelium potential, which then are differentiated to iHE, which are then differentiated into ipro-T or T cells. Alternatively, the invention provides a method of generating pluripotent stem cell-derived T cell progenitors or T cells, which comprises differentiating pluripotent stem cell-derived mesodermal cells with definitive hemogenic endothelium potential to iHE, which are then differentiated into ipro-T or T cells. Further, the invention provides a method of generating pluripotent stem cell-derived T cell progenitors (ipro-T) or T cells that comprises differentiating pluripotent stem cell-derived THE into ipro-T or T cells. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors. In some embodiments, the Notch factors including, but not limited to, Jag1, Jag2, DLL-1, DLL-3 and DLL-4 can be introduced as soluble peptide, peptide conjugated to beads, peptide conjugated to the surface, or peptide presented by cells.

In one embodiment of the method of generating pluripotent stem cell-derived T cell progenitors (ipro-T) or T cells (iT) from pluripotent stem cell, the method comprises (1) differentiating the seeded pluripotent stem cells to mesoderm by contacting the cells with a medium comprising a BMP activator, and optionally bFGF; (2) differentiating the mesoderm to mesodermal cells with definitive hemogenic endothelium potential by contacting the cells with a medium comprising a BMP activator, a Wnt pathway activator and bFGF; (3) differentiating the mesodermal cells with definitive hemogenic endothelium potential to definitive HE cells by contacting the cells with a medium comprising a ROCK inhibitor, and one or more of the growth factors and cytokines selected from the group consisting of VEGF, bFGF, SCF, IL6, and IL11, and (4) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the above method further comprises seeding and expanding pluripotent stem cells by contacting the cells with a medium comprising a MEKi, a GSKi, and a ROCKi. In some embodiments, the pluripotent stem cells are iPSCs. In some embodiments, the iPSCs are naïve iPSCs. In some embodiments, the method above further comprises differentiating the definitive HE cells to pre-proT by contacting the HE cells with a medium comprising a BMP activator, a ROCK inhibitor, and one or more of the growth factors and cytokines selected from the group consisting of SCF, Flt3L, IL7, VEGF, and bFGF. In other embodiments, the method comprising differentiating the definitive HE cells to pre-proT, further comprises differentiating the pre-proT to ipro-T or iT by contacting the pre-proT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiment, the above method comprising pluripotent stem cell-derived pro-T with one or more Notch factors. In some embodiments, the Notch factor is Jag1, Jag2, DLL-1, DLL-3, or DLL-4. In some embodiments, DLL-1 and -4 can be introduced as soluble peptide, peptide conjugated to beads, peptide conjugated to the surface, or peptide presented by cells. In some embodiments, the method above further comprises subjecting the seeded pluripotent stem cell, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, and/or CXCR4. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells from pluripotent stem cell-derived mesoderm, the method comprises (1) differentiating the mesoderm to mesodermal cells with definitive hemogenic endothelium potential by contacting the cells with a medium comprising a BMP activator, a Wnt pathway activator and bFGF; (2) differentiating the mesodermal cells with definitive hemogenic endothelium potential to definitive HE cells by contacting the cells with a medium comprising a ROCK inhibitor, one or more of the growth factors and cytokines selected from the group consisting of VEGF, bFGF, SCF, IL6, and IL11; and (3) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-proT by contacting the HE cells with a medium comprising a BMP activator, a ROCK inhibitor one or more of the growth factors and cytokines selected from the group consisting of SCF, Flt3L, IL7, VEGF, and bFGF. In other embodiments, the method comprising differentiating the definitive HE cells to pre-pro-T, further comprises differentiating the pre-proT to ipro-T or iT by contacting the pre-proT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiment, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, and/or CXCR4. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells (iT) from pluripotent stem cell-derived mesodermal cells with definitive hemogenic endothelium potential, the method comprises (1) differentiating the mesodermal cells with definitive hemogenic endothelium potential to definitive HE cells by contacting the cells with a medium comprising a ROCK inhibitor, and one or more of the growth factors and cytokines selected from the group consisting of VEGF, bFGF, SCF, IL6, and IL11; and (2) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-proT by contacting the HE cells with a medium comprising a BMP activator, a ROCK inhibitor, and one or more of the growth factors and cytokines selected from the group consisting of SCF, Flt3L, IL7, VEGF, and bFGF. In other embodiments, the method comprising differentiating the definitive HE cells to pre-pro-T further comprises differentiating the pre-iproT to pro-T or iT by contacting the pre-proT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiment, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, and/or CXCR4. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells (iT) from pluripotent stem cell-derived HE cells, the method comprises differentiating the definitive HE cells to ipro-T or T by contacting the definitive HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-proT by contacting the HE cells with a medium comprising a BMP activator, a ROCK inhibitor, and one or more of the growth factors and cytokines selected from the group consisting of SCF, Flt3L, IL7, VEGF, and bFGF. In other embodiments, the method comprising differentiating the definitive HE cells to pre-pro-T further comprises differentiating the pre-iproT to pro-T or iT by contacting the pre-proT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiment, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the pluripotent stem cell-derived HE cells under a low oxygen tension between about 2% and about 10%. In some embodiments, the THE cells obtained from the above method express CD34. In some embodiments, the above method further comprises sorting the obtained THE cells using CD34, CD43, CD73, and/or CXCR4. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

6. Obtaining Pluripotent Stem Cell-Derived NK Cell Progenitors (Ipro-NK) or NK Cells—iCD34 Platform and iNK Platform One aspect of the invention provides a method of using an optimized multistage process to generate pluripotent stem cell-derived NK cell progenitors (ipro-NK) or NK cells (iNK). Generally, the method begins with pluripotent stem cells, which in some embodiments are seeded. The pluripotent stem cells are developed into mesoderm cells which are expanded and subsequently differentiated to mesodermal cells with definitive hemogenic endothelium potential. Definitive hemogenic endothelium are then differentiated and expanded from the mesodermal cells with definitive hemogenic endothelium potential. The HE cells are capable of being differentiated to pre-proNK, and then to NK cell progenitors (pro-NK), which can be continuously differentiate into NK cells in the same medium. Alternatively, the invention provides a method of generating pluripotent stem cell-derived NK cell progenitors (ipro-NK) or NK cells that comprises differentiating seeded pluripotent stem cells to mesoderm, differentiating mesoderm to mesodermal cells with definitive hemogenic endothelium potential, then the mesodermal cells with definitive hemogenic endothelium potential are differentiated to iHE, which are then differentiated into NK cell progenitors. The invention further provides a method of generating pluripotent stem cell-derived NK cell progenitors (ipro-NK) or NK cells that comprises differentiating pluripotent stem cell-derived mesoderm to mesodermal cells with definitive hemogenic endothelium potential, then the mesodermal cells with definitive hemogenic endothelium potential are differentiated to iHE, which are then differentiated into ipro-NK or iNK. Alternatively, the invention provides a method of generating pluripotent stem cell-derived NK cell progenitors or iNK comprises differentiating pluripotent stem cell-derived mesodermal cells with definitive hemogenic endothelium potential to iHE, which are then differentiated into ipro-NK or iNK. Further, the invention provides a method of generating pluripotent stem cell-derived NK cell progenitors (ipro-NK) or NK cells comprises differentiating pluripotent stem cell-derived THE into ipro-NK or iNK. In some embodiments, the pluripotent stem cells are iPSCs. In some embodiments, the iPSCs are naïve iPSCs. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. The methods disclosed herein utilize the optimized iCD34 culture platform, which is free, or essentially free, of TGFβ receptor/ALK inhibitors.

In one embodiment of the method of generating pluripotent stem cell-derived NK cell progenitors (ipro-NK) or NK cells (iNK) from seeded iPSC, the method comprises (1) differentiating and expanding mesodermal cells from pluripotent stem cells by contacting the cells with a medium comprising a BMP activator, and optionally bFGF; (2) obtaining definitive hemogenic endothelium potential in the mesodermal cells by contacting the mesodermal cells with a medium comprising a BMP activator, a Wnt pathway activator and bFGF; (3) differentiating and expanding definitive HE cells from the mesodermal cells with definitive hemogenic endothelium potential by contacting the cells with a medium comprising a ROCK inhibitor, and one or more of the growth factors and cytokines selected from the group consisting of VEGF, bFGF, SCF, IL6, and IL11; and (4) differentiating the definitive HE cells to ipro-NK or iNK by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, IL3, IL7, IL15, VEGF, and bFGF. In other embodiments, the method comprising differentiating the definitive HE cells to pre-proNK, further comprises differentiating the pre-proNK to pro-iNK or iNK by contacting the pre-proNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In one embodiment, the above method further comprises seeding and expanding naïve pluripotent cells by contacting the pluripotent cells with a medium comprising a MEKi, a GSKi, and a ROCKi. In some embodiments, the method above further comprises subjecting the seeded iPSC, mesoderm, and/or mesodermal cells with definitive hemogenic endothelium potential under a low oxygen tension between about 2% and about 10%. In some embodiments, the THE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived mesoderm, the method comprises (1) differentiating the mesoderm by contacting the mesoderm with a medium comprising a BMP activator, a Wnt pathway activator and bFGF to obtain mesodermal cells having definitive hemogenic endothelium potential; (2) differentiating the mesodermal cells with definitive hemogenic endothelium potential by contacting the cells with a medium comprising a ROCK inhibitor, and one or more of the growth factors and cytokines selected from the group consisting of VEGF, bFGF, SCF, IL6, and IL11, to obtain definitive HE cells; and (3) differentiating the definitive HE cells by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor to obtain ipro-NK or iNK. In some embodiments, the pluripotent stem cells are iPSCs. In some embodiments, the iPSCs are naïve iPSCs. In some embodiments, the method above further comprises differentiating the definitive HE cells to pre-proNK by contacting the HE cells with a medium comprising a BMP activator, a ROCK inhibitor, and one or more of the growth factors and cytokines selected from the group consisting of SCF, Flt3L, IL3, IL7, IL15, VEGF, and bFGF. In other embodiments, the method comprising differentiating the definitive HE cells to pre-proNK, further comprises differentiating the pre-proNK to ipro-NK or iNK by contacting the pre-proNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived mesodermal cells with definitive hemogenic endothelium potential, the method comprises: (1) differentiating and expanding definitive HE cells by contacting the mesodermal cells with definitive hemogenic endothelium potential with a medium comprising a ROCK inhibitor, and one or more of the growth factors and cytokines selected from the group consisting of VEGF, bFGF, SCF, IL6, and IL11; and (2) differentiating the definitive HE cells to ipro-NK or iNK by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, IL3, IL7, IL15, VEGF, and bFGF. In other embodiments, the method comprising differentiating the definitive HE cells to pre-pro-NK, further comprises differentiating the pre-proNK to ipro-NK or iNK by contacting the pre-proNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the seeded pluripotent stem cells, mesoderm, and/or mesodermal cells with definitive hemogenic endothelium potential under a low oxygen tension between about 2% and about 10%. In some embodiments, the THE cells obtained from the above method express CD34. In some embodiments, the above method further comprises sorting the obtained iHE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived HE cells, the method comprises differentiating the definitive HE cells to ipro-NK or iNK by contacting the definitve HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, IL3, IL7, IL15, VEGF, and bFGF. In other embodiments, the method comprising differentiating the definitive HE cells to pre-ipro-NK, further comprises differentiating the pre-proNK to ipro-NK or iNK by contacting the pre-pro-NK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting ipro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the seeded pluripotent stem cell, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained THE cells using CD34, CD43, CD73, and/or CXCR4. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In light of the above, one of the advantages offered by the culture platforms contemplated herein is the enhanced viability and survival of culturing, passaging, and dissociating single pluripotent cells without EB formation for pluripotent stem cell differentiation. In some embodiments, the pluripotent stem cells are iPSCs. In some embodiments, the iPSCs are naïve iPSCs. Disassociation of cells into single cells, such as into a single cell suspension, can be accomplished by enzymatic or mechanical means. Any enzymatic agent known in the art to allow dissociation of cells into single cells may be used in the methods of the invention. In one embodiment, the dissociation agent is selected from Trypsin/EDTA, TrypLE-Select, Collagenase IV and Dispase. A chelator, such as EDTA, Accutase, or AccuMax, may also be used, alone or in combination with an enzymatic agent, in dissociating cells in accordance with the methods contemplated herein. The dissociation agent may be dissolved in calcium and magnesium free PBS to facilitate dissociation to single cells. To enhance the survival of the cells during and after dissociation, in some embodiments, a survival promoting substance is added, for example, one or more growth factors, inhibitors of cellular pathways involved in cell death and apoptosis, or conditioned media. In one embodiment, the survival promoting substance is a ROCK inhibitor, including but not limited to thiazovivin.

Techniques in cell culture and media collection are outlined in Hu et al., Curr. Opin. Biotechnol. 8:148, 1997; K. Kitano, Biotechnology 17:73, 1991; Curr. Opin. Biotechnol. 2:375, 1991; Birch et al., Bioprocess Technol. 19:251, 1991; "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cell Differentiation in vitro" (M. V. Wiles, Meth. Enzymol. 225:900, 1993); "Properties and uses of Embryonic Stem Cells: Prospects for Application to Human Biology and Gene Therapy" (P. D. Rathjen et al., al., 1993). Differentiation of stem cells is reviewed in Robertson, Meth. Cell Biol. 75:173, 1997; and Pedersen, Reprod. Fertil. Dev. 10:31, 1998.

In the present invention, strategies for enriching a population of cells with specific characterizations are provided at various stages of the methods. In one embodiment, the method of enriching pluripotent stem cells from a cell population comprises making a single cell suspension by dissociating the cells in the population and resuspending the cells. The dissociated cells may be resuspended in any suitable solution or media for maintaining cells or performing cell sorting. In particular embodiments, the pluripotent single cell suspension contains a GSK3 inhibitor, a MEK inhibitor, and a Rock inhibitor and lacks a TFGβ inhibitor. In certain embodiments, the GSK3 inhibitor is CHIR99021, the MEK inhibitor is PD0325901, and/or the Rock inhibitor is thiazovivin.

In a particular embodiment, a population of cells is sorted to positively select pluripotent cells, and/or the population is depleted of non-reprogrammed or non-pluripotent cells, thereby obtaining a population of cells enriched for pluripotent cells. In one embodiment, a single cell suspension is prepared, and then the single cells are prepared for sorting, such as by staining for markers of pluripotency using, e.g., appropriate antibodies. Cells may be sorted by any suitable method of sorting cells, such as by magnetic bead or flow cytometry (FACS) sorting.

Cells may be sorted based on one or more markers of pluripotency, or markers indicating cell differentiation, including without limitation, expression of SSEA3/4, TRA1-60/81, TRA1-85, TRA2-54, GCTM-2, TG343, TG30, CD9, CD29, CD133/prominin, CD140a, CD56, CD73, CD105, OCT4, NANOG, SOX2, KLF4, SSEA1 (Mouse), CD30, SSEA5, CD90 and/or CD50. In various embodiments, cells are sorted based on at least two, at least three, or at least four markers of pluripotency or differentiation. In certain embodiments, cells are sorted based on expression of SSEA4, and in certain particular embodiments based on expression of SSEA4 in combination with TRA1-81 and/or TRA1-60. In certain embodiments, cells are sorted based on SSEA4, TRA1-81, or TRA1-60, and/or CD30 expression. In one embodiment, cells are sorted based on SSEA4, TRA1-81 and CD30. In another embodiment, cells are sorted based on SSEA4, TRA1-60 and CD30. In certain embodiments, cells sorting using one or more surface markers of differentiation includes, but not limited to, CD13, CD26, CD34, CD45, CD31, CD46 and CD7, and pluripotent markers such as SSEA4, TRA1-81 and/or CD30.

In some embodiments, a population of cells undergoing reprogramming or a population of pluripotent cells is depleted of differentiated cells. In one embodiment, a population of pluripotent cells or cells induced to reprogram can be depleted of cells having one or more cells surface markers of differentiated cells. Illustrative examples of cell surface markers of differentiating cells include but are not limited to, CD13, CD26, CD34, CD45, CD31, CD46, and CD7. In particular embodiments, CD13 is used as a surface marker of differentiating cells.

In other embodiments, a population of cells is induced to differentiate into a desired lineage and is depleted of pluripotent cells to obtain an enriched population of differentiating or differentiated cells. In some embodiments, the population of differentiated cells comprises a population of cells, such as ESCs or iPSCs that has been induced to differentiate into a specific lineage. In some embodiment, a population of cells may be depleted of pluripotent cells using the negative cell sorting techniques described above ("panning"), such as sorting cells in the population according to magnetic beads or FACs based on markers of pluripotency. In some embodiments, a population of cells comprising differentiated cells is sorted by FACs using pluripotency markers, and a fraction is obtained that is depleted of cells expressing pluripotency markers. In other embodiments, a population of cells is sorted by FACs based on markers of differentiation, such as lineage-specific markers including, but not limited to, CD13, CD26, CD34, CD45, CD31, CD46, and CD7, to obtain a fraction depleted of markers of pluripotency. In some particular embodiments of the invention, CD13 is used as a surface marker of differentiating cells.

D. Cell Populations and Cell Lines Generated from the Methods and Platforms Provided Herein In some embodiments, the cells cultured after reprogramming are induced to differentiate for at least 1, 2, 3, 4, 5, 6, 7, 8, 9, 10, 11, 12, 15, 18, 20, 22, 24, 26, 28, 30, 32, 35, 40, 42, or 45 days, or any number of days in between. In some embodiment, the cells cultured after reprogramming are induced for about 1 to 42 days, 2 to 40 days, 2 to 35 days, 2 to 20 days, 2 to 10 days, 4 to 30 days, about 4 to 24 days, about 6 to 22 days, or about 8 to about 12 days. In some embodiments, the cells are pluripotent stem cells including iPSCs. In some embodiments, the iPSCs are naïve iPSCs. In one embodiment, enrichment provides a method for obtaining clonal pluripotent stem cell-derived differentiating cell colonies in a relatively short time, thereby improving the efficiency of generating pluripotent stem cell-derived differentiated cells at various stages. In one embodiment, enrichment provides a method for deriving CD34 expressing HE cells, CD34 expressing HSC cells, T or NK cell progenitors and T or NK cells, thereby improving the efficiency of generating each of the cell populations. Enrichment may comprise sorting a population of cells, to identify and obtain cells expressing specific characteristic marker(s) indicative of differentiation stage/cell types. In some embodiments, the sorting uses CD34, CD43, CD73, and/or CXCR4. In some embodiments, the sorting uses CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. An additional enrichment methodology comprises the depletion of cells expressing markers representing undesired cell types to obtain an enriched population of desired cell types.

As such, one aspect of the invention provides a composition comprising one or more cell populations, cell lines, or clonal cells of (i) pluripotent stem cell-derived CD34+ HE cells (iCD34), wherein the iCD34 cells have capacity to differentiate into multipotent progenitor cells, and wherein the iCD34 cells are CD34+CD43−; (ii) pluripotent stem cell-derived definitive hemogenic endothelium (iHE), wherein the iHE cell line or clonal cells are CD34+; (iii) pluripotent stem cell-derived definitive HSCs (iHSC), wherein the iHSC is CD34+CD45+, and is suitable for long-term engraftment; (iv) pluripotent stem cell-derived multipotent progenitor cells (iMPP), wherein the iMPP cells are CD34+CD45+; (v) pluripotent stem cell-derived T cell progenitors (iproT), wherein the T cell progenitors are CD34+CD7+; (vi) pluripotent stem cell-derived T cells (iTC), wherein the T cells are CD4+ or CD8+; (vii) pluripotent stem cell-derived NK cell progenitors (iproNK), wherein the NK cell progenitors are CD56+CD3−; and (viii) pluripotent stem cell-derived NK cells (iNK), wherein the NK cells are CD56+CD57+CD16+. In some embodiments, the above compositions, cell populations, cell lines or clonal cells are amenable to cryopreservation. In some embodiments, the compositions, cell populations, cell lines or clonal cells are amenable to ambient storage conditions for more than 12 hrs, 24 hrs, 36 hrs, 48 hrs, but not longer than 3 days, 4 days, 5 days, 6 days, or a week.

Another aspect of the invention provides a mixture comprising one or more of pluripotent stem cell derived (i) CD34+ HE cells (iCD34), and one or more culture medium selected from iMPP-A, iTC-A1, iTC-A2, iTC-B1, iTC-B2, iNK-A1, iNK-A2, iNK-B1 and iNK-B2; (ii) definitive hemogenic endothelium and one or more culture medium selected from iMPP-A, iTC-A1, iTC-A2, iTC-B1, iTC-B2, iNK-A1, iNK-A2, iNK-B1 and iNK-B2; (iii) definitive HSCs, and one or more culture medium selected from iMPP-A, iTC-A1, iTC-A2, iTC-B1, iTC-B2, iNK-A1, iNK-A2, iNK-B1 and iNK-B2; (iv) multipotent progenitor cells (iMPP), and iMPP-A; (v) T cell progenitors (iproT), and one or more culture medium selected from iTC-A1, iTC-A2, iTC-B1, and iTC-B2; (vi) T cells (iTC), and iTC-B1 or iTC-B2; (vii) NK cell progenitors (iproNK), and one or more culture medium selected from iNK-A1, iNK-A2, iNK-B1, and iNK-B2; and/or (viii) NK cells (iNK), and iNK-B1 or iNK-B2; (ix) HSC (iHSC), and iHSC-A, iHSC-B, and iHSC-C; wherein a. iHSC-A comprises a Wnt pathway activator, and a BMP activator;
b. iHSC-B comprises a Wnt pathway activator, a BMP activator, and optionally, a TGFβ receptor/ALK inhibitor;
c. iHSC-C comprises a BMP activator, and one or more growth factors and cytokines selected from the group consisting of VEGF, SCF, Flt3L, IL15, IL3, IL6, IGF, and TPO. In some embodiments, the composition is free of Wnt pathway activators and TGFβ receptor/ALK inhibitors;
d. iTC-A1 comprises a BMP activator, one or more growth factors and cytokines selected from the group consisting of SCF, Flt3L, IL7, IL2, IL3, and IL6, and one or more Notch pathway activators selected from the group consisting of Jag1, Jag2, DLL-1, DLL-3 and DLL-4; in some embodiments, the composition is free of VEGF and/or IL15;
e. iTC-B1 comprises one or more growth factors and cytokines selected from the group consisting of SCF, Flt3L, IL7, IGF, IL2, IL3, and IL6, and one or more Notch pathway activators selected from the group consisting of Jag1, Jag2, DLL-1, DLL-3 and DLL-4; (iHSC platform); in some embodiments, the composition is free of BMP activator;
f. iNK-A1 comprises a BMP activator, one or more growth factors and cytokines selected from the group consisting of SCF, Flt3L, VEGF, IL2, IL3, IL6, and IL15;
g. iNK-B1 comprises one or more growth factors and cytokines selected from the group consisting of SCF, Flt3L, IGF, IL7, IL2, IL3, IL6, and IL15;
h. iCD34-C comprises a ROCK inhibitor, and one or more growth factors and cytokines selected from the group consisting of bFGF, VEGF, SCF, IL6, and IL11; and is free of TGFβ receptor/ALK inhibitor;
i. iMPP-A comprises a BMP activator, a ROCK inhibitor, and one or more growth factors and cytokines selected from the group consisting of TPO, IL3, GMCSF, EPO, bFGF, VEGF, SCF, IL6 and IL11;
j. iTC-A2 comprises a BMP activator, a ROCK inhibitor, VEGF, and bFGF; and one or more growth factors and cytokines selected from the group consisting of SCF, Flt3L, and IL7;
k. iTC-B2 comprises one or more growth factors and cytokines selected from the group consisting of SCF, Flt3L, and IL7; wherein the composition is free of on eor more of VEGF, bFGF, BMP activators, and ROCK inhibitors;
l. iNK-A2 comprises a BMP activator, a ROCK inhibitor, VEGF, and bFGF, and one or more growth factors and cytokines selected from the group consisting of SCF, Flt3L, IL7, IL15; and
m. iNK-B2 comprises one or more growth factors and cytokines selected from the group consisting of SCF, Flt3L, IL7 and IL15.

EXAMPLES

The following examples are offered by way of illustration and not by way of limitation.

Example 1—hiPSC Generation and Maintenance

Somatic cells including fibroblast and blood cells were induced to reprogram towards a pluripotent state using various factor combinations including OCT4/SOX2/LargeT, OCT4/SOX2 or OCT4/SOX2/NANOG/LargeT in the presence of reprogramming medium containing ROCK, MEK, GSK3 pathway and TGFβ receptor inhibitors (Valamehr et al. Sci Rep. 2012; 2: 213). Fourteen days after induction, reprogramming populations were switched to maintenance medium containing ROCK, GSK3, and MEK pathway inhibitors, basic fibroblast growth factor (bFGF), and leukemia inhibitory factor (LIF) (Valamehr et al. Stem Cell Reports 2014, 2(3): 366-381). Cells were kept indefinitely in the maintenance medium.

Approximately three weeks after induction, the reprogramming populations were sorted into individual wells of a 96-well plate. Selected clones were characterized and fully reprogrammed clones representative of naïve hiPSCs were selected for differentiation studies (Valamehr et al. Stem Cell Reports 2014, 2(3): 366-381). To determine the percent undifferentiated cells during maintenance and post differentiation, flow cytometry analysis was conducted for co-surface expression of SSEA4, TRA181 and CD30.

Example 2—Hematopoietic Differentiation Using iHSC Culture Platform

To initiate differentiation towards hematopoietic cell lineage, naïve hiPSCs were seeded as a monolayer in the maintenance medium and allowed to expand until approximately 25% confluency was reached. At this point, hematopoietic differentiation was initiated by switching the culture medium to iHSC-A (see FIG. 1). As illustrated in FIG. 1, the culture was subsequently switched to iHSC-B, 48 hrs post the initiation of differentiation, followed by a switch to iHSC-C on day 4-5 post initiation of differentiation. The attached culture was maintained adherent and not perturbed during the medium changes.

Figure 4B:
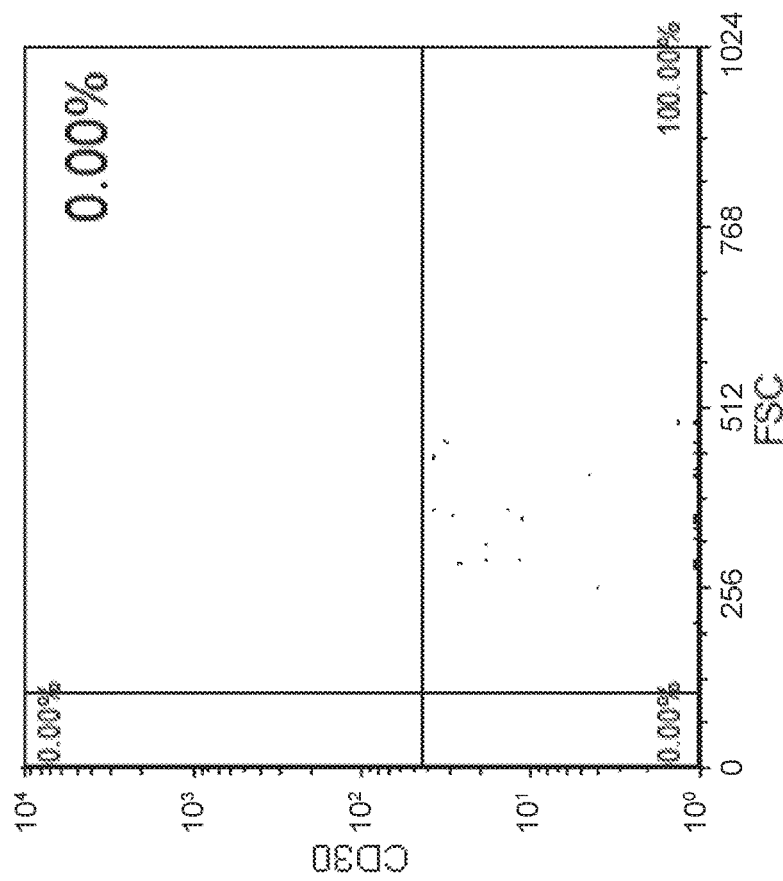
Figure 4A:
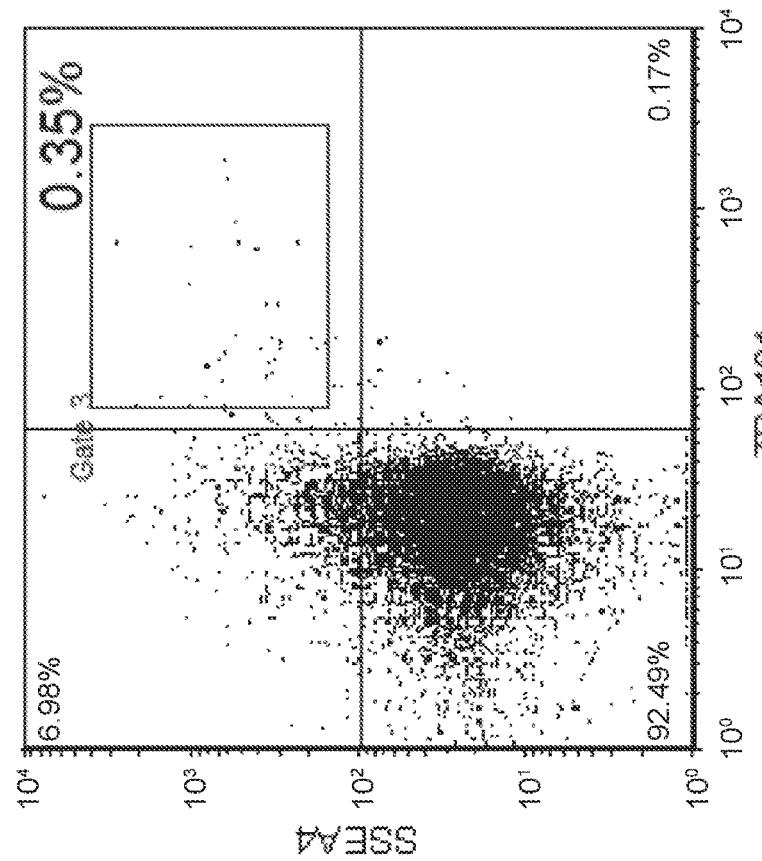
Figure 5A:
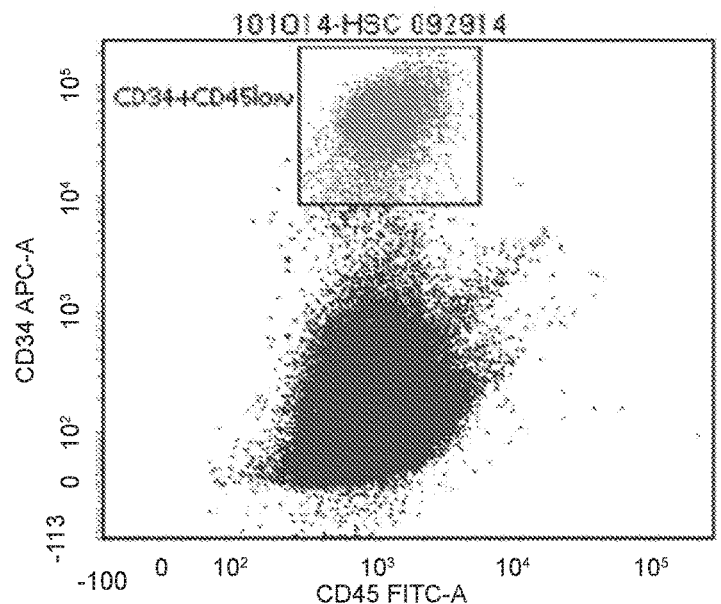
FIGS. 5A-5C show CD34/CD45 expression profile of hematopoietic cells differentiated from hiPSCs generated from various methods and starting input.
Figure 5B:
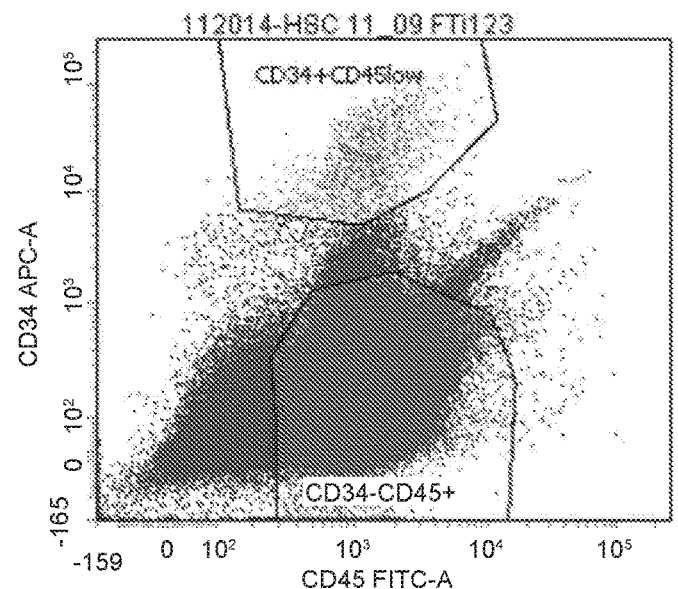
Figure 5C:
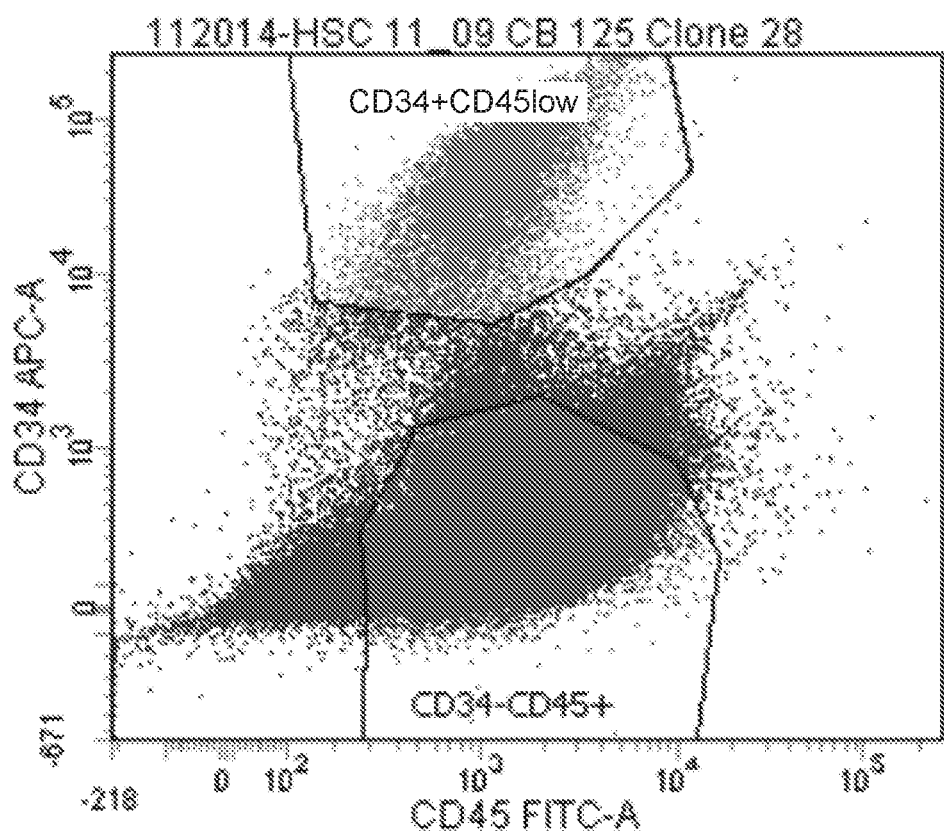

Early during the differentiation process, directed differentiation was monitored by lineage markers, CD57, NESTIN, SOX17 and BRACHYURY. FIG. 3 illustrates a directed differentiation shift towards the mesoderm lineage and away from ectoderm lineage. Through the subsequent differentiation stages, the hiPSC morphology was given to a differentiated population consisting of rounded cells, a morphology similar to clusters of hematopoietic cells (FIG. 4A), loss of hiPSC associated surface markers (FIG. 4B), and the appearance of surface markers such as Brachyury, CD34, CXCR4, and CD45 (FIGS. 4C and 4D). On day 9 (this time point can be extended, optimally by day 14), the cells were dissociated into single cells and analyzed for CD34 and CD45 surface expression (FIGS. 5A-5C). The single cell dissociation was most commonly aided by Accutase and filtered through a 40 μm mesh to collect the single cells. Using FACS Aria or MACS enrichment, CD34 positive or CD34 and CD45 positive cells were collected for further processing and testing.

Figure 6A:
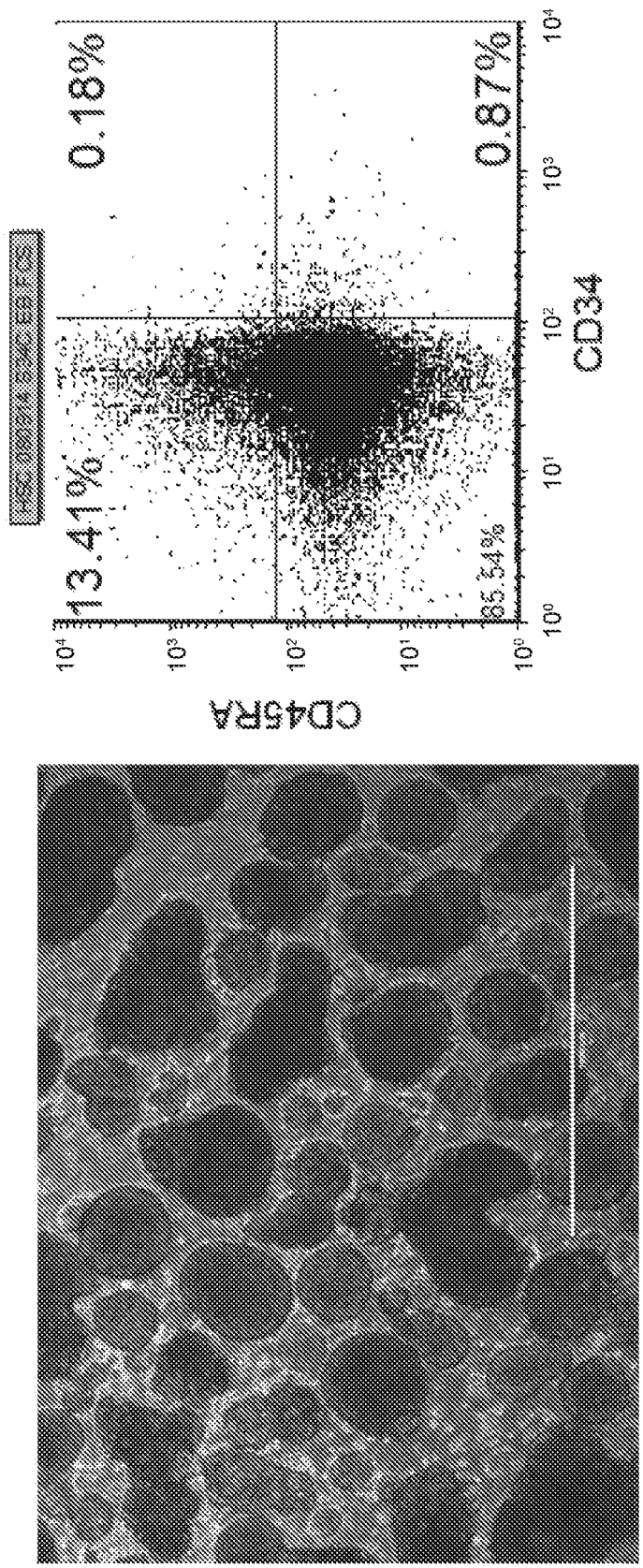
FIG. 6A-6C show improvement in CD34 differentiation efficiency when mediated as a monolayer in described differentiation culture media.
Figure 6B:
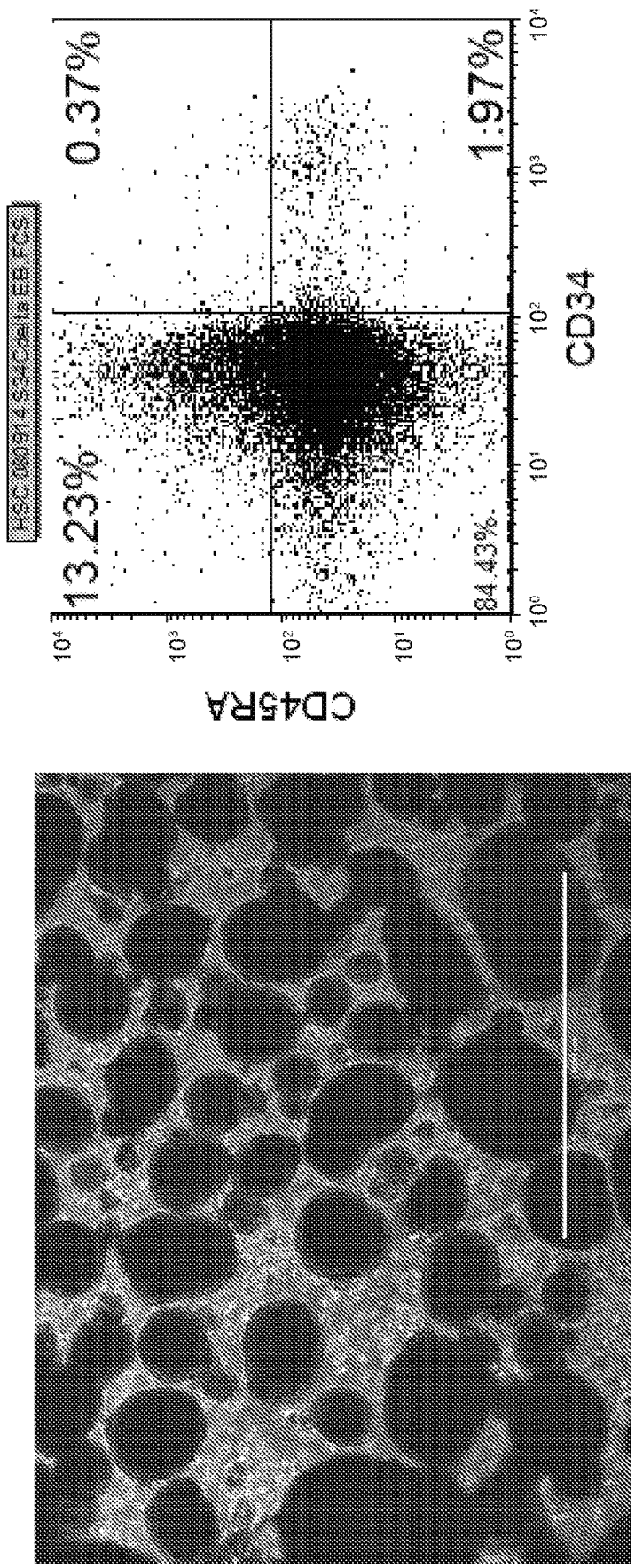
Figure 6C:
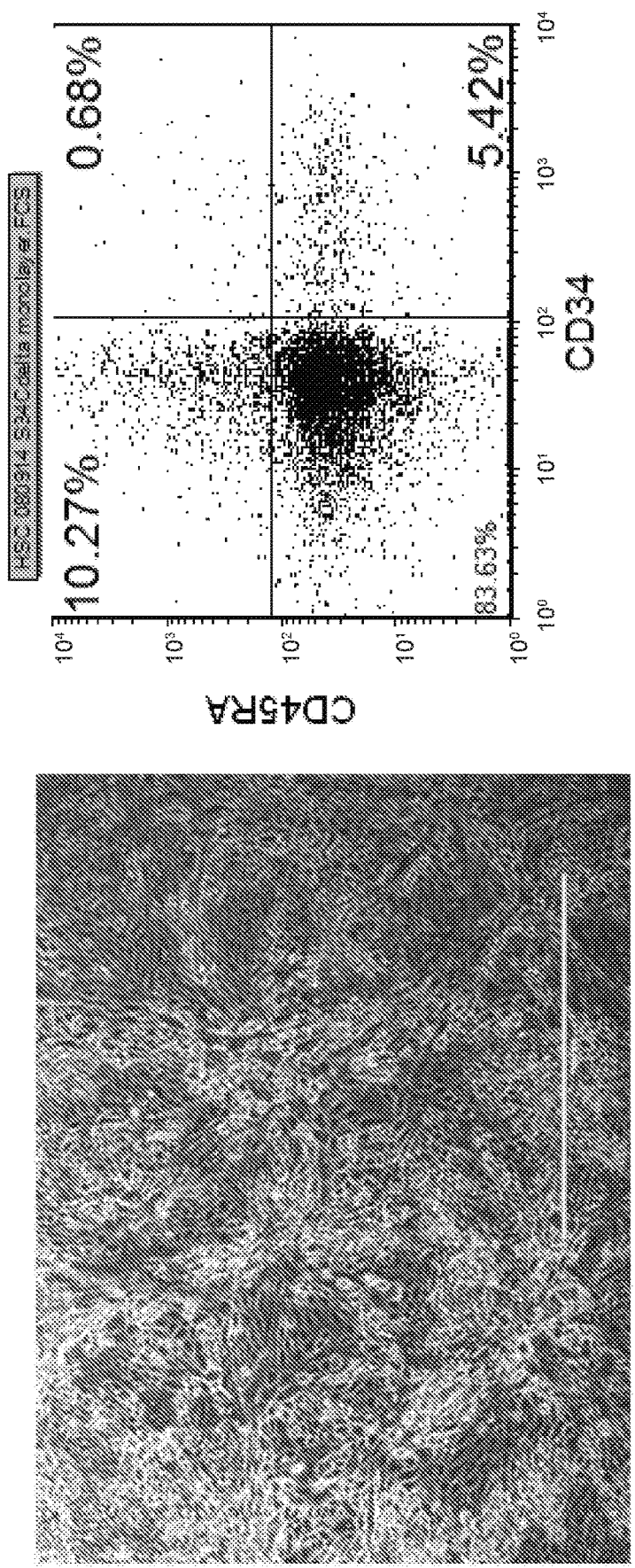
Figure 7:
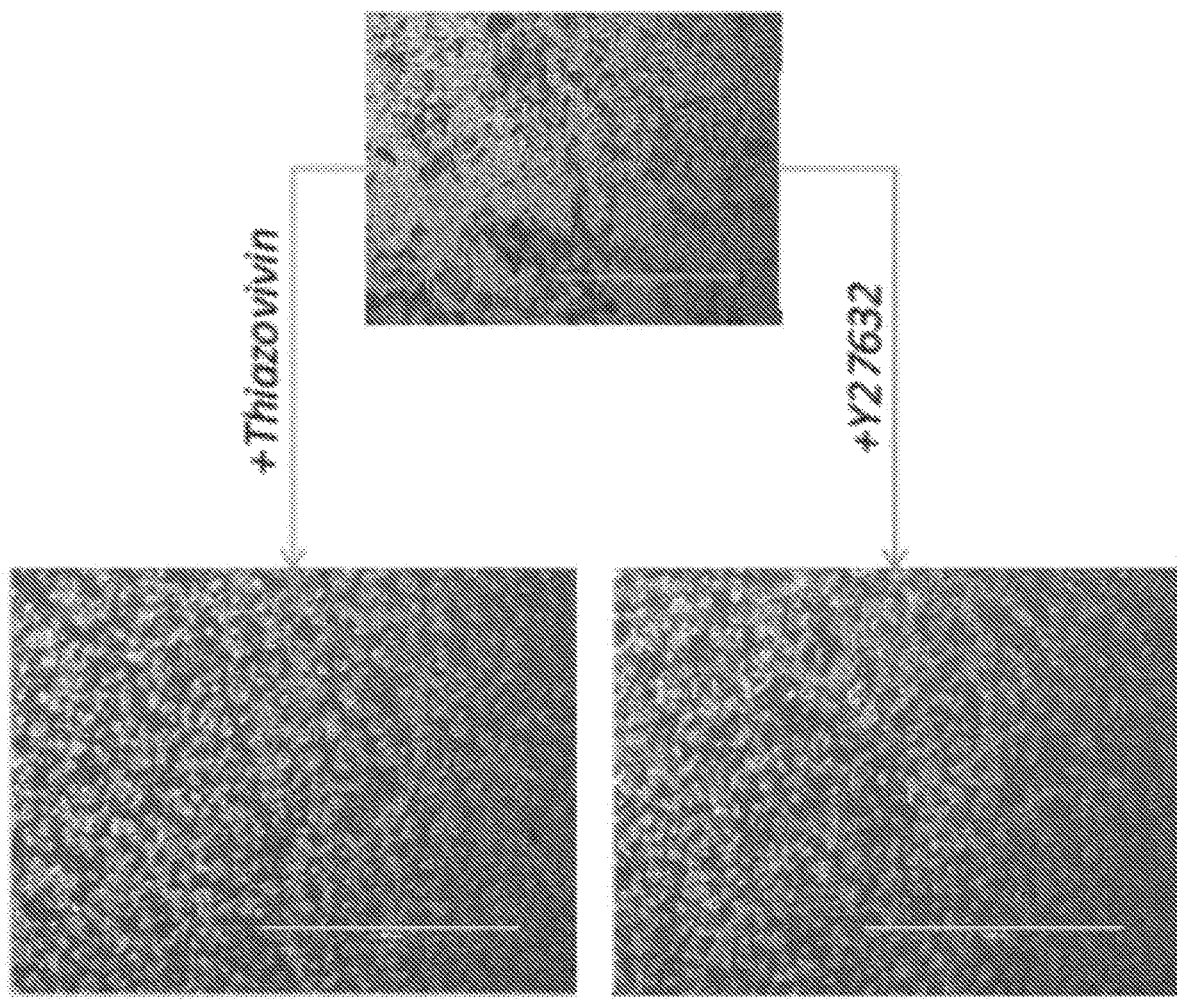
FIG. 7 shows survival and proliferation of hematopoietic differentiated cells under ROCK inhibition after single cell disassociation.
Figure 8:
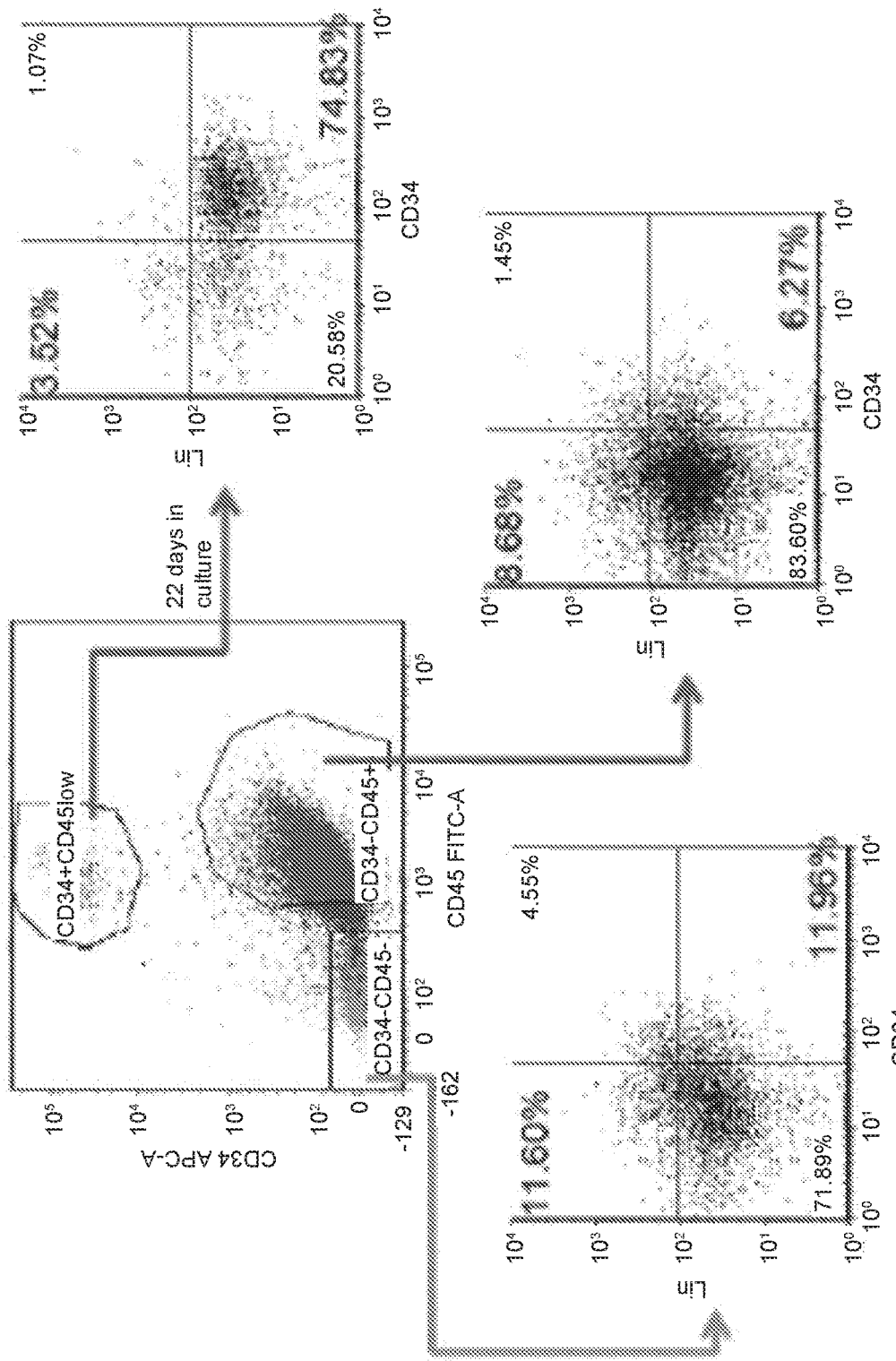
FIG. 8 shows maintenance of CD34 expression of hematopoietic cells differentiated from hiPSC after 22 days in culture.

Example 3—In Vitro Characterization and Testing Following Differentiation Using iHSC Culture Platform To determine the expandability and maintenance of the differentiated definitive hematopoietic stem cells, the CD34 sorted or enriched population was transferred into suspended culture supplemented with Stemspan hematopoietic stem cell culture medium (StemCell Technologies, Vancouver, Canada), 1× CC110 supplement (StemCell Technologies), 10 ng/mL bFGF and 5 μM Thiazovivin or 10 μM 27632 ROCK inhibitors (for the first few days in culture to improve survival). The culture was fed with fresh medium every other day and pipetted to break up the aggregates resulting from dividing CD34 positive sorted cells. After several weeks in culture, the scaled suspended culture was assessed and measured through surface marker expression and viable cell number. As demonstrated in FIG. 8, the CD34 sorted population was maintained for 22 days in culture with minimal loss of the CD34 population. To improve viability of suspension culture the small molecule inhibitor of the ROCK pathway was added. FIG. 7 illustrates survival and proliferation of cells post passage of single cell dissociation in the presence of ROCK inhibition. FIGS. 6A-6C illustrate improvements in the differentiation method described in FIG. 1 applied to both monolayer and EB culture, and a higher percent of CD34 cells were shown to present in monolayer format compared to EB meditated differentiation.

Figure 9A:
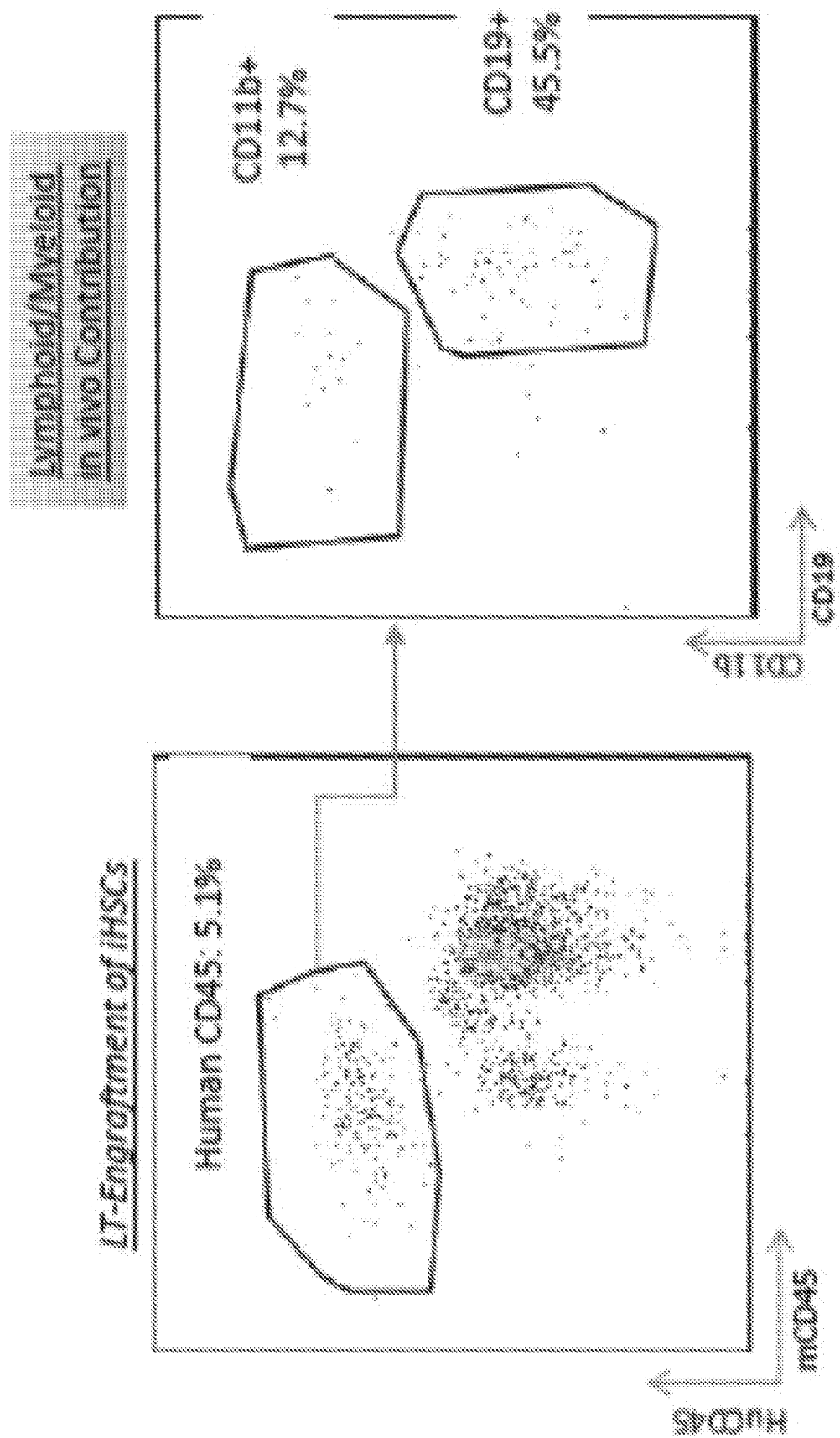
FIGS. 9A-9B show in vivo reconstitution of engrafted CD34 positive cells as seen with the presence of cells exclusively expressing human CD45 marker and reconstitution of CD34+ cells with the presence of both T and B cells. The CD34 positive cells are derived from naïve hiPSC cultured with GSK3 inhibitor and in monolayer format, without EB or aggregate intermediates.
Figure 9B:
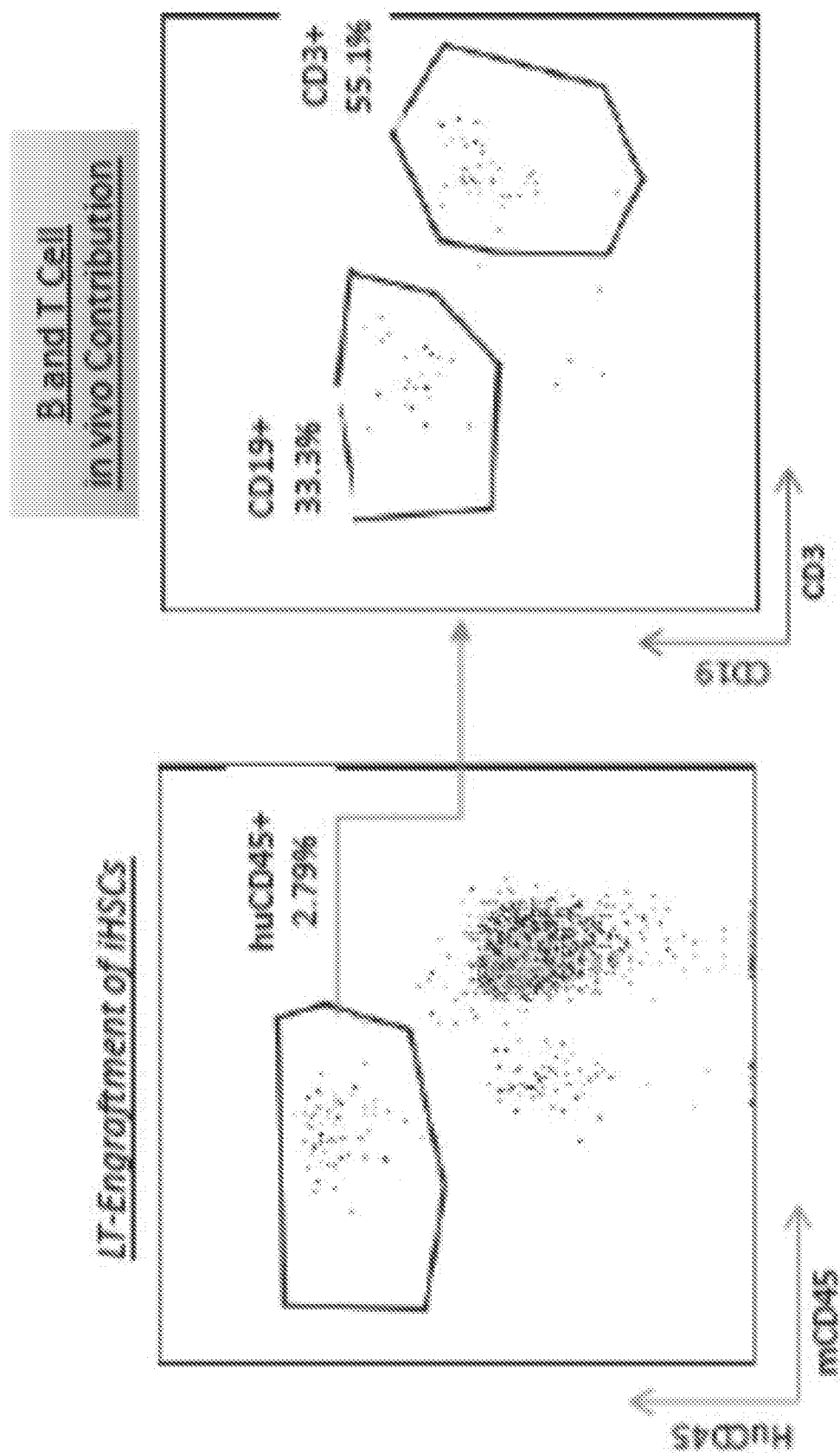

Example 4—In Vivo Reconstitution Following Differentiation Using iHSC Culture Platform To demonstrate in vivo functionality and engraftment potential of the derived definitive hematopoietic stem cells, CD34 positive cells derived from the hiPSC differentiated process described above were either sorted using FACS Aria or enriched using MACS beads. The collected cells were counted by trypan blue staining to determine viability. Approximately, 30,000 viable CD34 positive cells were resuspended in MSS and introduced into NSG mice via retro-orbital injection. The NSG mice were sub-lethally irradiated at 300 rad 24 hours prior to engraftment studies. In addition, unsorted differentiated populations (up to 250, 000) were also introduced into NSG mice as controls as well as human peripheral blood. Every two weeks, mice were bled and assessed for human blood contribution using human specific markers including CD45, CD11 b, CD19 and CD3. FIG. 9A demonstrates 12 week reconstitution of engrafted CD34 positive cells as seen with the presence of cells exclusively expressing human CD45 marker. The data also shows the multi-lineage capability of the engrafted cells to give rise to both myeloid and lymphoid population. FIG. 9B demonstrates 18 week reconstitution of CD34+ cells with the presence of both T and B cells.

Example 5—Small Molecule Modulation Following Differentiation Using iHSC Culture Platform To assess the ability of hiPSC-derived CD34 positive definitive hematopoietic stem cells to respond to pharmacological modulation, CD34 sorted or enriched cells were treated with known modulators. After an overnight incubation at 37° C., the CD34 positive cells were flow cytometry assessed for pharmacological response, including upregulation of surface PDL1 expression. In comparison to vehicle control, significantly more treated CD34 cells demonstrated up-regulation of PDL1 surface protein in addition to increased total expression in the general population (see FIG. 11), which is an indication of immunoregulatory potential of the CD34 positive cells derived from naïve hiPSCs using the disclosed methods.

Figure 10:
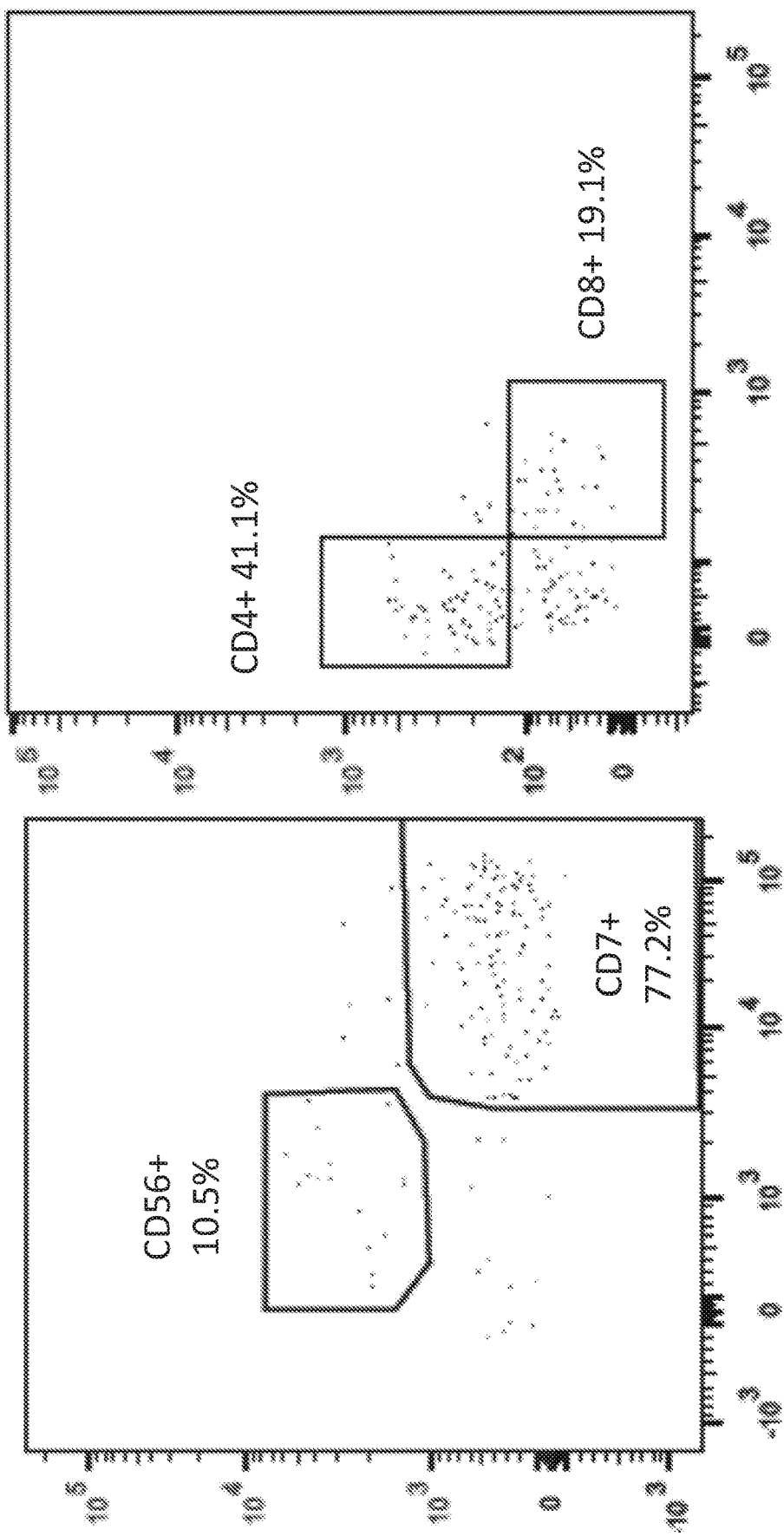
FIG. 10 shows CD56 positive cells and single positive CD4 and CD8 cells, derived from CD56-/CD7+/CD3+/TCRαβ+ gating strategy, were identified when hiPSC-derived CD34 positive cells were further cultured in differentiation medium in the absence of stromal cells and in the presence of soluble DLL1 and DLL4 recombinant peptide (for T cell only).

Example 6—Continuation of Differentiation for Specific Hematopoietic Lineages Following Differentiation Using iHSC Culture Platform Sorted or enriched CD34 positive cells were further differentiated down the hematopoietic lineage towards various specific cell types including T cells and NK cells. Specific to T cells, upon enrichment, CD34 positive cells were transferred into suspension culture containing no feeder cells or adherent culture containing OP9 stromal cells or matrigel coated surface. Regardless of the setting, the culture was supplemented with iTC-A1 (FIG. 1) containing soluble DLL1 and DLL4. After approximately 10 days, the culture setting was switched to iTC-B1 to complete T cell maturation. After approximately 30-40 days (post original induction of differentiation), the cell population was assessed for the composition of T cells including surface expression of CD3, CD7, TCRαβ, CD4 and CD8. FIG. 10 illustrates the in vitro differentiation capability of the derived CD34 positive cells to give rise to distinct populations of T cells as defined by expression of CD4 and CD8 from the CD7 population.

Specific to NK cells, CD34 positive cells were treated with differentiation medium including IL15, iNK-A1 medium for approximately 10 days (FIG. 2) and switched to iNK-B1 medium (FIG. 2) for an additional 10-20 days (see CD56 positive population in FIG. 10). The culture was performed in suspended format.

Figure 11:
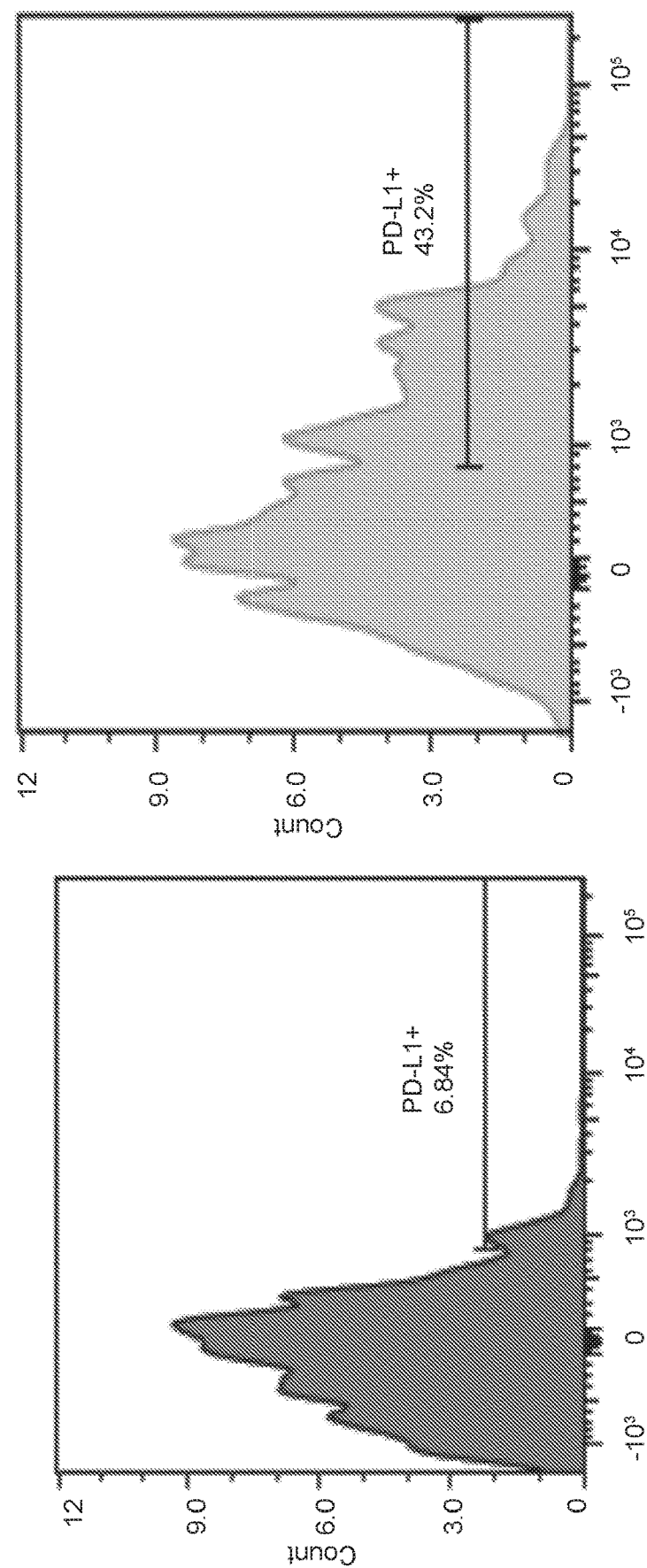
FIG. 11 shows hiPSC-derived CD34 positive cells can respond to pharmacological modulation as seen with enhanced expression of PD-L1 surface expression.

The multi-stage differentiation platform described here showed the process of deriving definitive hematopoietic stem cells from a variety of stem, progenitor or transdifferentiated cells, including pluripotent stem cells, using a sequential differentiation method. The derived CD34 positive hematopoietic stem cells can be kept in suspended culture for scaling and give rise to multi-lineage hematopoietic cell types including hematopoietic stem cells, T cells and NK cells. Moreover, the derived CD34 positive definitive hematopoietic stem cells were shown to respond to pharmacological modulation by upregulating the immune-modulatory surface protein PDL1 (FIG. 11). Furthermore, when engrafted, the derived CD34 positive cells were capable of in vivo reconstitution comprising of both myeloid and lymphoid population (FIG. 9). The definitive hematopoietic stem cells derived from various populations including pluripotent stem cells are ideal candidates for patient specific therapy and regenerative medicine applications.

Example 7—Hematopoietic Differentiation Using iCD34 Culture Platform and Identification of HE Population Having Engraftment Potential The above iHSC platform was further optimized for hematopoietic lineage cells differentiation. To initiate differentiation towards the hematopoietic lineage, hiPSCs were seeded as a monolayer on Day (D) 0 in the maintenance medium and allowed to adhere and expand for about 24 hours. At this point, the maintenance medium was removed and replaced with base medium without maintenance factors at D1. Hematopoietic differentiation was initiated at around D2 by switching the culture medium to iCD34-A (see FIG. 12). As illustrated in FIG. 12, the culture medium was supplemented with the growth factor bFGF at D3 and switched to iCD34-B medium subsequently for differentiation. The monolayers were maintained until around D5-D6 at which point they were dissociated into single cells and seeded as a low density monolayer in iCD34-C medium until differentiation around D10. Low oxygen tension (2-10% $O_2$) was maintained from the onset of hematopoietic differentiation around D2 up until around D10 of differentiation.

Figure 15A:
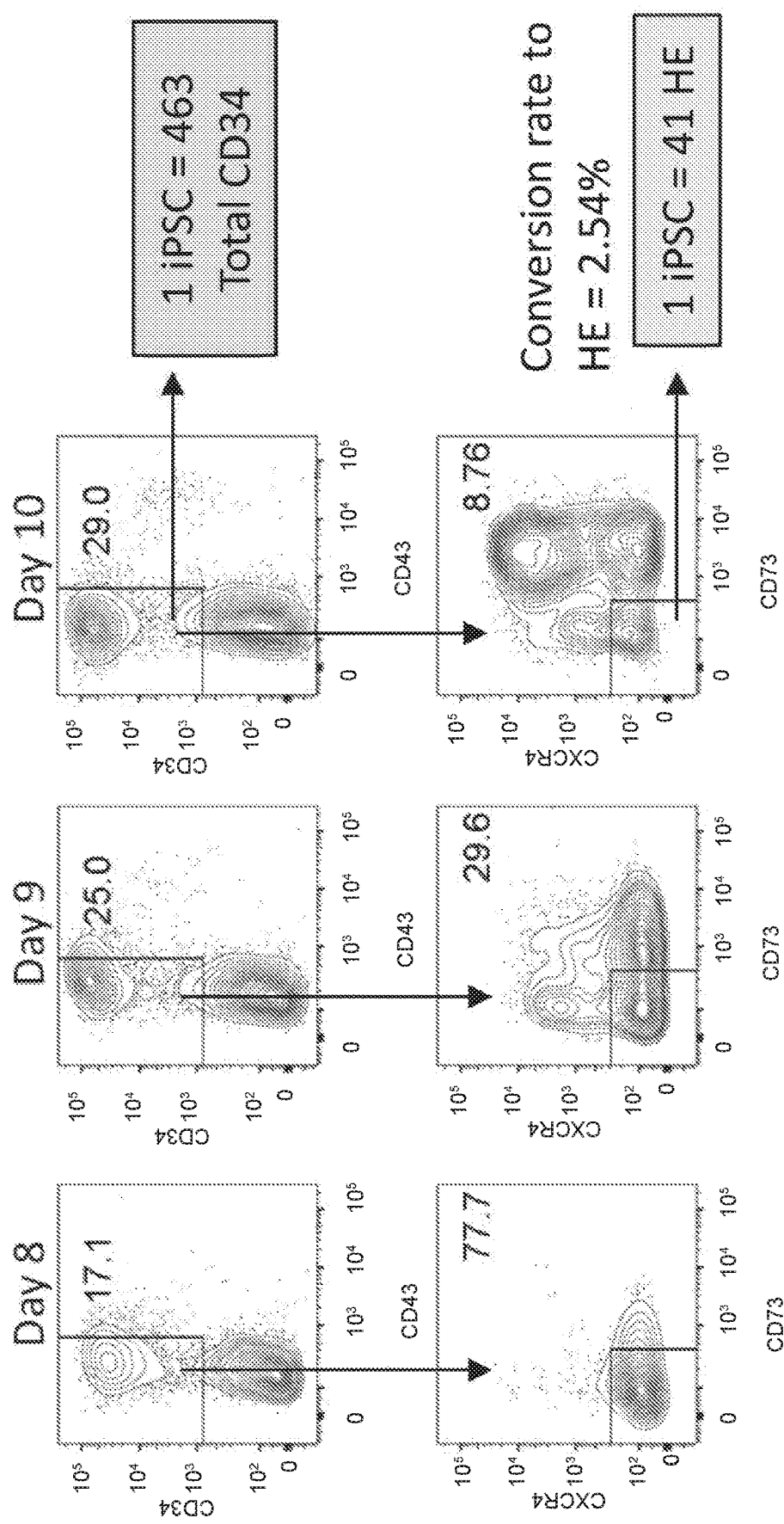
FIG. 15A-C shows flow cytometric profiles depicting the emergence of iHE over a 10 day time course and the output of iCD34 and iHE cells per iPSC differentiation. Calculations are based on snapshot of representative cultures and not optimized cultures.
Figure 15B:
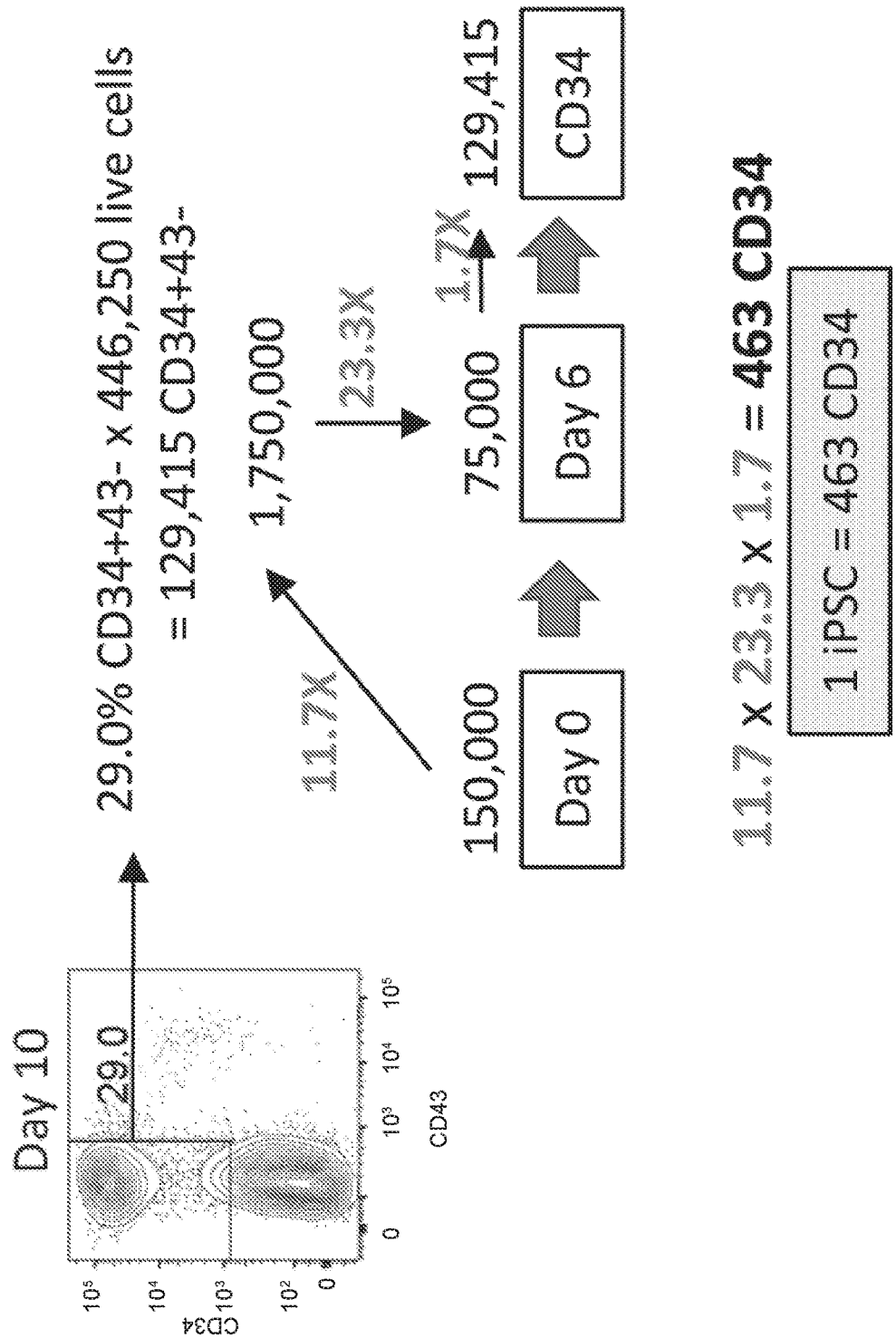

During the culture process, the directed differentiation towards the hematopoietic lineage was monitored by the dissociation of the monolayers into single cells and analysis for the surface marker expression of CD34, and optionally, CD43, CD45, CXCR4 and CD73 (FIG. 15A). At around D8 of differentiation, the appearance of a cell population representing HE was observed by the cell surface expression signature CD34+. CD43−CXCR4−CD73− was also observed in the CD34+ cells. The CD34+ population was maintained until around D10 (FIG. 15A). At D10, which time point can be shortened to about D9 or extended until about D12, the cells were dissociated into single cells and the CD34+ HE population was sorted by FACS using a BD FACS Aria for further analysis and functional assessment. As an example of hematopoietic output capacity, 463 total CD34+ cells (FIG. 15A) and 41 CD34+CD43−CXCR4−CD73− cells (FIG. 15A) were generated for every input of a single iPSC, a conversion rate to definitive HE cells of at least 2.5%.

Figure 33:
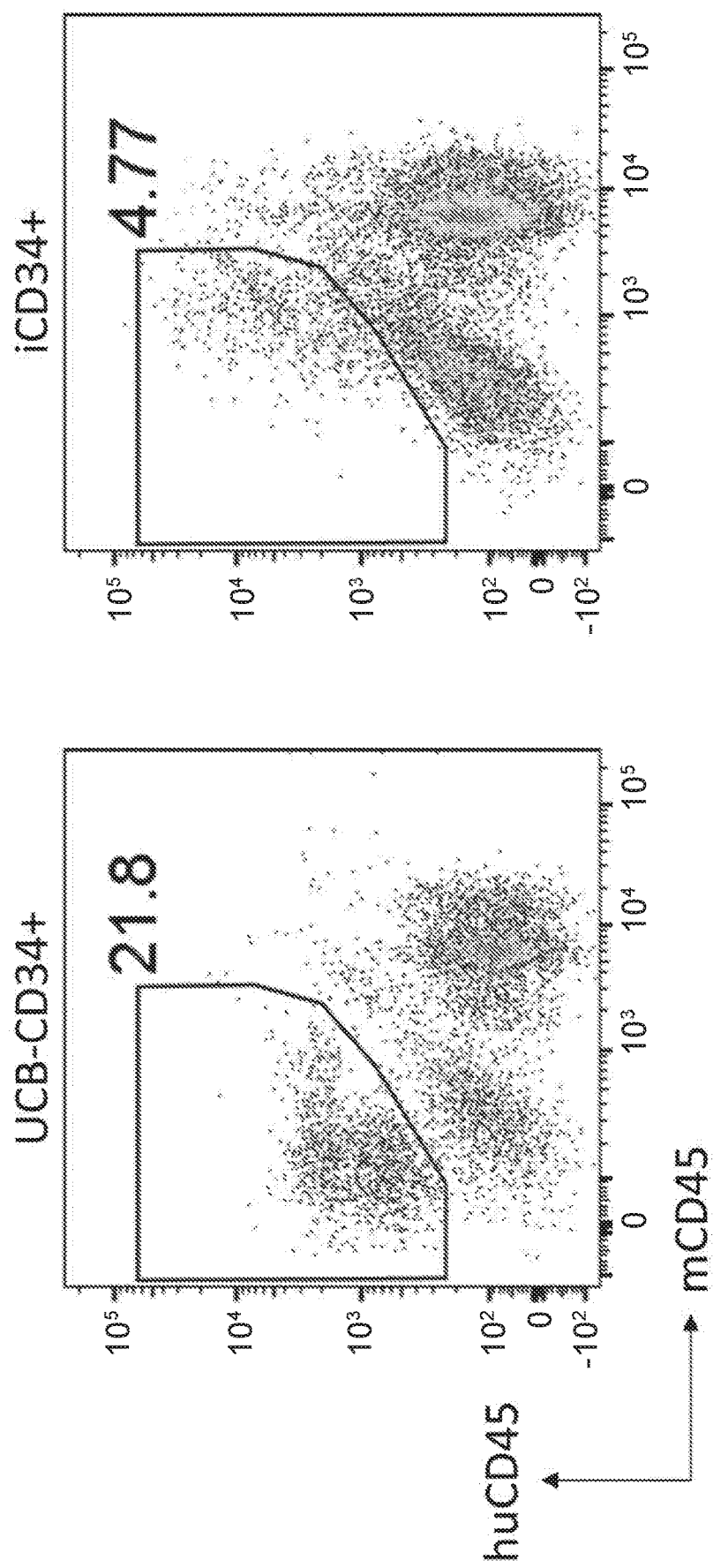
FIG. 33 shows engraftment of hiPSC-derived iCD34+ cells.

To demonstrate the engraftment potential of hiPSC-derived iHE, Day 10 CD34+ cells were sorted and cultured in the iMPP assay for 7 days as described above. After a total of 17 days in culture (10 days of iCD34 plus 7 days of iMPP) approximately 400,000 cells were injected into NSG via retro-orbital injection. 200,000 umbilical cord blood CD34+ cells were injected into separate mice as a control. FIG. 33 demonstrates 5 week reconstitution of engrafted CD34 positive cells as seen by the presence of cells expressing the human CD45 marker in the peripheral blood of the mouse.

Figure 15C:
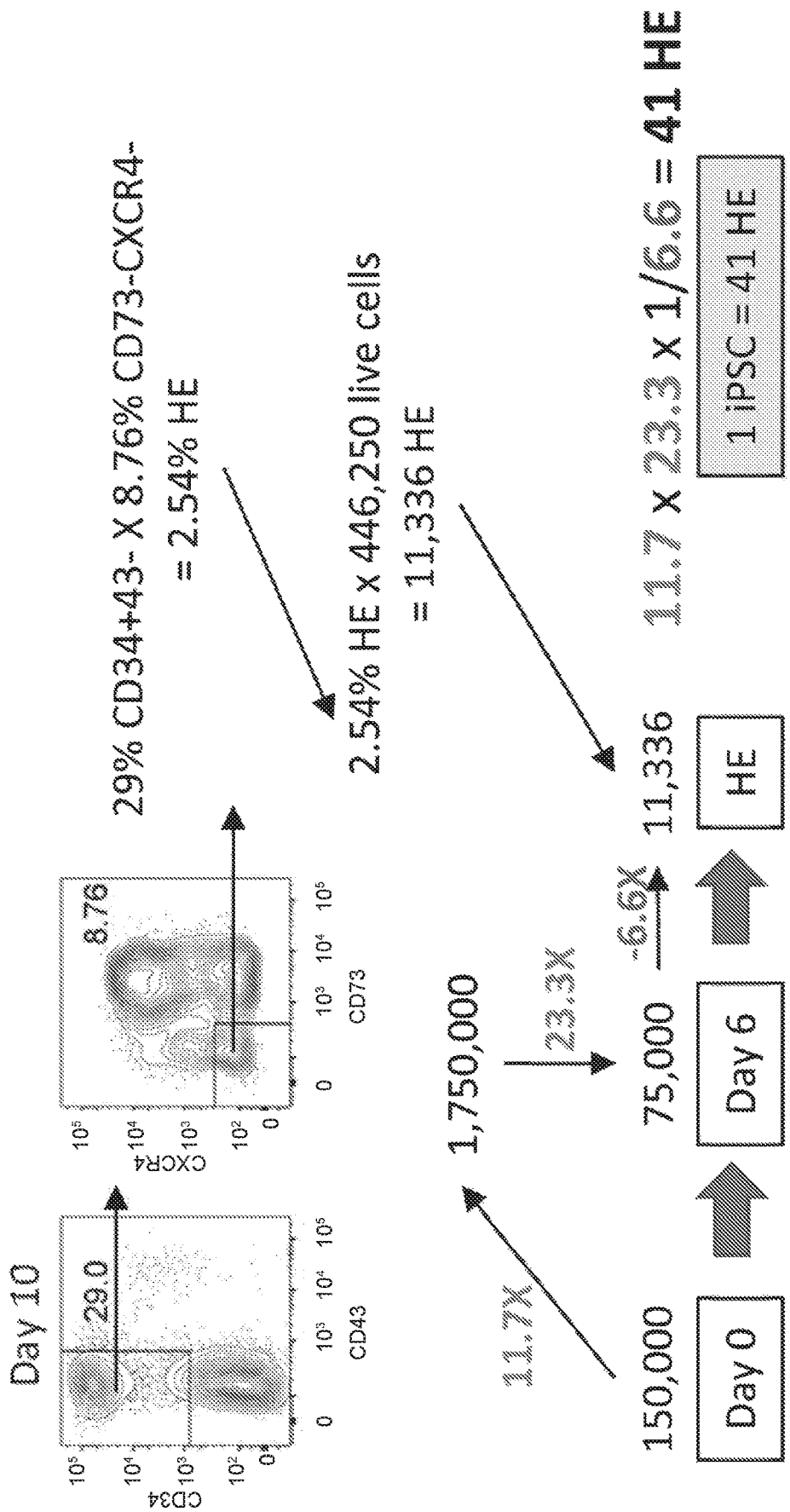
Figure 16A:
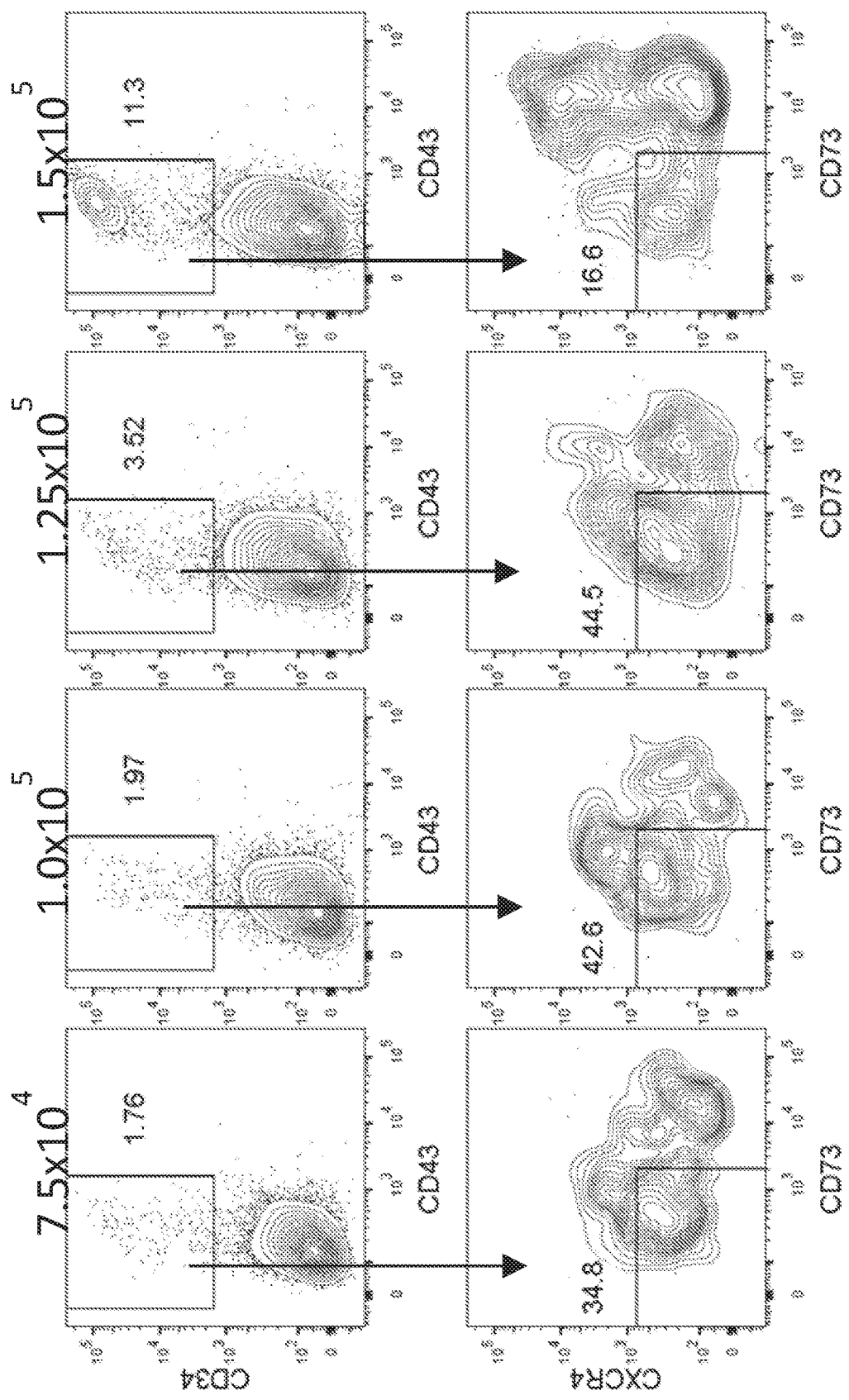
FIG. 16A-E shows modifications to the protocol, including plating density and growth factor titrations, to improve the output of HE at Day 10. A) Plating density at Day 0 influences HE population at Day 10. B) Concentration of BMP4 from Day 2-Day 6 influences HE population at Day 10. C) Concentration of CHIR at Day 3.75 influences HE population at Day 10. D) Plating density at Day 6 influences HE population at Day 10. E) Addition of IGF1 and EPO at Day 8 decreases HE at Day 10.
Figure 16B:
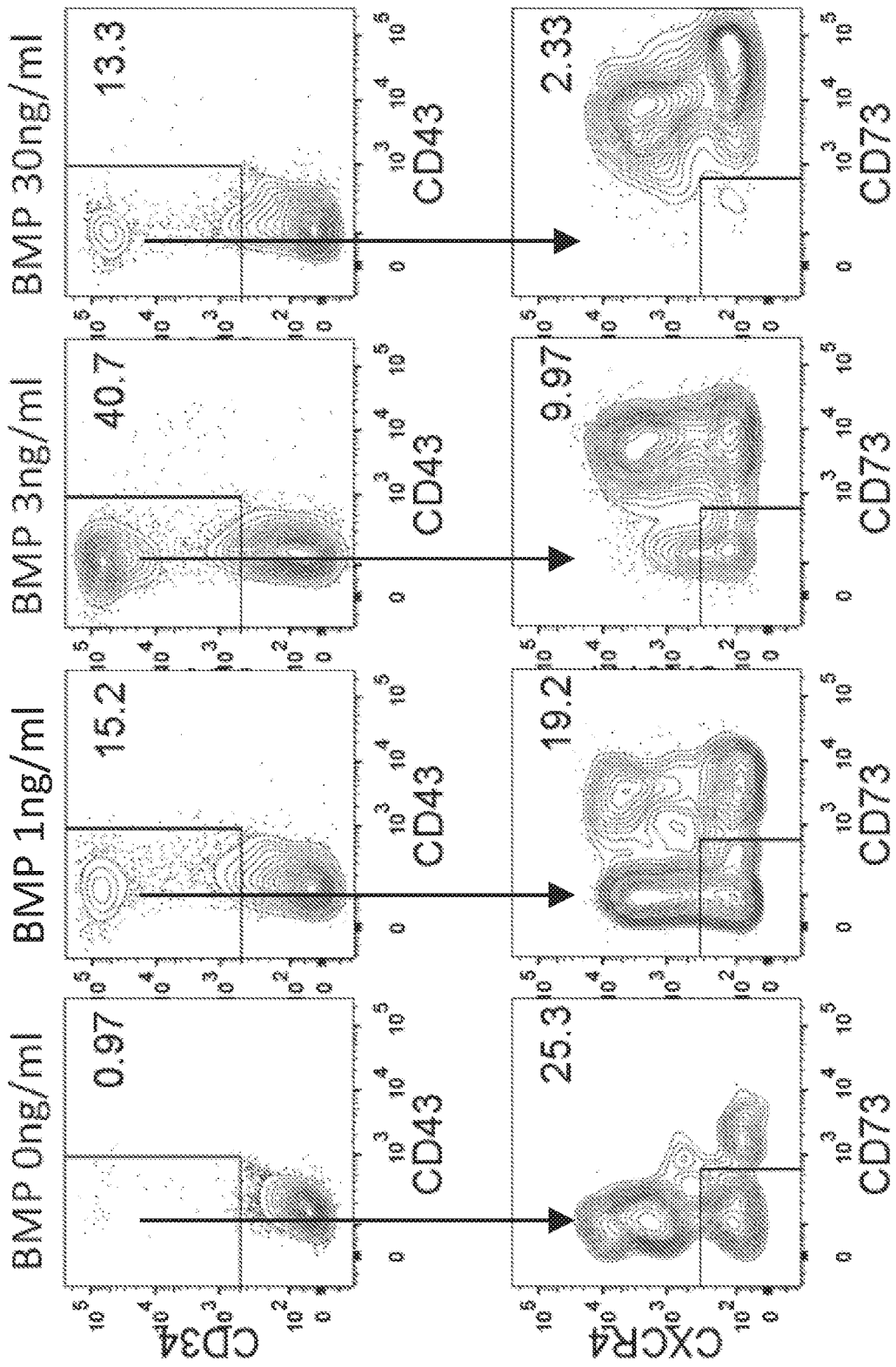

Example 8—Optimization of HE Generation by Small Molecule, Cytokine and Plating Density Modulation To optimize the efficient generation of HE from hiPSCs after around 10 days of differentiation several parameters were examined. The optimal plating density of the monolayers at D0 of differentiation was assessed by plating increasing amounts of hiPSCs from $7.5 \times 10^4$/well to $1.5 \times 10^5$/well on Matrigel™-coated 6 well culture dishes and then analyzing the generation of the CD34+ HE population at about D10. FIG. 16A demonstrates that increasing the cellular plating density increases the total percentage of CD34+ cells but decreases the CXCR4−CD73− HE subpopulation. Despite this decrease, the highest conversion rate of hiPSCs to HE after 10 days of monolayer differentiation was at the highest plating density tested at $1.5 \times 10^5$/well (FIG. 15C).

Figure 16C:
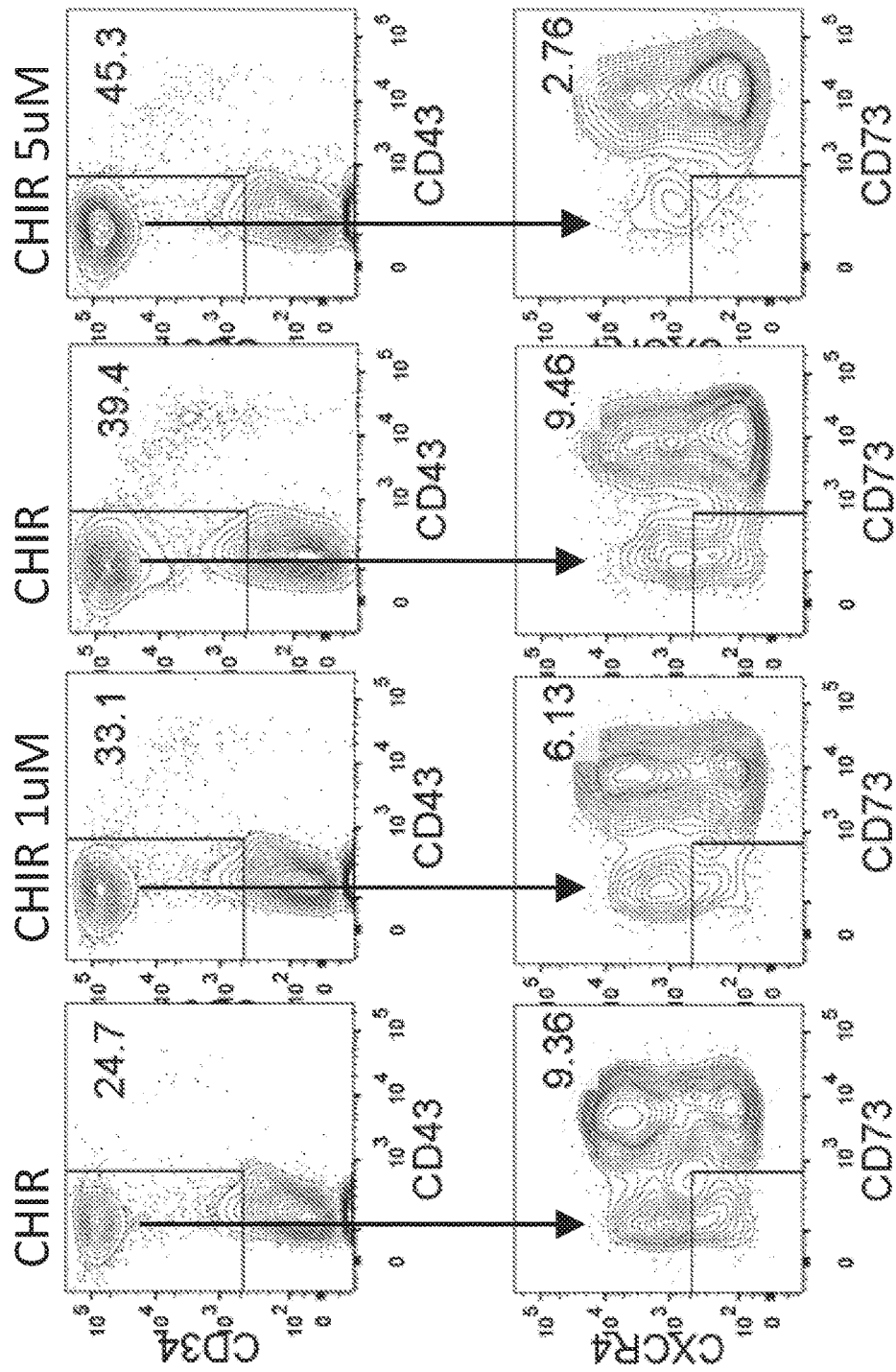

The effect of the concentration of BMP4 modulation during the initial stages of hematopoietic differentiation on the generation of HE was assessed by treating the cultures with increasing concentrations of BMP4 ranging from 0 ng/ml to 30 ng/ml from about D2 to about D6 of differentiation. The generation of HE at D10 was assessed by the detection of the CD34+ HE population. FIG. 16C demonstrates that increasing concentrations of BMP4 from D2 to D6 increases the HE population at D10 below a threshold BMP4 concentration indicating an optimal concentration of about 3 ng/mL.

Figure 16D:
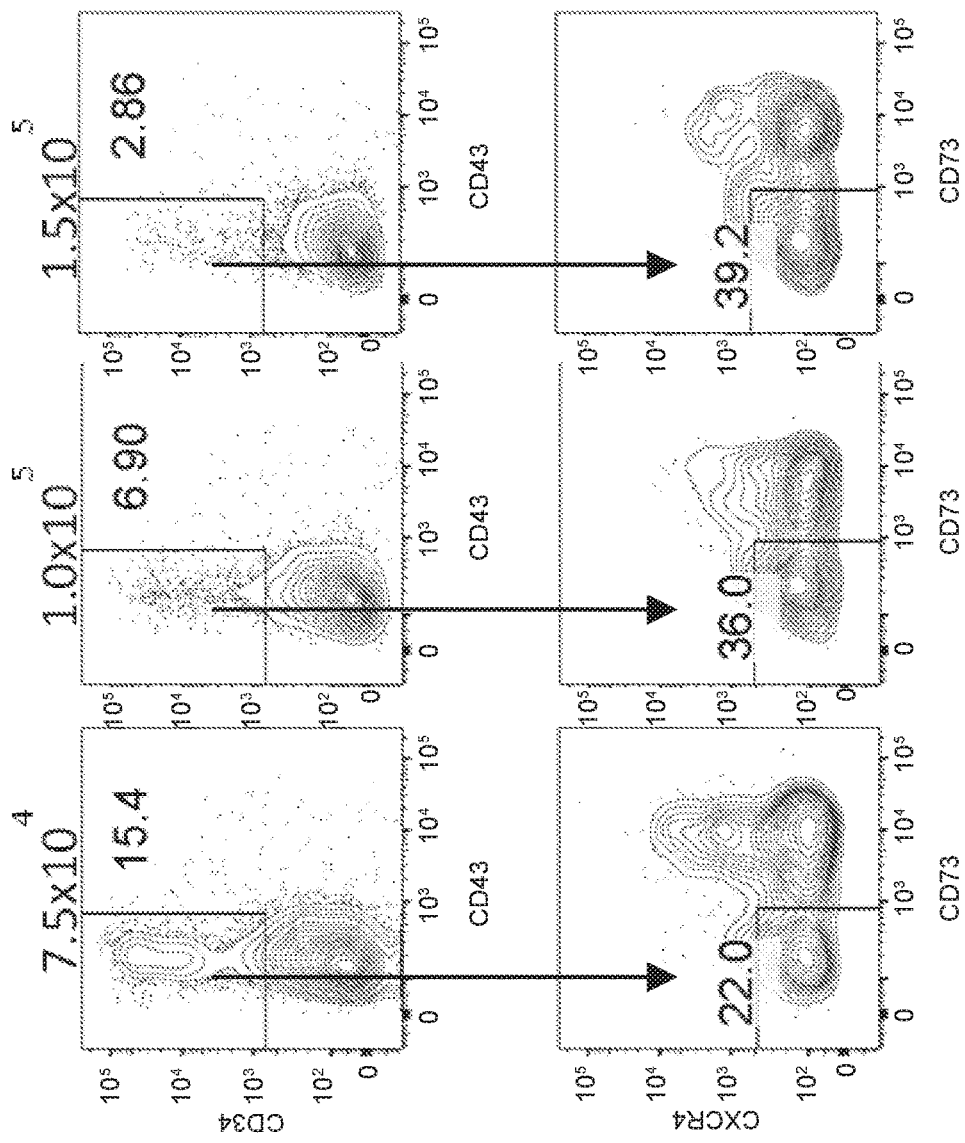

The Wnt pathway activator CHIR99021 is responsible for the induction of the definitive hematopoetic program from hiPSCs. The effect of the modulation of CHIR during the induction phase of the hematopoietic differentiation protocol was assessed by treating the cultures with increasing concentrations of CHIR from about D3.75 to about D6. FIG. 16D demonstrates that while increasing the concentration of CHIR99021 increases the total percentage of CD34+ cells it decreases the percentage of the HE subpopulation with the optimal concentration of CHIR99021 being approximately 1 uM.

Figure 16E:
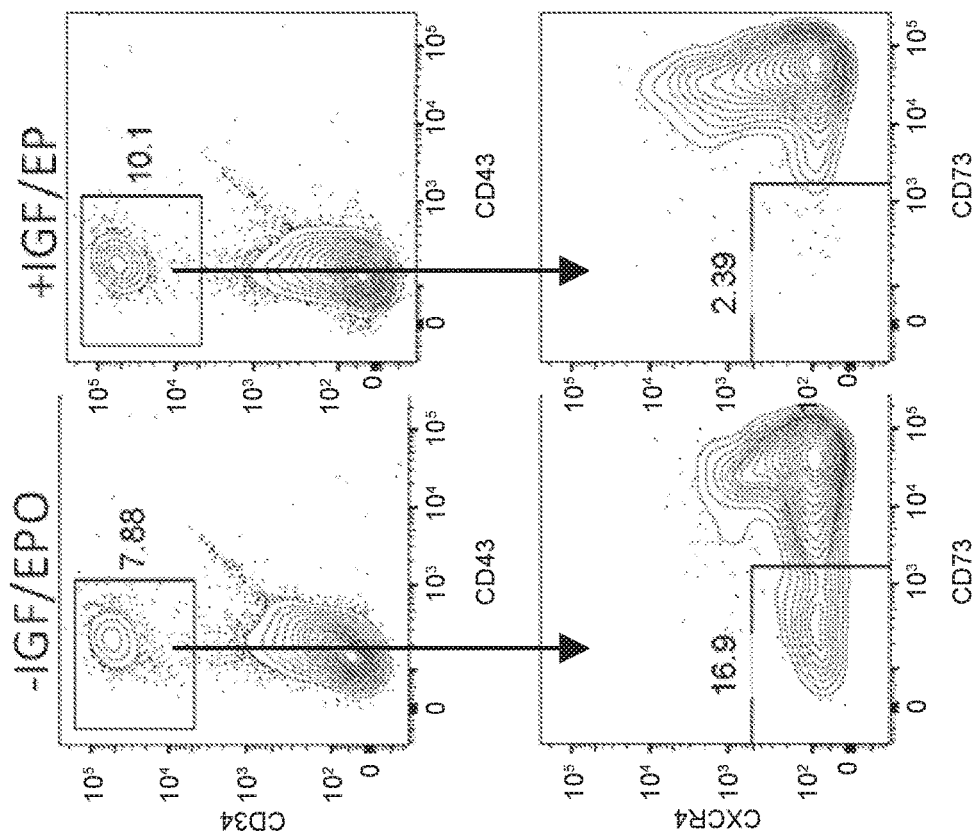

At D6 of the directed differentiation protocol the monolayer cultures dissociated to single cells and were replated as a monolayer for further differentiation to HE. The plating density at D6 was shown to influence the generation of HE as demonstrated in FIG. 16E in which decreasing cellular concentrations from $1.5 \times 10^5$ to $7.4 \times 10^4$ increases the percentage of the HE population.

The previous protocols for directed differentiation called for the addition of IGF1 and EPO cytokines during the generation of HE. FIG. 16F illustrates that the addition of IGF1 and EPO decreases the percentage of HE observed at around D10 and the removal of these factors results in improvement in the differentiation method.

Figure 17A:
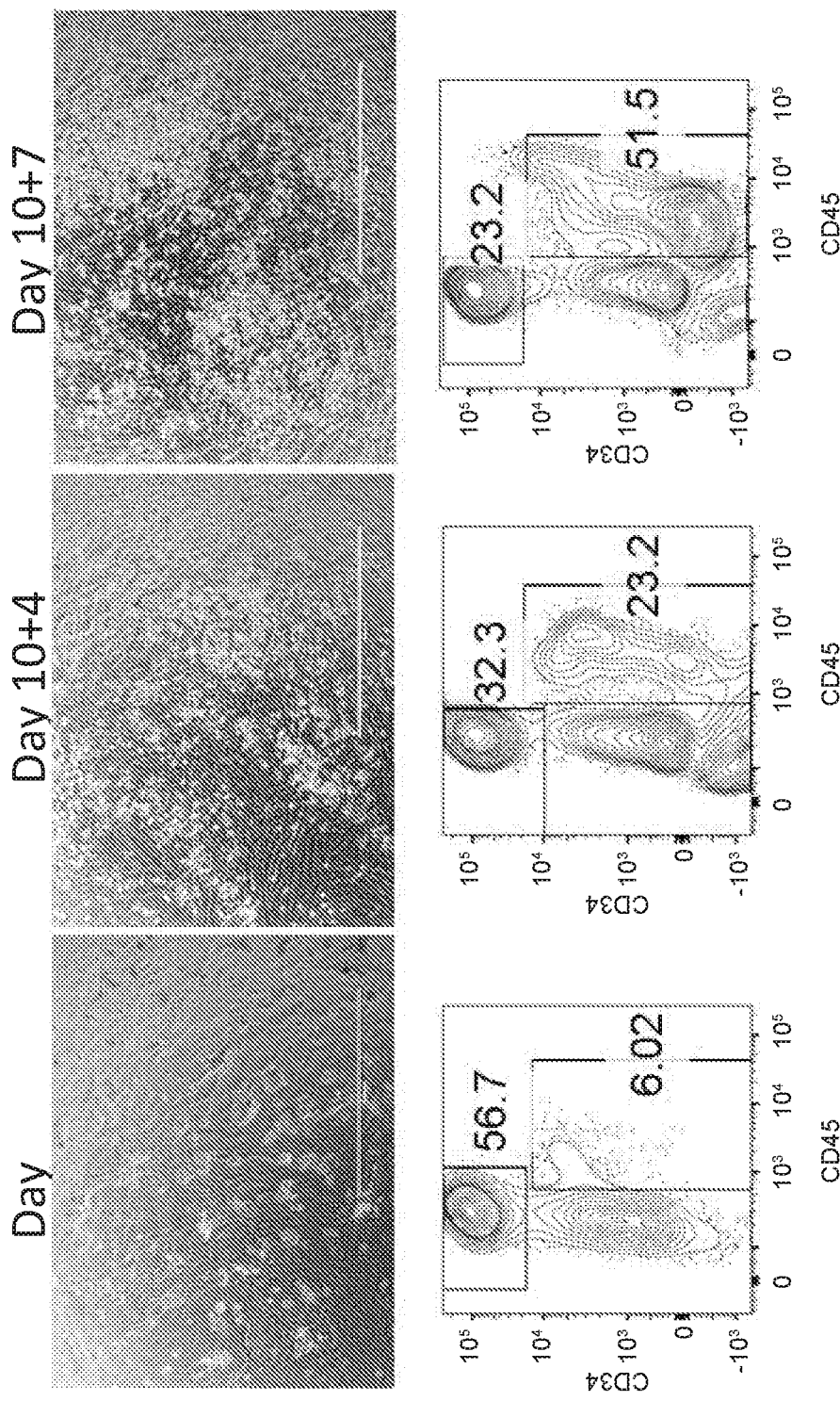
FIG. 17A-B shows the Day 10 HE represents definitive hematopoiesis that is multipotent and dependent upon the Notch signaling pathway. A) Morphological changes over the 7 day MPP assay with flow cytometric profiles of emerging CD45 hematopoietic cells. B) iPSC-derived CD34+ cells generate Notch-dependent definitive CD45+ cells during the iMPP assay.

Example 9—Determination of Hematopoietic Potential of HE by Notch-Dependent Hematopoiesis and MPP Differentiation To demonstrate the hematopoietic potential of the hiPSC-derived definitive population HE cells were sorted using FACS and assessed for their ability to undergo the endothelial to hematopoetic transition to generate CD45+ hematopoietic progenitors as described in the multipotent progenitor assay (iMPP) in FIG. 12. Approximately 30,000 CD34+ HE cells were cultured in suspension as aggregates overnight in iMPP-A media and then plated as a monolayer and further cultured for 6-8 days. FIG. 17A illustrates the phenotypic alterations in the monolayer cultures with the emergence of round hematopoietic cells and flow cytometric staining identifies the presence of CD45+ over the 6-8 day culture period.

Figure 17B:
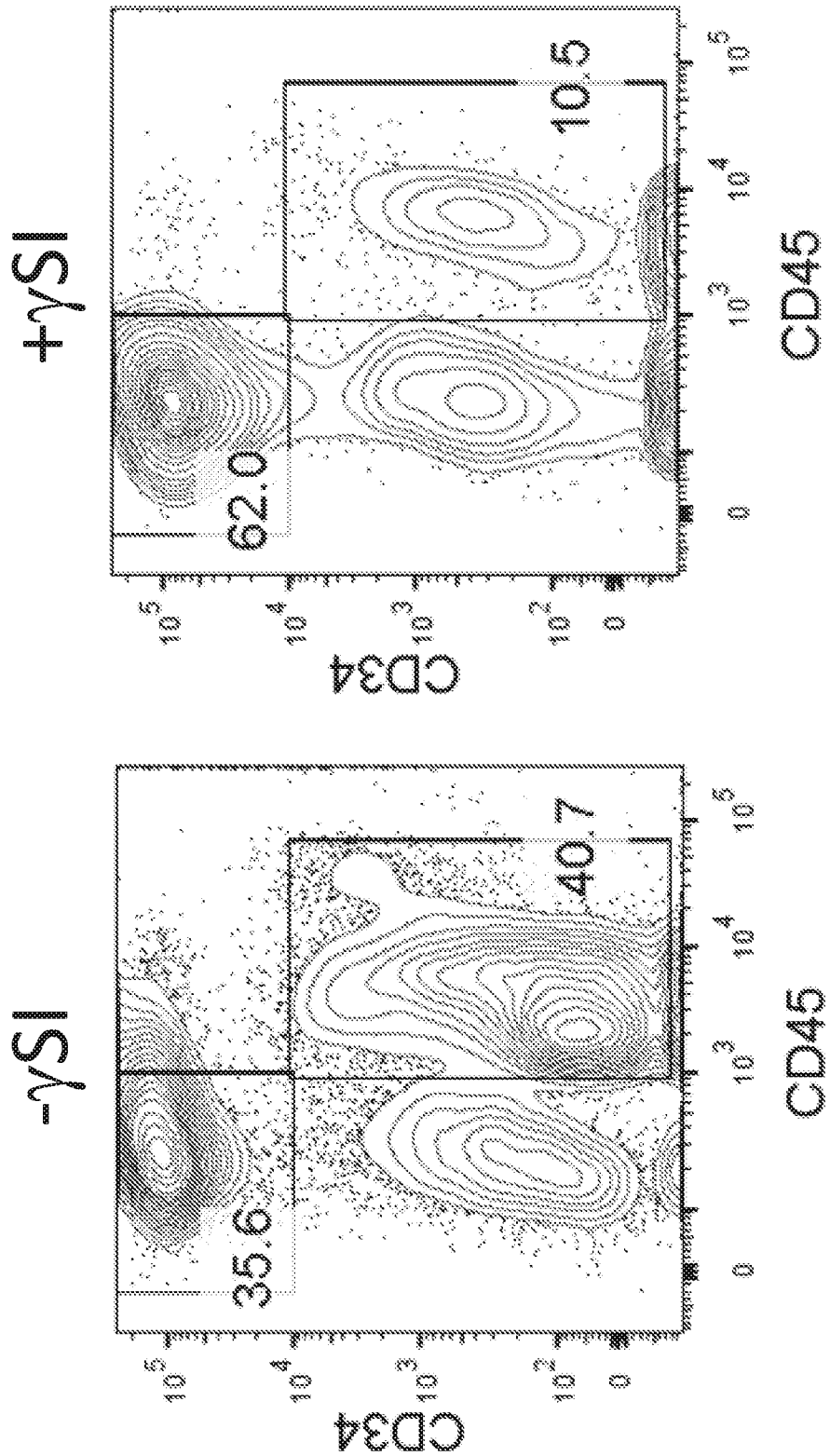

To assess whether the HE population generated at D10 of the directed differentiation protocol represents definitive HE, CD34+ HE sorted cells were treated with the Notch pathway inhibitor gamma secretase inhibitor (γSI) for the duration of the 7-9 day iMPP assay. Fresh γSI was added to the iMPP-A culture media every 2 days. After about 8 days the monolayers cultures were assessed by flow cytometry for the emergence of CD45+ hematopoietic cells. In comparison to vehicle control, significantly less CD45+ cells were seen in the γSI-treated cultures demonstrating a dependence upon the Notch signaling pathway and the presence of definitive HE (FIG. 17B).

Figure 18A:
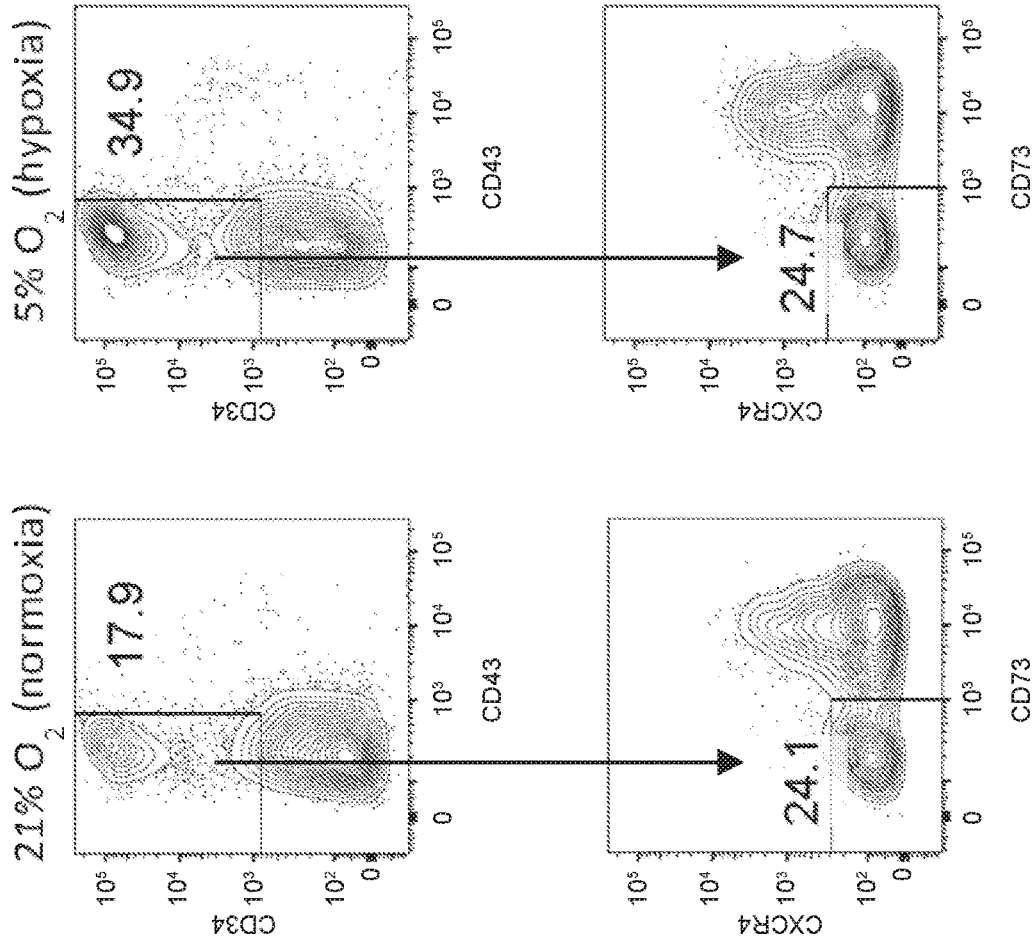
FIG. 18A-B shows the effect of differentiation under hypoxic conditions on the generation of iHE and iMPP hematopoietic progenitors. A) Monolayer differentiation in hypoxia increases both percentage of iCD34 positive cells and iHE cells at Day 10. B) Day 10 iCD34+ HE cells generated under hypoxic conditions can be further differentiated in the iMPP assay.
Figure 18B:
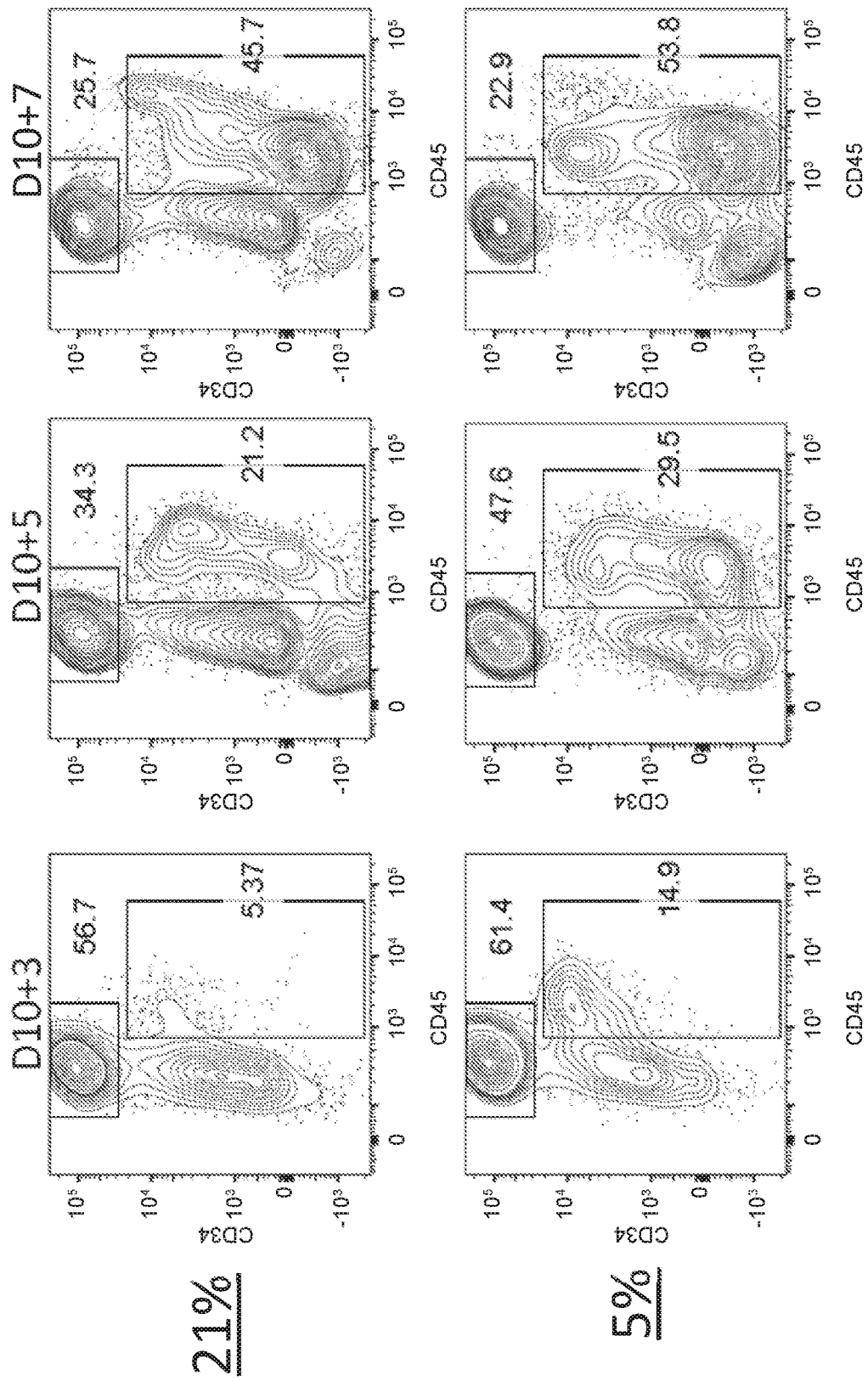

Example 10—Optimization of HE And iMPP Generation Through Manipulation of Oxygen Conditions To assess whether the oxygen environment affects the generation of definitive HE and iMPP hematopoietic progenitors, hiPSCs were differentiated as described in FIG. 12 under either normoxic (21% $O_2$) or hypoxic (5% $O_2$) conditions. At around D10 of differentiation the monolayers were counted and assessed by flow cytometry for the presence of the CD34+ HE population. As seen in FIG. 18A differentiation under hypoxic conditions resulted in an increase in the amount of CD34+ HE generated. To confirm that the HE generated under hypoxic conditions retained the potential to generate CD45+ hematopoietic progenitors, CD34+ cells were isolated by FACS from normoxic and hypoxic differentiation conditions and assessed by the iMPP assay. HE generated under both conditions have equivalent iMPP potential indicating that hematopoietic differentiation under hypoxic conditions increases the output of definitive HE (FIG. 18B)

Example 11—Cryopreservation of Day 8 Differentiation Cultures and HE

Figure 19A:
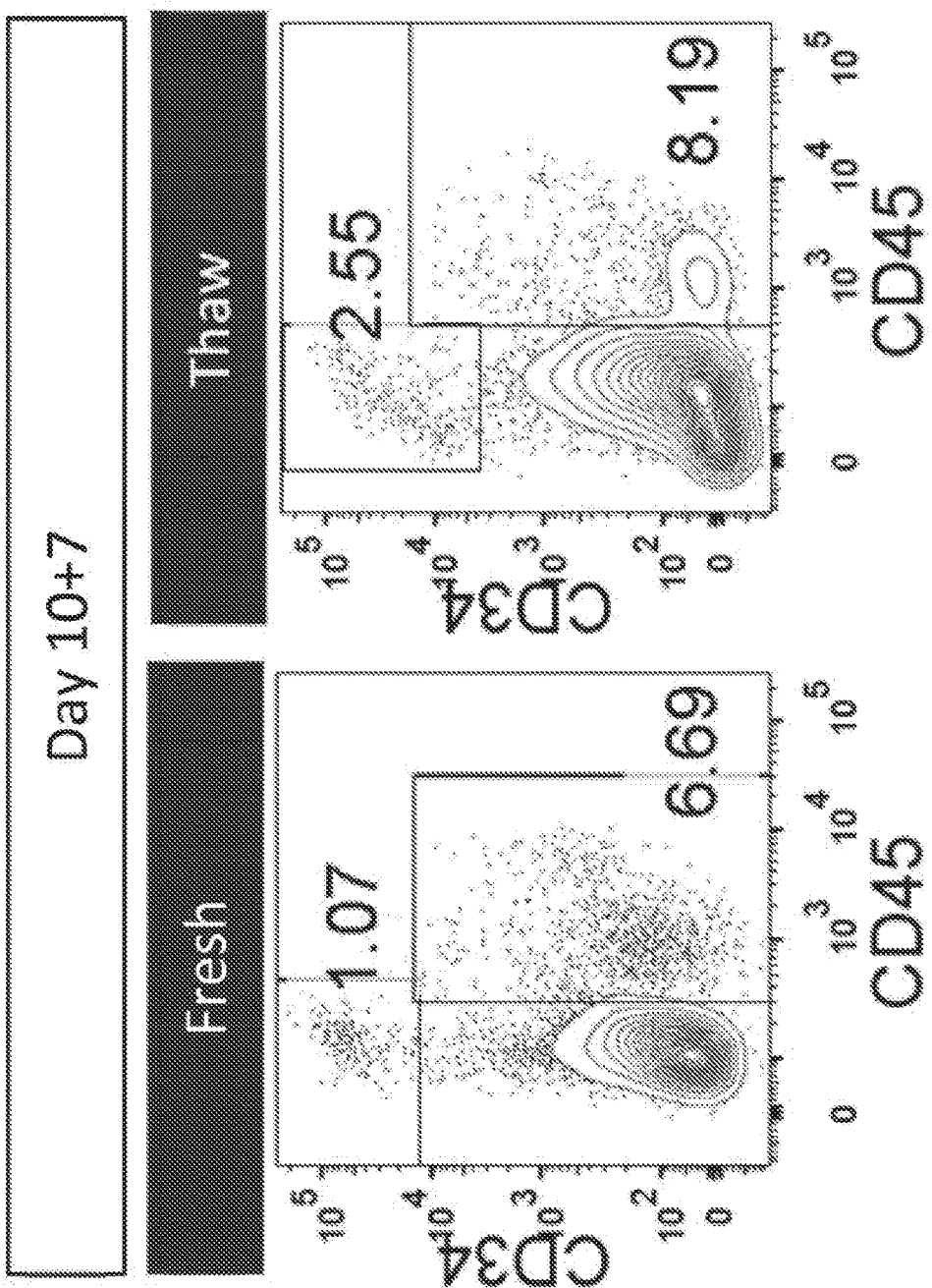
FIG. 19A-D shows the ability of unsorted or sorted Day 10 cultures to be cryopreserved and maintain hematopoietic potential. A) Cryopreserved Day 10 unsorted differentiation cultures can survive and generate CD45+ hematopoietic cells during iMPP assay. B), C) and D) Cryopreserved Day 10 iCD34+ sorted cells can survive and generate CD45+ hematopoietic cells during iMPP assay.

At around day 10 of the direct differentiation protocol, entire cultures were dissociated to assess their ability to maintain hematopoietic potential following cryopreservation in day 8 medium supplemented with 10% DMSO. Thawed cells were resuspended and subsequently cultured in iMPP-A media as described in FIG. 12 for 7 days prior to flow analysis. As seen in FIG. 19A, cryopreserved D10 cells survived the freeze/thaw process and had comparable hematopoietic potential to unfrozen controls as seen by the presence of CD45+ cells.

Figure 19B:
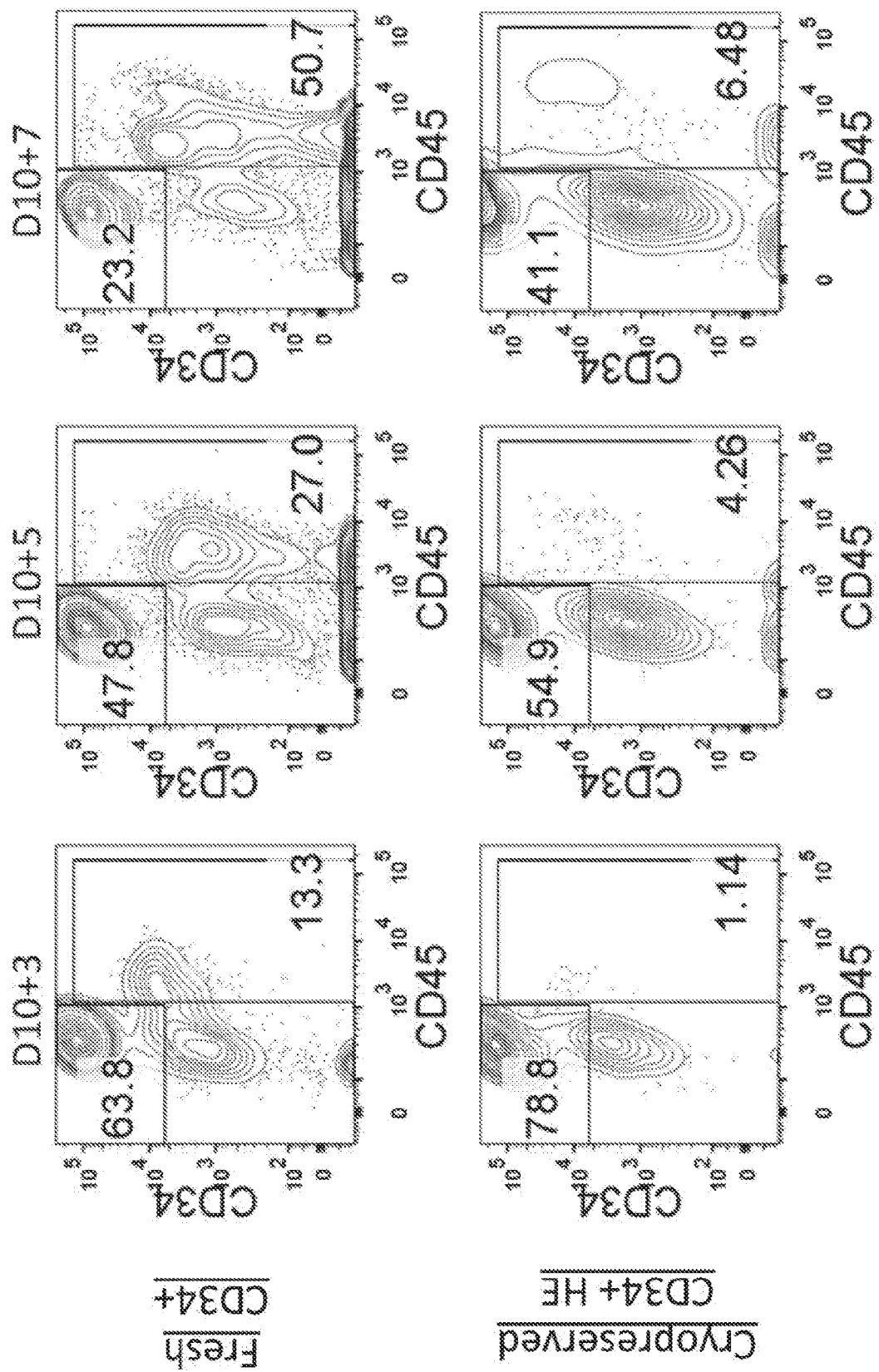
Figure 19C:
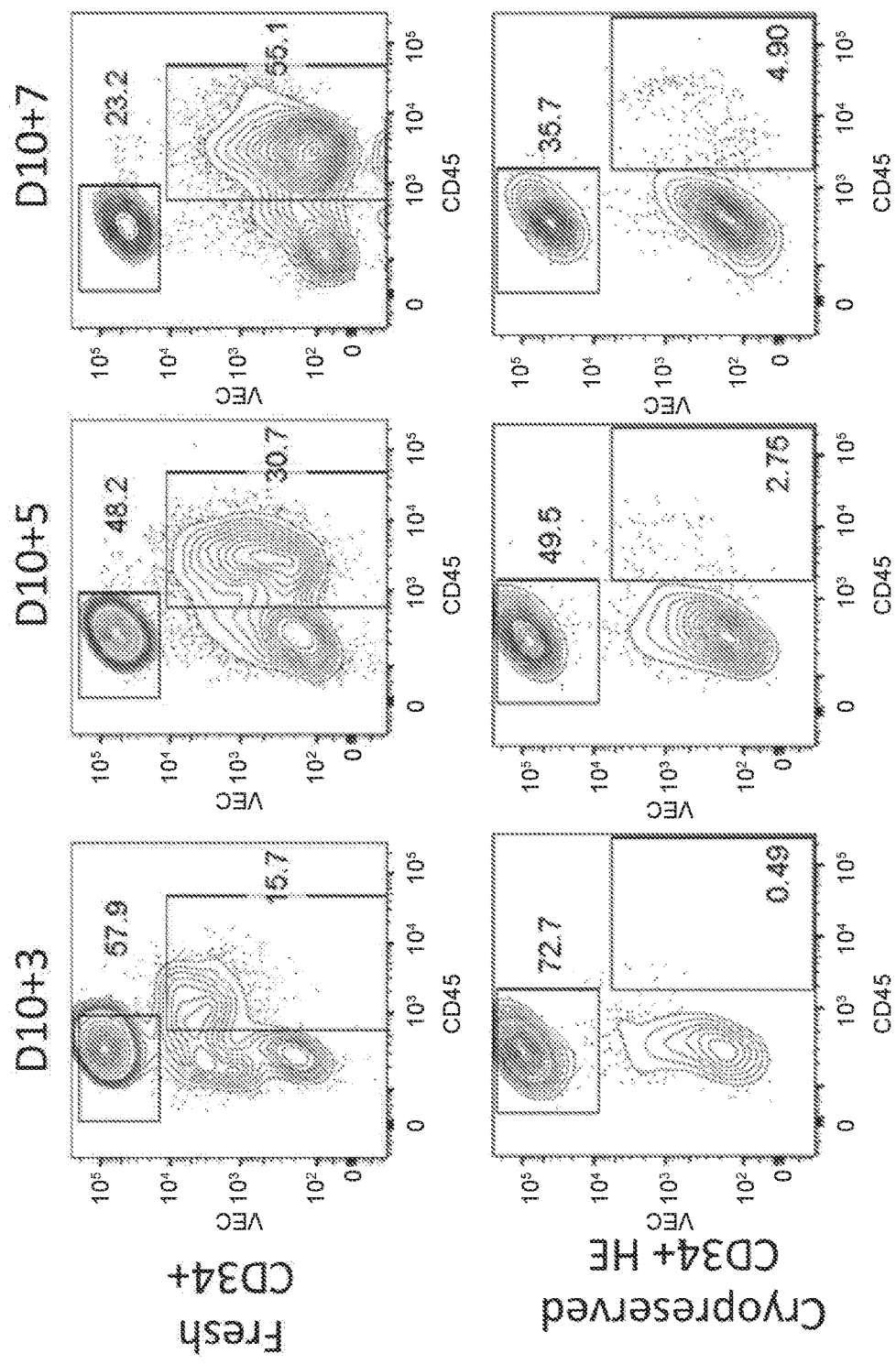
Figure 19D:
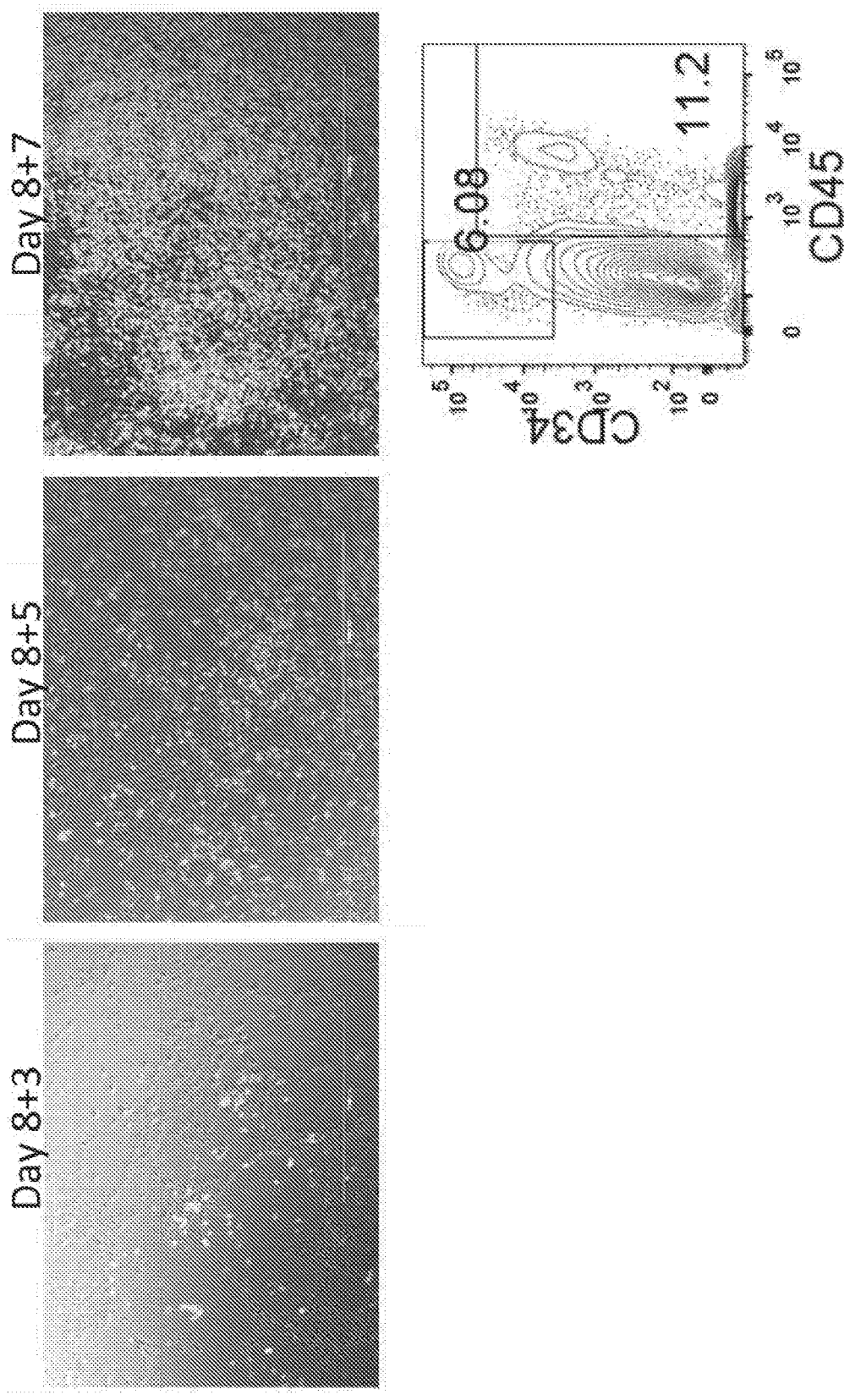

Sorted CD34+ cells were assessed for their ability to maintain hematopoietic potential following cryopreservation. D10 iCD34 generated under hypoxic conditions was isolated and plated directly into the iMPP assay as described in FIG. 12 or cryopreserved in iMPP-A media for 7 days and then thawed and plated in the iMPP assay. As seen in FIG. 19B, the cryopreserved HE survived the freeze/thaw process and was able to maintain hematopoietic potential as seen by the presence of CD45+ cells, although with decreased efficiency compared to the unfrozen control (FIG. 19B top panel). Cryopreserved iCD34 were also plated at a higher density (200,000 cells/well) which appeared to increase the output of CD45+ cells (FIG. 19D).

Example 12—Recovery of Day 8 Differentiation Cultures After Overnight Shipment

Figure 20A:
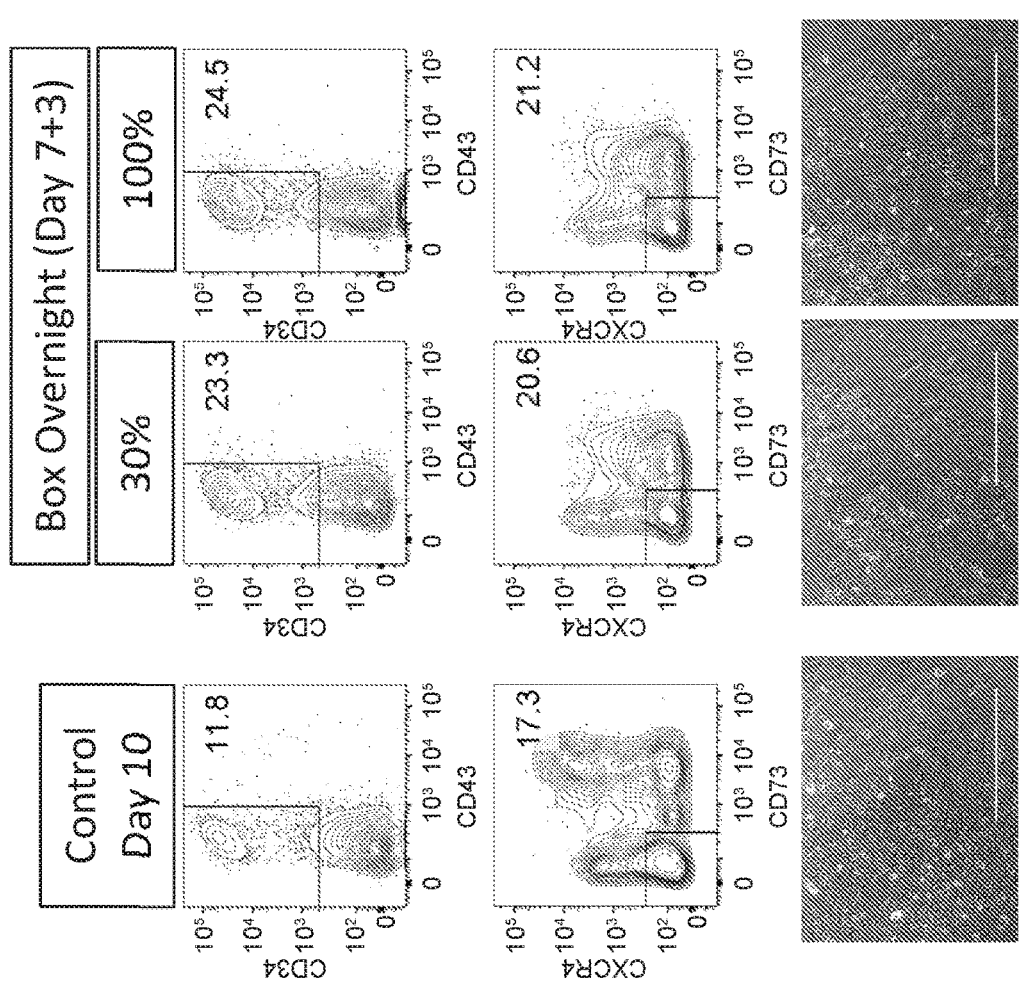
FIG. 20A-B shows that Day 10 differentiation cultures can be shipped overnight in ambient temperature without loss of HE potential. A) Cultures at day 7 were either maintained in the incubator (Control) or processed for overnight shipment followed by reintroduction into an incubator for the following two additional days. The cultures, both at day 10 were then analyzed for the presence of iCD34 and iHE cells. In the overnight shipped cultures, the T-flasks either contained 30% culture medium with 70% base or 100% culture medium. B) Calculations for number of cells.
Figure 20B:
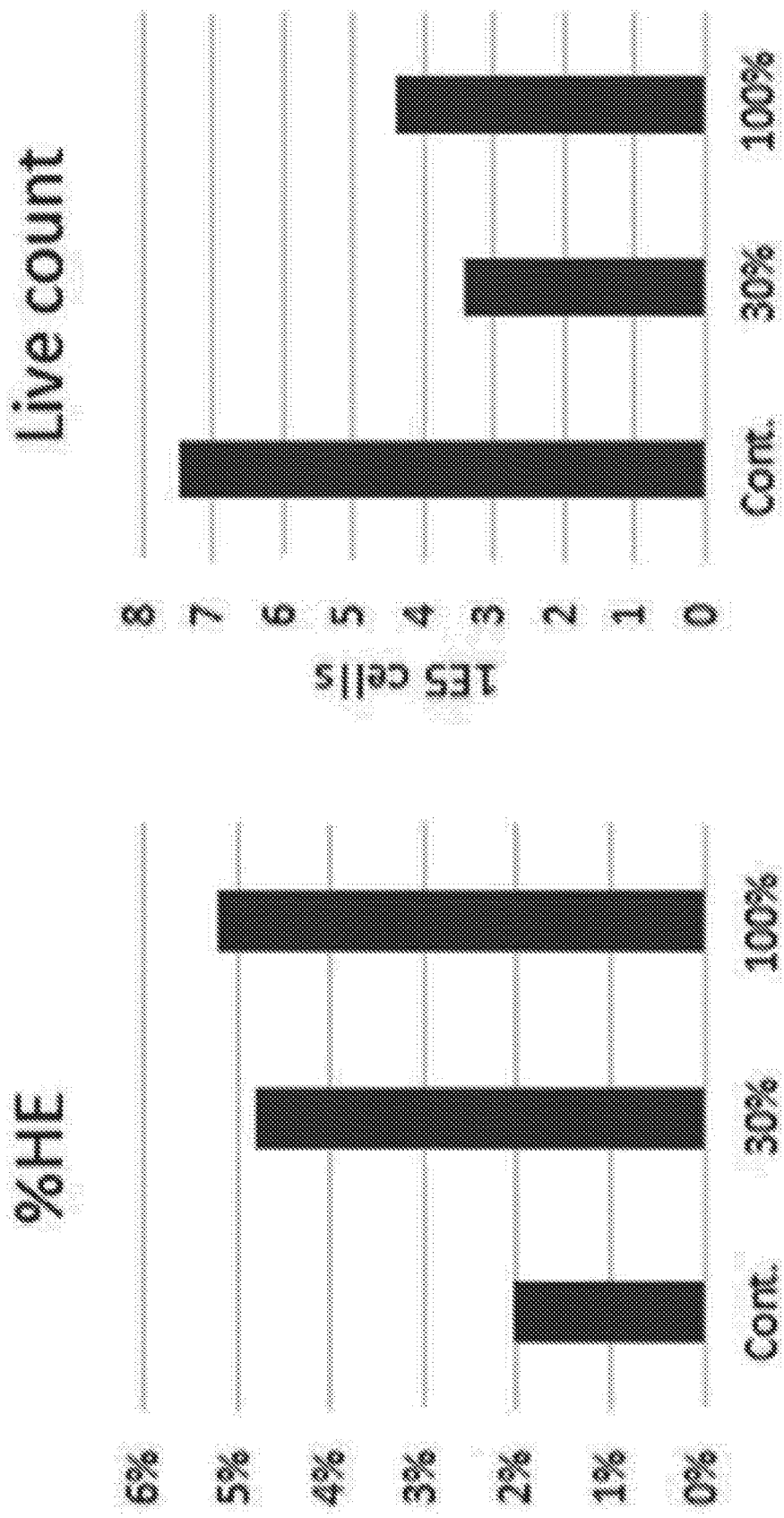

Day 6 differentiation cultures from 6 well plates were passaged into T25 cultures flasks at a seeding density of 200,000 cells/flask and then filled up completely with medium at Day 8 and kept in a Styrofoam box overnight to assess the feasibility of shipping fresh cells directly without the need for cryopreservation. Cold packs initially kept in a 37° C. water bath were also added to the Styrofoam box in order to preserve a 37° C. temperature for as long as possible. Two medium compositions were tested alongside a control flask kept in a 37° C. incubator: a flask with 30% concentration of the cytokines and morphogens utilized in the Day 8 step (FIG. 12) and a flask with 100% concentration. On Day 9, the flasks were removed from the box, medium replaced with 10 mL of Day 8 medium, along with new caps placed on the flasks and allowed to recover before processing for flow analysis on Day 10 for the presence of the CD34+ HE population. As seen in FIG. 20 the overall output of HE was comparable between all conditions demonstrating the feasibility of fresh overnight shipment of Day 8 cultures as an effective means for delivering HE cells.

Figure 21A:
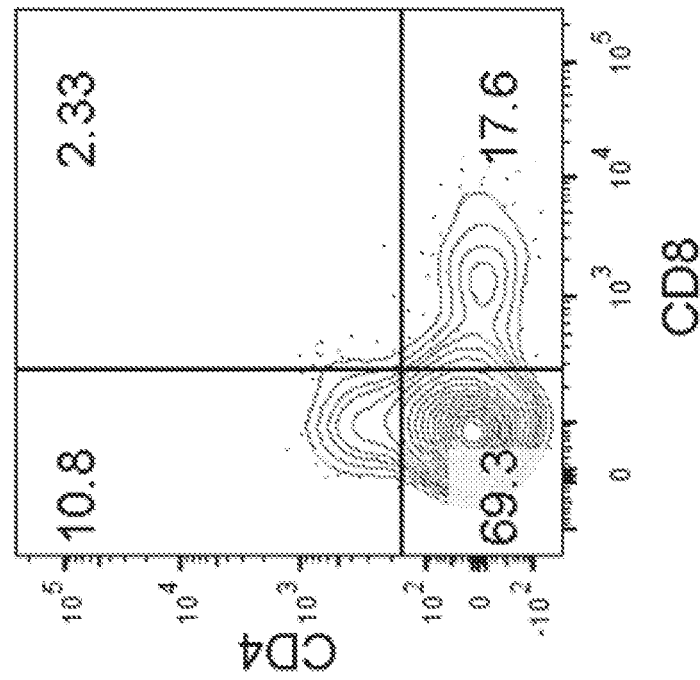
FIG. 21A-C shows early CD34+CD7+ T cell progenitors and mature CD4+ and CD8+ T cell subsets derived from hiPSCs utilizing a CD45+CD56– gating strategy. A) Early T cell lineage markers mark the presence of iproT cells as defined by CD34+/CD7+. B) Mature T cell markers mark the presence of mature T cells as defined by CD4+ or CD8+ cells. C) 5 day T cell differentiation comparing the potential of CD34 positive cells from umbilical cord blood and iCD34 positive cells to give rise to iproT cells.
Figure 21B:
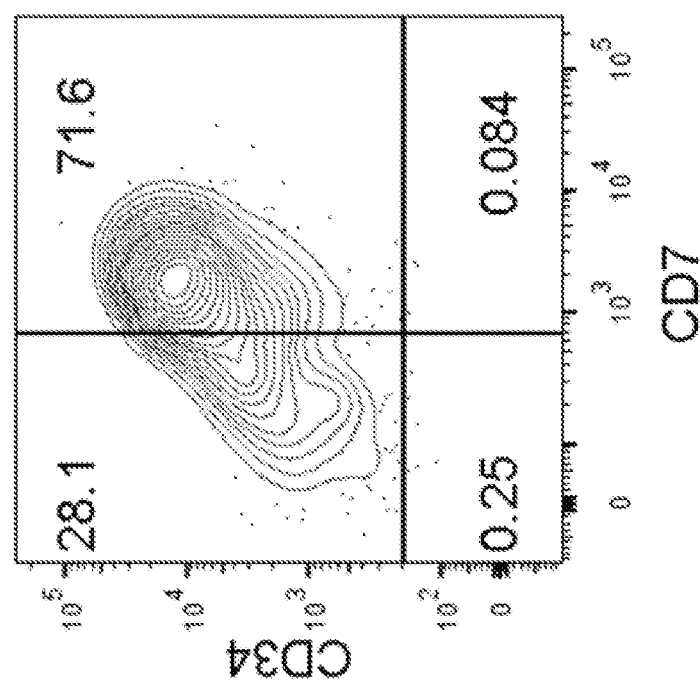
Figure 21C:
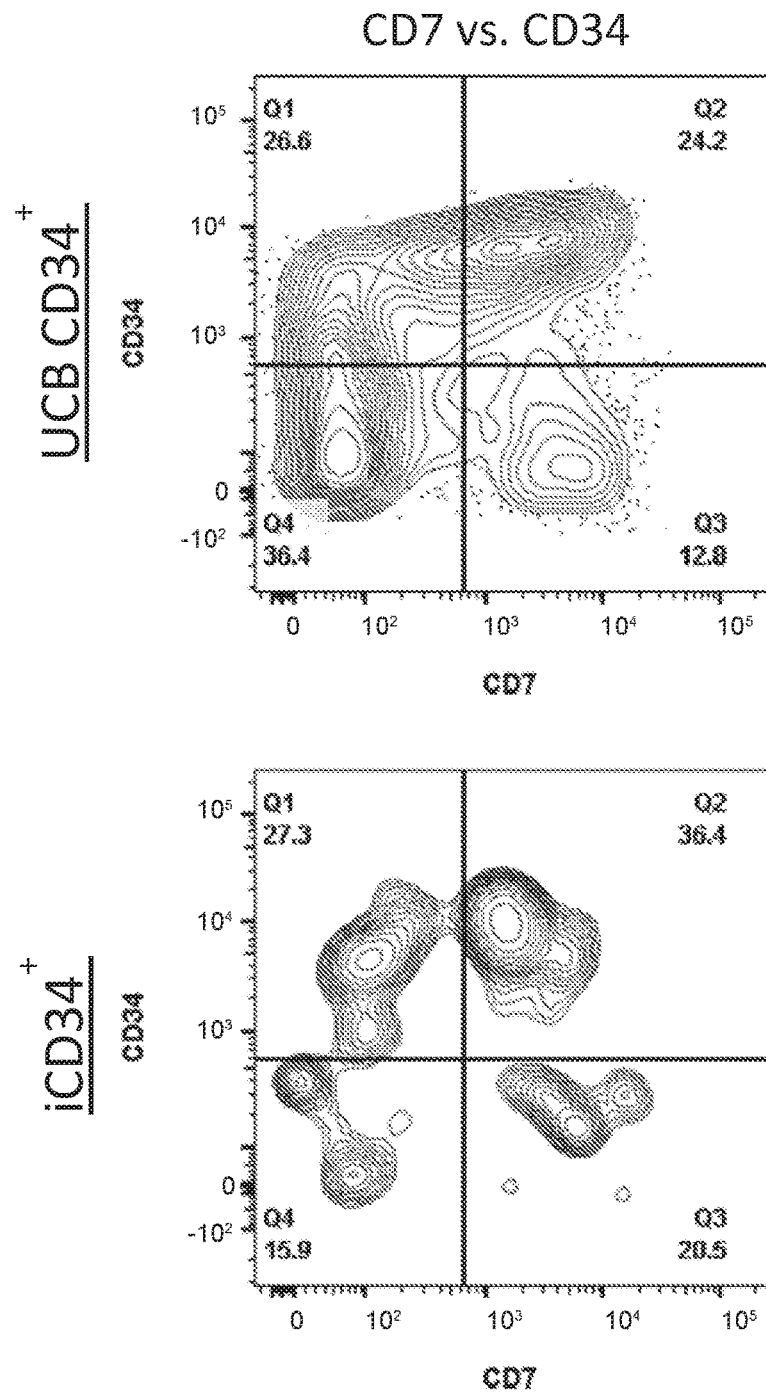
Figure 26:
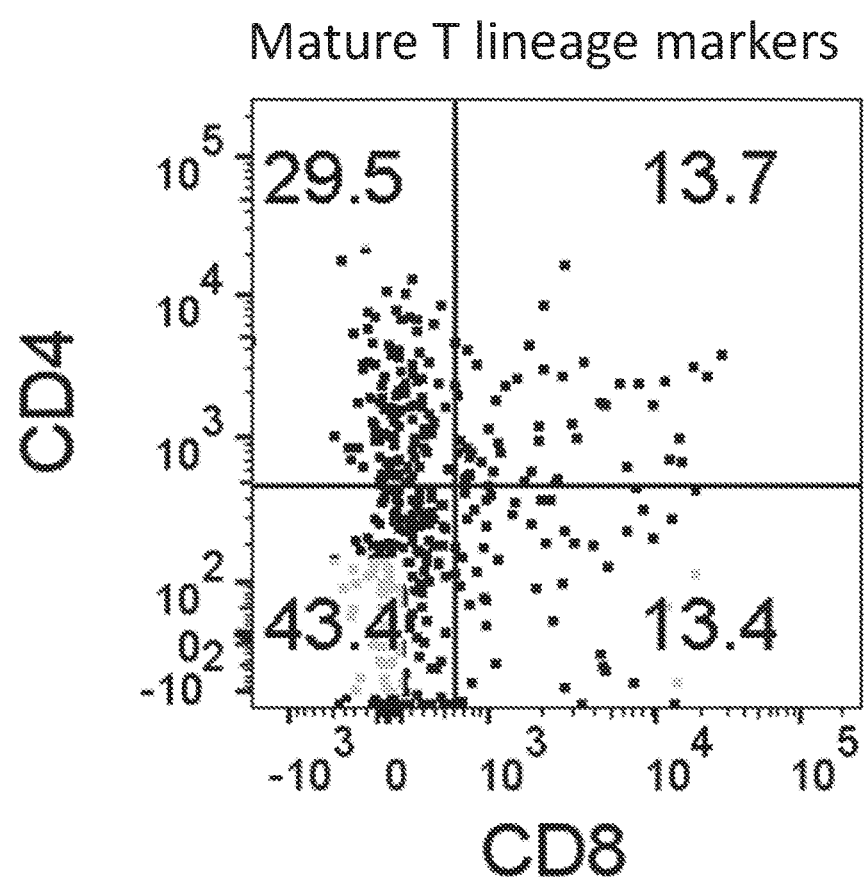
FIG. 26 shows mature CD4+ and CD8+ T cell subsets derived from hiPSCs using a CD45+CD56– gating strategy.

Example 13—Continuation of Differentiation of HE Towards Mature T and NK Lymphoid Lineages Using DLL4-Expressing Stromal Cells Sorted CD34+ HE cells were further differentiated towards the T and NK lymphoid lineages. Specific to T cells, upon sorting the HE cells were cultured as aggregates for 16 hours on low attachment tissue culture plates in iTC-A serum-free differentiation media containing BMP4, SCF, Flt3L and IL7 (FIG. 13). After 16 hrs the aggregated cells were transferred to adherent cultures containing DLL4-expressing stromal cells in iTC-B differentiation media containing SCF, Flt3L and IL7. After 5 days the iTC-B medium was maintained to complete T cell differentiation. After approximately 10 days of culture (post HE isolation) the culture was assessed for the generation of T cell progenitors by the co-expression of the cell surface markers CD34 and CD7. After further differentiation for approximately 15-20 days these CD34+CD7+ T cell progenitors gave rise to distinct populations of mature T cells as seen by the expression of CD4 and CD8. FIG. 21 depicts the in vitro differentiation capability of the Day 10 HE population to give rise to early T cell progenitors and mature T cell subsets by analysis of a CD45+CD56− population generated in the co-cultures. FIG. 26 depicts the in vitro differentiation capability of the Day 10 HE population to give rise to mature T cell subsets by analysis of a CD45+CD56− population generated in the co-cultures after approximately 30 days of culture (post HE isolation).

Figure 27:
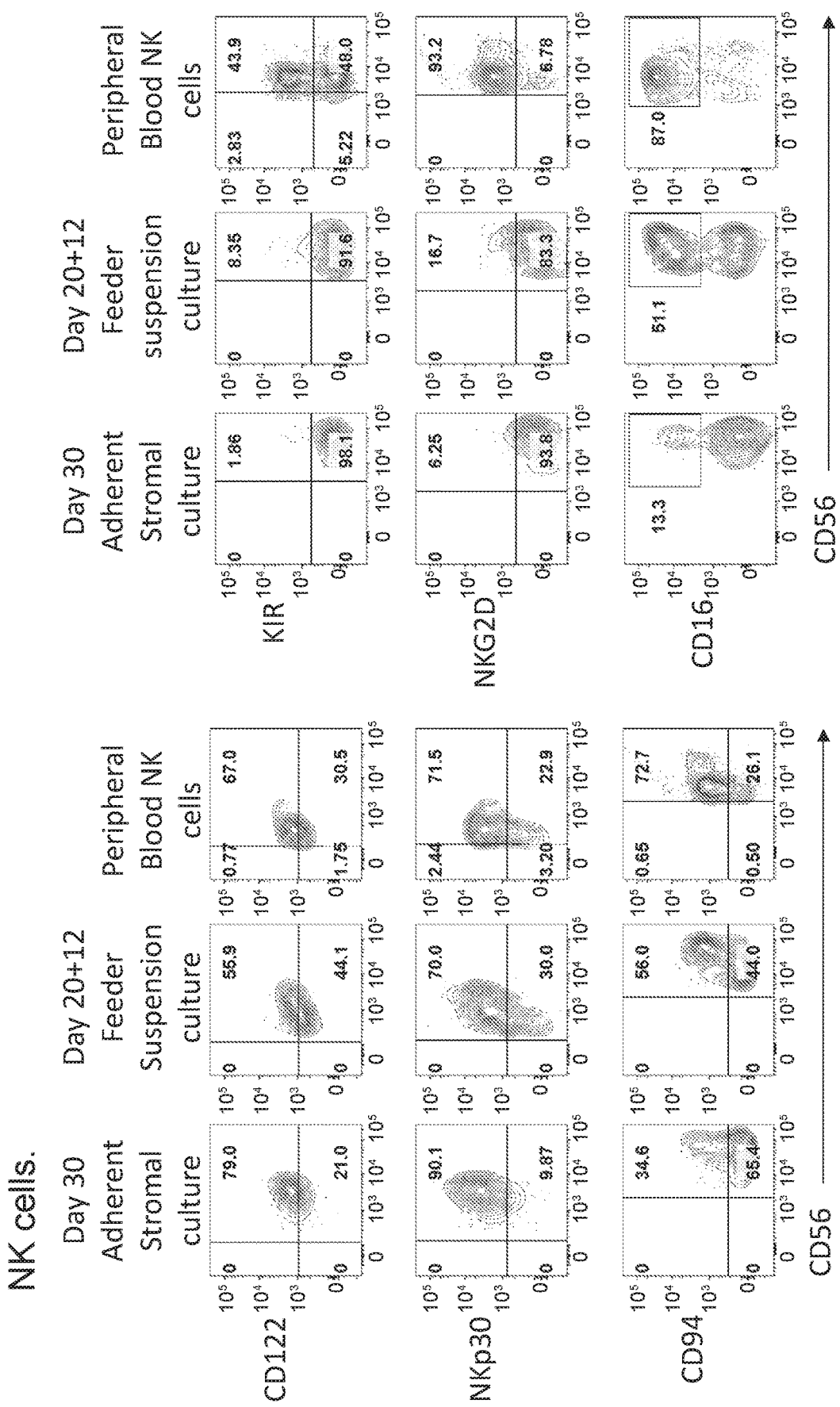
FIG. 27 shows feeder-based suspension culture supports the maturation of iCD34-derived NK cells.

Specific to NK cells, upon sorting, the HE cells were cultured as aggregates for 16 hours on low attachment tissue culture plates in iNK-A serum-free differentiation media containing BMP4, SCF, IL3, IL15, Flt3L and IL7 (FIG. 14). After 16 hrs the aggregated cells were transferred to adherent cultures containing DLL4-expressing stromal cells in iNK-B differentiation media containing SCF, IL3, IL15, Flt3L and IL7. After 5 days the iNK-B medium was maintained to complete NK cell differentiation. After approximately 10-15 days of culture (post HE isolation) the culture was assessed for the generation of NK cell progenitors followed by mature NK subsets following an additional 10-15 days of culture. CD56 and CD161 (NKR-P1A) are the first cell surface markers to be expressed during early NK cell development followed by the expression of CD16, KIR, CD8 and NKG2D (CD314) on later mature NK cell subsets. FIG. 22 depicts the in vitro differentiation capability of the Day 10 HE population to give rise to early NK cell progenitors and mature NK cell subsets by analysis of a CD45+ population generated in the co-cultures. An alternative method to enhance the maturation of NK cell progenitors is co-culture with feeder cells in a suspension culture. Day 20 iNK cells were transferred from DLL4-stromal cell culture to feeder-based suspension cultures in iNK-B media containing SCF, IL15, FLT3L and IL7 for an additional 12 days in culture. FIG. 27 depicts the in vitro differentiation capability of the Day 10 HE population to give rise to mature NK cell subsets using feeder suspension culture by analysis of a CD45+ population generated in the stromal and feeder-based co-cultures compared to peripheral blood-derived NK cells. HiPSC-derived CD34+ cells were differentiated towards the NK cell lineage for 20 days and then placed in suspension culture for further maturation. Mature NK lineage markers identify the presence of mature NK cells as defined by CD56, CD122, NKp30, CD94, CD16, NKG2D and MR.

Figure 23A:
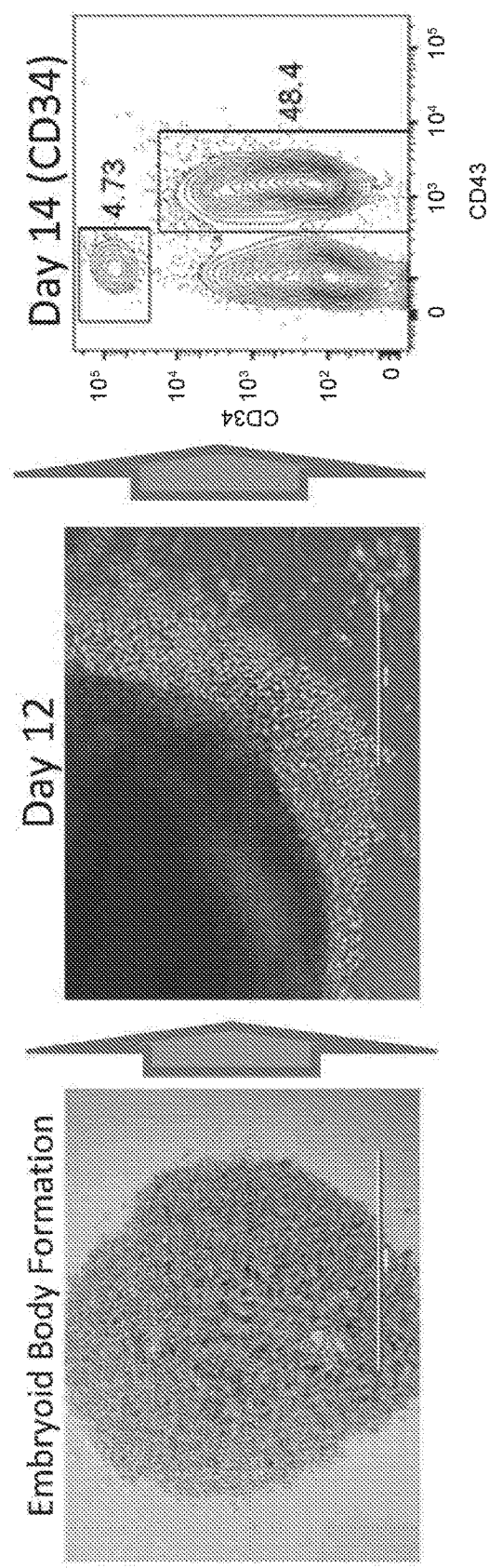
FIG. 23A-C shows monolayer hiPSC hematopoietic differentiation platform allows for a scalable expansion strategy that is not seen during EB formation. A. hiPSCs were aggregated to form Embryoid bodies and differentiated for 14 days prior to analysis for CD34 and 43 expression. B. hiPSCs were seeded as monolayer and differentiated for 8 days prior to analysis for CD34, 43, CXCR4 and CD73. C. CD34 positive cells were counted and plotted over time for both monolayer and EB mediated hematopoietic differentiation.
Figure 23B:
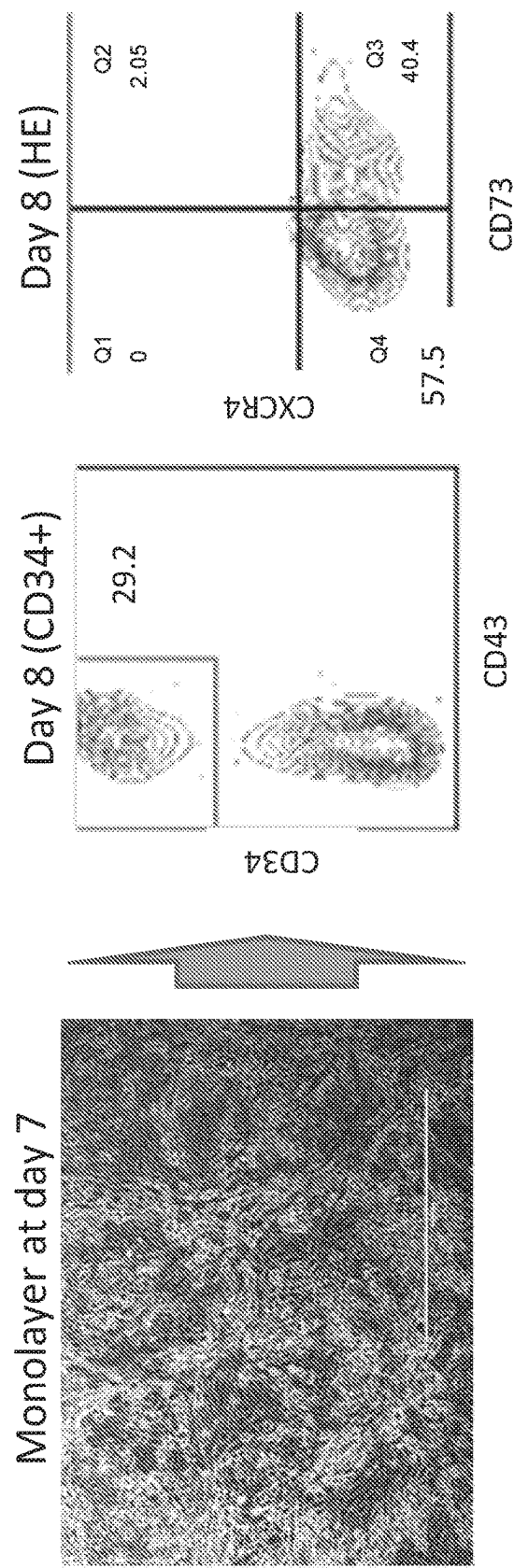
Figure 23C:
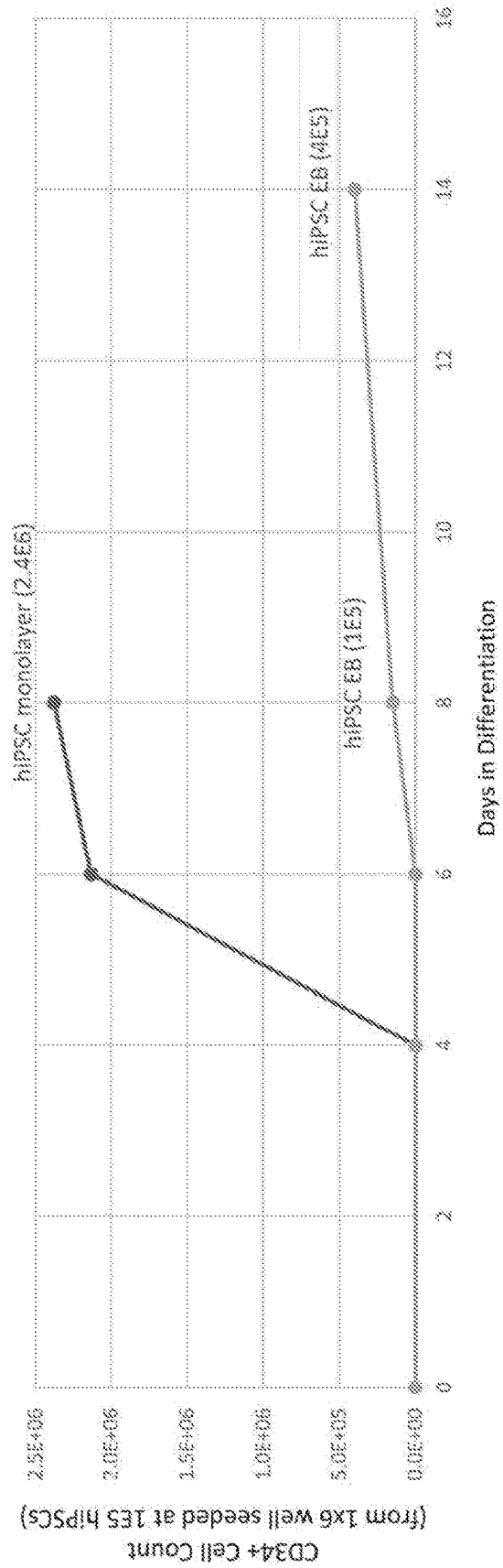
Figure 24:
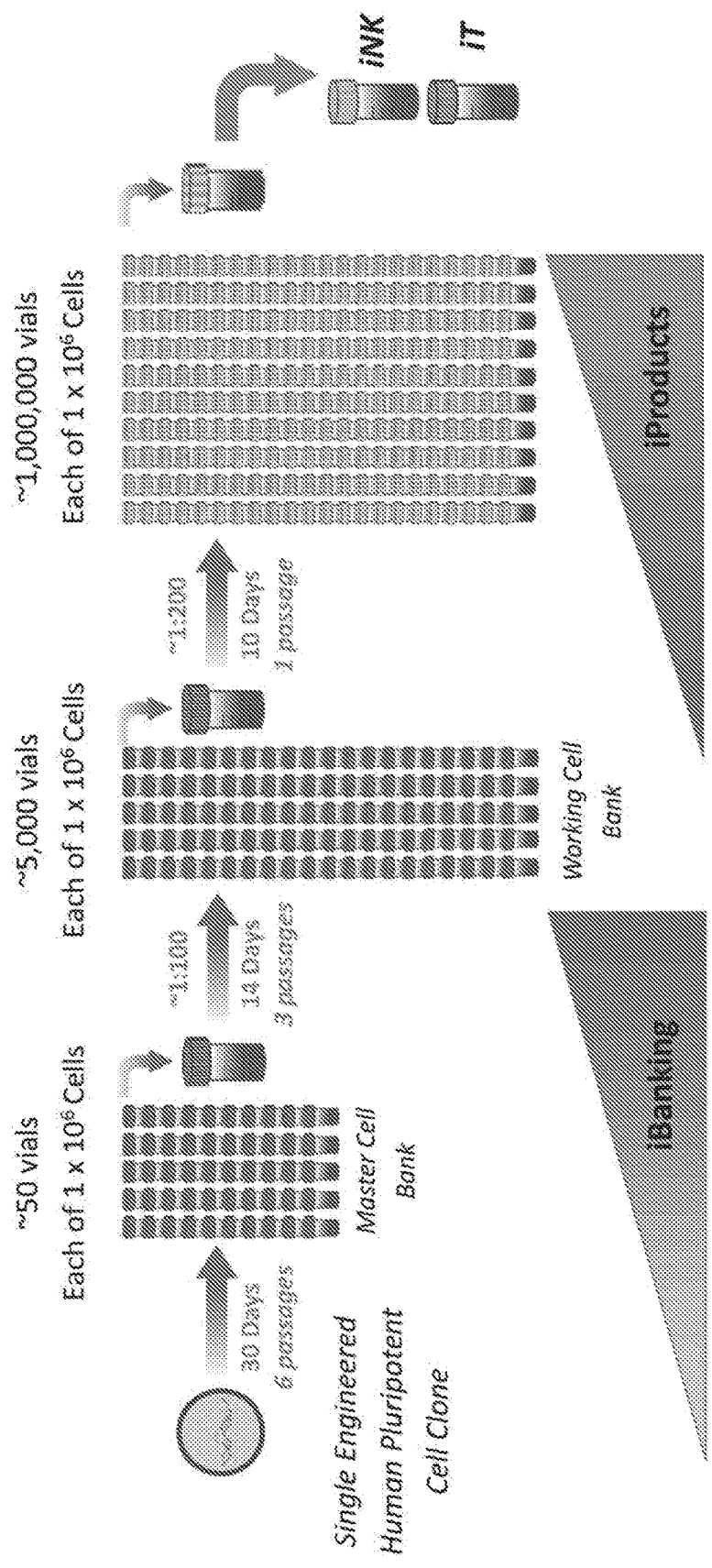
FIG. 24 shows a schematic diagram for the scalable expansion strategy of the monolayer hiPSC hematopoietic differentiation platform for the production of off-the-shelf iNK and iT cells. Calculations are based on a snapshot of representative cultures and not optimized cultures.

Example 14—Monolayer hiPSC Hematopoietic Differentiation Platform Allows for a Highly Scalable Expansion Strategy hiPSCs were seeded as monolayer and differentiated towards hematopoietic cells in defined, serum-free and feeder-free culture as described in FIGS. 12-14 and compared to hiPSCs setup in aggregates to form embryoid bodies prior to the initiation of hematopoietic differentiation (Kennedy et al., Cell Reports 2012:1722-1735). Both culture sets used 100,000 hiPSCs as the initial starting number. During the hematopoietic differentiation process, cell counts and phenotype assessment was conducted routinely to demonstrate the expansion potential of each system. As shown by FIG. 23, by day 6 of differentiation, a significant number of CD34 positive cells were detected in the monolayer culture—over 2 million CD34+ cells, versus the EB format where no CD34 positive cells were detected. On day 8 of differentiation, the monolayer format had generated approximately 2.4 million cells while in the EB format only approximately 100,000 CD34 positive cells were detected, despite roughly the same number of iPSCs as the starting material, a difference of approximately 24-fold. In addition, as the time of assessment, while the monolayer format produced only CD34+CD43− cells, suggestive of definitive hematopoiesis, the EB format produced majority CD34+ CD43+ cells suggestive of primitive hematopoiesis (Kennedy et al., 2012). FIG. 24 further illustrates the scalable expansion of the monolayer hiPSC hematopoietic differentiation platform as disclosed herein for the production of off-the-shelf iNK and iT cells. The pluripotent cell clonal expansion platform provided herein ensures off-the-shelf scalability, for example, from a single pluripotent cell clone to about one million vials of therapeutic doses, each having no less than $10^6$ NK or T cells that are therapeutically functional. The clonal expansion as disclosed further provides extensive homogeneity and therefore ensures product consistency, quality control and quality assurance. In some embodiments, the single pluripotent cell clone is genetically engineered.

Example 15—Immune-Regulatory Properties of iCD34+ Cells

Figure 25:
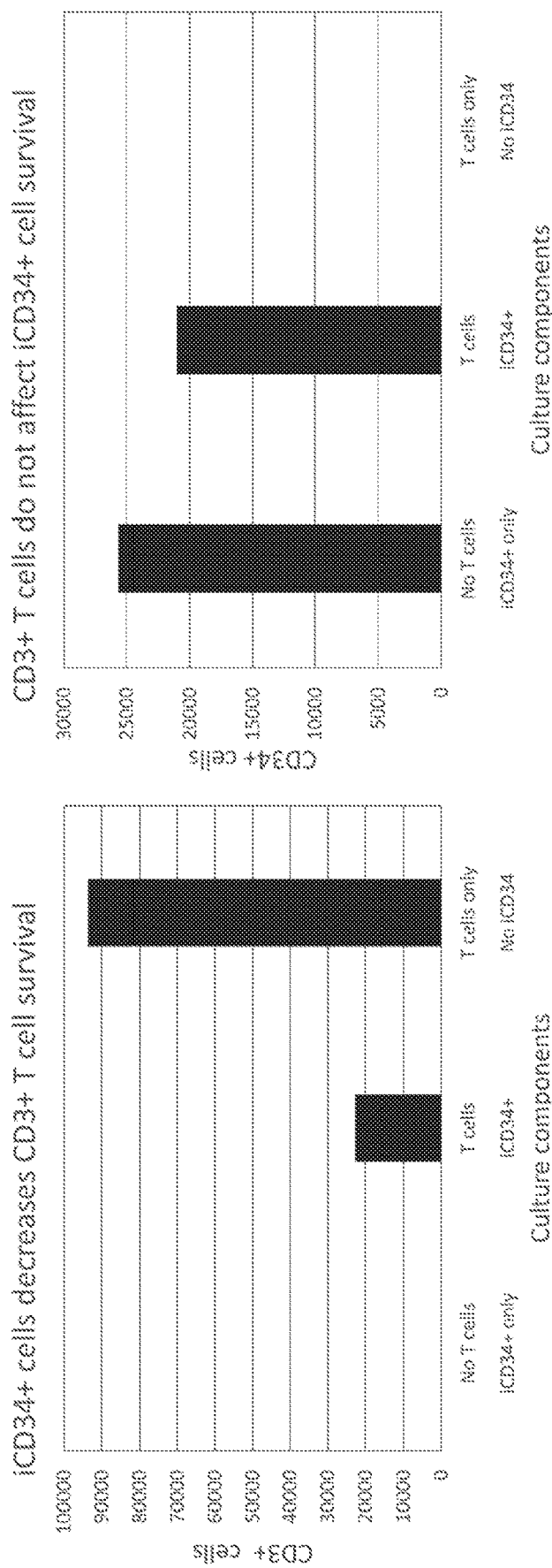
FIG. 25 shows hiPSC-derived CD34 positive cells have immune-regulatory properties by the suppression of CD3+ T cell survival.

To determine the immune-regulatory capacity of the hiPSC-derived CD34 positive cells (iCD34), CD34 sorted cells were co-cultured with activated peripheral blood-derived CD3-expressing T cells in iMPP-A media. After 5 days incubation at 37° C., the cocultures were mixed with counting beads and assayed via flow cytometry to determine the absolute number of cells in each sample. FIG. 25 depicts the immune-regulatory potential of the hiPSC-derived CD34+ cells as seen by comparison to cultures containing CD3+ T cells alone, the CD3+ T cells cocultured with hiPSC-derived CD34+ cells had decreased cellular survival while the total number of CD34+ cells in the culture was unaffected.

Figure 28:
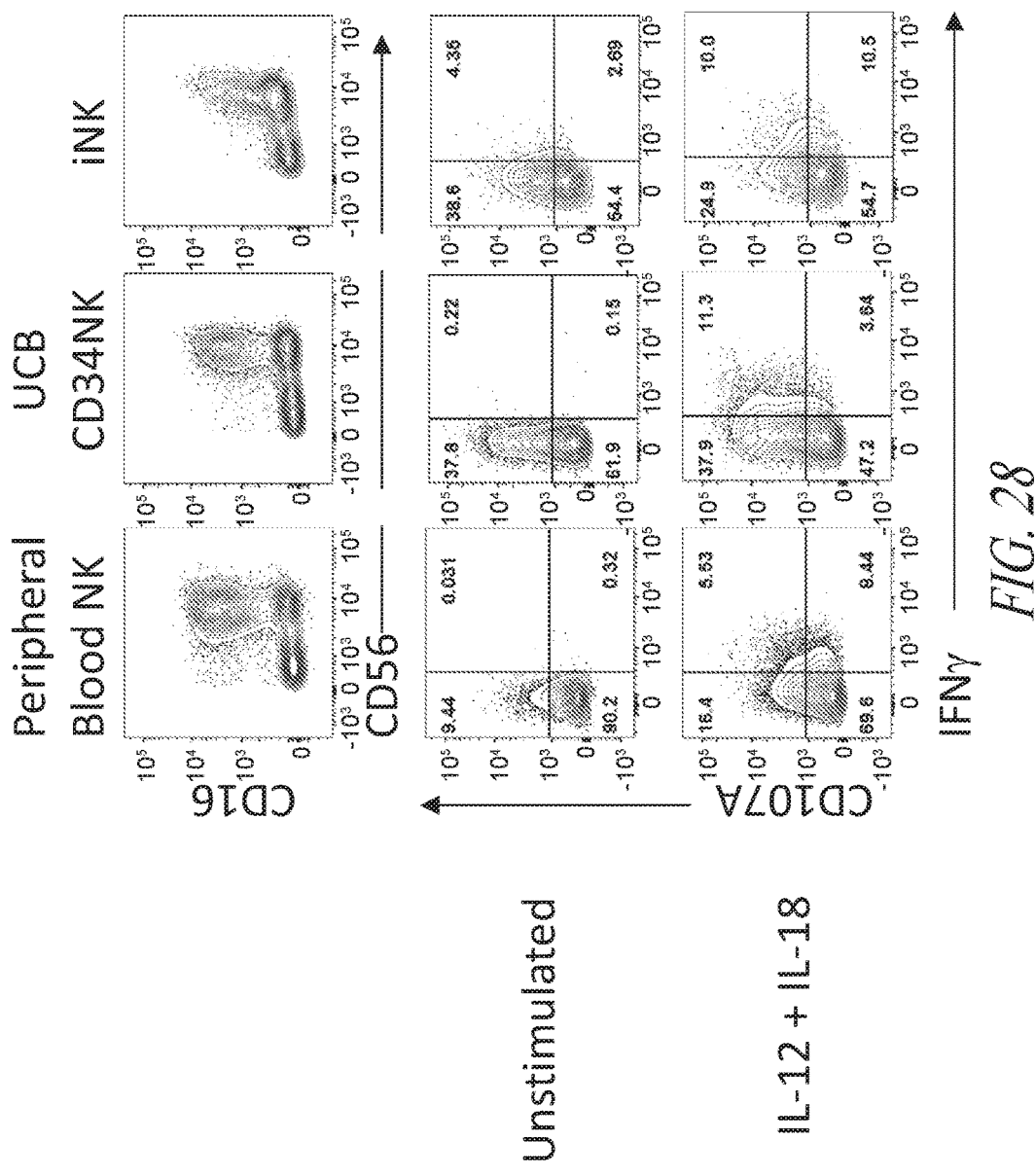
FIG. 28 shows iCD34-derived iNK can respond to cytokine stimulation to secrete pro-inflammatory cytokines in a similar manner to peripheral blood NK cells.

Example 16—Determination of iNK Cell Function by Cytokine-Induced Activation as Seen by Cytokine Release and Degranulation To demonstrate the functionality of the hiPSC-derived mature iNK cells, Day 20 (after HE isolation) iNK cells were transferred to feeder-based suspension cultures for an additional 10 days in iNK-B media containing SCF, IL15, IL7 and Flt3L. After 10 days of additional culture, iNK cells were stimulated with IL12 and IL18 to induce iNK cell activation. iCD34-derived iNK responded to cytokine stimulation and secreted pro-inflammatory cytokines in a similar manner to peripheral blood NK cells. FIG. 28 depicts the activation of iNK cells as seen by the expression of CD107A (a cell surface marker representative of degranulation) and the intracellular staining for interferon gamma based on a CD45+CD56+ gating strategy as compared to umbilical cord blood-derived NK cells generated using the same stromal and feeder suspension co-cultures and peripheral blood-derived NK cells.

Example 17—Establishment of Stromal-Free Differentiation Cultures for the Generation of T and NK Cells The above T and NK lymphoid differentiation platform was further optimized for the generation of umbilical cord blood-derived and hiPSC-derived iT and iNK progenitors using a stromal-free differentiation platform.

Figure 29:
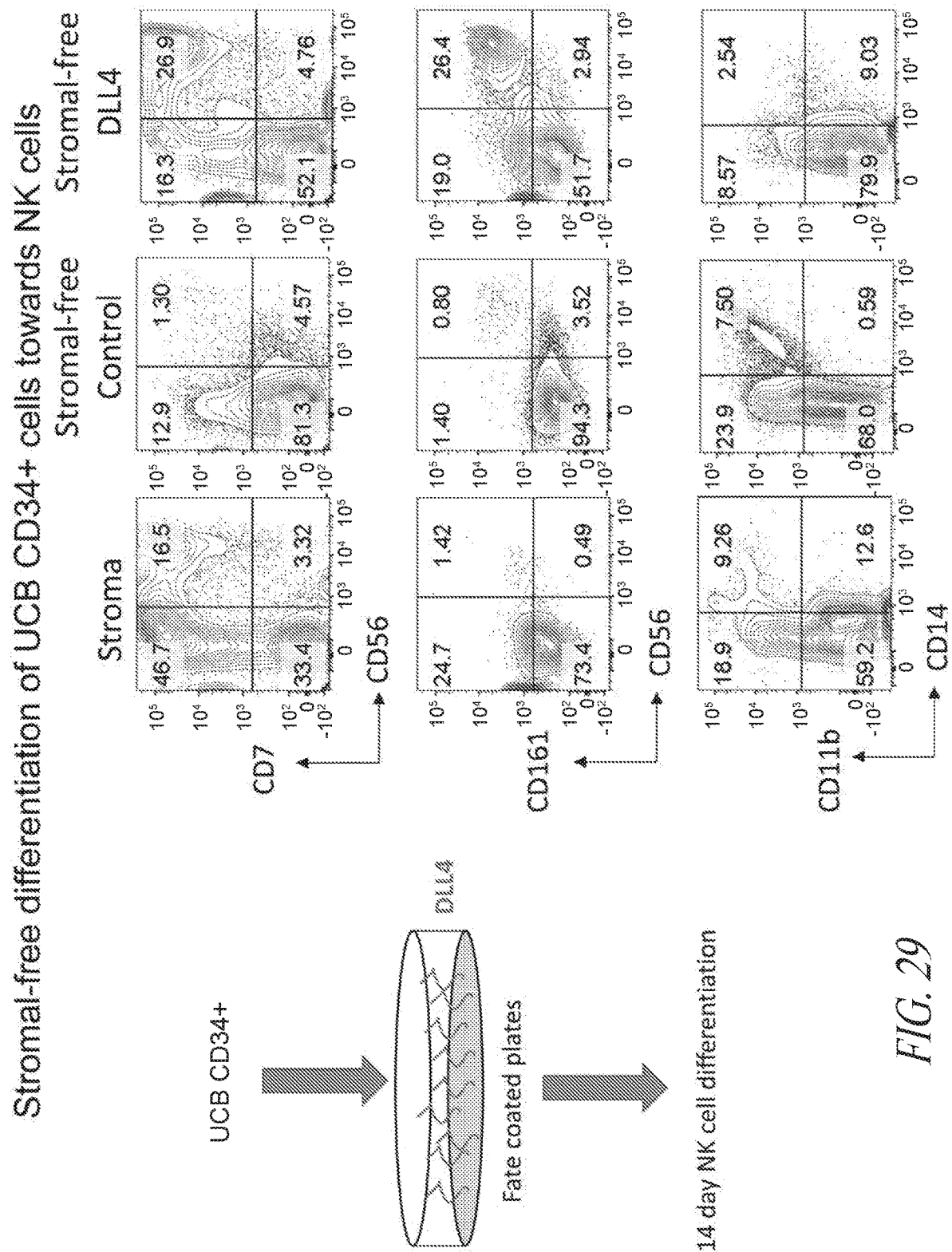
FIG. 29 shows the stromal-free differentiation of pro-NK cells derived from umbilical cord blood CD34 positive cells is more rapid than conventional stromal-based differentiation platform using a CD45+ gating strategy.

Specific to NK cells, enriched umbilical cord blood CD34+ cells were plated in iNK-A serum-free differentiation media containing SCF, Flt3L, IL3, IL15 and IL7 in culture plates containing DLL4 protein or control protein. After 5 days the iNK-B medium was maintained to complete NK cell differentiation. After approximately 10-15 days of culture, the culture was assessed for the generation of NK cell progenitors and the absence of myeloid cells. CD56, CD7 and CD161 are the first cell surface markers to be expressed during NK cell development. CD11b and CD14 are cell surface markers expressed on myeloid cell subsets. FIG. 29 depicts stromal-free differentiation of umbilical cord blood CD34+ cells towards NK cells. It was shown that the plate-bound DLL4 supports a more rapid and efficient differentiation of CD56+CD7+CD161+ NK cell progenitors compared to stromal-based cultures and stromal-free control cultures, and that the umbilical cord blood CD34+ cells have the in vitro differentiation capacity to give rise to early NK cell progenitors (pro-NK) in a DLL4-expressing stromal-free differentiation platform in a similar manner (in terms of phenotype) to conventional stromal-based differentiation platform using a CD45+ gating strategy. Early NK lineage markers identify the presence of proNK cells as defined by CD56, CD7 and CD161 and the absence of myeloid markers CD11b and CD14.

Figure 30:
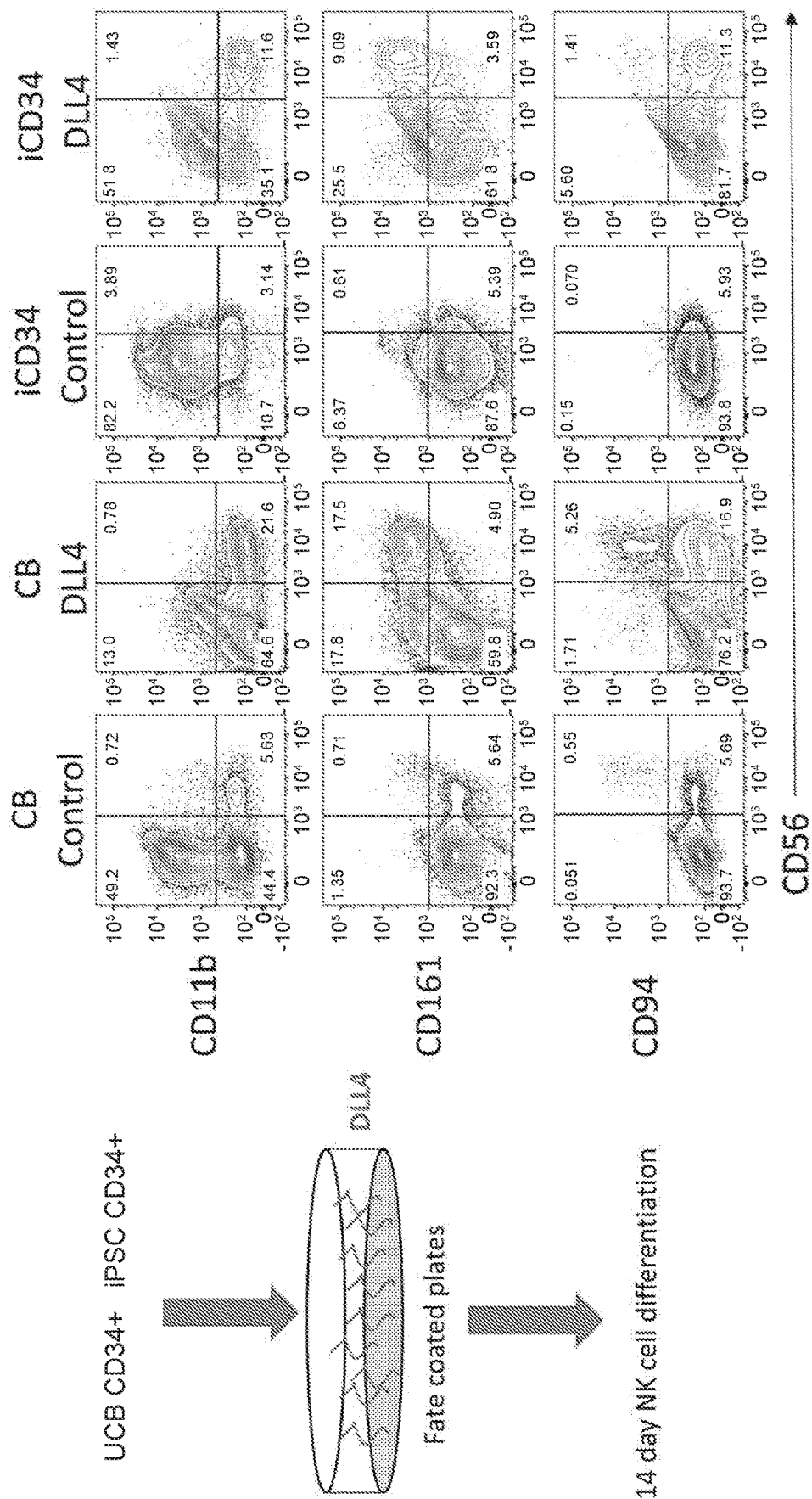
FIG. 30 shows stromal-free differentiation of iPSC-derived iCD34+ cells towards NK cells. Plate bound DLL4 supports the differentiation of CD56+CD7+CD161+ NK cell progenitors but not CD11 b+ myeloid cells.

To demonstrate the capacity of hiPSC-derived HE cells in giving rise to iNK cell progenitors in the stromal-free differentiation platform, Day 10 CD34+ iHE sorted cells were cultured in iNK-A2 media in cultures containing DLL4 protein or control protein. Then the hiPSC-derived CD34+ cells were differentiated towards the NK cell lineage for 20 days and then placed in suspension culture for further maturation. FIG. 30 illustrates the capability of hiPSC-derived iHE to give rise to iNK cell progenitors as seen by the expression of CD56, CD161 and CD94 using a CD45+ gating strategy. Plate bound DLL4 supports the differentiation of CD56+CD7+CD161+ NK cell progenitors but not CD11 b+ myeloid cells. After 5 days iNK-B2 media was maintained to complete NK cell differentiation. The maturation of hiPSC-derived iNK cells in a feeder-based suspension cultures results in mature NK cells that phenotypically resemble peripheral blood NK cells using a CD45+ gating strategy. Mature NK lineage markers identify the presence of mature NK cells as defined by CD56, CD122, NKp30, CD94, CD16, NKG2D and MR.

Figure 31:
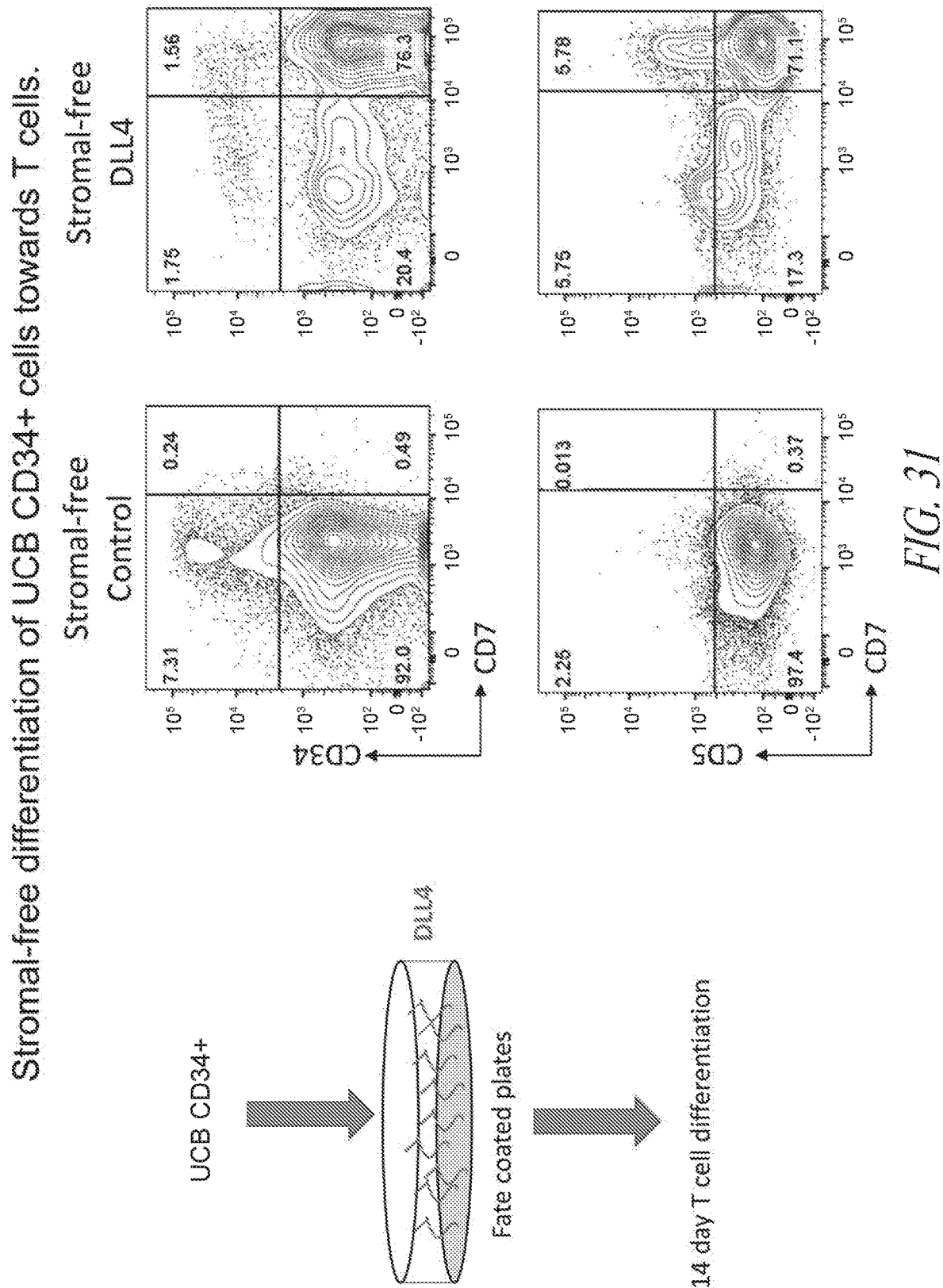
FIG. 31 shows stromal-free differentiation of UCB CD34+ cells towards T cells.

Specific to T cells, enriched CD34+ cells from umbilical cord blood were plated in iT-A2 media in cultures containing DLL4 protein or control protein. After 5 days iT-B2 media was maintained for the generation of T cell progenitors (proT). After approximately 10-15 days of culture the cultures were assessed for the generation of T cell progenitors by the co-expression of the cell surface markers CD34 and CD7. FIG. 31 depicts the ability of CD34+ umbilical cord blood cells to give rise to T cell progenitors in a DLL4-expressing stromal-free differentiation platform using a CD45+ gating strategy. The stromal-free differentiation platform of proT cells derived from umbilical cord blood CD34 positive cells was shown to be more rapid than conventional stromal-based differentiation platform using a CD45+CD56-gating strategy. Early T lineage markers identify the presence of proT cells as defined by CD34, CD5 and CD7.

Figure 32:
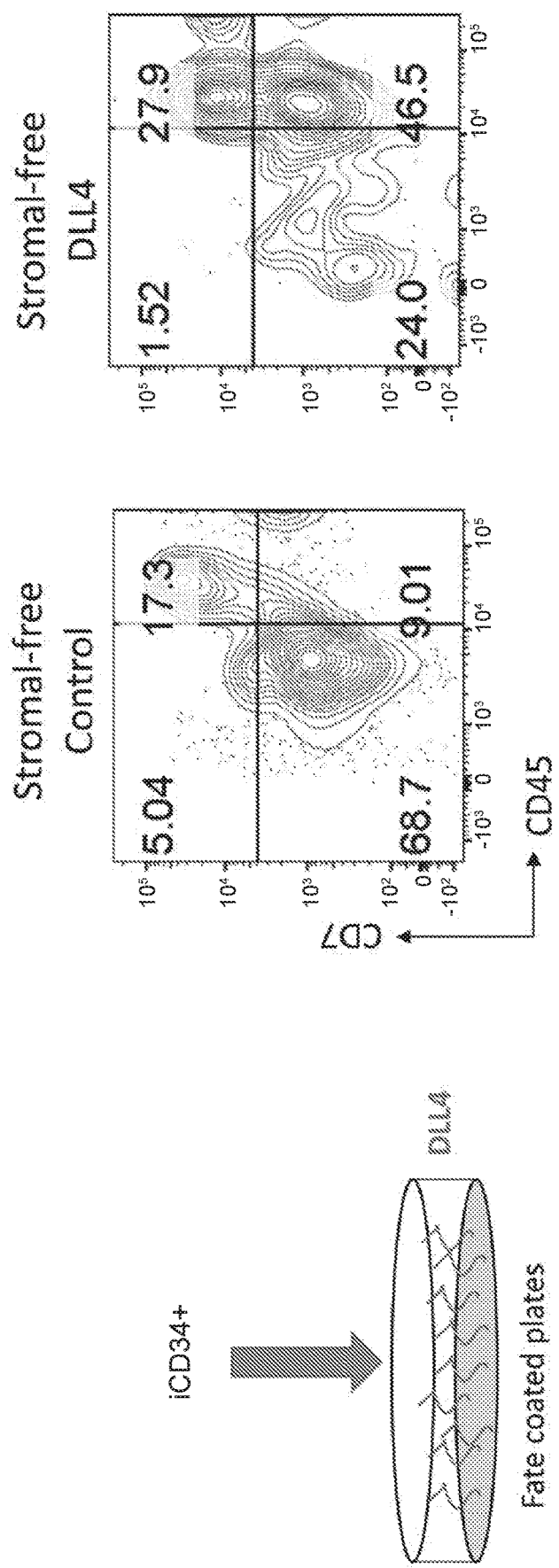
FIG. 32 shows stromal-free differentiation of iPSC-derived iCD34+ cells towards T cells.

To demonstrate the capacity of hiPSC-derived HE cells to give rise to iT cells in the stromal-free platform, Day 10 CD34+ iHE sorted cells were cultured in iT-A2 media in cultures containing DLL4 protein or control protein. FIG. 32 illustrates the capacity of hiPSC-derived iHE to give rise to iT progenitors as seen by the expression of CD45 and CD7.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An in vitro method for generating human pluripotent stem cell-derived Natural Killer (NK) lineage cells comprising:
   (i) contacting human pluripotent stem cells with a composition comprising a BMP activator, to allow cell differentiation and expansion to obtain human pluripotent stem cell-derived mesodermal cells;
   (ii) contacting the human pluripotent stem cell-derived mesodermal cells with a composition comprising a BMP activator, bFGF, and a GSK3 inhibitor, to allow cell differentiation and expansion, to obtain human pluripotent stem cell-derived mesodermal cells having definitive hemogenic endothelium (HE) potential;
   (iii) contacting the human pluripotent stem cell-derived mesodermal cells having definitive HE potential with a composition comprising a ROCK inhibitor, and one or more growth factors and cytokines selected from the group consisting of bFGF, VEGF, SCF, IL6 and IL11, to allow cell differentiation and expansion, wherein the composition is free of TGFβ receptor/ALK inhibitor to obtain human pluripotent stem cell-derived definitive hemogenic endothelium; and
   (iv) contacting the human pluripotent stem cell-derived definitive hemogenic endothelium with a composition comprising one or more growth factors and cytokines selected from the group consisting of SCF, Flt3L, IL3, IL7, and IL15, wherein the composition is free, or essentially free, of one or more of VEGF, bFGF, BM' activators and ROCK inhibitors for generating the human pluripotent stem cell-derived NK lineage cells.

2. The method of claim 1, wherein the method further comprises subjecting human pluripotent stem cells, pluripotent stem cell-derived mesodermal cells, mesodermal cells with hemogenic endothelium potential, and/or definitive hemogenic endothelium under low oxygen tension between about 2% to about 10%.

3. The method of claim 2, wherein the human pluripotent stem cell-derived NK lineage cells comprise pluripotent stem cell-derived (i) pre-NK cell progenitors, (ii) NK cell progenitors or (iii) NK cells.

4. The method of claim 1, wherein the human pluripotent stem cells are iPSCs or naïve iPSCs.

5. The method of claim 1, wherein the composition contacting the human pluripotent stem cells further comprises bFGF.

6. The method of claim 1, wherein the composition contacting the human pluripotent stem cell-derived mesodermal cells is free of TGFβ receptor/ALK inhibitor.

7. The method of claim 1, wherein the method further comprises contacting human pluripotent stem cells with a composition comprising a MEK inhibitor, a GSK3 inhibitor, and a ROCK inhibitor, to seed and expand the cells, wherein the composition is free of TGFβ receptor/ALK inhibitors.

8. The method of claim 1, wherein generating human pluripotent stem cell-derived NK lineage cells is void of generation of embryoid bodies.

9. The method of claim 1, wherein generating human pluripotent stem cell-derived NK lineage cells is under monolayer culturing.

10. The method of claim 1, wherein generating human pluripotent stem cell-derived NK lineage cells is under feeder-free condition.

11. The method of claim 1, wherein generating human pluripotent stem cell-derived NK lineage cells is under stromal-free condition.

12. A differentiation platform for generating human pluripotent stem cell-derived NK cells comprising:
  (i) a culture medium that comprises a BMP activator, and optionally bFGF, wherein the medium is suitable for differentiating and expanding human pluripotent stem cell-derived mesodermal cells from human pluripotent stem cells;
  (ii) a culture medium comprising a BMP activator, bFGF, and a GSK3 inhibitor, wherein the medium is suitable for obtaining definitive hemogenic endothelium potential in the human pluripotent stem cell-derived mesodermal cells;
  (iii) a culture medium comprising a ROCK inhibitor, one or more growth factors and cytokines selected from the group consisting of bFGF, VEGF, SCF, IL6, and IL11, wherein the medium is suitable for differentiating human pluripotent stem cell-derived definitive hemogenic endothelium from human pluripotent stem cell-derived mesodermal cells having definitive hemogenic endothelium potential; and
  (iv) a medium comprising one or more growth factors and cytokines selected from the group consisting of SCF, Flt3L, IL3, IL7, and IL15, wherein the medium is free of one or more of VEGF, bFGF, BMP activators and ROCK inhibitors and is suitable for differentiating human pluripotent stem cell-derived definitive hemogenic endothelium to human pluripotent stem cell-derived NK cell progenitors or NK cells.

13. The differentiation platform of claim 12, further comprising:
  (v) a culture medium that comprises a MEK inhibitor, a GSK3 inhibitor, and a ROCK inhibitor, and is free of TGFβ receptor/ALK inhibitors, wherein the medium is suitable for seeding and expanding human pluripotent stem cells.

14. The differentiation platform of claim 12, wherein the culture medium comprising a BMP activator, bFGF, and a GSK3 inhibitor, is free of TGFβ receptor/ALK inhibitor.

15. The differentiation platform of claim 12, wherein the culture medium comprising a ROCK inhibitor, one or more growth factors and cytokines selected from the group consisting of bFGF, VEGF, SCF, IL6, and IL11, is free of TGFβ receptor/ALK inhibitor.

16. The differentiation platform of claim 12, wherein the human pluripotent stem cells are iPSCs or naive iPSCs.

* * * * *

UNITED STATES PATENT AND TRADEMARK OFFICE
CERTIFICATE OF CORRECTION

PATENT NO. : 10,626,372 B1
APPLICATION NO. : 15/545243
DATED : April 21, 2020
INVENTOR(S) : Bahram Valamehr and Raedun Clarke Page 1 of 1

It is certified that error appears in the above-identified patent and that said Letters Patent is hereby corrected as shown below:

In the Claims

Column 92, Line 59, in the twenty-eighth Line of Claim 1, delete "one or more of VEGF, bFGF, BM'" and insert --one or more of VEGF, bFGF, BMP--

Signed and Sealed this
Fourth Day of February, 2025

Coke Morgan Stewart
*Acting Director of the United States Patent and Trademark Office*